US009399776B2

(12) United States Patent
Friedrich et al.

(10) Patent No.: US 9,399,776 B2
(45) Date of Patent: Jul. 26, 2016

(54) ***CHLOROGLOEOPSIS* SP. HOST CELL FOR PRODUCING ETHANOL AND METHOD FOR PRODUCING ETHANOL USING THE SAME**

(71) Applicant: Algenol Biofuels Inc., Fort Myers, FL (US)

(72) Inventors: Alexandra Friedrich, Berlin (DE); Irina Piven, Berlin (DE); Frank Uliczka, Berlin (DE); Heike Enke, Berlin (DE)

(73) Assignee: Algenol Biotech LLC, Fort Myers, FL (US)

( * ) Notice: Subject to any disclaimer, the term of this patent is extended or adjusted under 35 U.S.C. 154(b) by 4 days.

(21) Appl. No.: 14/839,359

(22) Filed: Aug. 28, 2015

(65) Prior Publication Data

US 2016/0032294 A1 Feb. 4, 2016

Related U.S. Application Data

(63) Continuation of application No. PCT/EP2013/077496, filed on Dec. 19, 2013.

(51) Int. Cl.

| | |
|---|---|
| ***C12N 1/13*** | (2006.01) |
| ***C12N 15/52*** | (2006.01) |
| ***C12N 15/74*** | (2006.01) |
| ***C12N 9/88*** | (2006.01) |
| ***C12N 9/04*** | (2006.01) |

(52) U.S. Cl.

CPC ............. *C12N 15/52* (2013.01); *C12N 9/0006* (2013.01); *C12N 9/88* (2013.01); *C12N 15/74* (2013.01); *C12Y 101/01001* (2013.01); *C12Y 401/01001* (2013.01)

(58) Field of Classification Search

None

See application file for complete search history.

(56) References Cited

U.S. PATENT DOCUMENTS

| | | | |
|---|---|---|---|
| 5,750,380 | A | 5/1998 | Itakura et al. |
| 6,306,639 | B1 | 10/2001 | Woods et al. |
| 6,472,184 | B1 | 10/2002 | Hegemann et al. |
| 6,699,696 | B2 | 3/2004 | Woods et al. |

FOREIGN PATENT DOCUMENTS

| | | |
|---|---|---|
| WO | WO2009/098089 | 8/2009 |
| WO | WO2009/105714 | 8/2009 |
| WO | WO2011/103277 | 8/2011 |
| WO | WO2013/098265 | 7/2013 |
| WO | WO2013/098267 | 7/2013 |
| WO | WO2015/090422 | 6/2015 |

OTHER PUBLICATIONS

Mitra et al. (1967), "On a new genus of the blue-green alga *Chlorogloeopsis* with remarks on the production of heterocysts in the alga," Phykos 5:106-114.

Mitra et al. (1950), "Two new algae from Indian soils," Ann. Bot. London. N.S. 14: 457-464.

Stucken et al. (2012), "Transformation and Conjugal Transfer of Foreign Genes into the Filamentous Multicellular Cyanobacteria (Subsection V) Fischerella and Chlorogloeopsis," Curr Microbiol., 65:552-560.

International Search Report and Written Opinion for PCT/EP2013/077496, dated Feb. 20, 2014 (9 pages).

*Primary Examiner* — Jim Ketter

(74) *Attorney, Agent, or Firm* — Lawrence B. Ebert; Suzanne G. Jepson; David J. Lorenz

(57) ABSTRACT

One embodiment of the invention provides a genetically enhanced *Chlorogloeopsis* sp. host cell comprising at least one first recombinant gene encoding a first protein for the production of ethanol under the transcriptional control of a first inducible promoter, having at least 85%, 90% or 95% sequence identity to an endogenous inducible promoter of the *Chlorogloeopsis* sp. host cell.

19 Claims, 33 Drawing Sheets

*Chlorogloeopsis* sp. PCC 6912+ TK18 Ethanol production at 37° C

5´-gatttcaaaatagacagaataataatcattctaacatctgaatatatattcagatattga gataactATGttaaacttcaaaggagttattcttcagcgacttactgaaacggctATG

1.ATG 2.ATG

*Chlorogloeopsis* PCC9212

*CHLOROGLOEOPSIS* SP. HOST CELL FOR PRODUCING ETHANOL AND METHOD FOR PRODUCING ETHANOL USING THE SAME

CROSS-REFERENCE TO RELATED APPLICATIONS

This patent application is a continuation of International Application No. PCT/EP2013/077496, filed Dec. 19, 2013, the disclosure of which is hereby incorporated by reference.

STATEMENT REGARDING FEDERALLY SPONSORED RESEARCH

Not Applicable.

REFERENCE TO SEQUENCE LISTING

This application contains a sequence listing comprising 36 sequences, submitted by EFS-Web, thereby satisfying the requirements of 37 C.F.R. §§1.821-1.825. The sequence listing file, named "*Chlorogloeopsis*—_ST25.txt", was created on Aug. 25, 2015, and is 286 kb in size.

FIELD OF THE INVENTION

The present invention relates to the genetic enhancement of *Chlorogloeopsis* sp. host cells in order to produce ethanol as a compound of interest.

BACKGROUND OF THE INVENTION

Cyanobacteria are small, prokaryotic, generally aquatic organisms. Some cyanobacterial species can be genetically engineered in order to produce compounds of interest by utilizing light and carbon dioxide. These compounds of interest can include biofuels, industrial chemicals, pharmaceuticals, nutrients, carotenoids, food supplements and other compounds such as lipids. Owing to the fact that cyanobacteria are capable of fixing carbon dioxide as a carbon source for photoautotrophic growth, they do not require the input of organic carbon as feedstock and generally only need few nutrients. Some cyanobacterial species such as *Synechococcus* or *Synechocystis* have been genetically engineered in order to produce various compounds of interest such as ethanol (see for example U.S. Pat. No. 6,699,696 and U.S. Pat. No. 6,306,639, as well as PCT patent application WO 2009/098089 A2). Cyanobacterial cells can grow under a large variety of different growth conditions including sweet water as well as brackish water and can also thrive at very different temperatures.

The cyanobacterial genus *Chlorogloeopsis* belongs to the subsection V of cyanobacteria and is a heterocyst forming nitrogen fixing cyanobacterial genus, which can among others be isolated from hot springs (original publications: Mitra, A. A. and Pandey, D. C. (1967) "On a new genus of the blue-green alga *Chlorogloeopsis* with remarks on the production of heterocysts in the alga"; Phykos 5: pages 106 to 114 and Mitra, A. K. (1950): Two new algae from Indian soils. Ann. Bot. London. N. S. 14: 457-464).

The scientific publication Stucken et al.: "Transformation and Conjugal Transfer of Foreign Genes into the Filamentous Multicellular Cyanobacteria (Subsection V) *Fischerella* and *Chlorogloeopsis*"; Curr Microbiol., 2012 November; 65(5): 552-560, describes successful transformation of Cyanobacteria of subsection V by introducing the gene coding for the green fluorescent protein GFP into *Fischerella* and *Chlorogloeopsis* so that these cells were able to express the GFP reporter protein under two different promoters: the nitrogen regulated PglnA and the strong constitutive *E. coli* promoter Ptrc. For both strains partial removal of the exopolysaccharide sheath by salt washing was a critical step. However, the expression of the green fluorescent protein, which is not an enzyme, does not greatly affect the metabolism of the cyanobacterial cells because it does not consume metabolically important intermediates. This is in contrast to enzymes which are expressed to catalyze the production of chemical compounds of interest. Therefore this publication does not disclose any information on how a stable production of chemical compounds such as ethanol in *Chlorogloeopsis* can be achieved.

What is needed in the art is a new cyanobacterial strain for the production of ethanol, which can withstand hard culturing conditions and the metabolic stress associated with the production of chemical compounds of interest.

SUMMARY OF INVENTION

One aspect of the invention is directed to a genetically enhanced *Chlorogloeopsis* sp. host cell comprising at least one first recombinant gene encoding a first protein for the production of ethanol under the transcriptional control of a first inducible promoter, having at least 85%, 90% or 95% sequence identity to an endogenous inducible promoter of the *Chlorogloeopsis* sp. host cell.

Further, the genetically enhanced *Chlorogloeopsis* sp. host cell can be *Chlorogloeopsis fritschii* PCC6912, *Chlorogloeopsis* sp. PCC 9212, or *Chlorogloeopsis* sp. ABICyano3, preferably *Chlorogloeopsis fritschii* PCC6912.

A second aspect of the invention describes a method for producing ethanol, comprising the method steps of:

a) culturing the genetically enhanced *Chlorogloeopsis* sp. host cells described in the patent application in a culture medium, the host cells thereby producing ethanol,
b) retrieving ethanol at least from either one of: the host cells, the medium or the headspace above the medium.

In particular, the host cells are cultured under at least one of the following culturing conditions:

temperatures between 20° C. to about 55° C., preferably between 30° C. to 45° C., and/or
a salinity of the culture medium of between 0.2 to 35.0 psu, in particular 0.2, 5.0, 8.75 and 17.5 psu.

A third aspect of the invention is directed to a method for producing genetically enhanced *Chlorogloeopsis* sp. host cells comprising introducing a first and if present second recombinant gene into the host cell.

This method can comprise the method steps of:

a) providing a recombinant nucleic acid sequence including the first and if present second recombinant gene and protecting said recombinant nucleic acid sequence against endogenous restriction endonucleases of the host cell,
b) introducing the first and if present second recombinant gene into the host cell.

BRIEF DESCRIPTION OF THE DRAWINGS AND THE SEQUENCE LISTING

Figure 3A:
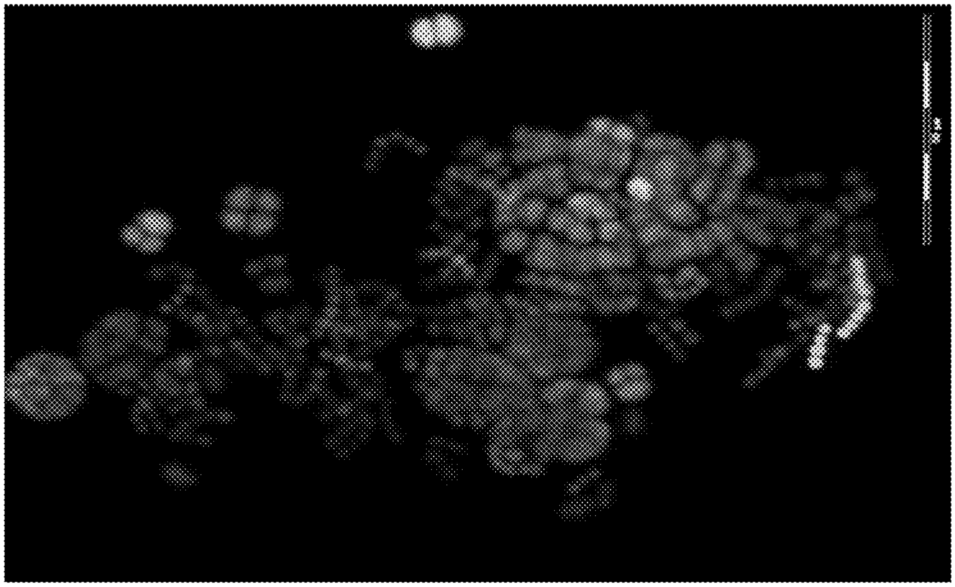
Figure 3B:
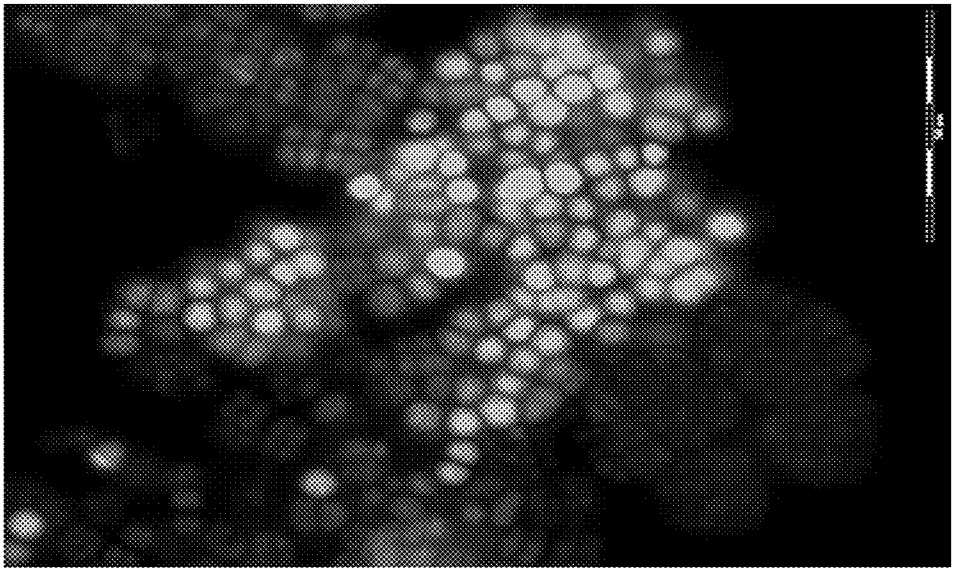

FIG. 3A and FIG. 3B show fluorescence photography of *Chlorogloeopsis* sp. ABICyano3 cells transformed with an extrachromosomal pDU1 based plasmid harboring the gene encoding the green fluorescent protein under the transcriptional control of a promoter inducible by nitrogen starvation. FIG. 3A: non-induced; FIG. 3B: induced by nitrogen-starvation.

Figure 4A:
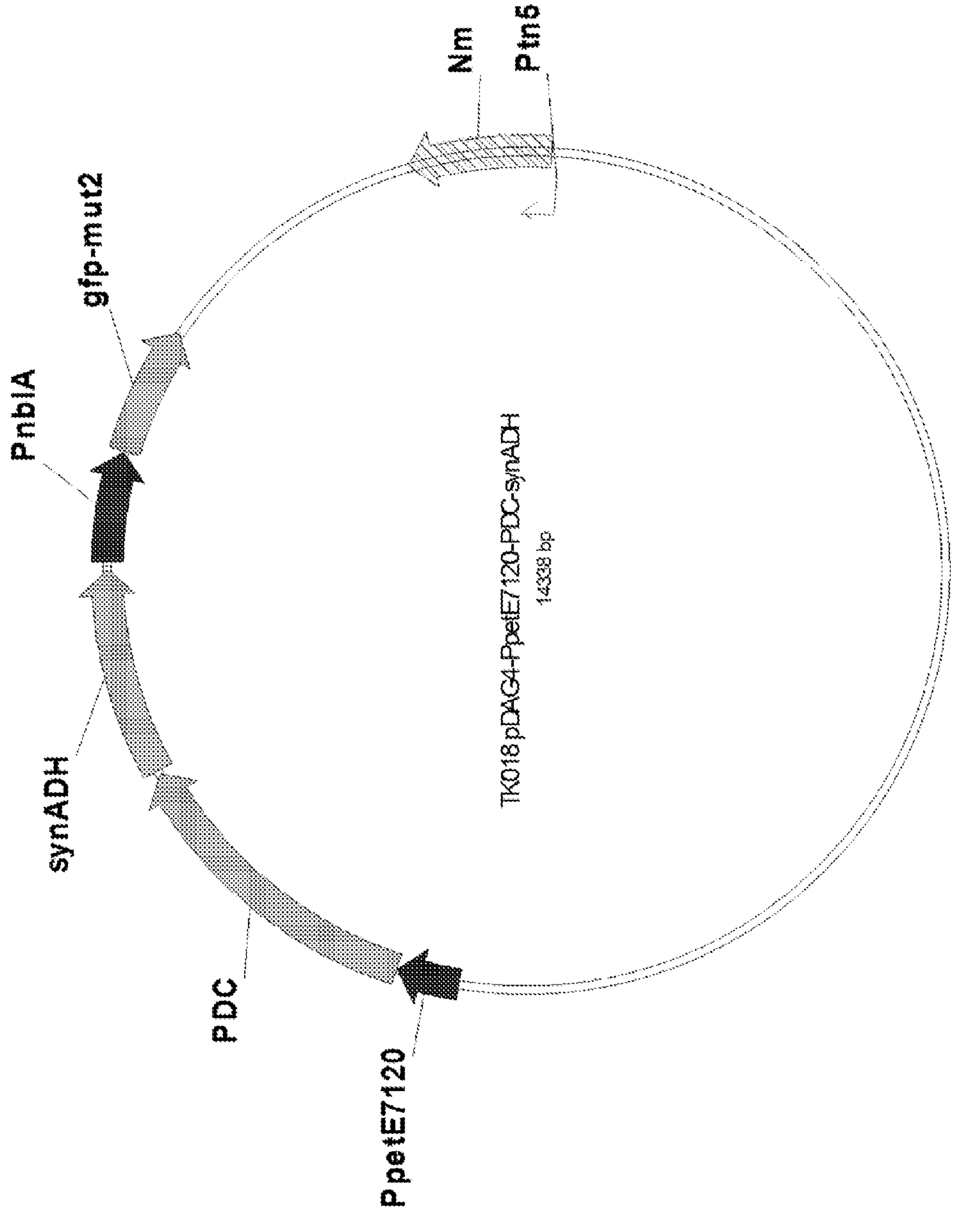

FIG. 4A shows the plasmid map of the pDU1 based plasmid TK18 harboring a gene encoding pyruvate decarboxylase enzyme and also a second recombinant gene encoding the alcohol dehydrogenase from *Synechocystis* PCC6803 under the transcriptional control of the petE promoter from *Nostoc* PCC7120, which was shown to be a constitutive promoter in *Chlorogloeopsis* PCC6912. This plasmid also includes PnblA controlling a gfp gene. The nucleotide sequence of this plasmid is shown in SEQ ID No. 1. The gene encoding the green fluorescent protein runs from nucleotides 628 to 1338, the complementary sequence of the gene conferring neomycin resistance "Nm" is located at nucleotides 2910 to 3701, the promoter PnblA stretches from the nucleotides 18 to 621, the gene encoding the *Synechocystis* alcohol dehydrogenase denoted "synADH" is located at the nucleotides 13201 to 14337, the gene encoding pyruvate decarboxylase denoted "PDC" runs from nucleotides 11472 to 13178, and the promoter PpetE from *Nostoc/Anabaena* PCC7120 labeled as "PpetE7120" runs from nucleotides 11124 to 11470.

Figure 4B:
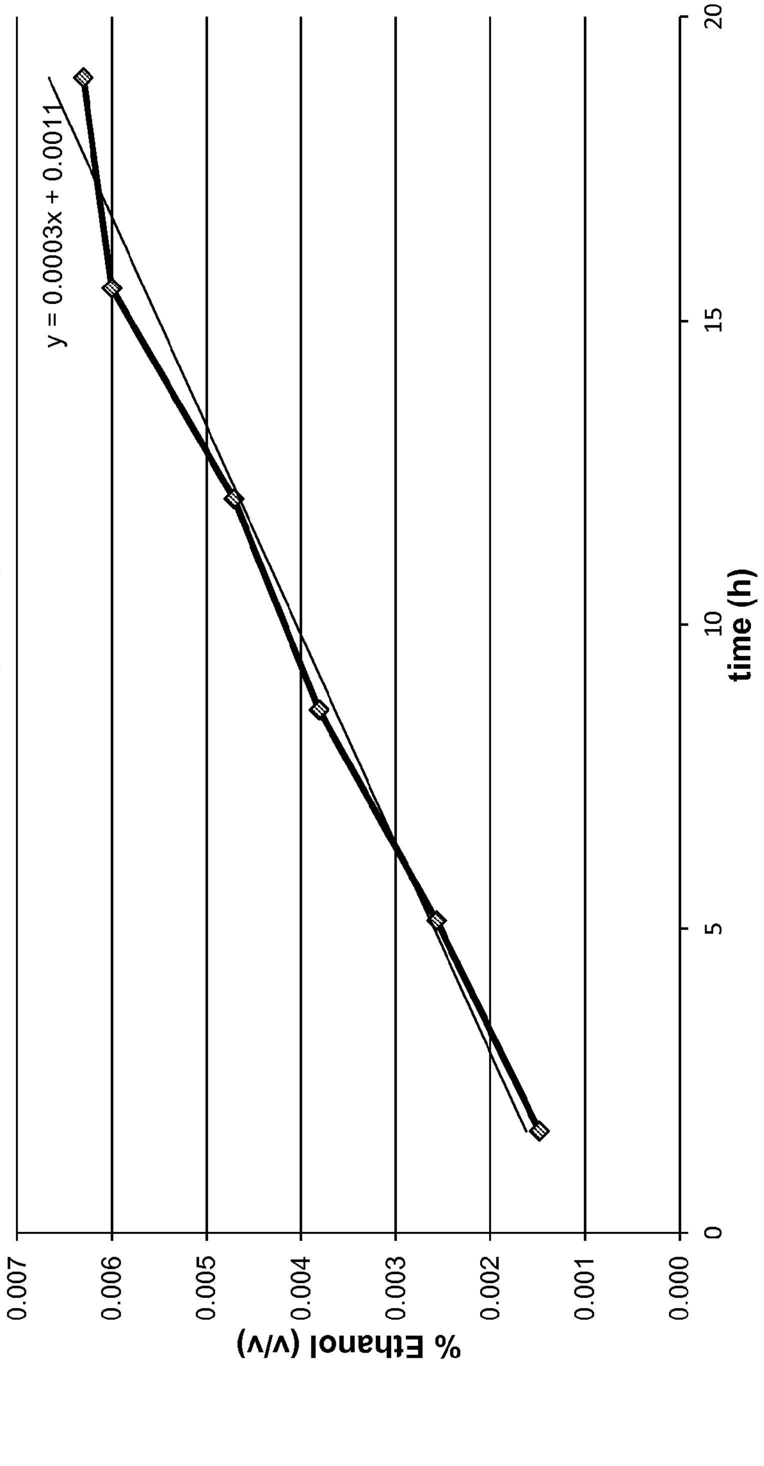

FIG. 4B shows the accumulation of ethanol measured via GC online experiments over a course of nearly 20 hours in *Chlorogloeopsis* PCC6912 cells harboring/containing the plasmid TK18.

Figure 4C:
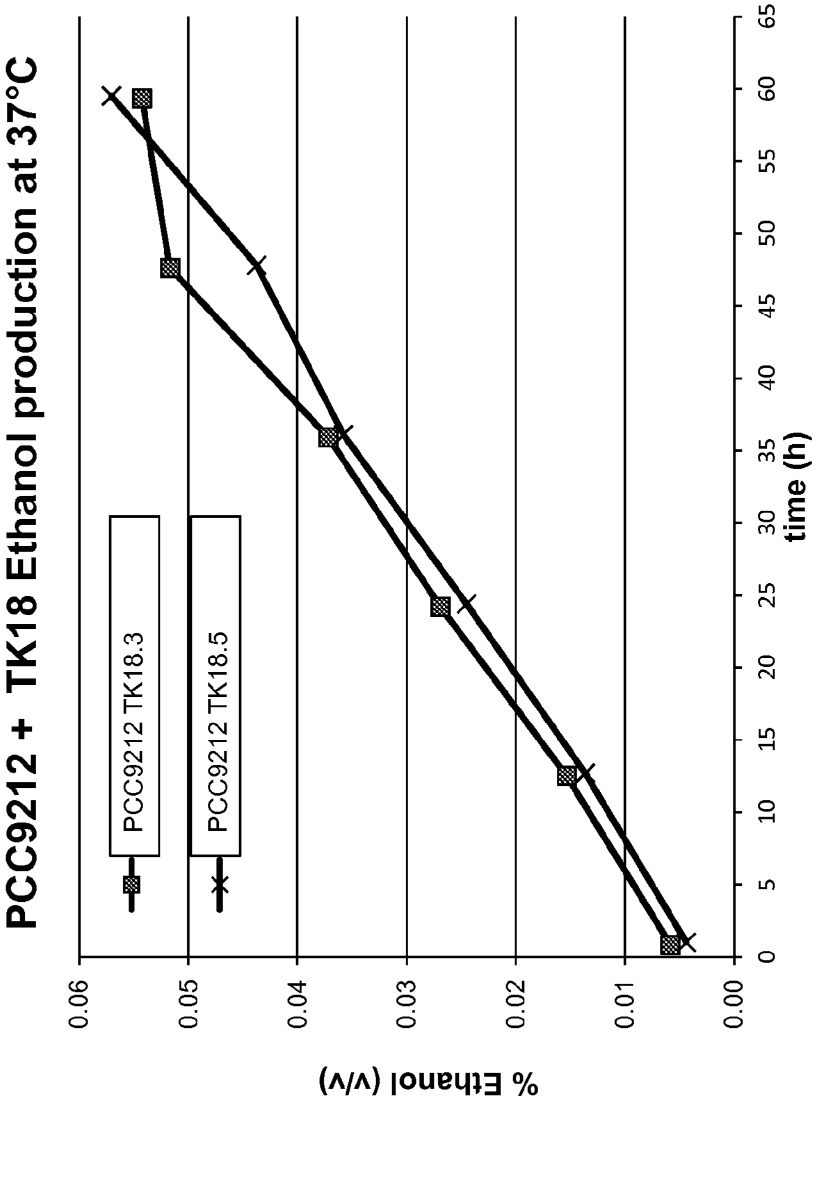

FIG. 4C depicts the accumulation of ethanol during the course of a 60 hour cultivation of *Chlorogloeopsis* PCC9212 including the plasmid TK18 measured via GC online experiments.

Figure 5:
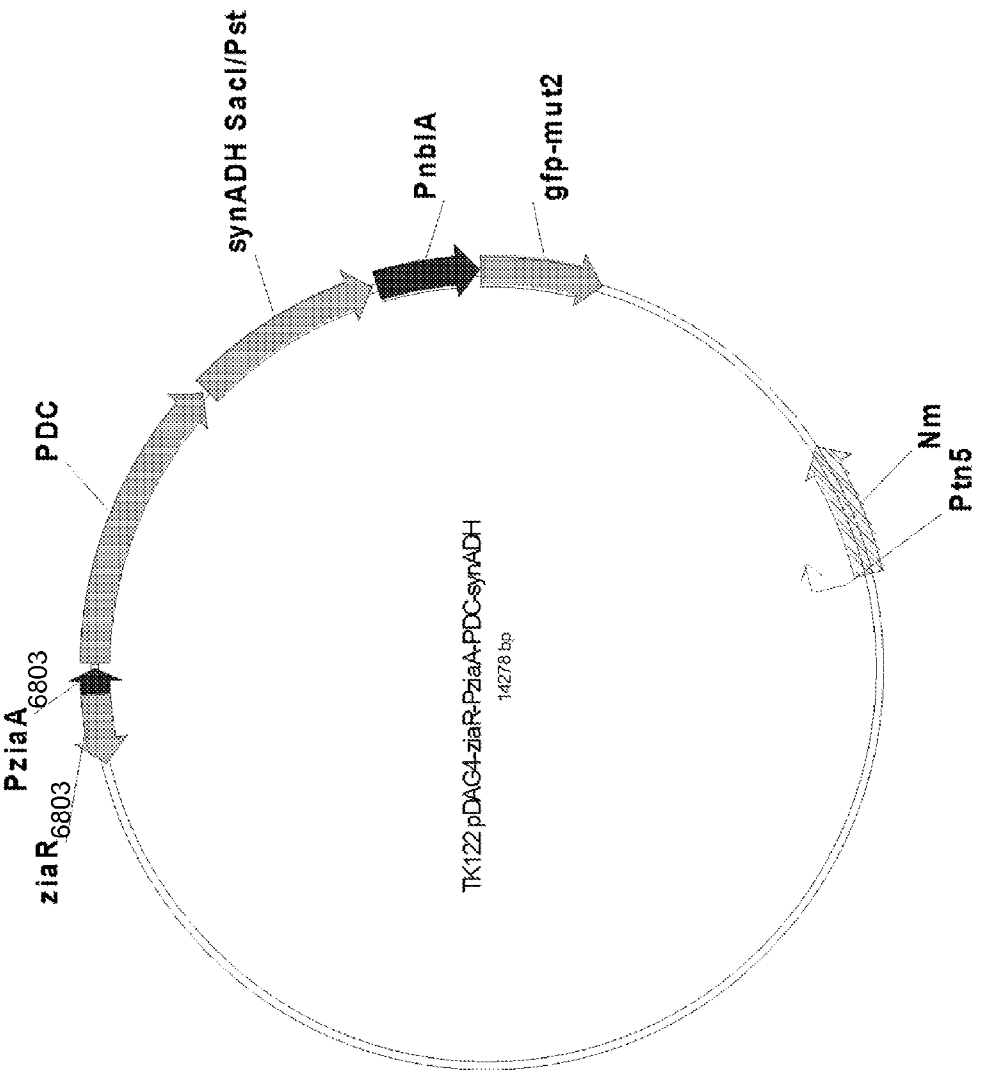

FIG. 5 shows the plasmid map of the plasmid TK122 including a $Zn^{2+}$ inducible heterologous promoter PziaA from *Synechocystis* PCC6803 including its respective repressor ZiaR controlling the transcription of both a PDC and *Synechocystis* ADH enzyme encoding gene. This plasmid, similar to many other plasmids disclosed in this patent application, also includes a gene coding for a green fluorescent protein (gfp-mut2) under the control of the promoter PnblA from *Nostoc* 7120. In PCC6912 and PCC9212 the PnblA promoter is constitutive (which is not the case for *Chlorogloeopsis* sp. ABICyano3). Gfp was included to detect the presence of the plasmid in the cyanobacterial cells. The nucleotide sequence of the plasmid TK122 is shown in SEQ ID NO. 2. In this plasmid the following important genes are located: the gene coding for pyruvate decarboxylase "PDC" is located between nucleotides 5 to 1705, the *Synechocystis* alcohol dehydrogenase encoding gene "synADH" runs from nucleotides 1730 to 2867, and the promoter controlling the transcription of this gene PnblA is located at nucleotides 2900 to 3503, the promoter PziaA is between nucleotides 14132 to 14275 and the complementary sequence of the corresponding repressor gene ziaR runs from the nucleotides 13726 to 14124.

FIG. 6 shows two possible annotations for a start codon (ATG) of a protein encoding gene in a genomic region including a putative endogenous $Zn^{2+}$ inducible promoter PziaA from *Chlorogloeopsis* PCC6912. The putative gene ziaA in *Chlorogloepsis* was identified based on the sequence homologies of the deduced protein to the $Zn^{2+}$ transporting ATPase, ZiaA, from *Synechocystis* sp. PCC6803 (SEQ ID NO. 3). Cloning of the shorter region up to the first ATG, resulted in plasmid TK186 while cloning of the longer version up to the second ATG resulted in TK187. Hybrids harboring TK186 did not produce any ethanol whereas hybrids containing TK187 achieved high ethanol production rates.

Figure 7A:
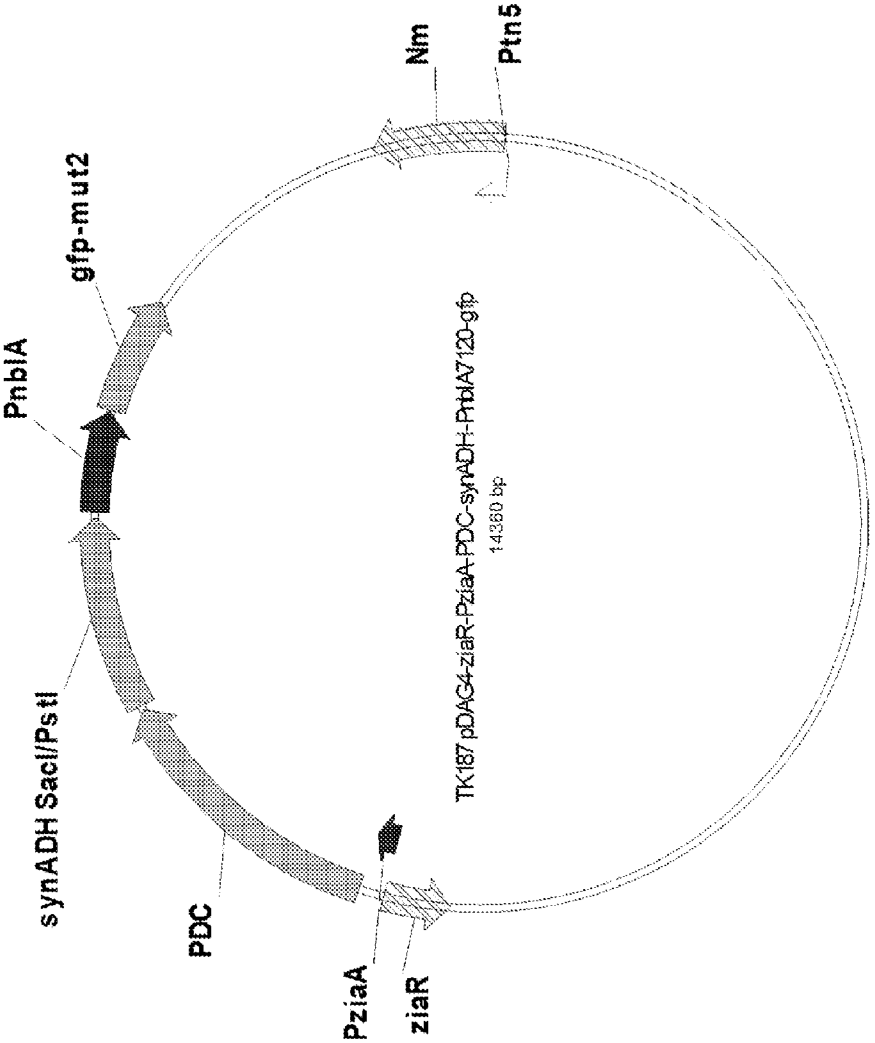

FIG. 7A shows the plasmid map of the plasmid TK187 including an endogenous $Zn^{2+}$ inducible promoter from *Chlorogloeopsis* PCC6912, which controls in the PCC6912 genome a gene whose deduced protein shows homologies to ZiaA of PCC6803. The promoter was called/named in analogy to PCC6803 PziaA. In addition to PziaA from *Chlorogloeopsis* PCC6912, TK187 also includes the respective repressor gene ziaR. This promoter controls the transcription of both the first and second recombinant genes, encoding for PDC enzyme and *Synechocystis* alcohol dehydrogenase enzyme. The nucleotide sequence of the plasmid TK187 is shown in SEQ ID NO. 4. In this plasmid the following important genes are located: the gene coding for pyruvate decarboxylase "PDC" is located between nucleotides 11498 to 13198, the *Synechocystis* alcohol dehydrogenase encoding gene "synADH" runs from nucleotides 13223 to 14360, and the promoter controlling the transcription of this gene PnblA is located at nucleotides 33 to 636, the endogenous promoter PziaA is between nucleotides 11348 to 11492 and the complementary sequence of the corresponding endogenous repressor gene ziaR runs from the nucleotides 10945 to 11346.

Figure 7B:
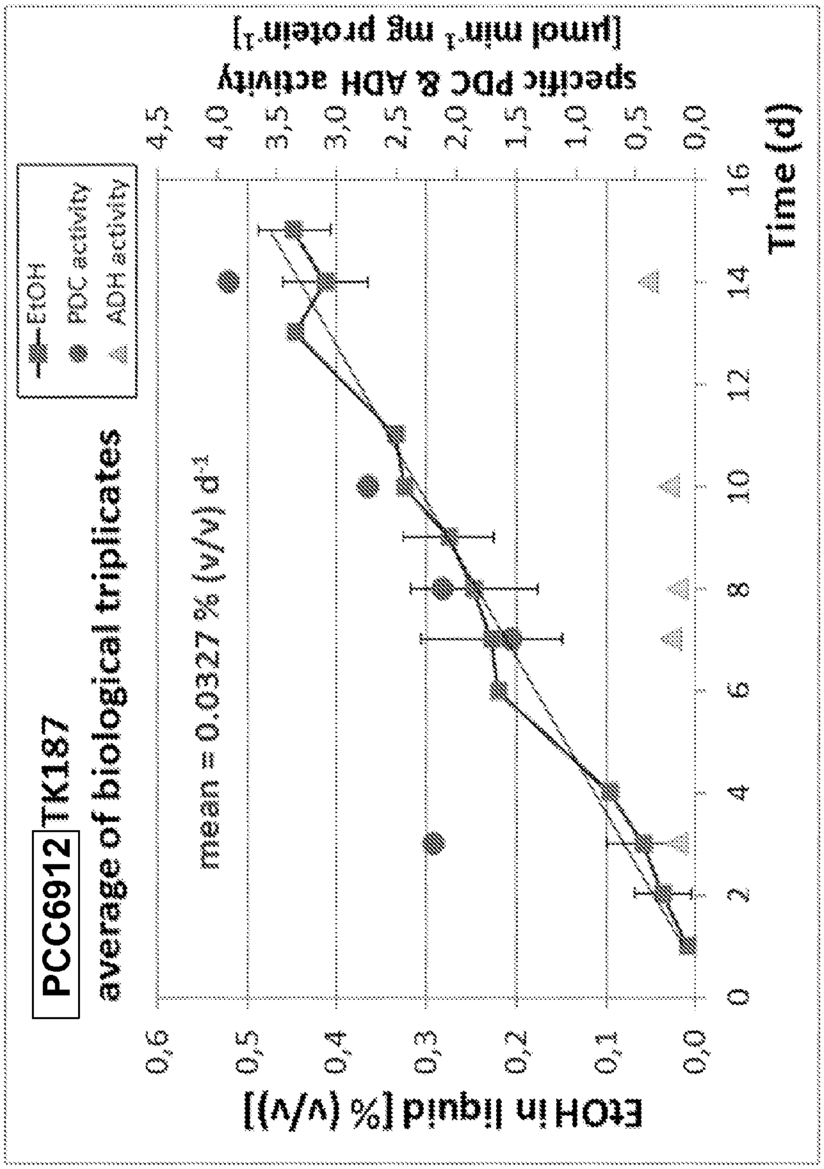
Figure 7C:
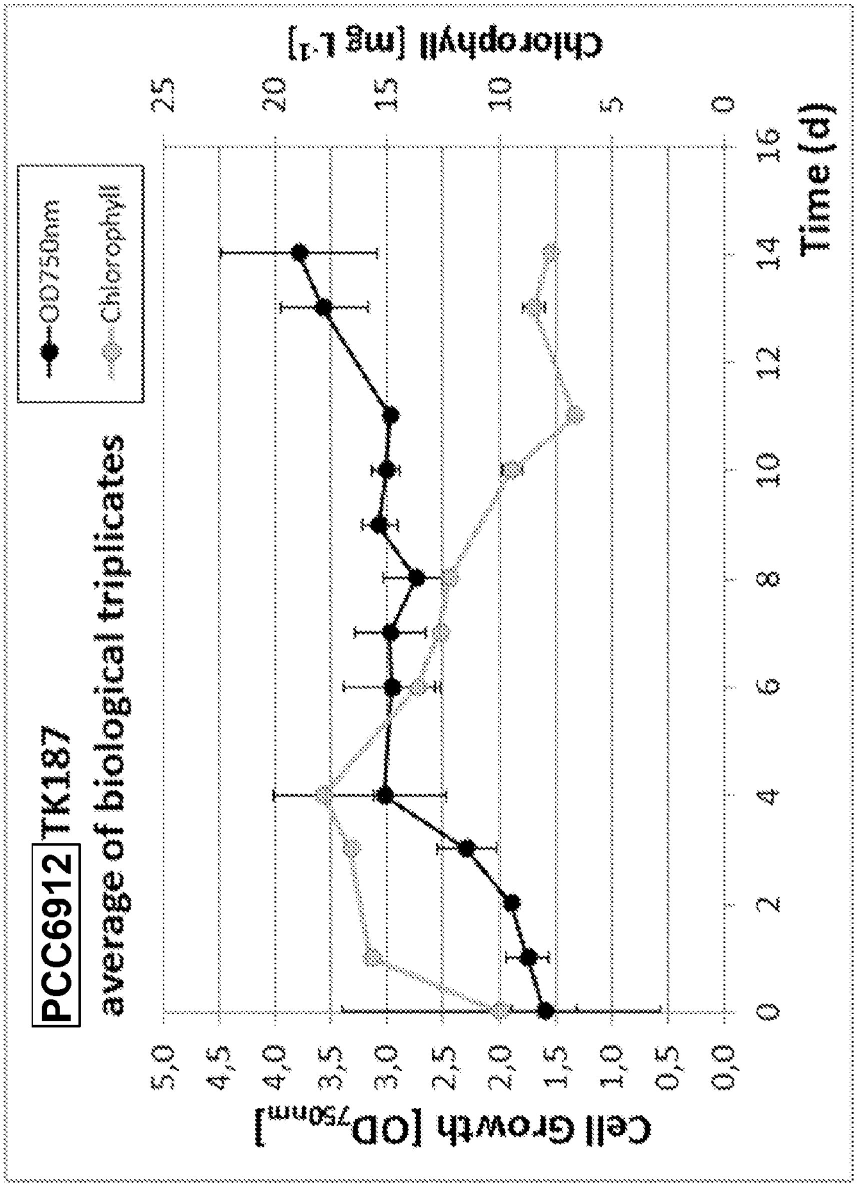
Figure 7D:
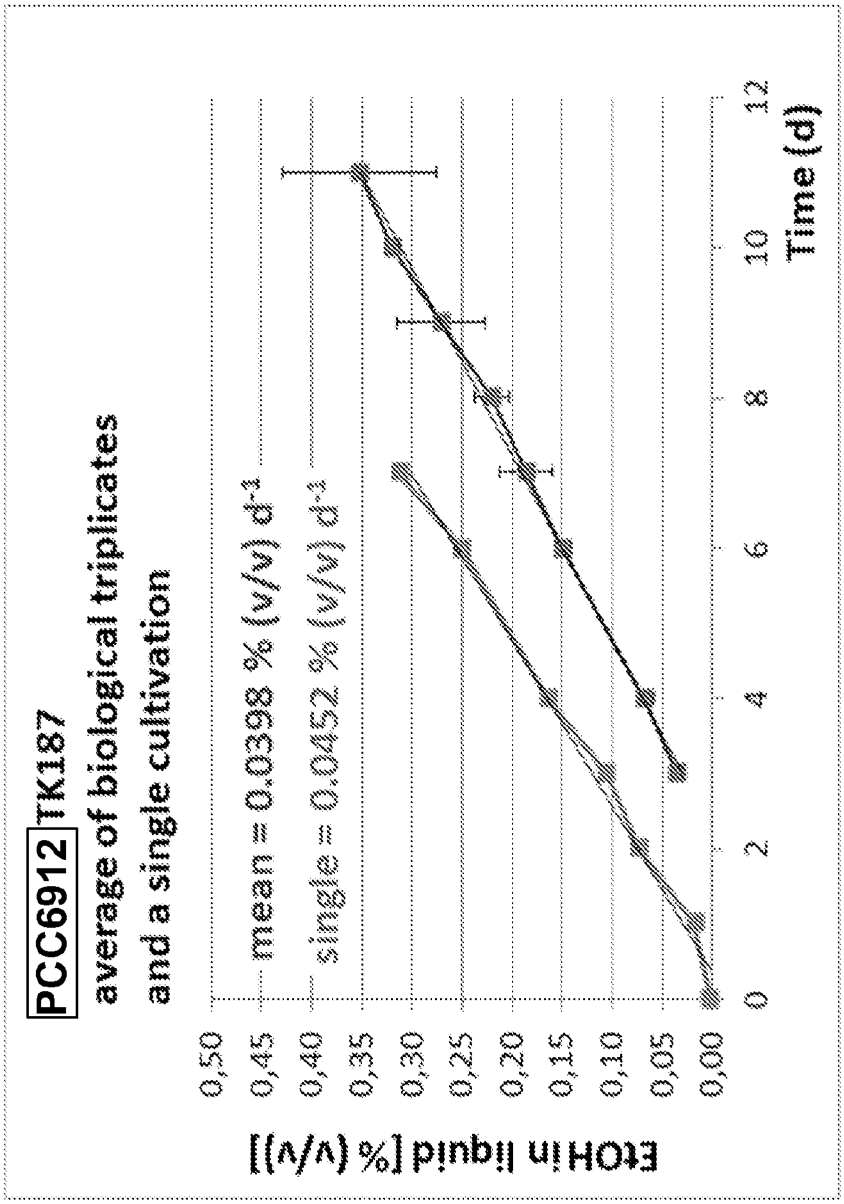

FIG. 7B to FIG. 7D depict the accumulation of ethanol (FIG. 7B and FIG. 7D) (% (v/v), the activities of ADH enzyme and PDC enzyme (FIG. 7B), the growth of the cells given by $OD_{750\ nm}$, (FIG. 7C), and the chlorophyll content of cells of *Chlorogloeopsis* PCC6912 genetically enhanced with the plasmid TK187 in mBG11 medium (FIG. 7C). FIG. 7B shows the accumulation of ethanol over 14 days (day 1 to day 15). Data are given as an average of biological triplicates. The mean productivity of the three cultivations (0.0327% (v/v)/d) is also indicated. In addition the ethanol accumulation over the course of the first 7 days is shown (7D) for a single cultivation leading of a peak production rate of 0.0452% (v/v) $d^{-1}$. The highest ethanol production rate as an average of the three biological triplicates shown in FIG. 7B, calculated from day 3 to 11 is also indicated (7D). *Chlorogloeopsis* PCC6912 cells genetically enhanced with the plasmid TK187 were cultivated in 0.5 L photobioreactors and ethanol concentration determined via GC single measurements.

Figure 7E:
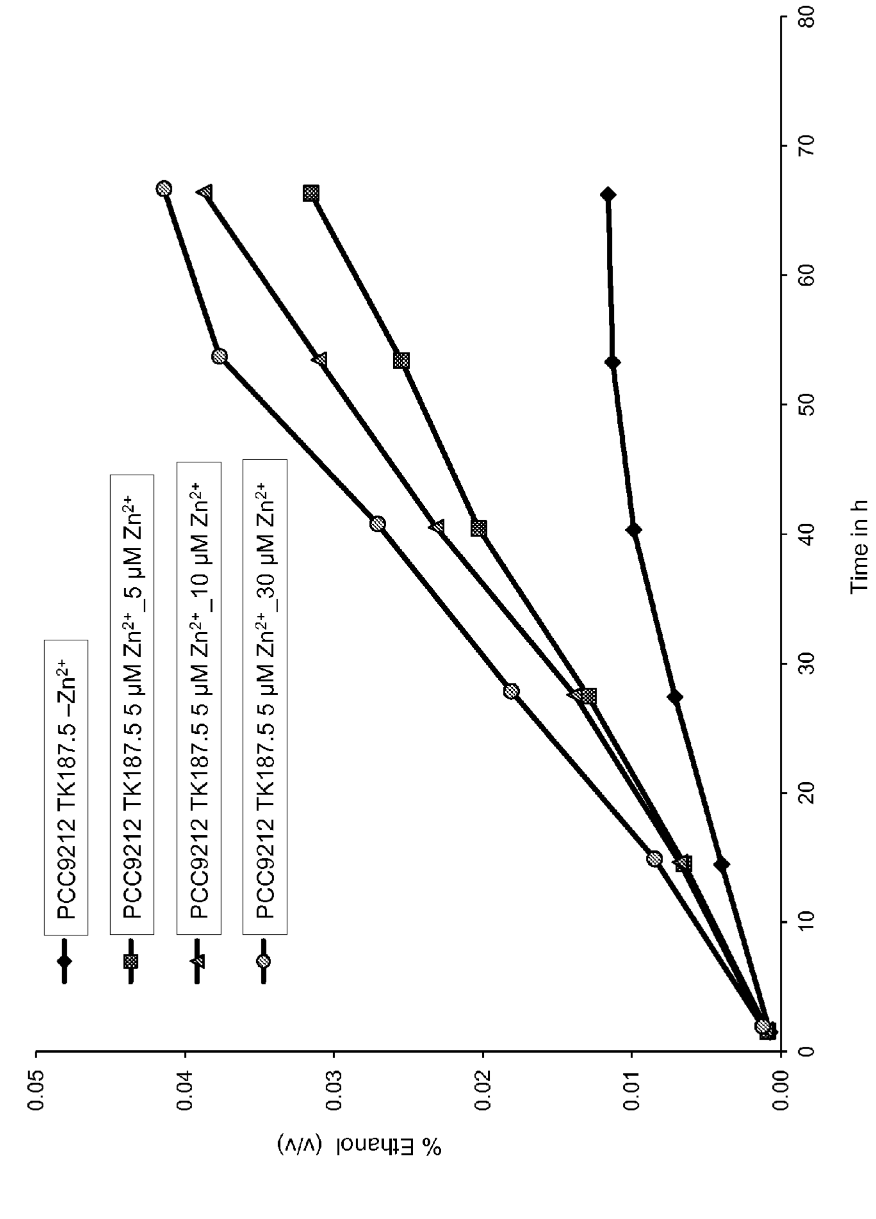

FIG. 7E shows the accumulation of ethanol measured via GC online measurements for *Chlorogloeopsis* PCC9212 cells also harboring the plasmid TK187 cultured for nearly 70 hours in the uninduced state (—Zn) and at different factors of induction via addition of different amounts of $Zn^{2+}$ to the medium (5 μM $Zn^{2+}$, 10 μM $Zn^{2+}$ and 30 μM $Zn^{2+}$).

Figure 8:
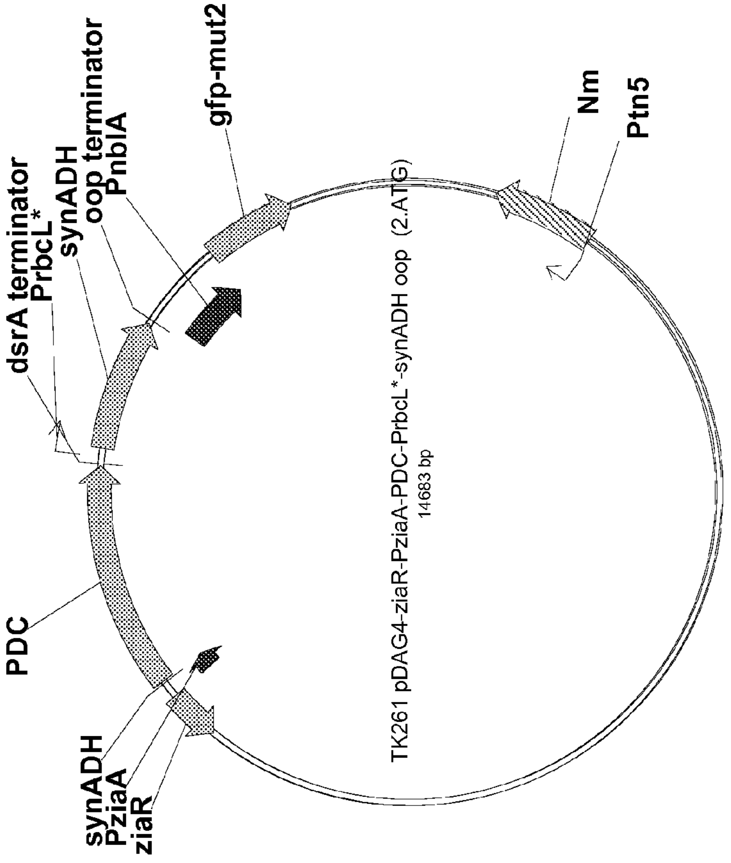

FIG. 8 shows the plasmid map of the plasmid TK261 including the $Zn^{2+}$ inducible promoter PziaA from *Chlorogloeopsis* PCC6912 only controlling the transcription of the PDC enzyme encoding first recombinant gene. The *Synechocystis* ADH enzyme encoding second recombinant gene is controlled by the constitutive promoter PrbcL. The nucleotide sequence of plasmid TK261 is shown in the sequence listing as SEQ ID NO. 5. Apart from the green fluorescent protein encoding gene and the neomycin resistance cassette, this plasmid includes from nucleotides 1418 to 2021 the promoter PnblA. Furthermore, the PDC gene runs from nucleotides 13152 to 178 and the promoter PziaA controlling this gene is located between nucleotides 12520 to 13153, and the respective complementary sequence of the repressor ziaR is located at nucleotides 12606 to 13007. The second recombinant gene for ethanol production encoding *Synechocystis* alcohol dehydrogenase is located between nucleotides 309 to 1319. Between both ethanologenic genes the terminator sequence "dsrA\terminator" is inserted between nucleotides 190 to 214 and the oop terminator between the *Synechocystis* ADH gene and the green fluorescent protein gene is at nucleotides 1349 to 1380.

Figure 9A:
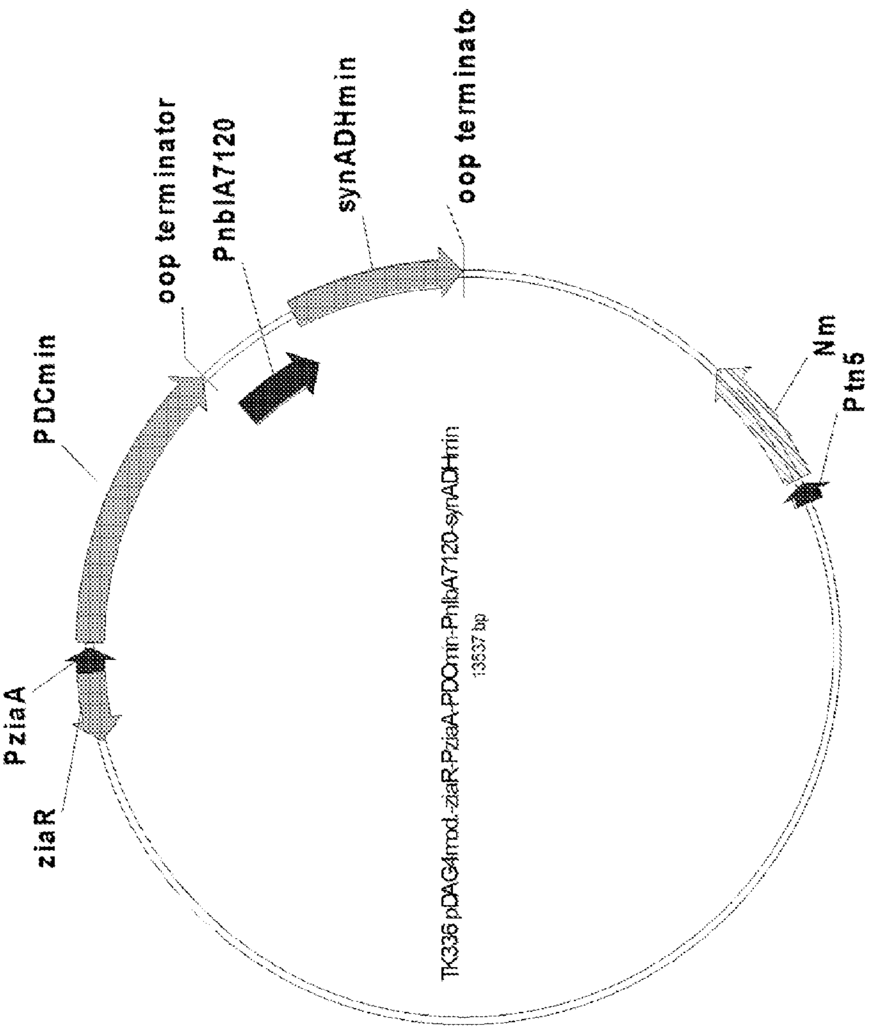

FIG. 9A shows the plasmid map of the plasmid TK336, which includes the $Zn^{2+}$ inducible PziaA promoter and its respective repressor ziaR from *Chlorogloeopsis* PCC6912 controlling the transcription of a codon improved version of the first recombinant gene encoding PDC enzyme. Transcription of a codon improved version of the second recombinant gene coding for *Synechocystis* alcohol dehydrogenase enzyme is controlled by the constitutive promoter PnblA from *Nostoc* PCC7120. SEQ ID NO. 6 shows the nucleotide sequence of this plasmid. The codon improved version of the pdc gene runs from nucleotides 1 to 1702 and the promoter PziaA controlling this gene is located between nucleotides 13386 to 13529, and the respective complementary sequence of the repressor ziaR is located at nucleotides 12984 to 13385. The second recombinant codon improved gene for ethanol production encoding *Synechocystis* alcohol dehydrogenase is located between nucleotides 2344 to 3357. Between both ethanologenic genes the oop terminator is inserted between nucleotides 1708 to 1740.

Figure 9B:
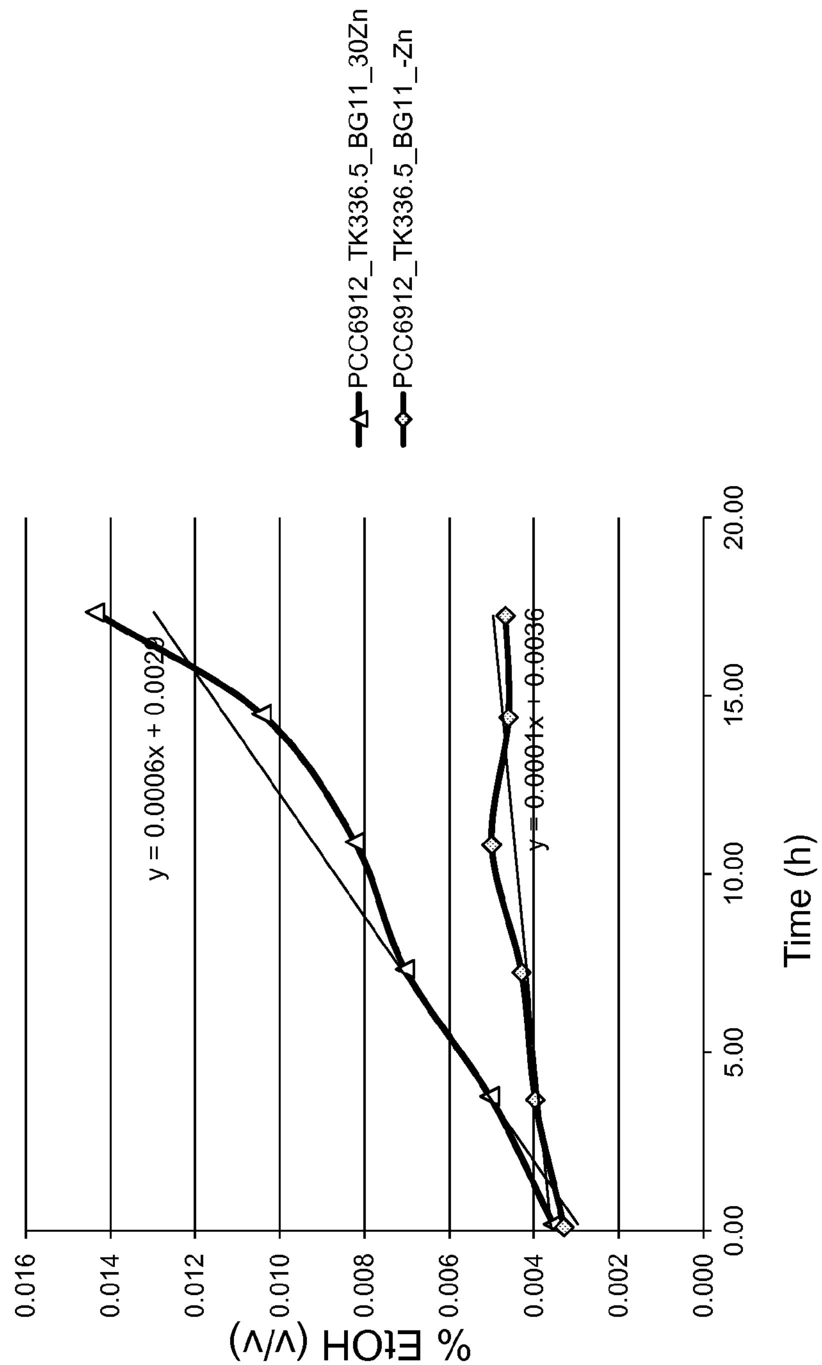

FIG. 9B is a graph showing the ethanol accumulation in cultures of *Chlorogloeopsis* PCC6912 harboring the plasmid TK336 over a time course of around 18 hours in the uninduced (0Zn) and the induced state (30 μM $Zn^{2+}$) measured via GC online measurements.

Figure 10A:
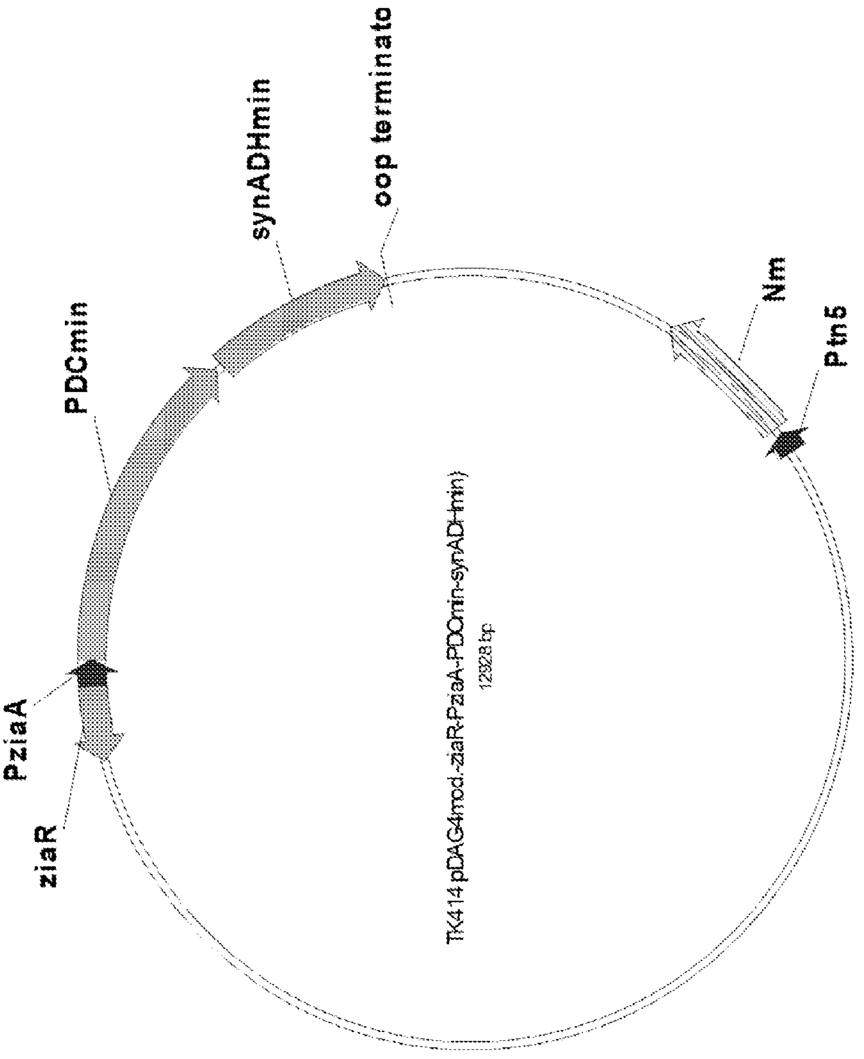

FIG. 10A shows the plasmid map of the plasmid TK414 including the $Zn^{2+}$ inducible promoter PziaA from *Chlorogloeopsis* PCC6912 (nucleotides 12777 to 12920) controlling the transcription of codon improved variants of pdc (nucleotides 12921 to 1702) and adh genes (nucleotides 12921 to 1702). In addition a terminator sequence (oop terminator between nucleotides 2754 to 2786) is located downstream of the *Synechocystis* ADH enzyme encoding gene in order to ensure a reliable transcription termination. SEQ ID NO. 7 shows the nucleotide sequence of this plasmid.

Figure 10B:
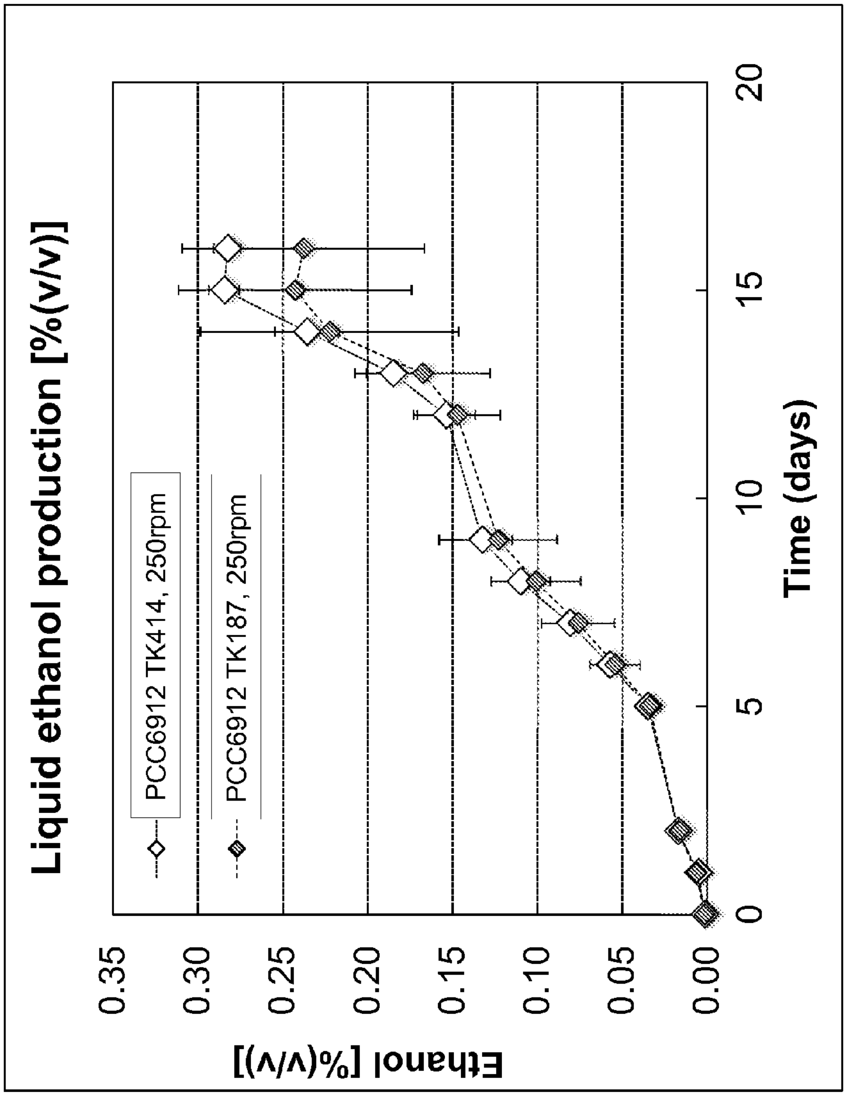

FIG. 10B includes a graph depicting a comparison of the ethanol accumulation (% (v/v) of *Chlorogloeopsis* PCC6912 hybrids containing the different plasmids TK414 and TK187 during 15 day cultivation in 0.5 liter photobioreactor. Ethanol concentration was determined via GC single measurements.

Figure 11:
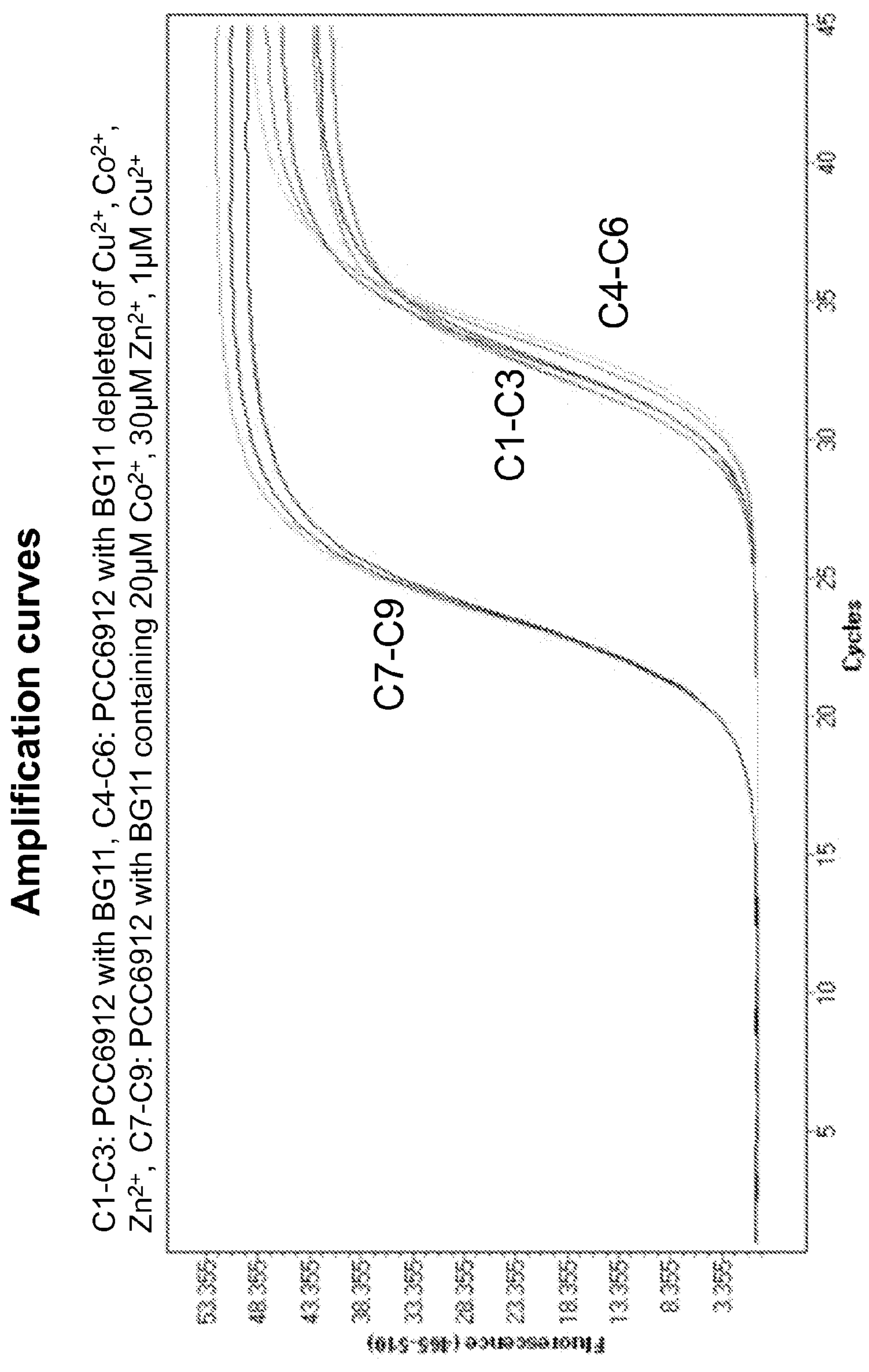
Figure 11:
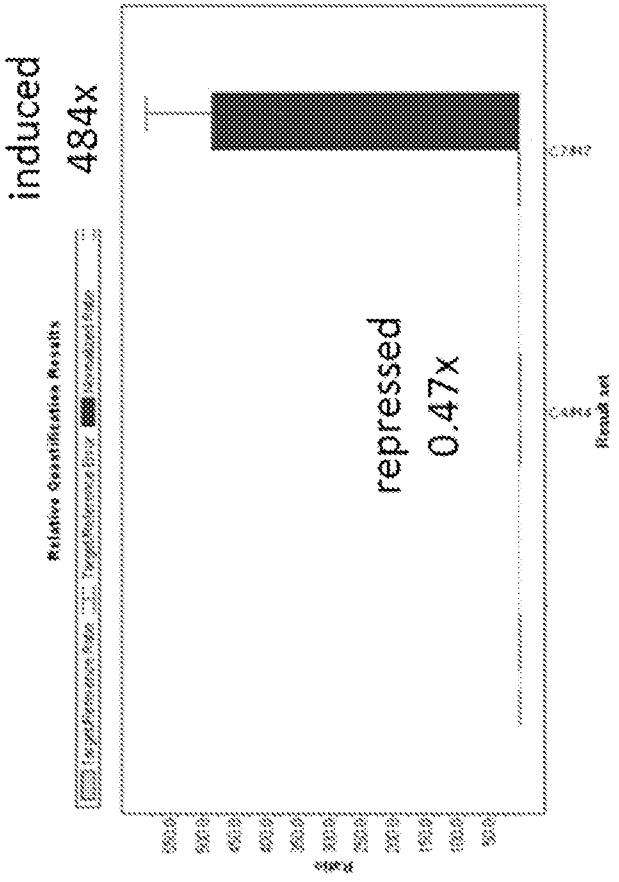

FIG. 11A shows the metal-ion dependent induction of orf7041 by qRT-PCR. qRT-PCR shows the significant upregulation of orf7041 by addition of the metal-ion mix containing 20 μM $Co^{2+}$, 30 μM $Zn^{2+}$, and 1 μM $Cu^{2+}$. The promoter of orf7041 can be considered as being regulated by at least one of these metal-ions.

FIG. 11B shows the relative quantification of orf7041 based on the amplification curves of the qRT-PCR. Expression levels were normalized to expression of a reference gene.

Figure 12A:
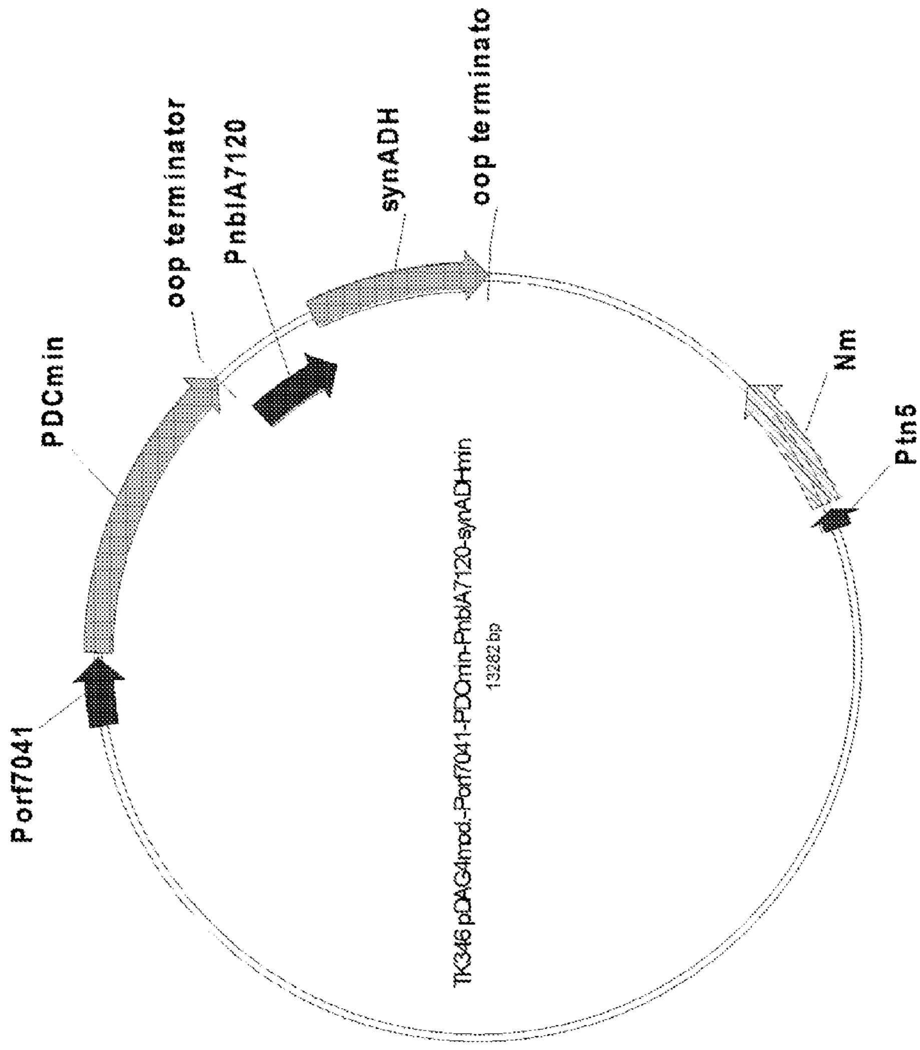

FIG. 12A depicts the plasmid map of the plasmid TK346 including the promoter of the open reading frame (orf) 7041 from *Chlorogloeopsis* PCC6912 running from nucleotides 12898 to 13274, which is both a $Co^{2+}/Zn^{2+}$ inducible promoter, but which mainly reacts to $Co^{2+}$ controlling the transcription of a codon improved version of the first recombinant gene encoding PDC enzyme (from nucleotides 1 to 1702). The *Synechocystis* ADH enzyme encoding second recombinant gene (from nucleotides 2344 to 3357) is controlled by the constitutive promoter PnblA from *Nostoc* (nucleotides 1747 to 2343) and a transcription terminator sequence (oop terminator between nucleotides 1708 to 1740) is present between both recombinant genes in order to decouple the transcriptional control of these genes. The DNA sequence of this plasmid is shown in the sequence listing as SEQ ID NO. 8.

Figure 12B:
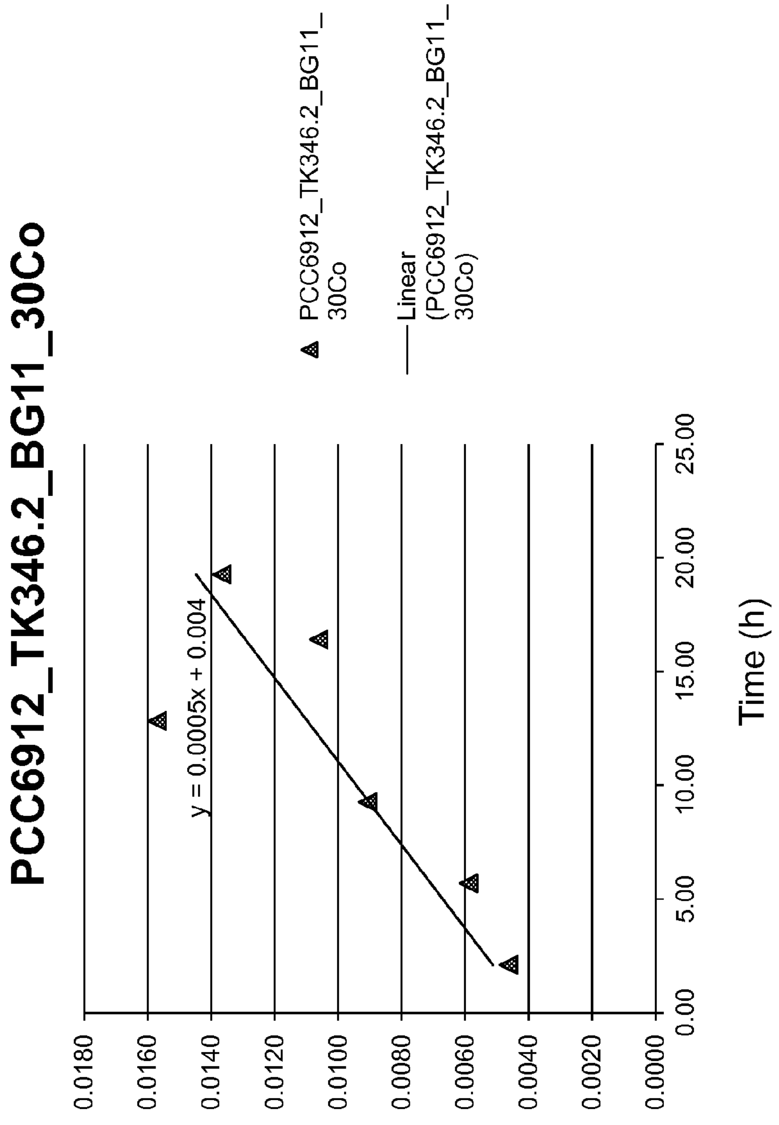

FIG. 12B is a graph showing the ethanol accumulation over a 20 hour cultivation of an induced culture of *Chlorogloeopsis* PCC6912 (30 μM $Co^{2+}$) harboring the plasmid TK346 determined via GC online measurements.

Figure 12C:
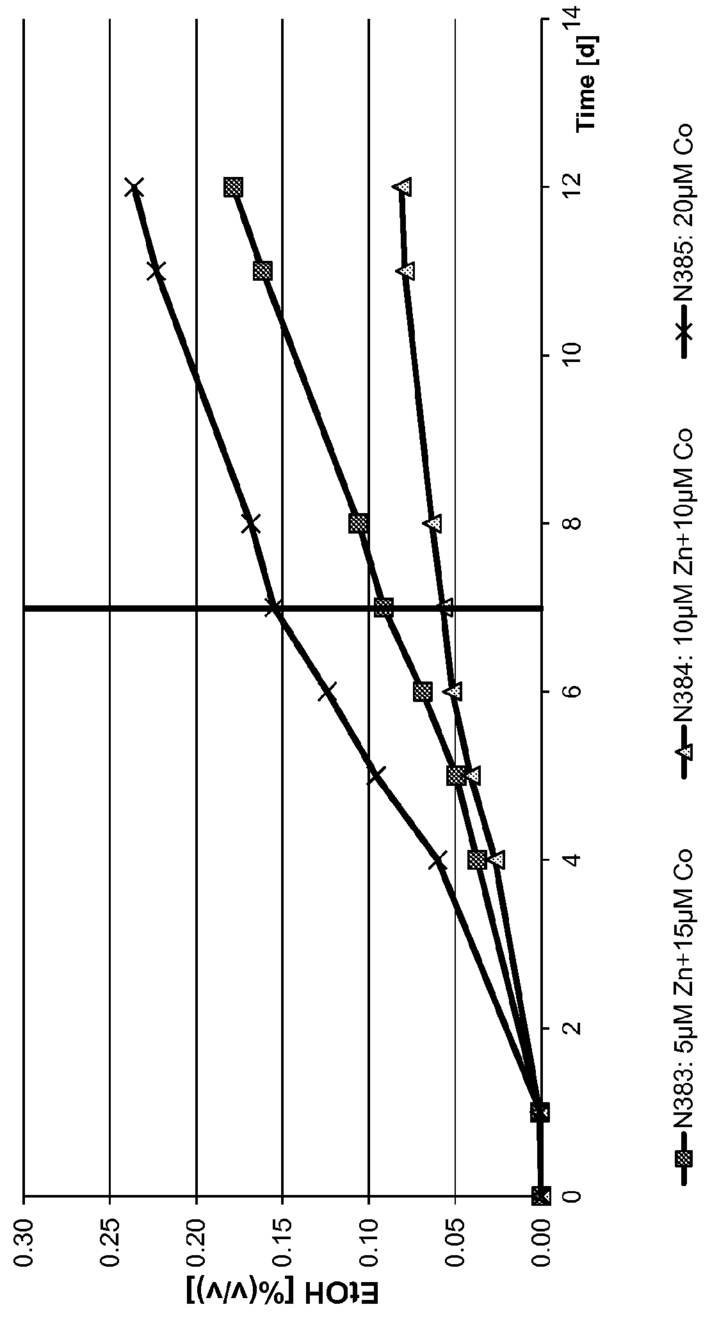

FIG. 12C depicts the ethanol accumulation over the time course of 12 days of the same hybrid as shown in FIG. 12B in larger 0.5 liter photobioreactors determined via GC single measurements. The best productivity was observed with 20 μM $Co^{2+}$.

Figure 13:
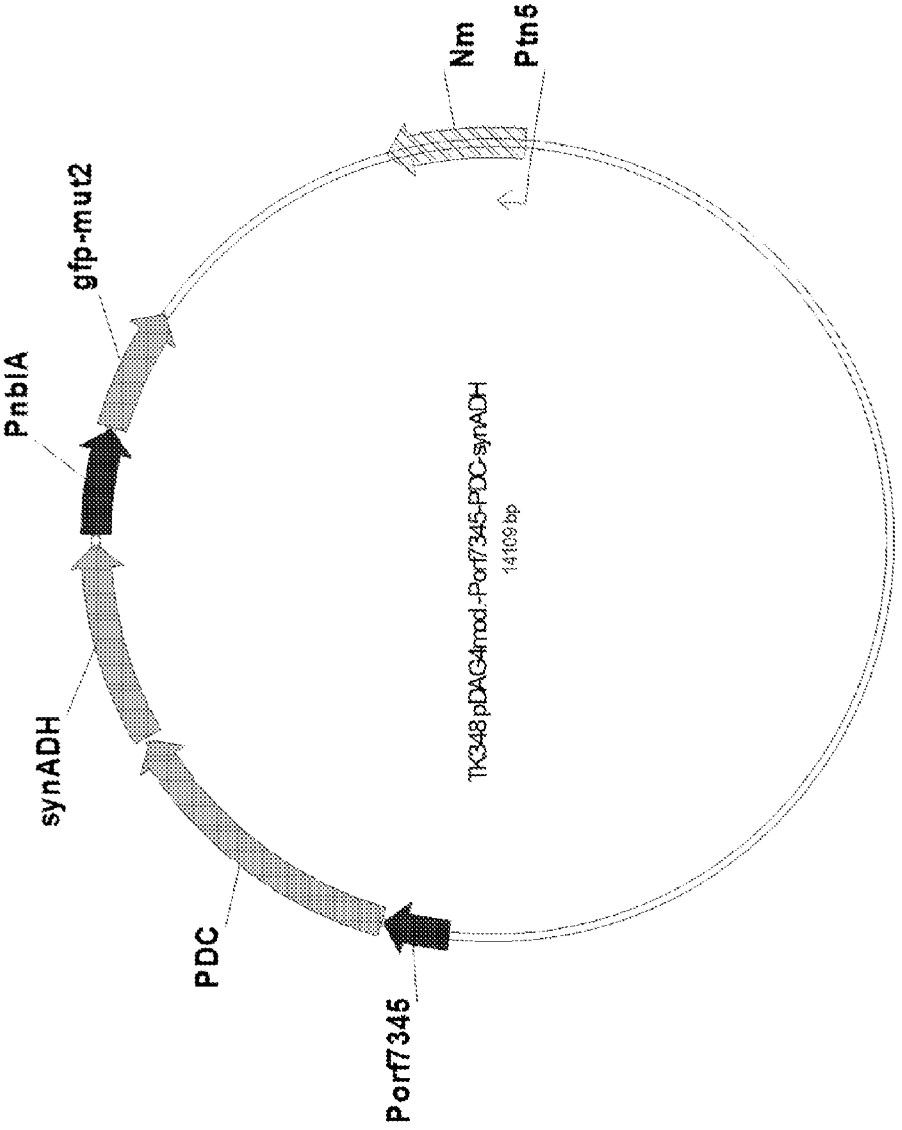

FIG. 13 shows the plasmid map of the plasmid TK348, including the promoter controlling the open reading frame (orf) 7345 of *Chlorogloeopsis* PCC6912 (from nucleotides 10832 to 11212), which is a promoter inducible by $Zn^{2+}$ and $Co^{2+}$, but mainly reacts to $Zn^{2+}$ and which controls the transcription of both the pdc (nucleotides 11220 to 12920) and the adh gene (nucleotides 12945 to 14082) encoding first and second recombinant enzymes. The DNA sequence of this plasmid is shown in the sequence listing as SEQ ID NO. 9.

Figure 14:
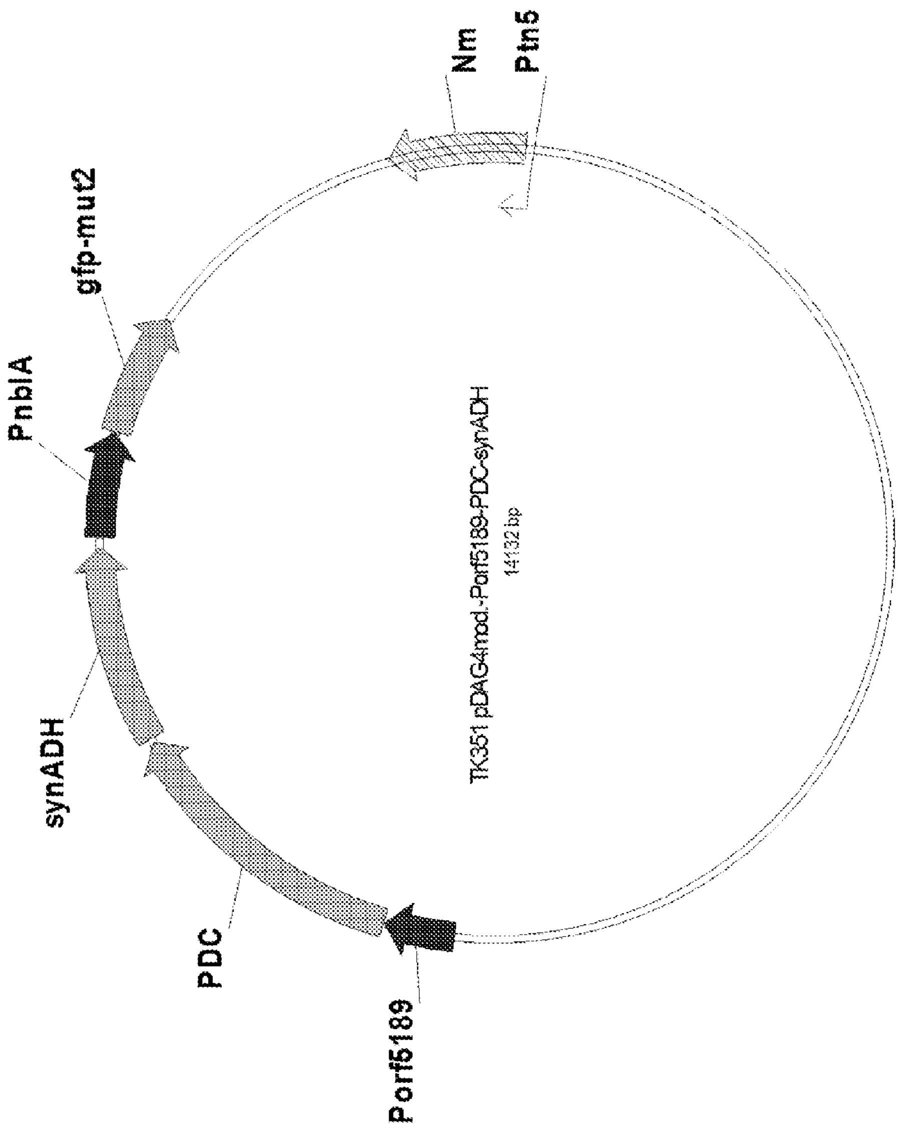

FIG. 14 shows the plasmid map of the plasmid TK351 including the $Zn^{2+}$ inducible promoter of the open reading frame (orf) 5189 of *Chlorogloeopsis* PCC6912 (running from nt 10832 to 11237) controlling the transcription of both the PDC enzyme (nucleotides 11243 to 12943) and *Synechocystis* ADH enzyme (nucleotides 12968 to 14105) encoding genes. SEQ ID NO. 10 depicts the nucleotide sequence of this plasmid.

Figure 15:
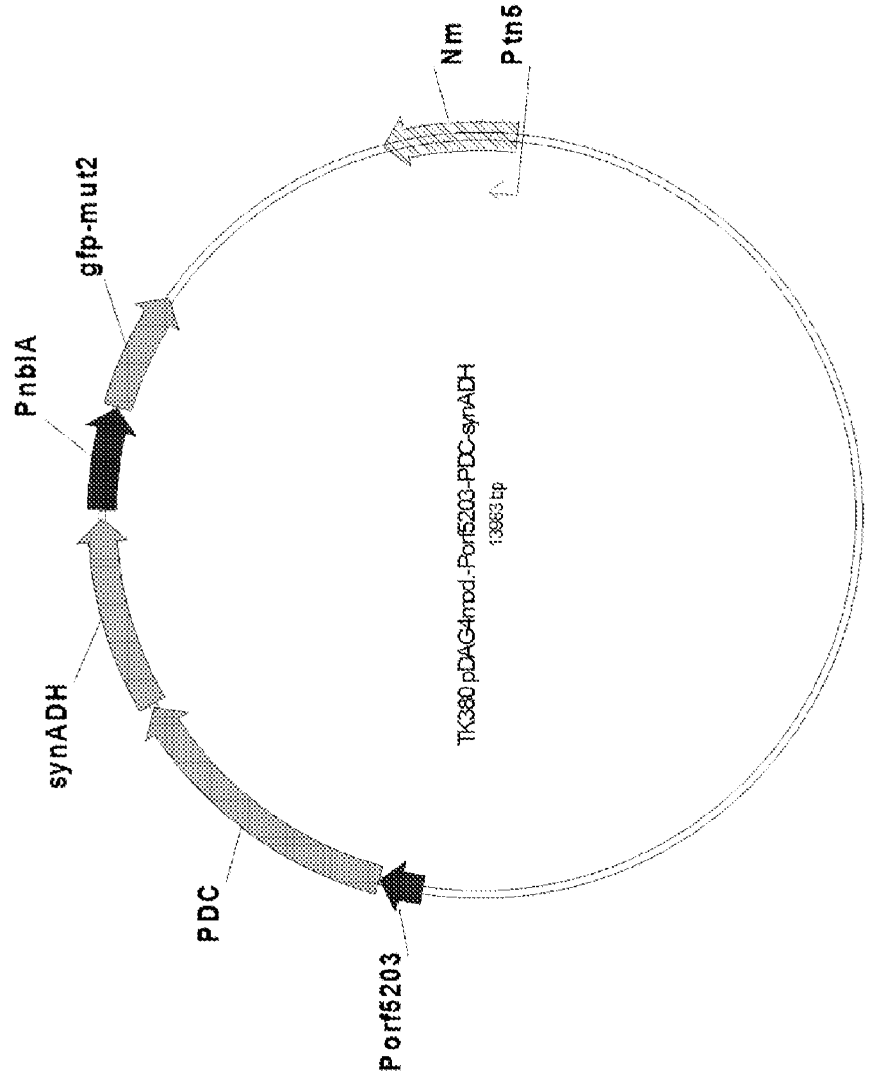

FIG. 15 shows the plasmid map of the plasmid TK380 including the $Zn^{2+}$ inducible promoter of the open reading frame (orf) 5203 of *Chlorogloeopsis* PCC6912 (running from nucleotides 10832 to 11088), controlling the transcription of both the first and second recombinant gene encoding PDC (nucleotides 11094 to 12794) and ADH enzyme (nucleotides 12819 to 13956). The nucleotide sequence of this plasmid is shown as SEQ ID NO. 11 in the sequence listing.

Figure 16A:
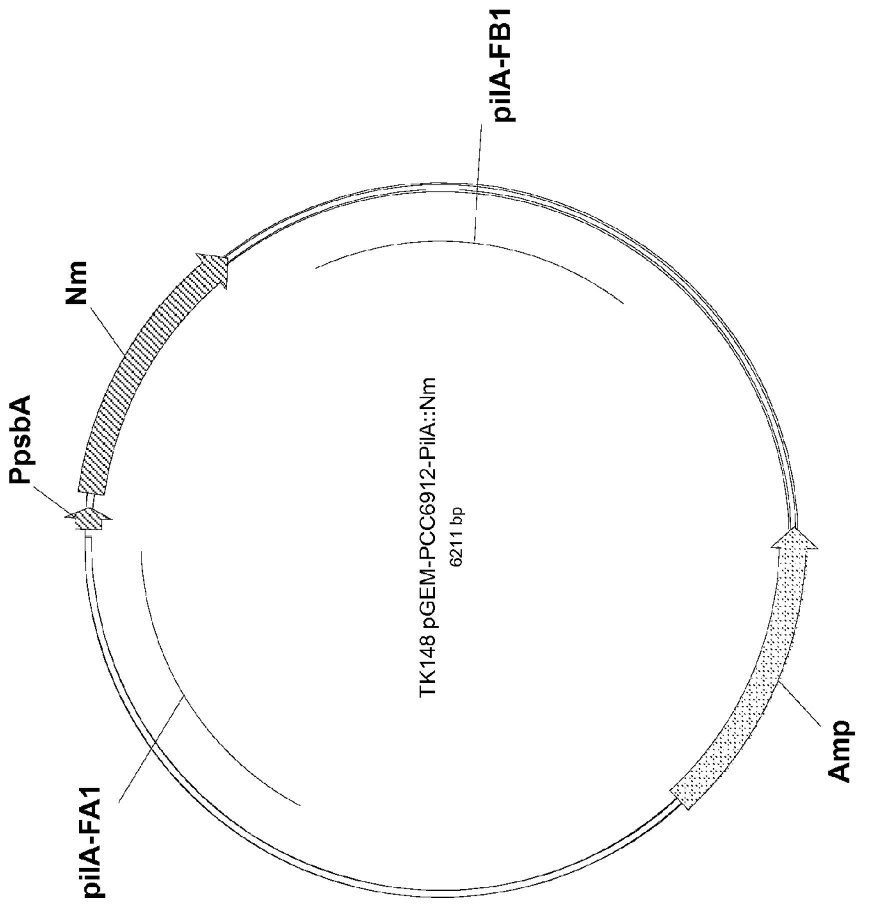

The plasmid map plasmid TK148 is shown in FIG. 16A. This plasmid cannot replicate in *Chlorogloeopsis*. It contains a neomycin resistance conferring gene (denoted Nm running from nucleotides 121 to 902) under the transcriptional control of PpsbA (nucleotides 21 to 81), which is flanked by two sequences which are homologous to parts of the chromosomal pilA gene of *Chlorogloeopsis fritschii* PCC6912. The pilA parts are needed for homologous recombination of the neomycin conferring resistance gene into the genome of the *Chlorogloeopsis* sp. host cells (platform pilA-FB1 from nucleotides 1115 to 2196 and platform pilA-FA1 from nucleotides 5140 to 6210). SEQ ID NO. 12 shows the DNA sequence of this plasmid.

Figure 16B:
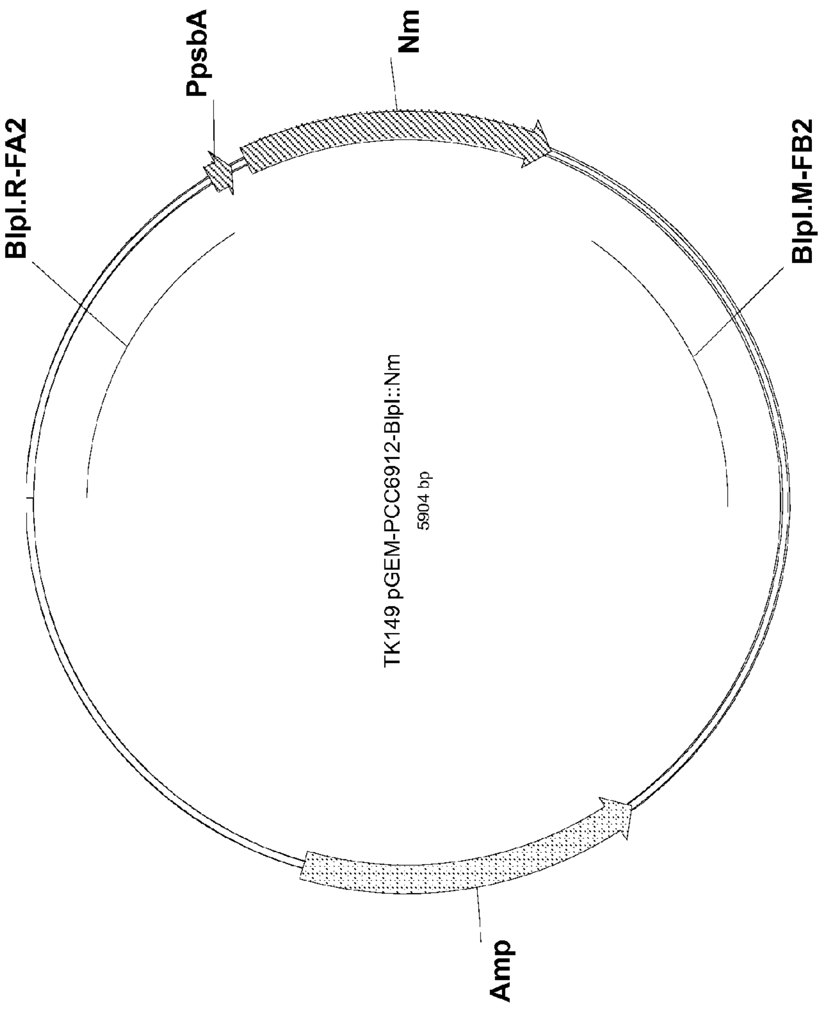

FIG. 16B depicts the plasmid map of the plasmid TK149, which, similar to plasmid TK148, harbors a neomycin resistance conferring gene (from nucleotides 1053 to 1834) under the transcriptional control of PpsbA (nucleotides 953 to 1013). This resistance gene is flanked by two sequences homologous to parts of the gene BlpI. The BlpI part is necessary for integration of the neomycin resistance conferring gene into the genome of the *Chlorogloeopsis* sp. host cells (platform BlpI.M FB2 from nucleotides 2047 to 2962 and platform—BlpI.R FA2\ from nt 2 to 931). SEQ ID NO. 13 shows the DNA sequence of this plasmid.

Figure 16C:
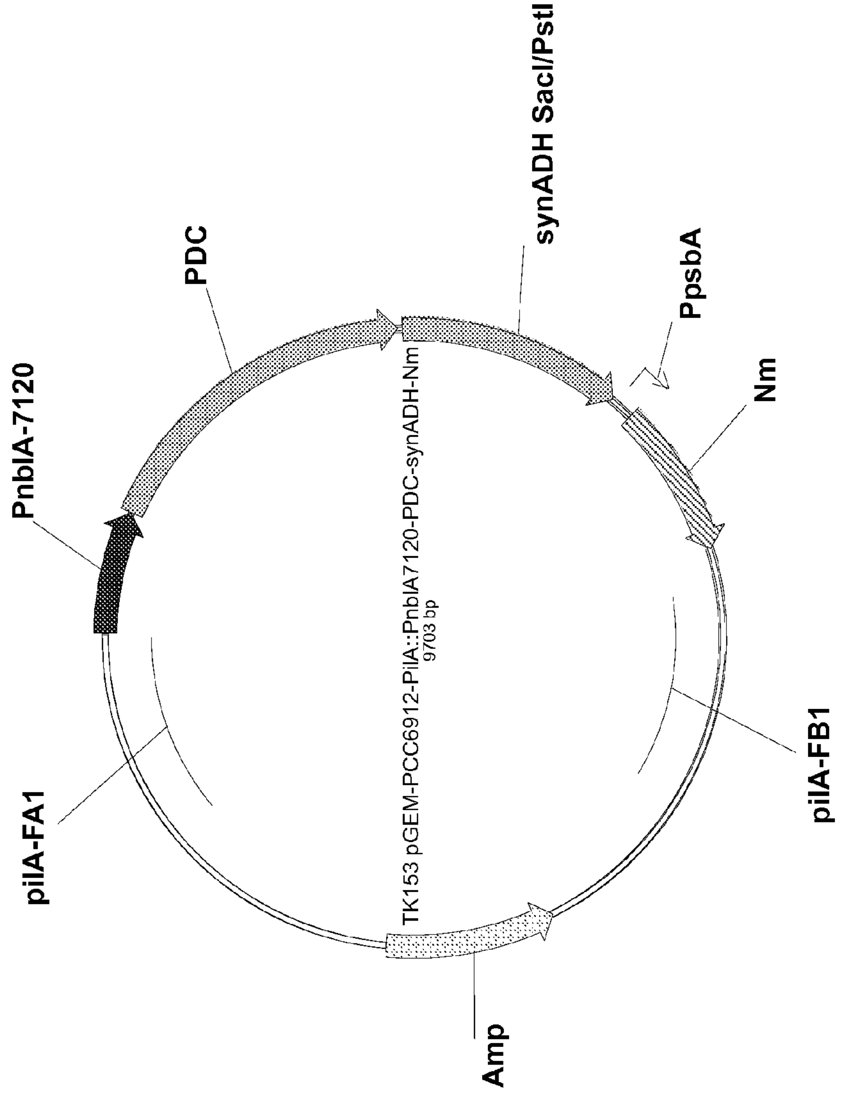

The plasmid map of the plasmid TK153 is shown in FIG. 16C. This plasmid is similar to TK148, but contains in addition an ethanologenic gene cassette including genes coding for PDC enzyme (nucleotides 626 to 2330) and ADH enzyme (nucleotides 2355 to 3492) under the transcriptional control of the promoter PnblA from *Nostoc/Anabaena* PCC7120

(nucleotides 6 to 622). Similar to plasmid TK148, two sequences for homologous recombination into the gene pilA are present upstream and downstream of the ethanologenic cassette and the neomycin resistance gene (denoted pilA-FA1) running from nucleotides 8632 to 9702 and pilA-FB1 (running from nucleotides 4607 to 5688). The nucleotide sequence of this plasmid is shown in the sequence listing as SEQ ID NO. 14.

Figure 17A:
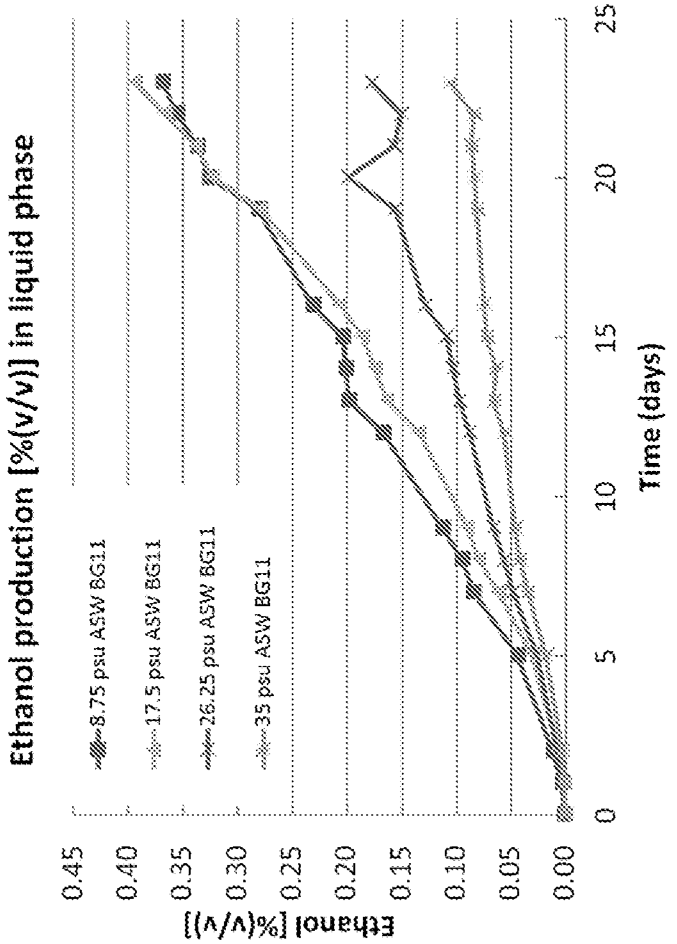

FIG. 17A shows the ethanol accumulation over a course of 23 days in *Chlorogloeopsis* PCC6912 hybrids containing the plasmid TK336 in medium at different salinities of 8.75, 17.5, 26.25 and 35 psu. Artificial seawater BG11 medium was used and modified to different salinities (aswBG11).

Figure 17B:
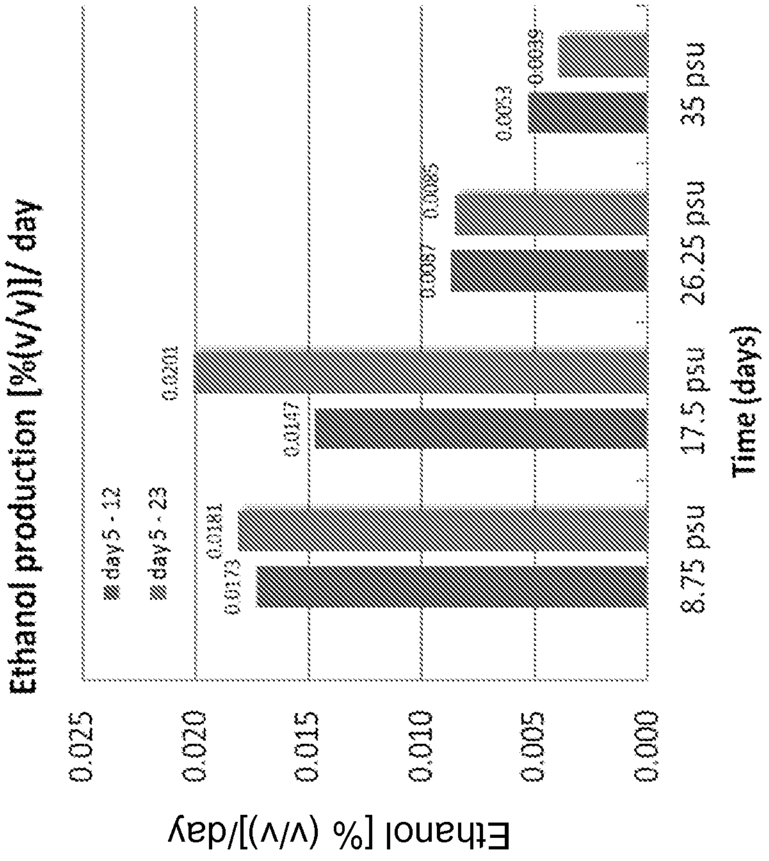

FIG. 17B shows a comparison of the ethanol production rate (% (v/v)$d^{-1}$) between days 5 to 12 and days 5 to 23 for the same experiment already shown in FIG. 17A at different salinities measured via GC single measurements.

Figure 18:
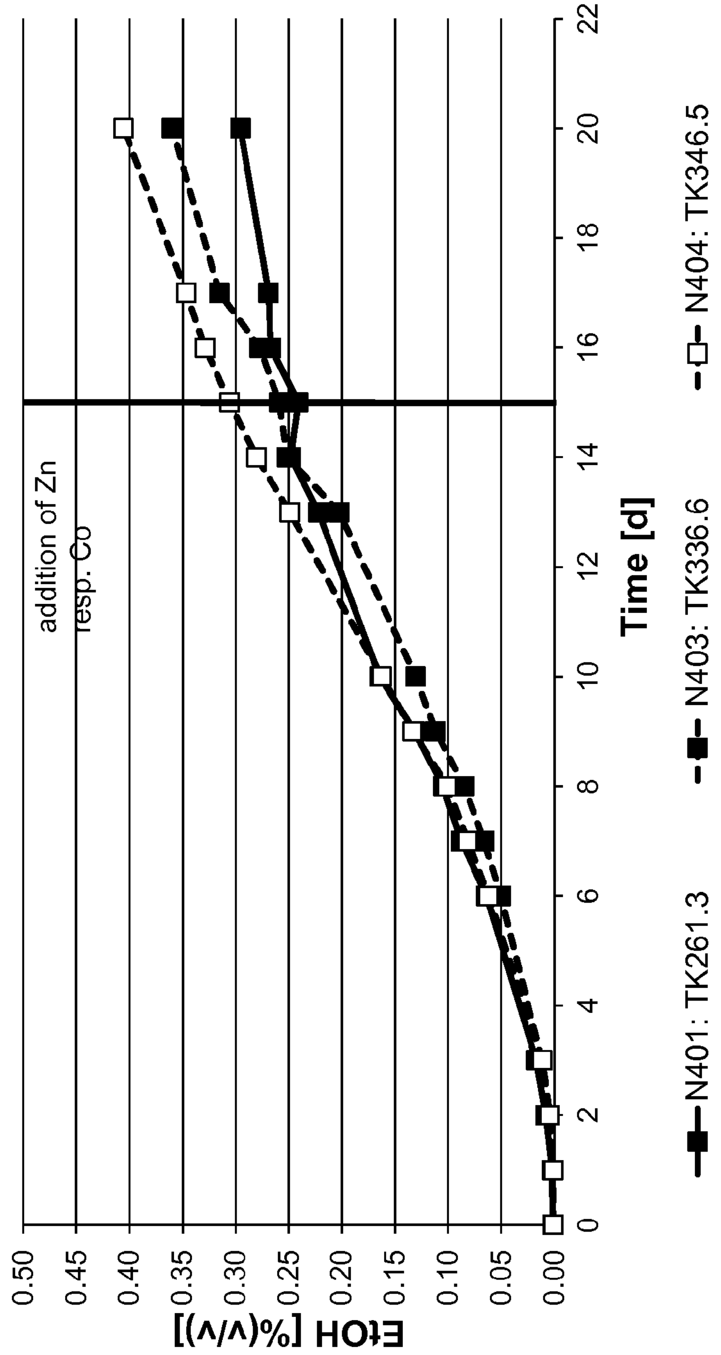

FIG. 18 shows the ethanol accumulation in 35 psu medium (artificial mBG11) at pH 8 of parallel cultivations of *Chlorogloeopsis* PCC6912 hybrids harboring the plasmids TK261, TK336 and TK346, respectively.

Figure 19B:
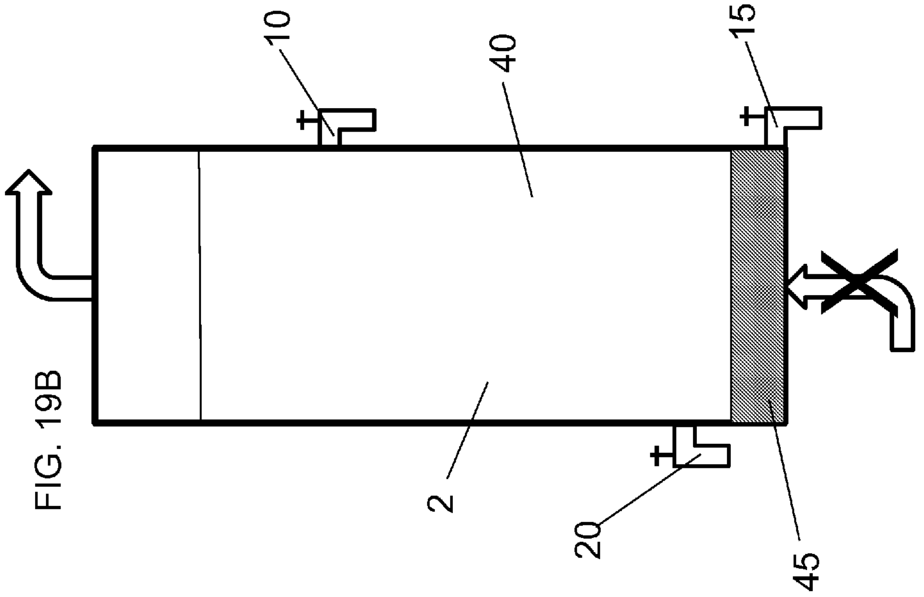
Figure 19A:
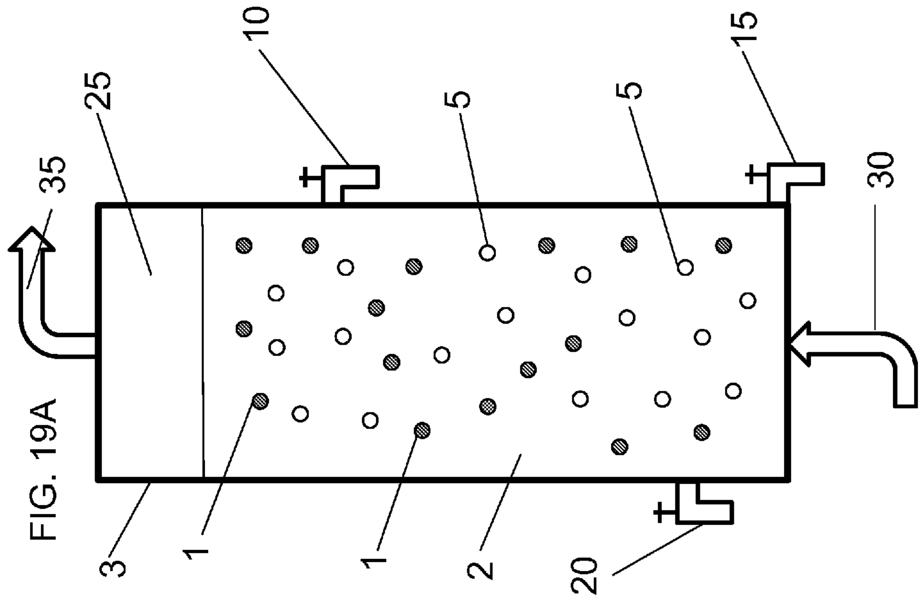

FIG. 19A is a schematic diagram showing a culture of PCC6912 and ABICyano3 during mixing of the culture.

FIG. 19B is a schematic diagram showing the settling of a culture of PCC6912 and ABICyano3 to the bottom of the container after mixing of the culture medium is discontinued.

DETAILED DESCRIPTION OF INVENTION

Several strains of the genus *Chlorogloeopsis* sp. were successfully transformed for the first time with plasmids by using conjugation and electroporation procedures, resulting in ethanol production. This task was achieved by a new transformation protocol taking into consideration the specifics of the genus *Chlorogloeopsis* sp., such as protection of the plasmids used for transformation against the endogenous restriction endonucleases SphI and BlpI. Surprisingly, no special treatment such as sonification or salt washing steps for transformation via conjugation was necessary for the EPS layer around the *Chlorogloeopsis* sp. cells in order for the plasmids to be introduced into the cyanobacteria. In particular, the individual species *Chlorogloeopsis* PCC6912 and *Chlorogloeopsis* PCC9212 as well as *Chlorogloeopsis* ABICyano3 could be genetically enhanced with ethanologenic plasmids. Although these cyanobacterial strains belong to the same genus *Chlorogloeopsis* sp., they show differences in their cultivation behavior as well as in their sensitivity to salinity and other typical growth parameters.

*Chlorogloeopsis* PCC6912 and *Chlorogloeopsis* ABICyano3 were shown to form aggregates during cultivation, whereas *Chlorogloeopsis* PCC9212 was more uniformly dispersed in the culture medium. *Chlorogloeopsis fritschii* PCC6912 was able to produce ethanol at reasonable quantities in a wide temperature range of between 20° C. to about 55° C. and/or at salinities of the culture medium of between 0.2 to 35.0 psu, in particular 0.2, 8.75 and 17.5 psu, which was not the case for the other two cyanobacterial strains, which required freshwater medium for ethanol production. In contrast to *Chlorogloeopsis* sp. PCC9212, ABICyano3 showed a higher salt tolerance, which was however not comparable to *Chlorogloeopsis fritschii* PCC6912. This makes *Chlorogloeopsis* PCC6912 especially suitable for cultivation in deserts where a large temperature difference between day and night is to be expected. Furthermore *Chlorogloeopsis* PCC6912 showed high ethanol production rates at medium salinities between 0.2, 8.75 and 17.5 psu, so that this strain can also be cultivated in a brackish medium.

GENERAL EXPLANATIONS AND DEFINITIONS

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture Biotechnology And Applied Phycology (2003) Richmond, A.; (ed.), Blackwell Publishing; and "The cyanobacteria, molecular Biology, Genomics and Evolution", Edited by Antonia Herrero and Enrique Flores, Caister Academic Press, Norfolk, UK, 2008.

It is well known to a person of ordinary skill in the art that large plasmids can be produced using techniques such as the ones described in the U.S. Pat. No. 6,472,184 B1 titled "method for producing nucleic acid polymers" and U.S. Pat. No. 5,750,380 titled "DNA polymerase mediated synthesis of double stranded nucleic acid molecules", which are hereby incorporated in their entirety.

Denominations of genes are in the following presented in a three letter lower case name followed by a capitalized letter if more than one related gene exists, for example ziaA. The respective protein encoded by that gene is denominated by the same name with the first letter capitalized, such as ZiaA.

Denominations for promoter sequences, which control the transcription of a certain gene in their natural environment are given by a capitalized letter "P" followed by the gene name according to the above described nomenclature, for example "PnblA" for the promoter controlling the transcription of the nblA gene.

Denominations for enzyme names can be given in a two or three letter code indicating the origin of the enzyme, followed by the above mentioned three letter code for the enzyme itself, such as SynADH ($Zn^{2+}$ dependent Alcohol dehydrogenase from *Synechocystis* PCC6803), ZmPdc (pyruvate decarboxylase from *Zymomonas mobilis*).

All publications and patent applications mentioned in this specification are herein incorporated by reference to the same extent as if each individual publication or patent application was specifically and individually indicated to be incorporated by reference.

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%, 10% or 5%.

The term "Cyanobacteria" refers to a member from the group of photoautotrophic prokaryotic microorganisms which can utilize solar energy and fix carbon dioxide. Cyanobacteria are also referred to as blue-green algae.

The term "terminator" refers to a nucleic acid sequence which is able to terminate the transcription of an mRNA. The terminators can exert their function in various ways including, but not limited to forming a hairpin structure in the mRNA transcript, which disrupts the mRNA-DNA RNA polymerase complex during transcription or via forming a recognition site for a transcription termination factor. Non-limiting examples are dsrA from *E. coli*, the oop terminator or the rho terminator.

The term "*Chlorogloeopsis* sp." refers to an unspecified cyanobacterial member of the genus *Chlorogloeopsis*, which was among other characterized by Mitra, A. A. and Pandey, D. C. (1967) "On a new genus of the blue-green alga *Chlorogloeopsis* with remarks on the production of heterocysts in the alga"; Phykos 5: pages 106 to 114 and Mitra, A. K. (1950): Two new algae from Indian soils. Ann. Bot. London. N. S. 14: 457-464.

The terms "host cell" and "recombinant host cell" are intended to include a cell suitable for metabolic manipulation, e.g., which can incorporate recombinant polynucleotide sequences, e.g., which can be transformed. The term is intended to include progeny of the cell originally transformed. In particular embodiments, the cell is a prokaryotic cell, e.g., a cyanobacterial cell. The term recombinant host cell is intended to include a cell that has already been selected or engineered to have certain desirable properties and suitable for further enhancement using the compositions and methods of the invention.

The term "genome" refers to the chromosomal genome as well as to extrachromosomal plasmids which are normally present in the wild type *cyanobacterium* without having performed recombinant DNA technology. For example, cyanobacteria such as *Synechococcus* PCC7002 can include at least up to 6 extrachromosomal plasmids in their wild type form.

"Competent to express" refers to a host cell that provides a sufficient cellular environment for expression of endogenous and/or exogenous polynucleotides.

As used herein, the term "genetically enhanced" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

As used herein, the term "recombinant" refers to nucleic acid sequences and in particular to genes which are changed by laboratory methods thereby creating combinations of nucleic acid sequences in a host cell which are not found in the respective wild type host cell. This term can apply nucleic acid sequences which are both endogenous as well as heterologous with respect to the host cell.

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "homology" refers to the percentage of identity between two polynucleotide or two polypeptide moieties. The correspondence between the sequences from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, "substantially similar" refers to nucleic acid fragments wherein changes in one or more nucleotide bases results in substitution of one or more amino acids, but do not affect the functional properties of the protein encoded by the DNA sequence. The term "substantially similar" also refers to modifications of the nucleic acid fragments of the instant invention such as deletion or insertion of one or more nucleotide bases that do not substantially affect the functional properties of the resulting transcript.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994 Nucleic Acid Research 22: 4673-4, 680). A nucleotide sequence or an amino acid sequence can also be used as a so-called "query sequence" to perform a search against public nucleic acid or protein sequence databases in order, for example, to identify further unknown homologous sequences, which can also be used in embodiments of this invention. Such searches can be performed using the algorithm of Karlin and Altschul (1999 Proceedings of the National Academy of Sciences U.S.A. 87: 2,264 to 2,268), modified as in Karlin and Altschul (1993 Proceedings of the National Academy of Sciences U.S.A. 90: 5,873 to 5,877). Such an algorithm is incorporated in the NBLAST and XBLAST programs of Altschul et al. (1999 Journal of Molecular Biology 215: 403 to 410). Where gaps exist between two sequences, gapped BLAST can be utilized as described in Altschul et al. (1997 Nucleic Acid Research, 25: 3,389 to 3,402).

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacteria." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "transformation" is used herein to mean the insertion of heterologous or endogenous genetic material into the host cell via recombinant methods. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent crossover events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at any of a large number of genomic locations.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell) such as extrachromosomal plasmids. Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "promoter" is intended to include a polynucleotide segment that can transcriptionally control a recombinant gene of interest, e.g., a pyruvate decarboxylase gene that it does or does not transcriptionally control in nature. In one embodiment, the transcriptional control of a promoter results in an increase in expression of the gene of interest. In an embodiment, a promoter is placed 5' to the gene-of-interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.) will induce the promoter leading to the transcription of the gene.

The phrase "operably linked" means that the nucleotide sequence of the nucleic acid molecule or gene of interest is linked to the regulatory sequence(s) in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence.

The term "endogenous" refers to genes or genetic regulatory elements, such as promoters, which are present in the respective wild type cyanobacterial species. "Recombinant" genes or regulatory elements can also be included in non-natural recombinant plasmids within these cyanobacterial species or inserted into the genome of its native host cell via recombinant methods. In another embodiment of the invention "endogenous" also refers to genes or genetic elements, which are not present in the respective wild type cyanobacterial species, but which are present in other wild type species of the same genus, for example *Chlorogloeopsis*. Therefore the term "endogenous promoter" also can refer to a native promoter of *Chlorogloeopsis* PCC6912 recombinantly included in for example *Chlorogloeopsis* PCC9212. In this context, the inventors could show that some of promoters, for example the PziaA homologs can be identical between different *Chlorogloeopsis* species for example *Chlorogloeopsis* PCC6912 and *Chlorogloeopsis* PCC9212. In addition the promoters used in the present invention also might be at least 85, 86, 87, 88, 89, 90, 91, 92, 93, 94, 95, 96, 97, 98, or 99 percent identical or can be 100% identical to endogenous promoters. Any nucleotide changes in comparison to the native endogenous promoters can occur at least in one of the following regions:

The TATA box, and/or
the ribosomal binding side
the operator side and/or
the 5'-untranslated region (5'-UTR).

Additionally, the nucleotides between these functional regions can also be altered, deleted or additional nucleotides can be introduced.

A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6 to about 1,500 or more consecutive nucleotides of a polynucleotide according to the invention.

The term "open reading frame" abbreviated as "ORF," refers to a length of nucleic acid sequence, either DNA, cDNA or RNA, that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term “downstream” refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The terms “restriction endonuclease” and “restriction enzyme” refer to an enzyme that binds and cuts within a specific nucleotide sequence within double stranded DNA.

The term “expression” as used herein, refers to the transcription and stable accumulation mRNA derived from a nucleic acid or polynucleotide. Expression may also refer to translation of mRNA into a protein or polypeptide.

An “expression cassette” or “construct” refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term “codon” refers to a triplet of nucleotides coding for a single amino acid.

The term “codon-anticodon recognition” refers to the interaction between a codon on an mRNA molecule and the corresponding anticodon on a tRNA molecule.

The term “codon bias” refers to the fact that different organisms use different codon frequencies.

The term “codon improvement” refers to the modification of at least some of the codons present in a heterologous gene sequence from a triplet code that is not generally used in the host organism to a triplet code that is more common in the particular host organism. This can result in a higher expression level of the gene of interest. In particular, codon improvement or codon optimization can mean that the overall usage of the codons of a gene is adapted to more closely resemble or even be identical to the codon usage table of a certain organism, for example *Chlorogloeopsis fritschii* PCC6912.

The term “reporter gene” means a nucleic acid encoding an identifying factor that can be identified based upon the reporter gene’s effect, in order to determine or confirm that a cell or organism contains the nucleic acid of interest, and/or to measure gene expression induction or transcription. Examples of reporter genes known and used in the art include but are not limited to luciferase (Luc), green fluorescent protein (GFP), chloramphenicol acetyltransferase (CAT), β-galactosidase (LacZ), β-glucuronidase (GUS), and the like. In embodiments of the present invention, recombinant genes coding for GFP can be included in the extrachromosomal plasmids harboring the ethanologenic cassettes so that the presence of the plasmids in the host cells can be detected easily via fluorescence. Selectable marker genes may also be considered reporter genes.

The term “selectable marker” means an identifying factor, usually an antibiotic or chemical resistance gene, that is able to be selected for based upon the marker gene’s effect, such as resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, spectinomycin, kanamycin, hygromycin, neomycin and the like.

A “polypeptide” is a polymeric compound comprised of covalently linked amino acid residues. A “protein” is a polypeptide that performs a structural or functional role in a living cell.

A “heterologous protein” refers to a protein not naturally produced in the cell.

An “isolated polypeptide” or “isolated protein” is a polypeptide or protein that is substantially free of those compounds that are normally associated therewith in its natural state (e.g., other proteins or polypeptides, nucleic acids, carbohydrates, lipids).

The term “fragment” of a polypeptide refers to a polypeptide whose amino acid sequence is shorter than that of the reference polypeptide. Such fragments of a polypeptide according to the invention may have a length of at least about 2 to about 300 or more amino acids.

A “variant” of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements.

As used herein, the phrase “increased activity” refers to any genetic modification resulting in increased levels of enzyme function in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme, which increases the half-life of the protein, leading to the presence of more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Biomedical Engineering Handbook (2000) Bronzino, J. D., Springer, ISBN 354066808X).

The terms “pyruvate decarboxylase” and “PDC” refer to an enzyme that catalyzes the decarboxylation of pyruvic acid to acetaldehyde and carbon dioxide. A “pdc gene” refers to the gene encoding an enzyme that catalyzes the decarboxylation of pyruvic acid to acetaldehyde and carbon dioxide.

The terms “Alcohol dehydrogenase” and “ADH” refer to an enzyme that catalyzes the interconversion between alcohols and aldehydes or ketones. An “adh gene” refers to the gene encoding an enzyme that catalyzes the interconversion between alcohols and aldehydes or ketones, “pdc/adh” refers to the pdc and adh genes collectively. A “pdc/adh cassette” refers to a nucleic acid sequence encoding a PDC enzyme and an Adh enzyme.

The term “primer” is an oligonucleotide that hybridizes to a target nucleic acid sequence to create a double stranded nucleic acid region that can serve as an initiation point for DNA synthesis under suitable conditions. Such primers may be used in a polymerase chain reaction.

Database entry numbers given in the following are from the NCBI database (National Center for Biotechnology Information; http://www.ncbi.nlm.nih.gov) or from the CyanoBase, the genome database for cyanobacteria ((http://bacteria.kazusa.orjp/cyanobase/index.html); Yazukazu et al. "CyanoBase, the genome database for *Synechocystis* sp. Strain PCC6803: status for the year 2000", Nucleic Acid Research, 2000, Vol. 18, page 72).

The EC numbers cited throughout this patent application are enzyme commission numbers which is a numerical classification scheme for enzymes based on the chemical reactions which are catalyzed by the enzymes.

The *Chlorogloeopsis* sp. host cells and other cyanobacterial strains described in this patent application can be obtained from the Pasteur Culture Collection (PCC) of cyanobacteria, France, from the Culture Collection of Autotrophic Organisms (CCALA), Institute of Botany, Academy of Sciences of the Czech Republic, or were deposited by Algenol Biofuels Inc.

DESCRIPTION OF EMBODIMENTS OF THE INVENTION

One embodiment of the invention is directed to a genetically enhanced *Chlorogloeopsis* sp. host cell comprising at least one first recombinant gene encoding a first protein for the production of ethanol under the transcriptional control of a first inducible promoter, having at least 85%, 90% or 95% sequence identity to an endogenous inducible promoter of the *Chlorogloeopsis* sp. host cell.

The inventors of the present invention found that first inducible endogenous promoters for transcriptional control of at least the first recombinant gene for ethanol production of *Chlorogloeopsis* are important in order to establish a relatively high, constant and stable ethanol production in the *Chlorogloeopsis* sp. host cells for more than 3 weeks, preferably more than 5 weeks. Heterologous first promoters from different cyanobacterial genera, such as *Synechocystis* PCC6803 or *Nostoc/Anabaena* PCC7120 did not allow for a relatively high and stable, respectively ethanol production.

For example, the $Zn^{2+}$ inducible PziaA promoter from *Synechocystis* PCC6803 was also found to be $Zn^{2+}$ inducible in *Chlorogloeopsis* sp. host cells such as *Chlorogloeopsis* PCC9212, but resulted in very low ethanol production rates of 0.004-0.007% (v/v)/OD*$d^{-1}$, when controlling at least the transcription of the first recombinant gene encoding PDC enzyme so that this promoter was not used further in *Chlorogloeopsis* sp. host cells (see for example the below mentioned results for plasmid TK122). A second promoter PpetE from *Nostoc/Anabaena* PCC7120, which in its native host is $Cu^{2+}$ responsive was shown to be a constitutive promoter if inserted directly upstream of a first recombinant gene for ethanol production such as a PDC enzyme encoding gene in an extrachromosomal plasmid transformed into *Chlorogloeopsis* sp. host cells (see for example the below results for plasmid TK18). This plasmid initially resulted in high ethanol production rates in *Chlorogloeopsis* sp. host cells, which however grew very slowly even during the upscaling process due to the constant ethanol production. After 2 to 3 weeks of cultivation ethanol production stopped, probably because the host cells reverted back to their wild-type.

In contrast to that, first promoters for transcriptionally controlling at least the first recombinant gene for ethanol production, which are inducible and endogenous to the *Chlorogloeopsis* sp. host cells were shown to enable a relatively high and constant ethanol production, which also could be maintained for at least three weeks or more.

The finding that endogenous inducible promoters are important for a successful ethanol production in *Chlorogloeopsis* sp. host cells is also not suggested by the prior art of Stucken et al., which shows that also constitutive heterologous promoters, for example the trc promoter from *E. coli* can be used for the recombinant overexpression of GFP protein in *Chlorogloeopsis*.

According to a further embodiment of the invention, the first inducible promoter can be a metal ion inducible promoter, especially a $Zn^{2+}$, or $Co^{2+}$ inducible promoter such as the promoter PziaA from *Chlorogloeopsis fritschii* PCC6912, or the promoters controlling the open reading frame orf7041, orf7345, orf5189 and also orf5203 all from *Chlorogloeopsis* PCC6912. These endogenous metal ion inducible promoters can lead to relatively high and stable ethanol production rates (see for example the below experimental data showing higher ethanol production rates for plasmids TK187, TK261, TK414, TK336 and TK346 transformed into *Chlorogloeopsis* sp. host cells including either PziaA or Porf7041 from *Chlorogloeopsis fritschii* PCC6912 upon $Zn^{2+}$/$Co^{2+}$ induction, and data showing some ethanol production for the plasmid TK351 including the $Zn^{2+}$ inducible promoter from orf5189 from *Chlorogloeopsis fritschii* PCC6912).

In a further embodiment of the invention, the first endogenous inducible promoter can be generalized PziaA promoter with the following sequence:

$N_{61}$AACATCTGAATATATATTCAGATATT$N_{13}$TAAACT$N_{26}$ACTGAAA$N_5$ATG (SEQ ID NO: 36)

wherein the underlined sequence is the operator sequence, the boxed sequence is the TATA box and the underlined boldfaced sequence is the ribosomal binding site and wherein each of the nucleotides N is independently selected from a group consisting of A, T, C and G and wherein the 3'-ATG is the start codon for the first recombinant gene transcriptionally controlled by this promoter.

Furthermore, the *Chlorogloeopsis* sp. host cell can be a host cell from the well established strains *Chlorogloeopsis fritschii* PCC6912, *Chlorogloeopsis* PCC9212 or *Chlorogloeopsis* sp. ABICyano3.

A deposit of the Algenol Biofuels Inc. proprietary strain of *Chlorogloeopsis* sp. ABICyano3, disclosed in the present application and recited in the appended claims has been made with the American Type Culture Collection (ATCC), 10801 University Boulevard, Manassas, Va. 20110. The date of deposit was Oct. 10, 2013. The ATCC Accession Number is PTA-120619.

Preferably the *Chlorogloeopsis* sp. host cell is *Chlorogloeopsis fritschii* PCC6912. This cyanobacterial strain can produce ethanol in brackish water in ranges of salinity between 6 to 20 psu, preferably 8.75 to 17.5 psu. Furthermore *Chlorogloeopsis* PCC6912 can also form aggregates during cultivation which sink rapidly to the bottom of the photobioreactors, when mixing by for example stirring or bubbling is stopped, so that old medium can easily be removed from the upper parts of the medium having a lower concentration of the *Chlorogloeopsis* sp. host cells. Following this procedure ensures that not too many *Chlorogloeopsis fritschii* PCC6912 cells are removed by exchanging parts of the medium. In addition ethanol can easily be removed from top parts of the medium having a lower concentration of *Chlorogloeopsis fritschii* PCC6912 cells.

In addition, the *Chlorogloeopsis* sp. host cells can show high ethanol production rates of at least 0.01%(v/v) $d^{-1}$, preferably at least 0.025%(v/v) $d^{-1}$, most preferred at least 0.028% (v/v) $d^{-1}$ and up to at least 0.05%(v/v) $d^{-1}$ for at least 7 days of cultivation (see FIG. 7D for the single cultivation). The accumulated ethanol production can reach over 0.4% (v/v) over 14 days of cultivation in BG11 medium corresponding to a production rate of 0.033% (v/v) $d^{-1}$ (see FIG. 7B).

The ethanol production of *Chlorogloeopsis fritschii* PCC6912 e.g. in brackish media with a salinity of between 8.7 and 17.5 psu resulted in about 0.36 to 0.39% (v/v) ethanol after 23 days (FIG. 17A) of cultivation and is higher compared to the ethanol production rate of the other *Chlorogloeopsis* sp. host cells, such as *Chlorogloeopsis* sp. PCC9212, in brackish media.

In a further variant of the invention, the *Chlorogloeopsis* sp. host cell can also comprise at least one second recombinant gene encoding a second protein for the production of ethanol in addition to the first recombinant gene for ethanol production. For example the first recombinant gene can encode pyruvate decarboxylase converting pyruvate into acetaldehyde and the second recombinant gene can encode alcohol dehydrogenase further converting acetaldehyde into ethanol.

Alternatively or in addition, the first recombinant gene can also encode alcohol dehydrogenase E enzyme (AdhE enzyme) which can directly convert acetyl-Coenzyme A into ethanol. Genes encoding alcohol dehydrogenase E are for example disclosed in the PCT application WO 2009/098089 A2, which is incorporated for this purpose.

In this context, it is possible that the same first endogenous inducible promoter controls the transcription of both the first and second recombinant gene. This is for example the case in one of the plasmids which enable a high ethanol production rate in *Chlorogloeopsis* sp. host cells, for example the plasmid TK187.

Furthermore, it is also possible that the first and second recombinant genes are under the transcriptional control of separate first and second promoters. In this case it might be preferred if the induction mechanism of the second promoter is different from the first endogenous inducible promoter, i. e. either the second promoter is inducible by a different inductor in comparison to the first promoter or the second promoter is a constitutive promoter. In this case the second recombinant gene, for example the alcohol dehydrogenase, is permanently produced during the scale up and cultivation of the *Chlorogloeopsis* sp. host cells, so that the harmful acetaldehyde can be quickly converted to the less toxic ethanol once the first recombinant gene, for example pyruvate decarboxylase is produced in high quantities, when the first promoter is induced.

Alternatively, the second promoter can also be an inducible promoter, which can be induced by different inductors, for example other metal ions in comparison to the first inducible endogenous promoter.

In the case that the second promoter is a constitutive promoter it can be selected from a group consisting of PpetE, or PnblA from *Nostoc/Anabaena* PCC7120, which are used in many of the plasmids disclosed herein. The plasmid TK336 used herein contains the first recombinant gene encoding PDC enzyme under the control of the first $Zn^{2+}$ inducible PziaA promoter, whereas the second recombinant gene coding for alcohol dehydrogenase is under the control of the promoter PnblA from *Nostoc/Anabaena* PCC7120, which was shown to be a constitutive promoter in the *Chlorogloeopsis* PCC6912 host cells.

In addition, the at least one first and also if present the at least one second recombinant gene can be codon improved for enhancing translation by having a codon adaptation index of equal to or greater than 0.6, preferably equal to or greater than 0.7 most preferred greater than or equal to 0.8 based on the below codon usage table of the *Chlorogloeopsis* sp. host cell.

TABLE 1

| Codon Usage<br>Codon Usage table | | | | |
|---|---|---|---|---|
| Amino Acid | Codon | Number | /1000 | Fraction |
| Ala | GCG | 21513.00 | 10.38 | 0.13 |
| Ala | GCA | 56949.00 | 27.49 | 0.33 |
| Ala | GCT | 60693.00 | 29.30 | 0.36 |
| Ala | GCC | 30886.00 | 14.91 | 0.18 |
| Cys | TGT | 12937.00 | 6.24 | 0.59 |
| Cys | TGC | 8898.00 | 4.30 | 0.41 |
| Asp | GAT | 71751.00 | 34.63 | 0.75 |
| Asp | GAC | 23767.00 | 11.47 | 0.25 |
| Glu | GAG | 35182.00 | 16.98 | 0.27 |
| Glu | GAA | 94948.00 | 45.83 | 0.73 |
| Phe | TTT | 64339.00 | 31.06 | 0.76 |
| Phe | TTC | 19940.00 | 9.62 | 0.24 |
| Gly | GGG | 17992.00 | 8.68 | 0.13 |
| Gly | GGA | 37399.00 | 18.05 | 0.28 |
| Gly | GGT | 50906.00 | 24.57 | 0.38 |
| Gly | GGC | 27994.00 | 13.51 | 0.21 |
| His | CAT | 22815.00 | 11.01 | 0.58 |
| His | CAC | 16302.00 | 7.87 | 0.42 |
| Ile | ATA | 23782.00 | 11.48 | 0.17 |
| Ile | ATT | 82747.00 | 39.94 | 0.59 |
| Ile | ATC | 34003.00 | 16.41 | 0.24 |
| Lys | AAG | 28873.00 | 13.94 | 0.29 |
| Lys | AAA | 72057.00 | 34.78 | 0.71 |
| Leu | TTG | 52946.00 | 25.56 | 0.23 |
| Leu | TTA | 67444.00 | 32.56 | 0.30 |
| Leu | CTG | 29147.00 | 14.07 | 0.13 |
| Leu | CTA | 29246.00 | 14.12 | 0.13 |
| Leu | CTT | 27727.00 | 13.38 | 0.12 |
| Leu | CTC | 20752.00 | 10.02 | 0.09 |
| Met | ATG | 38148.00 | 18.41 | 1.00 |
| Asn | AAT | 58913.00 | 28.44 | 0.66 |
| Asn | AAC | 30157.00 | 14.56 | 0.34 |
| Pro | CCG | 11772.00 | 5.68 | 0.12 |
| Pro | CCA | 33050.00 | 15.95 | 0.34 |
| Pro | CCT | 31169.00 | 15.05 | 0.32 |
| Pro | CCC | 20628.00 | 9.96 | 0.21 |
| Gln | CAG | 32669.00 | 15.77 | 0.29 |
| Gln | CAA | 78214.00 | 37.75 | 0.71 |
| Arg | AGG | 6979.00 | 3.37 | 0.06 |
| Arg | AGA | 17363.00 | 8.38 | 0.16 |
| Arg | CGG | 12623.00 | 6.09 | 0.12 |
| Arg | CGA | 17024.00 | 8.22 | 0.16 |
| Arg | CGT | 24665.00 | 11.91 | 0.23 |
| Arg | CGC | 28950.00 | 13.97 | 0.27 |
| Ser | AGT | 30130.00 | 14.54 | 0.23 |
| Ser | AGC | 21582.00 | 10.42 | 0.17 |
| Ser | TCG | 10220.00 | 4.93 | 0.08 |
| Ser | TCA | 20353.00 | 9.82 | 0.16 |
| Ser | TCT | 33178.00 | 16.01 | 0.26 |
| Ser | TCC | 12875.00 | 6.21 | 0.10 |
| Thr | ACG | 11429.00 | 5.52 | 0.10 |
| Thr | ACA | 37859.00 | 18.27 | 0.33 |
| Thr | ACT | 43814.00 | 21.15 | 0.38 |
| Thr | ACC | 22203.00 | 10.72 | 0.19 |
| Val | GTG | 29904.00 | 14.43 | 0.21 |
| Val | GTA | 41715.00 | 20.14 | 0.30 |
| Val | GTT | 48038.00 | 23.19 | 0.34 |
| Val | GTC | 20305.00 | 9.80 | 0.15 |
| Trp | TGG | 30046.00 | 14.50 | 1.00 |
| Tyr | TAT | 39044.00 | 18.85 | 0.61 |
| Tyr | TAC | 25181.00 | 12.15 | 0.39 |
| End | TGA | 1668.00 | 0.81 | 0.22 |
| End | TAG | 2076.00 | 1.00 | 0.27 |
| End | TAA | 3815.00 | 1.84 | 0.50 |

The column titled "/1000" shows the frequency of the respective codon per 1000 bases of a coding DNA sequence in *Chlorogloeopsis* PCC6912. The column titled "number" denotes the overall number of the respective codon in the genome of *Chlorogloeopsis fritschii* PCC6912. The column titled "fraction" denotes the fractional amount of one codon coding for a particular amino acid in relation to the fractional amounts of the other codons coding for the same amino acid. The sum of all fractional amounts of the codons for one amino acid is 1.

It might be advantageous to include a transcription terminator between the first and second recombinant gene in order to disconnect the transcriptional control of the first and second recombinant gene as for example shown in the plasmid TK336 where the oop terminator is present between the first and second recombinant gene if the first recombinant gene and the second recombinant gene are controlled by different first and second promoters.

The first and if present second recombinant genes including their promoters can be either located on an extrachromosomal plasmid or can be integrated into a chromosome of the *Chlorogloeopsis* sp. host cell.

Furthermore, the inventors realized that extrachromosomal plasmids containing the ethanologenic cassettes need to contain an origin of replication from a closely related species such as *Nostoc/Anabaena*, for example the origin of replication pDU1 (the protein sequence of the replication protein of the pDU1 plasmid from *Nostoc* sp. PCC 7524 is shown as SEQ ID NO. 15, the protein sequence of the integrase/resolvase recombinase from *Nostoc* sp. PCC 7524 is shown in SEQ ID NO. 16, and the nucleic acid sequence of the respective origin of replication is included in the sequence listing as SEQ ID NO. 17) in order to independently replicate in the *Chlorogloeopsis* sp. host cells. Extrachromosomal plasmids based on a different origin of replication such as the origin of replication of RSF1010 such as pVZ321 did not result in genetically enhanced *Chlorogloeopsis* sp. host cells.

The *Chlorogloeopsis* sp. host cells were found to tolerate very harsh culturing conditions concerning both the concentration of ethanol in the medium as well as the range of temperature for cultivation and oxygen stress. In particular, the *Chlorogloeopsis* sp. host cells can withstand at least 1% (v/v) ethanol in the culture medium for at least 6, 12, 16 and up to 27 weeks. Furthermore the cells can withstand at least 48° C., preferably at least 50° C. or at least 53 to 55° C. for at least 2 hours peaks over at least 7 days in brackish media up to 15 to 17 psu. *Chlorogloeopsis* PCC 6912 can also withstand a purging of the culture medium with 60 to 70% oxygen.

The test for ethanol tolerance was performed by adding 1% ethanol to the medium of the *Chlorogloeopsis* sp. host cells. Additional ethanol was added throughout cultivation, in the case that the ethanol level decreased in order to keep the ethanol level at 1%. Cyanobacterial cultures were then examined for example under the microscope after a pre-determined period of time for example 6, 12 or 16 weeks and cyanobacterial cultures were deemed to have passed the ethanol tolerance test if at least more than 50% of the cyanobacterial cells were found to be intact and viable according to microscopic analysis, meaning that the cell morphology did not change significantly; the cells were still green and the cells were not lysed.

The test for temperature tolerance was conducted with the *Chlorogloeopsis* sp. host cells in a medium under conditions of light illumination and omitting light illumination (day/night cycle) at maximum temperatures between 45 to 55° C. for a certain period of time, for example 1 to 2 hours during illumination. Cyanobacterial cells were deemed to have passed the test if the cultures were still growing after having been subjected to 7 days of day/night cycles as described above. Growth could be detected for example by an increase in the chlorophyll content of the cyanobacterial cultures. *Chlorogloeopsis fritschii* PCC6912 for example was found to withstand 48° C., 50° C. or at least 53 to 55° C. for at least 2 hours per day over a time period of at least 7 days even in medium with a salinity of 35 psu.

In addition, an oxygen tolerance test was carried out which showed that *Chlorogloeopsis fritschii* PCC6912 can tolerate purging of the medium with 60% to 70% oxygen resulting an oxygen levels of up to 650 μmol/l in cultures during the day, when cultured a temperatures between 28° C. to 37° C. and then being illuminated with a light intensity of between 200 $\mu E \times m^{-2} \times s^{-1}$ to 400 $\mu E \times m^{-2} \times s^{-1}$.

The results for the ethanol tolerance tests and temperature tolerance tests for various different cyanobacterial strains including the *Chlorogloeopsis* sp. host cells of the present invention are shown in the following Table 2:

TABLE 2

Strain Characterization

| Cyanobacterial species | Growth in marine medium (35 psu) | 1% EtOH tolerance test [weeks] | Thermotolerance test (each test for 1 week) 2 hours 45° C. | 2 hours 48° C. | 2 hours 50° C. | Additional characterization (each test for 1 week) 2 hours 53° C. | 2 hours 55° C. |
|---|---|---|---|---|---|---|---|
| *Chlorogloeopsis* ABICyano3 | pos. | >11 (in (marine BG11 30 psu) | pos. (up to 27 psu) | pos. (up to 27 psu) | pos. (up to 27 psu) | pos. (up to 27 psu) | pos. (up to 27 psu) |
| *Chlorogloeopsis* PCC6912 | pos. | 27 (in (marine BG11 30 psu) | pos. (35 psu) | pos. (35 psu) | pos. (35 psu) | pos. (35 psu) | pos. (35 psu) |
| *Chlorogloeopsis* PCC9212 | neg. | 11* | pos. (7.5 psu) | pos. (15 psu) | pos. (7.5 psu) | pos. (7.5 psu) | pos. 7.5 psu) |
| *Thermosynechococcus elongates* BP-1 | neg. | <1 | pos. (BG11) | pos. (BG11) | n.d. | pos. (BG11) | pos. (BG11) |
| *Chroococcidiopsis thermalis* | pos. | 3 | n.d. | n.d. | n.d. | n.d. | n.d. |

TABLE 2-continued

Strain Characterization

| Cyanobacterial species | Growth in marine medium (35 psu) | 1% EtOH tolerance test [weeks] | Thermotolerance test (each test for 1 week) 2 hours 45° C. | 2 hours 48° C. | 2 hours 50° C. | Additional characterization (each test for 1 week) 2 hours 53° C. | 2 hours 55° C. |
|---|---|---|---|---|---|---|---|
| CCALA187 | | | | | | | |
| *Chroococcidiopsis thermalis* | pos. | 3 | n.d. | n.d. | n.d. | n.d. | n.d. |
| CCALA50 | | | | | | | |
| *Chroococcidiopsis thermalis* | pos. | 3 | pos. (Z) | pos. (Z) | neg. (Z) | | |
| CCALA48 | | | | | | | |

Pos. = positive
Neg. = negative
N.d. = Not determined
Z = Z medium
* = test was done in BG11 medium The table clearly shows that *Chlorogloeopsis* PCC6912 appears to be the most salt and ethanol tolerant cyanobacterial strain in the table and can withstand 1% ethanol in marine BG 11 medium for 27 weeks, whereas other thermotolerant strains such as *Chroococcidiopsis thermalis* can only tolerate 1% ethanol in BG11 medium for three weeks. The two other *Chlorogloeopsis* strains PCC9212 and ABICyano3 are less salt tolerant compared to PCC6912 in the thermotolerance test, because they can only withstand the same high temperatures as PCC6912 in media with lower salt concentration. *Chlorogloeopsis* PCC6912 was also the most sturdy strain in the thermotolerance test because it was able to tolerate two hours at 45° C. for one week, two hours 48° C. for one week and also two hours at 50° C. for one week in marine medium (35 psu).

Another aspect of the present invention is directed to a method for producing ethanol comprising the method steps of:

A) culturing any of the above described genetically enhanced *Chlorogloeopsis* sp. host cells in a culture medium, the host cells thereby producing ethanol, B) retrieving ethanol from at least either one of the host cells, the medium or the head space above the medium.

Due to the sturdiness of the *Chlorogloeopsis* sp. host cells during method step A) the host cells can be cultured under at least one of the following culturing conditions:

Temperatures between 20° C. to about 55° C., preferably between 25° C. to 45° C. and/or a salinity of the culture medium of between 0.2 to 35 psu, in particular between 8.7 to 17.5 psu. In particular, the *Chlorogloeopsis fritschii* PCC6912 host cells can therefore also be cultivated in brackish medium. This finding is particularly surprising, because *Chlorogloeopsis fritschii* PCC6912 is known to be a freshwater strain.

*Chlorogloeopsis* sp. host cells can tolerate a wide range of temperatures, for example moderate temperatures of around 20° C. to more extreme temperatures of around 55° C., so that these cells can easily be cultivated under desert-like conditions, where during daytime high temperatures can be reached and during night time much lower temperatures can be expected.

Since the *Chlorogloeopsis* sp. host cells can form nitrogen fixing heterocysts, the culture medium does not need to include nitrogen as a source for growth, which is a clear advantage to the culturing of other cyanobacterial strains which require nitrogen for growth such as *Synechococcus* or *Synechocystis.*

In the case that *Chlorogloeopsis fritschii* PCC6912 cells or ABICyano3 cells are cultured, a mixing of the culture medium during the method step A), for example via stirring or via introducing gases from the bottom of the bioreactor, can be advantageous, in order to avoid a settlement of the cells at the bottom of the photobioreactor.

Without stirring, during the cultivation method step A), a larger fraction of the *Chlorogloeopsis fritschii* PCC6912 cells and ABICyano3 cells settle in bottom sections of the culture medium compared to a smaller fraction of the host cells being located in top sections of the culture medium. If a settlement of the cells occur, one of the following method steps can be performed very easily:

During method step A):

culture medium in the top section is removed and fresh culture medium is added

*Chlorogloeopsis* sp. host cells are removed from the bottom section of the culture medium and/or During method step B):

ethanol is harvested in the top section of the culture medium.

*Chlorogloeopsis* PCC6912 and ABICyano3 form aggregates during cultivation; if mixing is stopped, those aggregates $t_{end}$ to settle more on the bottom of the photobioreactor, so that for example from the top sections of the culture medium, used medium can be removed and can be replenished by new medium, thereby easing the whole cultivation procedure. With reference to FIG. 19A, the cultivation can be done in vessels, for example bioreactors (3) harboring the culture medium (2) and containing an enclosed headspace (25) above the culture medium (2), including gases such as carbon dioxide and air or evaporated ethanol, which can be removed via the pipe (35). The top section of the culture medium is in contact with the headspace (25) and the bottom section of the culture medium is located below the top section. The top sections of the culture medium can be removed for example by using plug valves (10 and 20) located in the top sections of the photobioreactor for pumping the medium out of the photobioreactor by opening the valve. As long as gases (5), such as air or carbon dioxide are introduced from the bottom of the photobioreactor into the medium via a supply pipe (30) as shown in FIG. 19A, the PCC6912 or ABICyano3 cells are evenly distributed in the medium in aggregates (1).

Once the bubbling of gases is discontinued as shown in FIG. 19B (crossed out supply pipe 30), the cells settle in the bottom section (45) if allowed to settle for a period of time between 5 minutes to 60 minutes, at most 120 minutes. In contrast to the bottom section (45), the top section (40) is nearly free of the cells (less than 5% of the total cell mass of the cells, preferably less than 1% of the total mass of the cells would be located in the top section after settlement of the cells). Ethanol can now be more easily harvested from the top section (40) using for example the plug valves (10 and/or 20) so that the purification of ethanol is simplified. Removing more concentrated biomass of the *Chlorogloeopsis* sp. host cells from the bottom section (45) of the culture medium via for example the plug valve (15) is also easier.

Since most of the cells have settled in the bottom section, centrifuging the medium of the top section, which is normally done in order to remove the cells from the medium, is not necessary. The final separation of the ethanol from the medium of the top section can, for example, be done by vapor compression steam stripping as described in the PCT patent application WO 2011/103277 A1, which is hereby incorporated with regard to the separation procedure or via distillation.

In particular, the separation of the ethanol from the culture medium can be done via steam stripping process described in WO 2011/103277 A1, in which the culture medium, containing the ethanol is a dilute feed solution, the steam stripping process comprising the following method steps:

(a) counter-current contacting of the dilute feed solution and a vapor phase with a counter-current vapor-liquid contactor;

(b) condensing in a condensor of the vapor phase output of the counter-current vapor-liquid contactor with transfer of the latent heat released by condensation to an evaporator;

(c) evaporating of a liquid feed to provide the vapor phase input to the counter-current contactor; and (d) compressing of the vapor phase, wherein compression of the vapor phase may occur before the contactor, after the contactor, or both before and after and wherein the action of the compressor must result in a pressure that is higher in the condenser than in the evaporator.

The vapor phase can be saturated with water and strips off the ethanol from the dilute feed solution upon counter-current contacting, resulting in a vapor phase enriched with ethanol, which then can be condensed.

Long-term cultivation of the *Chlorogloeopsis* PCC6912 and ABICyano3 cells can therefore be maintained by alternating between two modes of operation, mixing or discontinue mixing so that the cells settle. During the mixing, the cell cultures can grow and can therefore produce ethanol, whereas if mixing is stopped, either medium can be replenished, new cells can be introduced into the cell culture or the ethanol can be harvested very easily as described above. Afterwards mixing can be resumed.

In the case that the first endogenous inducible promoter is a metal ion inducible promoter, method step A) can include the substeps of:

A1) culturing the *Chlorogloeopsis* sp. host cells in an uninduced state, and the further method step of A2) inducing the *Chlorogloeopsis* sp. host cells by adding metal ions to the culture medium.

This method is very simple and can easily be used for a reliable induction procedure. During the uninduced state, the *Chlorogloeopsis* sp. host cells can grow quickly so that the upscaling can easily be achieved.

Another aspect of the invention is directed to a method of producing the genetically enhanced *Chlorogloeopsis* sp. host cells comprising introducing said first and if present said second recombinant gene into the host cell. In general, said first and if present said second recombinant gene can be either be introduced into the chromosome of the host cell, into endogenous plasmids or can be introduced into the cell as a part of a heterologous extrachromosomal plasmid.

In particular the following method steps can be included in such a method:

a) Providing a recombinant nucleic acid sequence including said first and if present second recombinant gene and protecting said recombinant nucleic acid sequence against endogenous restriction endonucleases of the host cells, and the further method step of:

b) Introducing said first if present second recombinant gene into the genome of the host cell.

Such a protection step can for example be performed by methylating the plasmids for transformation of the *Chlorogloeopsis* sp. host cells using certain methylases in order to mask the specific restriction sites for the restriction endonucleases. Specific testing of the *Chlorogloeopsis* sp. host cells, especially the three strains *Chlorogloeopsis fritschii* sp. PCC6912, *Chlorogloeopsis* sp. PCC9212, and *Chlorogloeopsis* sp. ABICyano3 for restriction endonucleases, provided evidence that the restriction enzymes SphI and BlpI are present. Therefore, the methylases M. CviPI and M. SssI (New England Biolabs) can be used in order to protect the restriction sites against the action of these enzymes by in vitro methylation.

Alternatively, the recombinant nucleic acid sequence can be protected against endogenous restriction endonucleases by deleting and/or altering the specific recognition sequences of the endonucleases for example by in vitro gene synthesis.

Furthermore, during method step b) electroporation or conjugation can be used, preferably electroporation.

It was shown that especially *Chlorogloeopsis* PCC6912 host cells include a capsule or an extracellular polymer layer (EPS), which often can hinder an introduction of recombinant nucleic acids into the host cell. In the present case, however, the inventors found that neither sonification of the host cells nor incubation with a salt solution for at least one hour was necessary in order to enable a successful introduction of recombinant nucleic acids such as plasmids via conjugation or electroporation into the *Chlorogloeopsis* sp. host cells. This finding is also in clear contrast to the prior art document Stucken et al., which describes that sonification and a salt wash were critical steps for successful conjugation.

Another embodiment of the invention is directed to a construct for transformation of *Chlorogloeopsis* sp. host cells comprising:

at least one first recombinant gene encoding a first protein for the production of ethanol under the transcriptional control of a first inducible promoter, having at least 85%, 90% or 95% sequence identity to an endogenous inducible promoter of the *Chlorogloeopsis* sp. host cell.

Such a construct is well suited in order to produce genetically enhanced *Chlorogloeopsis* sp. host cells for ethanol production using the transformation protocols as described in this patent application. In particular, the endogenous promoter of the *Chlorogloeopsis* sp. host cells enables a stable and high ethanol production as described above.

The construct can be a plasmid, for example an extrachromosomal plasmid including an origin of replication for replication of the construct independently of the genome of the *Chlorogloeopsis* sp. host cells. Alternatively, the construct can also be an integrative plasmid containing DNA sequences homologous to genomic sequences of the host cell for integration of a recombinant region flanked by these homologous regions into the chromosomes of the host cell. The recombinant region can include an ethanologenic cassette with said first recombinant gene and if necessary also antibiotic resistance conferring genes.

The first inducible promoter can be a metal-ion inducible promoter, especially a $Zn^{2+}$, or $Co^{2+}$ inducible promoter as already described above.

The recombinant construct can also further include all the features already described with regard to the genetically enhanced *Chlorogloeopsis* sp. host cells, such as second recombinant gene for ethanol production and also the various different promoters.

EXAMPLES

Example 1

Bacterial Strains, Growth Conditions, and Selection of Transformants

*Escherichia coli* strains J53, HB101 (Promega), XL10-Gold (Stratagene), and α-select (Bioline) were grown in Luria-Bertani (LB) medium at 37° C. Ampicillin (50 μg/ml), kanamycin (25-50 μg/ml), and chloramphenicol (34 μg/ml) were used when appropriate. *E. coli* cultures were continuously shaken overnight at 200 rpm and at 100 rpm, respectively, when used for conjugation.

For transformation experiments cyanobacterial wild-type axenic strains were cultured at 28-35° C. in liquid BG11 fresh water on a reciprocal shaker at 150 rpm under continuous illumination of approximately 30-40 μmol photons/$m^2$ s.

*Chlorogloeopsis* transformants (derived from *Chlorogloeopsis fritschii* PCC6912, *Chlorogloeopsis* sp. PCC 9212, and *Chlorogloeopsis* sp. ABICyano3) were maintained on solid BG11 medium containing 25-50 μg/ml neomycin.

The liquid culture medium, BG11 and artificial seawater BG11 (aswBG11) for culturing either the wildtype or the genetically enhanced *Chlorogloeopsis* sp. host cells can be prepared as follows:

TABLE 3

Composition of BG-11 medium

| Compound | Amount (per liter) | Final Concentration |
|---|---|---|
| $NaNO_3$ | 1.5 g | 17.6 mM |
| $K_2HPO_4$ | 0.04 g | 0.23 mM |
| $MgSO_4 \cdot 7H_2O$ | 0.075 g | 0.3 mM |
| $CaCl_2 \cdot 2H_2O$ | 0.036 g | 0.24 mM |
| Citric acid | 0.006 g | 0.031 mM |
| Ferric ammonium citrate | 0.006 g | — |
| EDTA (disodium salt) | 0.001 g | 0.0030 mM |
| $NaCO_3$ | 0.02 g | 0.19 mM |
| Trace metal mix A5 | 1.0 ml | — |

TABLE 4

1000× Trace Metal Composition of BG-11 medium

| 1000× Trace Metal mix A5 | Amount | Final Concentration in Working Medium |
|---|---|---|
| $H_3BO_3$ | 2.86 g | 46.26 μM |
| $MnCl_2 \cdot 4H_2O$ | 1.81 g | 9.15 μM |

TABLE 4-continued

1000× Trace Metal Composition of BG-11 medium

| 1000× Trace Metal mix A5 | Amount | Final Concentration in Working Medium |
|---|---|---|
| $ZnSO_4 \cdot 7H_2O$ | 0.222 g | 0.772 μM |
| $NaMoO_4 \cdot 2H_2O$ | 0.39 g | 1.61 μM |
| $CuSO_4 \cdot 5H_2O$ | 0.079 g | 0.32 μM |
| $Co(NO_3)_2 \cdot 6H_2O$ | 49.4 mg | 0.170 μM |
| Distilled water | 1.0 L | — |

Distilled water for BG11 or seawater (35 practical salinity units=psu; see Unesco (1981a). The Practical Salinity Scale 1978 and the International Equation of State of Seawater 1980. Tech. Pap. Mar. Sci., 36: 25 pp.) for mBG11 is added to the final volume of 1.0 L.

TABLE 5

Recipe for a 100× BG11 stock solution

| 100× BG11 | g/L | mL/L |
|---|---|---|
| Sodium nitrate, waterfree ($NaNO_3$) | 149.58 | — |
| Magnesium sulfate -heptahydrate ($MgSO_4 \cdot 7H_2O$) | 7.49 | — |
| Calcium chloride dihydrate ($CaCl_2 \cdot 2H_2O$) | 3.6 | — |
| Citric Acid | 0.6 | — |
| 0.25M EDTA disodiumsalt dihydrate ($Na_2EDTA \cdot 2H_2O$ (pH 8.0)) | — | 1.12 |

TABLE 6

Recipe for artificial seawater aswBG-11 (35 psu)

| 35 psu artificial marine BG11 | g/L | mL/L |
|---|---|---|
| Sodium chloride | 25.84 | — |
| Magnesium sulfate-heptahydrate | 6.36 | — |
| Magnesium(II)chloride | 5.06 | — |
| Potassium chloride | 0.62 | — |
| Calcium chloride dihydrate | 1.36 | — |
| 100× BG11 | — | 10 |
| 20 mg/mL Disodium carbonate ($Na_2CO_3$) | — | 1 |
| 40 mg/mL Dipotassium hydrogen phosphate trihydrate ($K_2HPO_4 \cdot 3H_2O$) | — | 1 |

Use de-ionized water for preparing the solutions. Autoclave for 20 min at 121° C. After the media is cooled down add 1 mL 6 mg/mL Ferric ammonium citrate and 1 mL of the 1,000× trace metal mix.

TABLE 7

Recipe for Z media (from "Algal Culturing Techniques" by Academic Press, 2005)

| Z media | mL/L L |
|---|---|
| 1.1 mol/L $NaNO_3$ | 5 |
| 0.25 mol/L $Ca(NO_3)_2$ | 1 |
| 0.178 mol/L $K_2HPO_4$ | 1 |
| 0.1 mol/L $MgSO_4$ | 1 |
| 0.2 mol/L $Na_2CO_3$ | 1 |
| 10 mmol L $EDTA\text{-}Na_2$ and $FeCl_3$ 0, 1N HCl | 1 |
| Gaffron micronutrients | 0.08 |

Use de-ionized water for media preparation. Autoclave for 20 min at 121° C.

TABLE 8

| Recipe for Gaffron Nutrient Stock Solution | |
|---|---|
| Stock solutions Gaffron micro_nutrients | g/L |
| $H_3BO_3$ | 3.100 |
| $MnSO_4 \cdot 4H_2O$ | 2.230 |
| $ZnSO_4 \cdot 7H_2O$ | 0.220 |
| $(NH_4)_6Mo_7O_{24} \cdot 4H_2O$ | 0.088 |
| $Co(NO_3)_2 . 6H_2O$ | 0.146 |
| $VOSO_4 \cdot 6H_2O$ | 0.054 |
| $Al_2(SO_4)_3K_2SO_4 \cdot 2H_2O$ | 0.474 |
| $NiSO_4(NH_4)_2SO_4 \cdot 6H_2O$ | 0.198 |
| $Cd(NO_3)_2 \cdot 4H_2O$ | 0.154 |
| $Cr(NO_3)_3 \cdot 7H_2O$ | 0.037 |
| $Na_2WO_4 \cdot 2H_2O$ | 0.033 |
| KBr | 0.119 |
| KI | 0.083 |

Example 2

Detection of a Capsule or an Extracellular Polymer Layer (EPS) Around *Chlorogloeopsis Fritschii* PCC6912

The procedure is based on the so called ConA-FITC fluorescence microscopy (Lectin-Fluorescein isothiocyanate conjugate from *Canavalia ensiformis*), which can be used for labelling of carbohydrate moieties on the cell surface of the cyanobacterial cells.

In particular, the cells were incubated in 1/1000 ConA/FITC (Sigma) for 30 min. Lectin was diluted in 50 mM phosphate buffer (pH 7.0), which contained 5 mM $MnCl_2$ and $CaCl_2$ ("lectin buffer"). The stained cells were then microscopically investigated with a fluorescence microscope. If FITC results in a high background fluorescence, cells were directly washed on the slide with a bit "lectin buffer" and extra volume sucked off with a tissue.

Figure 1:
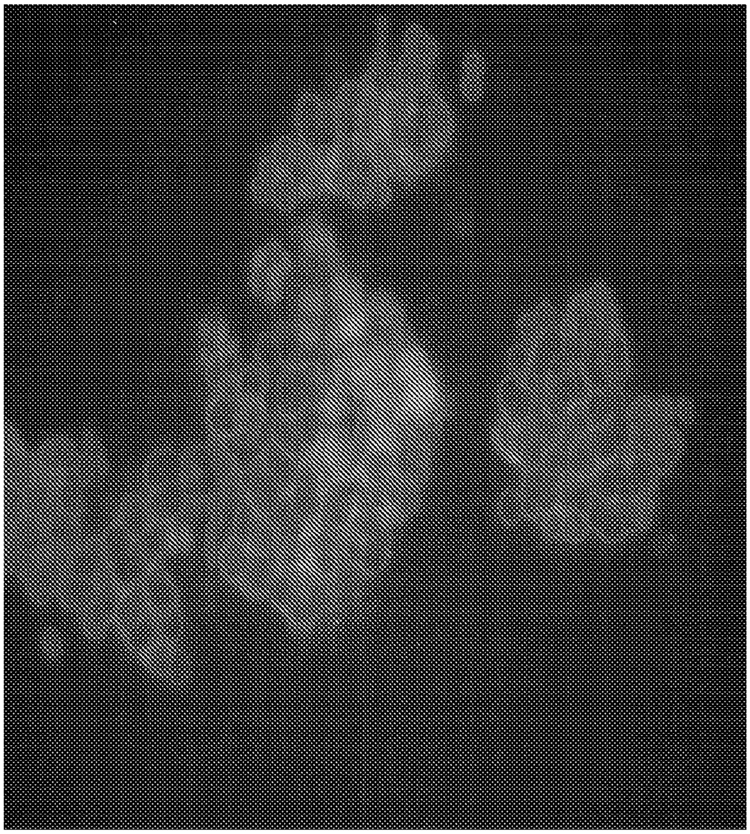
FIG. 1 shows a fluorescence photograph of the staining of *Chlorogloeopsis* PCC6912 cells with the lectin Concanavalin A-FITC (ConA-FITC) conjugated with a fluorescence marker showing the capsule or extracellular polymeric layer (EPS) of *Chlorogloeopsis* PCC6912. ConA-FITC can be used for labelling of carbohydrate moieties on the cell surface of the cyanobacterial cells.

FIG. 1 shows a fluorescence photograph of *Chlorogloeopsis fritschii* PCC6912 cells labeled with ConA-FITC. The extracellular capsule or EPS appears in a different color than the cyanobacterial cells itself (red fluorescence for the cells and green fluorescence for the capsule or EPS).

Example 3

Detection of Cyanobacterial Restriction Endonucleases (RENs)

Restriction analysis was performed using different plasmids, which were incubated with crude extracts of the *Chlorogloeopsis* strains. 600 ng of plasmids K230, K236Cm and K244, respectively (the DNA sequences of plasmid K230, K236Cm and K244, respectively are shown as SEQ ID Nos. 18, 19 and 20), were incubated in NEB buffer P4 with ~13 μg total protein over night at 28° C. in 40 μl reaction volume and analyzed by agarose gel electrophoreses. Digestion bands were indicative of specific RENs present in the crude extract. Smearing indicated unspecific nucleolytic activity. Sequencing of digested plasmids led to identification of respective restriction sites.

K230 was column purified after incubation in crude extract and fragments were sent to sequencing with primers #417 (230spannA) to #434 (230spannR) covering the whole plasmid (the DNA sequences of both primers #417 and #434 are included in the sequence listing as SEQ ID NOs. 22 and 23). A sharp signal drop down—which required complete digestion—in the obtained sequence was indicative of a restriction point.

Figure 2A:
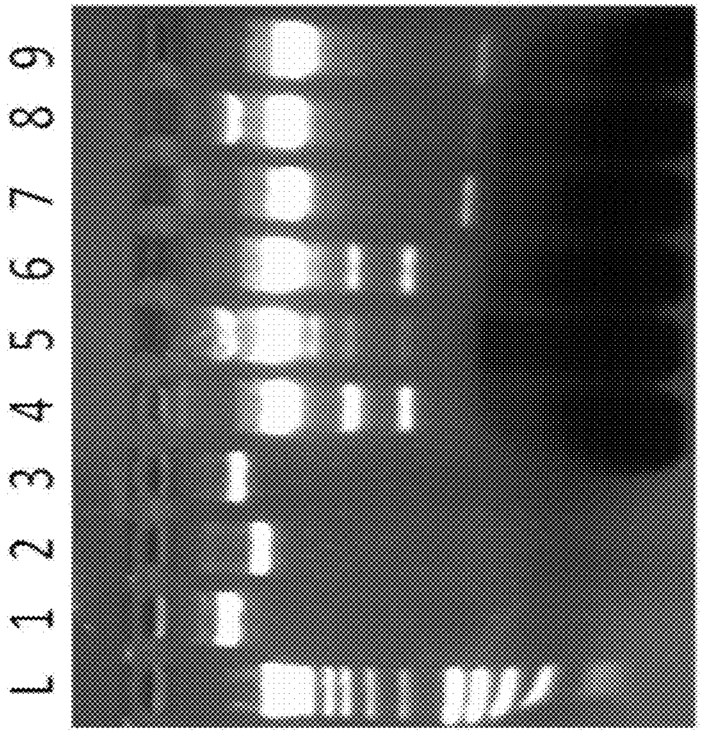
FIG. 2A and FIG. 2B are agarose gels showing the presence of endogenous restriction endonucleases resulting in digestion of certain plasmids after incubation with the crude extracts of the *Chlorogloeopsis* sp. cells.
Figure 2B:
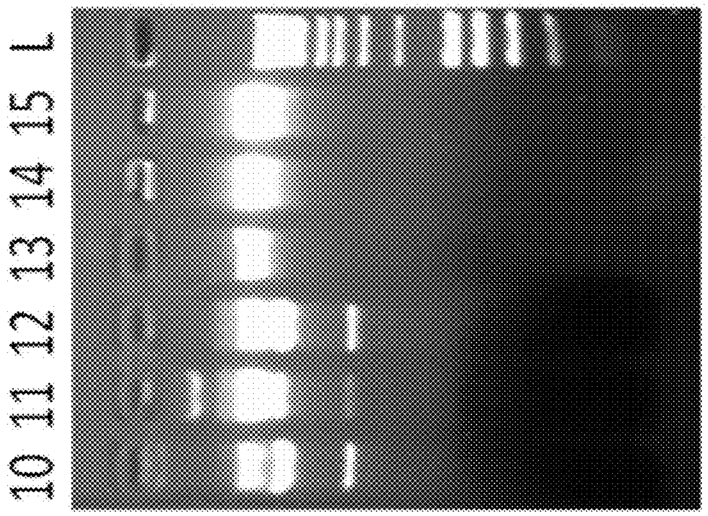

FIG. 2A and FIG. 2B show agarose gels evidencing the results of the incubation of the above mentioned plasmids with the crude extracts. A set of plasmids covering multiple different REN sites were incubated with crude extracts to identify RENs in the *Chlorogloeopsis* host cells. The lanes denote the following:

L: ladder, Lane 1: K230, lane 2: K236, lane 3: K244, lane 4: K230 plus *Chlorogloeopsis* sp. ABICyano3 crude extract, lane 5: K230 plus *Chlorogloeopsis fritschii* PCC6912 crude extract, lane 6: K230 plus *Chlorogloeopsis* sp. PCC9212 crude extract, lane 7: K236 plus *Chlorogloeopsis* sp. ABICyano3 crude extract, lane 8: K236 plus *Chlorogloeopsis fritschii* PCC6912 crude extract, lane 9: K236 plus *Chlorogloeopsis* sp. PCC9212 crude extract, lane 10: K244 plus *Chlorogloeopsis* sp. ABICyano3 crude extract, lane 11: K244 plus *Chlorogloeopsis fritschii* PCC6912 crude extract, lane 12: K244 plus *Chlorogloeopsis* sp. PCC9212 crude extract, lane 13: crude extract from *Chlorogloeopsis* sp. ABICyano3, lane 14: crude extract from *Chlorogloeopsis fritschii* PCC6912, lane 15: crude extract from *Chlorogloeopsis* sp. PCC9212. These gels clearly show that specific restriction pattern can be identified upon digestion of the plasmids with the three different cell extracts. Subsequent sequencing of these digested DNA patterns revealed the presence of the restriction endonucleases SphI and BlpI.

Example 4

Transformation of Cyanobacterial Strains

Gene transfer to *Chlorogloeopsis* strains was performed by conjugation and electroporation, respectively. Prior to electroporation DNA was protected by in vitro methylation using the commercially available methylates M. CviPI and M. SssI (New England Biolabs). In general, the transformation of the *Chlorogloeopsis* strains can be done in the same way using either extrachromosomal or integrative plasmids.

Methylations were conducted in 1× methylation buffer with 160-640 μM S-adenosylmethionine and methylase (1-5 U M.CviPI and/or 5 U M.SssI per 1 μg plasmid) for at least 4 hours at 37° C. Then, methylated DNA was extracted by phenol-chloroform-isoamylalcohol and precipitated by ethanol. After DNA pellet was dried at 65° C. for 10 minutes, the methylated DNA was resuspended in 30-100 μl $H_2O$ and dissolved at 65° C. for 20 min. Alternatively, methylated DNA was purified using the GeneJET™ gel extraction kit (Fermentas). The success of methylation was checked by specific restriction digests using commercial enzymes such as HaeIII (to confirm methylation by M. CviPI) and HpaII (to confirm methylation by M.SssI).

Conjugation:

For triparental mating, the *E. coli* strains J53 bearing a conjugative RP4 plasmid and HB101 bearing pDAG4 derivatives plus the pRL528 helper plasmid were used (DNA sequence of this plasmid is included as SEQ ID NO. 21, wherein M.AvaI is located between nucleotides 548 to 1996 and M.Eco47II is between nucleotides 3006 to 4259). 3-5 ml of each culture was centrifuged, washed twice with LB medium and suspended in 200 μl of LB-medium. Both *E. coli* strains were mixed, centrifuged and resuspended in 100 μl of LB-medium. 10-15 ml of exponentially growing cyanobacterial cultures were centrifuged, washed once with fresh BG11 medium and resuspended in 100-150 µl of BG11. The cyanobacterial and E. coli suspension was mixed and applied onto membrane filter (Millipore GVWP, 0.22 µm pore size) placed on the surface of the BG11 medium supplemented with 5% LB in a Petri dish. After incubation under dim light (5 µmol photons/m$^2$ s) for 2 days, cells were resuspended in fresh BG11 medium, plated onto selective medium (BG11 containing 25-35 µg/ml neomycin) and grown at 30° C. (light intensity approximately 20-40 µmol photons/m$^2$ s). Sonification and incubation with NaCl (0.5-2M) was not necessary in order to successfully complete the conjugation.

Electroporation:

10-15 ml of a late exponentially growing cyanobacterial culture were centrifuged at room temperature at 3.000×g for 5-10 min. The pellet was washed twice with 0.9% NaCl and then the culture was incubated on ice with 50 mM $CaCl_2$ solution for 15 min. After this step, cells were washed twice with 1.0 mM HEPES pH 7.5, resuspended in 80 µl of 1.0 mM HEPES and chilled on ice. Methylated DNA (0.5-5 µg) was added. Cells were electroporated in a cuvette with a 2-mm gap between the electrodes and pulsed once in a Gene Pulse X-cell (Bio-Rad) using exponential decay protocol (electric field strength 7 kV/cm or 12 kV/cm, capacitance 25 µF; resistance 200 ohms (time constant approximately 5 ms). After electroporation, 2 ml BG11 medium were immediately added to the cyanobacterial suspension, which was subsequently transferred to a 50 ml flask containing 15 ml fresh BG11 medium. After incubation for 2 days under normal light (30-40 µmol photons/2 m$^2$ s$^1$) with gentle shaking, recovered cultures were centrifuged, resuspended in 500 µl BG11 medium and placed onto selective media (BG11 containing 25-35 µg/ml neomycin). Cells were incubated under normal light intensity for 4 weeks until colonies were visible.

FIG. 3A and FIG. 3B show fluorescence photographs of Chlorogloeopsis sp. ABICyano3 cells transformed with an extrachromosomal plasmid harboring the gene encoding the green fluorescent protein under the transcriptional control of a promoter inducible by nitrogen starvation. For induction of the GFP reporter protein, cells were incubated in 1.0 ml of nitrogen-free BG11 medium (BG110) for 2 days. Subsequently, the culture was centrifuged and resuspended in 50-100 µl of BG110 medium. Approximately 10 µl aliquot of the culture was examined by fluorescence imaging microscopy. As negative control an aliquot of wild type culture (in BG11 and BG110 medium) and the non-induced transformant was used. Green fluorescence on a large scale was detected in FIG. 3B, where the cells were dispersed in nitrogen-free BG110 medium, leading to the induction of the GFP, whereas in FIG. 3A, less fluorescence was detected in cells suspended in BG11 medium containing nitrogen, due to a basal expression of GFP even in the non-induced state.

Example 5

Determination of Ethanol Production Using Headspace Gas Chromatography with Flame Ionization Detection (GC Online Vial Measurements and GC Single Measurements from Samples Taken from PBR Cultures)

Experimental Setup

Two kinds of GC headspace measurements were performed:
a) GC online vial measurements (applied for clone testing and short-term characterizations of cultures cultivated in GC vials with a duration of up to 72 hours,
b) single GC single measurements (applied for measurements of ethanol concentrations in samples daily taken from PBR cultures) by measuring the ethanol content after transferring 0.5 mL of the PBR cultures into GC vials after certain points of time of cultivation in the PBR.

GC single measurements do not involve the cultivation of the strains in the GC vials. GC single measurements were performed in order to characterize the long term ethanol production of strains, which are already known to produce ethanol in sufficient quantities in GC online vial measurements. GC single measurements further differ from GC online vial measurements in the volume of the culture (2 ml in GC online vial and 0.5 ml aliquots taken from a PBR culture in GC single measurements). In single GC measurements only the absolute amount of ethanol produced at a certain point of time is determined, whereas the GC online vial measurement determines the course of ethanol production during a certain period of time, up to 72 hours of growing the cells in a GC vial under constant illumination. For GC single measurements the sample was heated to 60° C. in order to transfer all ethanol from the liquid phase to the gas phase for the GC headspace chromatography, which resulted in a disruption of the culture. In contrast to that this 60° C. heating step was omitted during GC online vial measurements in order not to destroy the culture and in order to further continue with the culturing of the cells in the GC vial. In the following paragraphs, GC online vial measurements are described.

The GC online vial headspace measurement was performed on a Shimadzu GC-2010 gas chromatograph with Flame Ionization Detector. The detection limit for ethanol quantification is 0.0005%, but a calibration has to be done for detecting quantities below 0.001%. The instrument is connected in-line with a Shimadzu PAL LHS2-SHIM/AOC-5000 autosampler, comprising a gas-tight syringe for transfer of headspace aliquots from the culture samples to the analytical unit. Specific modifications were introduced as follows: Each sample tray was exposed with a LED acrylic sheet (length: 230 mm, wide: 120 mm, diameter: 8 mm, 24Chip, S4, 5300K), equipped with a dimmer by company Stingl GmbH. Below the sample tray a magnetic stirrer is installed (IKA RO 5 power) allowing for mixing of cultures which are cultivated in GC vials that stand in the sample tray. The sample trays are penetrating of maximum, so that the GC Vial stands in the Tray. A heating mat between an LED acrylic sheet and the magnetic stirrer (MOHR & Co, one heating circuit, 230 V, 200 Watt, length: 250 mm, wide: 150 mm, diameter: ca. 2.5 mm) with a temperature regulator (JUMO dTRON 316) allowed for the incubation of cultures in GC vials at specific temperatures. The gas chromatograph was connected to helium carrier gas as well as hydrogen and artificial air as a fuel gas and an oxidizer gas, respectively, for the flame ionization detector. Oxidizer air was generated with the generator WGAZA50 from Science Support. The gas chromatograph was equipped with a FS-CS-624 medium bore capillary with a length of 30 m, internal diameter of 0.32 mm and film thickness of 1.8 µm from the GC supplier Chromatographie Service GmbH.

The ethanol production in the culture has to be induced 1-2 days before the GC online vial experiment is performed by triggering the overexpression of the PDC enzyme and the ADH enzyme. For induction, hybrid cells grown under repressed conditions in aswBG11 or BG11 freshwater medium (without inductor), were induced when they reached an OD of ~2 by adding the inductor (e.g. metal-ions). The cells were incubated on a small shaker at 180 rpm for 48 hours at 28° C. The shaker was armed with a dimmable light table adjusted to 120 μE (300 μE-0 μE). After 48 h the tube was centrifuged at 20° C. for 10 minutes, 4,500 rpm, and the supernatant was discarded. The pellet was resuspended in aswBG11 medium or freshwater BG11 medium (in case of PCC9212) suppl. with 50 mM TES pH 7.3, 20 mM $NaHCO_3$, containing inductor (e.g. metal-ions) and no antibiotics. For hybrids under control of copper responsive promoters, the induction was realized by addition of 10-30 μM copper, for zinc inducible promoters the induction was realized by addition of 5-30 μM zinc sulfate (heptahydrate). The sample was adjusted to an $OD_{750}$ of about 0.7 (+/−0.1) for 4 replicates. 2 ml were filled in 20 ml GC vials equipped with a magnetic stir bar (12 mm) in which the lid was not completely tightened. 5 ml pure carbon dioxide was injected for 1-3 days with the 30 ml syringe through the septum, and then the lid tightly closed (gas tight). The tightly closed GC vials were placed into the headspace auto sampler rack which was temperature controlled at a given temperature for example 37° C. and were analyzed at the same day. After the GC measurements the final $OD_{750}$ was determined for the calculation of the ethanol production rate per average $OD_{750}$. The average $OD_{750}$ was calculated by addition of $OD_{750}$ at $t_{start}$ and $OD_{750}$ at $t_{end}$ divided by two.

When necessary, reference samples for the calibration of the gas chromatograph were prepared as 2 ml aliquots with 0.005, 0.01, 0.02, 0.05, 0.1, 0.2, 0.5, 1, 2, 5 and 10 mg/ml ethanol in 35 psu sodium chloride for marine media or without sodium chloride for freshwater media. Reference samples were placed into the same 20 ml sample containers with self-sealing silicon septum caps for headspace autosampling. For each reference sample at least six measurements were applied. After the measurements, the resulting peak areas of the reference samples were used for generating two calibration curves, the first in the concentration range from 0.005 to 0.5 mg/ml ethanol and the second one for the concentration range from 0.5 to 10 mg/ml ethanol. The calibration curves have to fulfill linearity.

The sample incubation temperature for the GC online measurements in the autosampler was adjusted to a given temperature for example 37° C. The illumination was set at 90 μE to 150 μE, preferably 120 μE. The magnetic stirrer was configured for interval mixing of the samples, with cycles of 2 minutes mixing at 400 rpm, followed by 90 minutes without mixing. An automated process follows, wherein after given periods aliquots of 500 μl of the headspace of the samples were automatically drawn with the gas-tight headspace syringe and injected via the injection port into the gas chromatograph for analysis. Before each headspace autosampling, the mixing was changed for 10 min to continuous mixing with 750 rpm at 37° C. incubation temperature. The syringe temperature was set at 70° C. The fill speed was 250 μl per second, following an initial lag time of 1 second after the septum of the samples has been pierced by the syringe needle. The injection of the aliquot into the gas chromatograph happens with an injection speed of 500 μl per second. Afterwards, the syringe flushes for 3 minutes with air to prevent sample carryover between two injections. The gas chromatograph run time was 4 minutes and 30 seconds. The injection temperature on the gas chromatograph was 230° C. The column temperature was 60° C. Detection was accomplished with the flame ionization detector at 250° C. process temperature. The makeup gas was nitrogen at 30 ml per minute, the fuel gas was hydrogen at 35 ml per minute and the oxidizer gas was artificial air at 400 ml per minute.

After the final GC online vial measurement, the final optical density at 750 nm of the samples was measured and an average cell density for each sample was determined by calculating the arithmetic mean of the optical density at the starting point and the optical density at the end point of the process divided by two. Afterwards, the average ethanol production rate per cell density was calculated.

For *Chlorogloeopsis fritschii* PCC6912 and *Chlorogloeopsis* sp. ABICyano3 the above described GC online protocol had to be modified in a way that less stirring/shaking of the agitator (only 250 rpm) was applied. Otherwise a major percentage of the cells aggregated above the liquid surface, subsequently sticking tightly to the wall of the GC vial, leading to an underestimation of the ethanol productivity.

Example 6

Ethanol Production in *Chlorogloeopsis fritschii* PCC6912 and *Chlorogloeopsis* sp. PCC9212 Strains Transformed with Various Plasmids Harboring Ethanologenic Cassettes Heterologous Promoters:

*Chlorogloeopsis fritschii* PCC6912 and the more accessible *Chlorogloeopsis* sp. PCC9212 were used for all additional transformation. Methylation of ethanologenic plasmids with M.CviPI followed by electroporation allowed generation of ethanologenic transformants of both *Chlorogloeopsis* strains. The first ethanologenic transformants were generated by use of the methylated plasmids TK18 and TK122. As shown in the FIG. 4A and FIG. 5, these plasmids contain the first and second recombinant gene for ethanol production encoding the PDC enzyme and ADH enzyme under the transcriptional control of PpetE from *Nostoc/Anabaena* PCC7120 (TK18) or under the transcriptional control of PziaA from *Synechocystis* PCC6803 (TK122).

Ethanol productivity of *Chlorogloeopsis fritschii* PCC6912 transformed with the plasmid TK18 was measured online in GC vials with high consistency, leading to a production rate of 0.008-0.01% EtOH (v/v)/OD*d in mBG11, whereas the production rate for *Chlorogloeopsis* sp. PCC9212 in BG11 was determined to be 0.01-0.015% EtOH (v/v)/OD*d. FIG. 4B shows two graphs of the ethanol accumulation during the time course of 18 hours of cultivation measured in GC online experiments with PCC6912 cells transformed with plasmid TK18 with two different starting ODs (graph with squares: start $OD_{750\ nm}$=around 0.5; graph with diamonds: start $OD_{750\ nm}$=around 1). FIG. 4C shows the accumulation of ethanol in two different cultures of PCC9212 during a cultivation of around 60 hours.

A comparison of the induced *Chlorogloeopsis fritschii* PCC6912 with TK18 to the non-induced control strain transformed with TK18 (data not shown) strongly indicated that PpetE7120 in PCC6912 is not regulated by copper; it appeared to be a constitutive promoter for both *Chlorogloeopsis* sp. strains. Furthermore, due to the constitutive expression of the PDC enzyme and the ADH enzyme, TK18 transformants of both *Chlorogloeopsis* strains grew very slowly during the upscaling due to the constitutive promoter. In addition, loss of productivity was observed after 2-3 weeks of cultivation, due to reversion of the cells to wild type cells.

In contrast to the PpetE promoter from *Nostoc*, the ziaR-PziaA promoter from *Synechocystis* PCC6803 included in the plasmid TK122 was not constitutive, but inducible by $Zn^{2+}$. Rates of 0.004-0.007% (v/v)/OD*d with TK122 were obtained after one day pre-induction with 10 μM $Zn^{2+}$ followed by GC online measurements with 20 μM $Zn^{2+}$ for *Chlorogloeopsis* PCC9212 cells transformed with this plasmid. As the production rate with TK122 was low, the construct was not transformed into *Chlorogloeopsis fritschii* PCC6912.

These data therefore show that the use of heterologous promoters from other cyanobacterial genera in *Chlorogloeopsis* sp. strains leads to either low production rates or to constitutive expression, which can even result in reversion of the genetically enhanced cells back to wild type cells and hence an unstable ethanol production.

Endogenous Promoters of the *Chlorogloeopsis* sp. Strains:

An additional plasmid TK187 was constructed for the *Chlorogloeopsis* sp. strains, which carries the ethanologenic gene cassette under the control of the endogenous putative promoter ziaR-PziaA from *Chlorogloeopsis fritschii* PCC6912 (see FIG. 7A). The genes ziaR-ziaA (orf5210-5209) were identified by a BLASTP search with the encoded proteins of the *Synechocystis* PCC6803 homologous ziaA and ziaR based on the method described for the additional promoter below. The product of ziaR is a $Zn^{2+}$ dependent transcriptional regulator of ziaA, which represses transcription of ziaA unless $Zn^{2+}$ concentrations are elevated. The product of ziaA encodes a $Zn^{2+}$ transporting ATPase, which transfers zinc tolerance by efficient export of $Zn^{2+}$.

The putative promoter-regulator combination ziaR-PziaA from *Chlorogloeopsis fritschii* PCC6912 was cloned in two variants: The plasmid TK186 contains a promoter region that covers the -35, -10 box and the first possible ATG start codon of ziaA, while plasmid TK187 contains a longer version, which additionally includes a second downstream located ATG (see FIG. 6 and FIG. 7A).

Plasmid TK186 which contains the shorter version of the promoter did not result in any ethanol production in both *Chlorogloeopsis* sp. strains PCC6912 and PCC9212, while plasmid TK187 led to a production of up to 0.012-0.015% (v/v)/OD*d in GC online measurements. It is assumed that plasmid TK186 contains a non-functional version of PziaA, due to an incorrect annotation.

FIGS. 7B to 7D show graphs of the ethanol accumulation, the activity of ADH and PDC enzyme, the cell growth measured as $OD_{750}$ nm, and the ethanol accumulation in the liquid medium for biological triplicates over 14 days (FIG. 7B) and a single cultivation for a 7 day cultivation period of *Chlorogloeopsis fritschii* PCC6912 transformed with plasmid TK187 in 0.5 L photobioreactors (Crison).

The culturing conditions in the Crisons were as follows: For upscale, all cultures were maintained under repressed conditions in order to allow a faster upscaling of the cell culture: The cells were scaled up in BG11 under repressed conditions and then transferred to mBG11 medium prepared with artificial seawater salts (35 psu) and deionized water. The medium was supplemented with Vitamins B1 and B12. Neomycin (100 mg $L^{-1}$) was used for plasmid retainment. Induction was initiated by the addition of 10 μM $Zn^{2+}$. It is beneficial to use a sufficiently high initial cell density for *Chlorogloeopsis fritschii* PCC6912. Otherwise, the culture behaves highly susceptible to light stress (caused by a high light regime or high mixing). For the standard set up, an initial $OD_{750}$ of about 2 proved well suited. Cells were cultivated in 0.5 L round Crison bottles. Mixing was achieved with a magnetic stir cross (250-450 rpm) and applied for 24 h. Cultures were run at pH 8.0. The pH was maintained by injection of 10-20% $CO_2$ in air into the liquid phase. The total gas flow rate was 15 ml $min^{-1}$ (applied only for pH control). There was no aeration or pH control during the night. A light: dark photoperiod of 12 h:12 h was applied. Illumination of cultures was done with LED lamps (which illuminate the round bottle from all sides). At the beginning of cultivation a light intensity of ca. 325-450 μmol $s^{-1}$ $m^{-2}$ was applied. Later during cultivation light was increased to 900 μmol $s^{-1}$ $m^{-2}$. The temperature regime was set to 25-28° C. during the night and 35-38° C. during the day. In all cultures, $OD_{750\ nm}$, chlorophyll and ethanol (as well as acetaldehyde) content were analyzed at least three times a week. PDC and ADH activities were recorded twice a week. Absorption spectra of cells were recorded weekly. Data on culture temperature and pH as well as oxygen saturation were automatically recorded online via probes.

For the biological triplicates of hybrid PCC6912 with TK187 a mean productivity of 0.0327% (v/v) $d^{-1}$ could be achieved for 14 days (see FIG. 7B). Furthermore, for a short time frame: of 7 day production period, a mean rate of 0.0398% (v/v) $d^{-1}$ was achieved for biological triplicates while another single cultivation resulted in a 7 day rate of 0.0452% (v/v) $d^{-1}$ (see FIG. 7D).

FIG. 7E shows the accumulation of ethanol (% (v/v)) during a nearly 70 hour cultivation of *Chlorogloeopsis* sp. PCC9212 transformed with the plasmid TK187 determined via GC online measurements. It is clearly visible that with an increasing degree of induction of the cells with $Zn^{2+}$ (5, 10 or 30 μM $Zn^{2+}$ denoted as 5Zn, 10Zn or 30Zn), higher ethanol accumulation can be achieved, leading to ethanol production rates of up to 0.0122% (v/v)/OD*d.

FIG. 8 denotes the plasmid map of the plasmid TK261 wherein the same regulator-promoter pair ziaR-PziaA as included in plasmid TK187 only controls the transcription of the first recombinant gene encoding PDC enzyme, whereas the constitutive promoter PrbcL* controls the transcription of the second recombinant gene coding for synADH enzyme. *Chlorogloeopsis fritschii* PCC6912 cells harboring this plasmid and cultivated in the 0.5 L Crison-photobioreactors achieved an ethanol production rate of 0.02%(v/v) $d^{-1}$ in the liquid phase over a period of 14 days, see FIG. 18 (conditions as follows: Media: mBG11 (35 psu (ASW) Neo100; Cultivation pH: 8.0; $CO_2$ supply: 10% pH dependent into liquid phase; Aeration: 10 mL min-1; Mixing: 250 rpm magnetic cross bar (comet); Light: fluorescence lamps starting with 275 μmol $s^{-1}$ $m^{-2}$, later increased to 450 from two sides 12/12 h).

Further derivatives of the initially successful plasmid TK187 were developed. The plasmid map of such a derivative TK336, (see FIG. 9A) shows its differences in comparison to TK187. In particular, the regulator-promoter pair ziaR-PziaA controls the transcription of a codon improved variant of the first recombinant gene coding for PDC enzyme. The second recombinant gene is also codon improved and is transcriptionally controlled by PnblA from *Nostoc/Anabaena* PCC7120, which is a constitutive promoter in the *Chlorogloeopsis* PCC6912 and PCC9212 host cells. In addition the transcriptional control of both recombinant genes for ethanol production is decoupled via an oop terminator present between both genes. FIG. 9B shows the ethanol accumulation of cultures of *Chlorogloeopsis fritschii* PCC6912 with TK336 as determined by GC online measurements without induction (graph denoted —Zn) and with induction by 30 μM $Zn^{2+}$ (graph denoted 30Zn) leading to a production rate of 0.015-0.02% (v/v)/OD*d. A rise in the accumulation of ethanol was clearly visible upon induction of PziaA. *Chlorogloeopsis* PCC6912 cells transformed with this plasmid and cultivated in the 0.5 L Crison-photobioreactors achieved an ethanol production rate of 0.022% (v/v) $d^{-1}$ in the liquid phase for 14 days (conditions as mentioned above for TK261). The cultivation of *Chlorogloeopsis* PCC 6912 cells transformed with TK336 in 0.5 L Crison-photobioreactors is shown in FIG. 18.

FIG. 10A shows the plasmid map of the plasmid TK414 including the $Zn^{2+}$ inducible promoter PziaA from *Chloroglоeopsis* PCC6912 controlling the transcription of codon improved variants of pdc and adh genes. This plasmid is a derivative of the initially successfully transformed plasmid. In addition, a terminator sequence (oop terminator) is located downstream of the *Synechocystis* ADH enzyme encoding gene in order to ensure a reliable transcription termination.

FIG. 10B includes a graph depicting a comparison of the ethanol accumulation (% (v/v) of *Chlorogloeopsis* PCC6912 hybrid cultures containing the different plasmids TK414 and TK187 during 15 day 0.5 liter photobioreactor cultivations determined via GC single measurements. The accumulation of ethanol in both cultures was very similar, indicating that TK414 results in slightly higher ethanol productivity, especially after 14 days of cultivation (and could be slightly advantageous with regard to long term production). The cultivation conditions were as follows: BG11, 250 rpm, light: fluorescence lamps starting with 2×160 μmol $s^{-1}$ $m^{-2}$, later increased to 2×360 μmol $s^{-1}$ $m^{-2}$, mixing: 250 rpm (no vitamins added).

Additional Inducible Endogenous Promoters of *Chlorogloeopsis fritschii* PCC6912 in Addition to PziaA:

In order to initially identify PziaA and other additional inducible promoters which could lead to higher ethanol productivity rates, the genome of *Chlorogloeopsis fritschii* PCC6912 cells was searched for genes encoding metal ion transporters and metallothioneins, respectively. ORFs were chosen by:

a) the degree of similarity to ZiaA and SmtA b) the genetic organization reflecting the adjacent localization of ziaR-ziaA.

11 putative genes plus a potential ziaA homolog, whose promoter is cloned in TK187, were selected and primers for qRT-PCR were designed. Cultures were treated with a metal mix containing 20 μM $Co^{2+}$, 30 μM $Zn^{2+}$ and 1 μM $Cu^{2+}$.

Total RNA from PCC6912 treated with the metal mix and from a control culture grown in BG11 medium and in BG11 medium without $Co^{2+}$, $Zn^{2+}$ and $Cu^{2+}$ (traces for preparation of BG11 medium were prepared without $Co^{2+}$, $Zn^{2+}$ and $Cu^{2+}$) were isolated and Quantitative reverse transcription PCR (qRT-PCR) was performed to analyze which of the 11 putative genes including ziaA respond upon induction with the metal ions in higher gene expression. In particular the following procedure was employed:

To remove traces of DNA, two DNase steps were applied. First an on-column digest according to Qiagen was performed, followed by a DNaseI (Roche) incubation for 1-2 h at 37° C. Success of DNase treatment was controlled using the primers T394 and T395 (the DNA sequences of both primers are included in the sequence listing as SEQ ID NO. 24 and 25, respectively) against the gapA reference gene. 1 μg DNase-free RNA was transcribed into cDNA using the QuantiTect Rev. Transcription Kit from Qiagen. Quantitative RT-PCR was performed in triplicates with RNA from three independent preparations using a LightCycler 480 (Roche) and the Roche LightCycler 480 SYBR Green I Master. Gene specific-primers used for qRT-PCR amplification (the qRT-PCR, orf7041 forward and reverse primers are shown as SEQ ID NOs. 26 and 27, the qRT-PCR, orf5189 forward and reverse primers are shown as SEQ ID NOs. 28 and 29, the orf7345 forward and reverse primers are shown as SEQ D NOs. 30 and 31, the qRT-PCR, orf5209 (ziaA) forward and reverse primers are SEQ ID NOs. 32 and 33, and orf5203 forward and reverse primers are shown as SEQ ID NOs. 34 and 35, respectively) were designed to produce a 120-150 bp amplicon. The amount of PCR product was quantified by measuring fluorescence of SYBR Green dye. Reported gene expression levels were normalized to levels of the gapA gene.

FIG. 11A shows the metal-ion dependent induction of orf7041 by qRT-PCR. PCC6912 was grown for 48 h in BG11 medium (C1, C2, C3), in BG11 medium without $Co^{2+}$, $Zn^{2+}$, $Cu^{2+}$ (C4, C5, C6) and in BG11 medium containing 20 μM $Co^{2+}$, 30 μM $Zn^{2+}$, and 1 μM $Cu^{2+}$ (C7, C8, C9). cDNA was prepared from cultures under all treatments. Gene specific-primers used for qPCR amplification are included in the sequence listing as SEQ ID 24-27. The amount of the PCR product was quantified by measuring fluorescence of the SYBR Green dye (y-axis) over the number of PCR cycles (x-axis). The fluorescence increases proportionally to the number of amplified fragments and can be measured when the fluorescence significantly rises above the background fluorescence. The higher the starting copy number of the nucleic acid target, the sooner a significant increase in fluorescence is observed. In this case, higher copy number of orf7041 from cultures treated with 20 μM $Co^{2+}$, 30 μM $Zn^{2+}$, and 1 μM $Cu^{2+}$ (C7, C8, C9) are observed compared to copy numbers from cultures grown in BG11 or BG11 medium without metal ions (C1-C6). qRT-PCR shows the significant upregulation of orf7041 by addition of the metal-ion mix containing 20 μM $Co^{2+}$, 30 μM $Zn^{2+}$, and 1 μM $Cu^{2+}$. The promoter of orf7041 can be considered as being regulated by at least one of these metal-ions.

FIG. 11B shows the 484 fold upregulation of orf7041 by metal-ions. Based on the amplification curves shown in FIG. 11A, relative quantification was performed by the light cycler 480 software (Roche). For this purpose, ratios of the target (orf7041) and reference (gapA) expression levels were calculated (light blue bars) for each growth condition i) BG11 (left bars), ii) without $Co^{2+}$, $Zn^{2+}$, $Cu^{2+}$ (middle bars), iii) plus 20 μM $Co^{2+}$, 30 μM $Zn^{2+}$ and 1 μM $Cu^{2+}$ (right bars). orf7041 expression ratios were further normalized to expression levels of PCC6912 grown in BG11 medium (red bars). Repression of orf7041 transcription was observed in PCC6912 grown without $Co^{2+}$, $Zn^{2+}$ or $Cu^{2+}$ (middle bars) whereas the mixture of 20 μM $Co^{2+}$, 30 μM $Zn^{2+}$ and 1 μM $Cu^{2+}$ induced the expression 484-fold. Primers for gap and orf7041 are included in the sequence listing as SEQ ID 24-27.

From the shown qRT-PCR results, the promoter of orf7041 can therefore be considered as regulated by at least one of these ($Cu^{2+}$, $Co^{2+}$, $Zn^{2+}$) metal-ions. Later experiments demonstrated $Co^{2+}$ as being the best inductor for Porf7041.

Promoters of those genes, which were found to be regulated upon induction with the metal ions, were cloned.

In the following, some of the plasmids including these endogenous promoters and experimental data obtained by introducing these plasmids into the *Chlorogloeopsis* sp. host cells will be described in more detail.

The plasmid map of TK346 is shown in FIG. 12A including the promoter of the open reading frame (orf) 7041 from *Chlorogloeopsis* PCC6912 which is a cobalt inducible promoter, controlling the transcription of a codon improved version of the first recombinant gene encoding PDC enzyme. The *Synechocystis* ADH enzyme encoding second recombinant gene is controlled by the constitutive promoter PnblA from *Nostoc* and a transcription terminator sequence (oop terminator) is present between both recombinant genes in order to decouple the transcriptional control of these genes. For *Chlorogloeopsis* PCC6912 cells harboring this plasmid ethanol production rates of about 0.012% (v/v)/OD*d could be determined after induction with 30 μM $Co^{2+}$. FIG. 12B shows a graph evidencing the ethanol accumulation over a 20 hour cultivation of an induced culture of this strain determined via GC online measurements. FIG. 12C depicts the ethanol accumulation over the time course of 12 days of these cultures in larger 0.5 liter photobioreactors determined via GC single measurements. FIG. 18 shows a comparison of PCC6912 hybrids containing either the $Co^{2+}$ inducible plasmid/promoter TK346 or one of the PziaA containing plasmids (TK261, TK336). Under the cultivation conditions used for the cultivation shown in FIG. 18, it can be seen that the ethanol yield of TK346, with a production rate of 0.025% (v/v) $d^{-1}$ over 14 days and 0.02% (v/v) $d^{-1}$ over 18 days (from day 2-20) was even slightly better than the PziaA constructs.

FIG. 13 shows the plasmid map of the plasmid TK348 including the promoter controlling the open reading frame (orf) 7345 of *Chlorogloeopsis* PCC6912, which is primarily a $Zn^{2+}$ but also a $Co^{2+}$ inducible promoter and which controls the transcription of both the PDC enzyme and the *Synechocystis* ADH enzyme encoding first and second recombinant genes.

FIG. 14 shows the plasmid map of the plasmid TK351 including the $Zn^{2+}$ inducible promoter of the open reading frame (orf) 5189 of *Chlorogloeopsis* PCC6912 controlling the transcription of both the PDC enzyme and *Synechocystis* Adh enzyme encoding genes. *Chlorogloeopsis* PCC6912 cells including this plasmid achieved an ethanol production rate of around 0.008% (v/v)/OD*d upon induction in GC vials.

FIG. 15 shows the plasmid map of the plasmid TK380, including the $Zn^{2+}$ inducible promoter of the open reading frame (orf) 5203 of *Chlorogloeopsis* PCC6912, controlling the transcription of both the first and second recombinant gene encoding the PDC and ADH enzyme.

The above described procedure can be used to identify further endogenous metal ion inducible promoters in the *Chlorogloeopsis* sp. host cells.

Example 7

Transformation of *Chlorogloeopsis* sp. Host Cells Using Integrative Plasmids

In the following, the design of three different constructs will be discussed, which were prepared in order to transform *Chlorogloeopsis* sp. host cells in the future by integrating genes into their genomes.

In particular, integration of a resistance marker into the genome of the *Chlorogloeopsis* sp. host cells, such as *Chlorogloeopsis fritschii* PCC6912 is conducted with the help of plasmids TK148, TK149, (see FIG. 16A and FIG. 16B for plasmid maps of both constructs) which were generated to integrate a neomycin/kanamycin resistance gene into orf1237 (pilA) or orf3194 (blpI) of the *Chlorogloeopsis* sp. host cells via homologous recombination, respectively. In general, the integrative plasmids contain two platforms (homologous sequence regions) for homologous recombination into the *Chlorogloeopsis* sp. host cells, which flank a DNA sequence to be introduced into the genome of the cyanobacteria. These plasmids are based on the cloning vector pGEM and contain flanking regions (down and upstream) of orf1237/orf3194 upstream and downstream of the neomycin/kanamycin resistance gene to generate a double crossover event in the *Chlorogloeopsis* sp. host cells.

Integration of other target genes, such as recombinant genes for ethanol production, into the genome of the *Chlorogloeopsis* sp. host cells is achieved with the integrative plasmid TK153 (see FIG. 16C for the plasmid map of this vector), which was generated to integrate a PnblA7120-PDC-synADH cassette as well as a neomycin/kanamycin resistance gene into orf1237 (pilA). The pGEM based plasmid contains a flanking region of orf1237 of PCC6912 upstream of PnblA7120-PDC-synADH as well as a flanking region of orf1237 of PCC6912 downstream of the neomycin/kanamycin resistance gene. TK153 was designed to generate a double crossover event via homologous recombination in PCC6912 in order to insert PnblA7120-PDC-synADH as well as a neomycin/kanamycin resistance gene into the genome of PCC6912. The promoter PnblA from *Nostoc/Anabaena* PCC7120 is a constitutive promoter in PCC6912 and PCC9212.

In general, the transformation using integrative plasmids could be done in the same way as the transformation using the extrachromosomal plasmids.

Example 8

Salt- and Freshwater Cultivation of *Chlorogloeopsis* PCC6912 Cells Transformed with Plasmid TK336

Since *Chlorogloeopsis* PCC6912 was isolated from a freshwater habitat, its ability to grow and produce ethanol under saltwater conditions is of great importance. The use of saltwater as a culture medium would greatly ease the cultivation and would reduce cultivation costs in comparison to cultivation in fresh water medium.

For the cultivations shown in FIGS. 17A and 17B, *Chlorogloeopsis* PCC6912 cells transformed with the plasmid TK336 where slowly adapted to the salt concentrations. From solid BG-11 plates, cells were directly inoculated in liquid BG-11, without $Zn^{2+}$ (repressed conditions). After two days, the cells were transferred to artificial seawater media with 8.75 psu and 17.5 psu ASW BG-11 and were set to an identical $OD_{750\,nm}$. For the higher salt concentrations, cells grown in 17.5 psu were transferred to media with 26.25 psu and 35 psu and were set to an identical $OD_{750\,nm}$. Cells were kept under these conditions for one more week and subjected to relatively low illumination intensities from two fluorescence lamps with 125 μmol $s^{-1}$ $m^{-2}$ each. Furthermore, no vitamins were added to the culture medium. For plasmid retainment and contamination control, kanamycin was used, adjusted to the salt concentration, as well. 8.75 psu kanamycin 37.5 mg/L, 17.5 psu kanamycin 50 mg/L, 26.25 psu kanamycin 100 mg/L.

FIG. 17A shows the ethanol accumulation over a course of 22 days in *Chlorogloeopsis* PCC6912 cells containing the plasmid TK336 growing in medium with different salinities of 8.75, 17.5, 26.25 and 35 psu. This graph evidences that the ethanol accumulation was the highest at lower salinities, e.g. between salinities of 8.75 to 17.5 psu, which shows that *Chlorogloeopsis* PCC6912 cells, although isolated from freshwater, can grow and produce ethanol in brackish water, although ethanol production in freshwater medium was higher compared to brackish medium.

FIG. 17B shows a comparison of the ethanol production rate (% (v/v) $d^{-1}$) between days 5 to 12 and days 5 to 23 for the same cells already shown in FIG. 17A at different salinities measured via GC single measurements. Again it can be seen that the ethanol production rate was the highest for salinities between of 8.75 to 17.5 psu.

FIG. 18 shows the ethanol accumulation in 35 psu medium (artificial mBG11) at pH 8 of parallel cultivations of *Chlorogloeopsis* PCC6912 cells harboring the plasmids TK261, TK336 ($Zn^{2+}$ inducible promoter regulator pair PziaA-ziaR controlling pdc gene in both plasmids TK261 and TK336) and TK346 (Porf7041 controlling pdc gene), respectively.

Cultivations were done in 0.5 L Crison photobioreactors with stirring at 250 rpm. The cells were subjected to an illumination intensity of 2×275 μmol $s^{-1}$ $m^{-2}$, (275 μmol $s^{-1}$ $m^{-2}$ from two different sides of the photobioreactor) increasing to 2×450 μmol $s^{-1}$ $m^{-2}$. The induction was initiated by adding 10 μM $Zn^{2+}$ and 10 μM $Co^{2+}$ (TK346), respectively. This graph clearly shows that during a 20 day cultivation, ethanol accumulation values of between 0.3 to 0.4% (v/v) could be reached, which was significantly higher compared to the experiments shown in the FIG. 17A and FIG. 17B in 35 psu BG11 medium.

Although the present invention has been described in considerable detail with reference to certain embodiments thereof, other embodiments are possible. Therefore, the spirit and scope of the appended claims should not be limited to the description of the embodiments contained therein.

We claim:

1. A genetically enhanced *Chlorogloeopsis* sp. host cell comprising at least one first recombinant gene encoding a first protein for the production of ethanol under the transcriptional control of a first inducible promoter, wherein said first inducible promoter has at least 85% sequence identity to nucleotides 62-87, 101-106, and 133-139 of SEQ ID NO: 36.

2. The genetically enhanced *Chlorogloeopsis* sp. host cell of claim 1, wherein the host cell is *Chlorogloeopsis fritschii* PCC6912, *Chlorogloeopsis* sp. PCC9212, or *Chlorogloeopsis* sp. ABICyano3ATCC #PTA-120619).

3. The genetically enhanced *Chlorogloeopsis* sp. host cell of claim 2, wherein the host cell is *Chlorogloeopsis fritschii* PCC6912.

4. The genetically enhanced *Chlorogloeopsis* sp. host cell of claim 1, further comprising at least one second recombinant gene encoding a second protein for the production of ethanol.

5. The genetically enhanced *Chlorogloeopsis* sp. host cell of claim 1, wherein the first recombinant gene encodes pyruvate decarboxylase.

6. The genetically enhanced *Chlorogloeopsis* sp. host cell of claim 4, wherein the second recombinant gene encodes alcohol dehydrogenase.

7. The genetically enhanced *Chlorogloeopsis* sp. host cell of claim 1, wherein the first recombinant gene encodes alcohol dehydrogenase E (AdhE) converting Acetyl-CoA into ethanol.

8. The genetically enhanced *Chlorogloeopsis* sp. host cell of claim 4, wherein both the first and second recombinant gene are under the transcriptional control of the same first endogenous inducible promoter.

9. The genetically enhanced *Chlorogloeopsis* sp. host cell of claim 4, wherein the first and second recombinant genes are under the transcriptional control of separate first and second promoters.

10. The genetically enhanced *Chlorogloeopsis* sp. host cell of claim 9, wherein the second promoter is a constitutive promoter.

11. The genetically enhanced *Chlorogloeopsis* sp. host cell of claim 9, wherein the second promoter is an inducible promoter.

12. The genetically enhanced *Chlorogloeopsis* sp. host cell of claim 4, wherein the second promoter is a constitutive promoter selected from a group consisting of PpetE, PnblA from *Nostoc*.

13. The genetically enhanced *Chlorogloeopsis* sp. host cell of claim 4, wherein the at least one first and/or second recombinant gene is codon improved for enhancing translation by having a codon adaptation index (CAI) of ≥0.60.

14. The genetically enhanced *Chlorogloeopsis* sp. host cell of claim 4, wherein a transcription terminator is present between the first and second recombinant gene.

15. The genetically enhanced *Chlorogloeopsis* sp. host cell of claim 4, wherein the at least one first recombinant gene and at least one second recombinant gene are located on an extrachromosomal plasmid of the host cell.

16. The genetically enhanced *Chlorogloeopsis* sp. host cell of claim 13, wherein the extrachromosomal plasmid contains an origin of replication which is at least 90% identical to the origin of replication of the pDU1 plasmid.

17. The genetically enhanced *Chlorogloeopsis* sp. host cell of claim 4, wherein the at least one first recombinant gene and at least one second recombinant gene are integrated into a chromosome of the host cell.

18. The genetically enhanced *Chlorogloeopsis* sp. host cell of claim 1, which can withstand at least one of the following culturing conditions:

a) At least 1% (v/v) ethanol in the medium for at least 6, 12, 16 or 27 weeks, b) at least 48° C. for at least 2 hours peaks over at least 7 days in brackish medium, and c) purging with 60% (v/v) to 70% oxygen.

19. A construct for transformation of *Chlorogloeopsis* sp. host cells comprising:

at least one first recombinant gene encoding a first protein for the production of ethanol under the transcriptional control of a first inducible promoter, wherein said first inducible promoter has at least 85% sequence identity to nucleotides 62-87, 101-106, and 133-139 of SEQ ID NO: 36.

* * * * *

SEQUENCE LISTING

```
<160> NUMBER OF SEQ ID NOS: 36

<210> SEQ ID NO 1
<211> LENGTH: 14338
<212> TYPE: DNA
<213> ORGANISM: Artificial Sequence
<220> FEATURE:
<223> OTHER INFORMATION: plasmid TK18

<400> SEQUENCE: 1

tcgactctag aggatccgat aacatcaccg tcgttatcgt cgctttagaa taacgttccc     60

aaaatagctc atttccaact ggcaactcac aaccaaaaac cgcattttta gtaaatatac    120

tcagcaattt gttcaacctg agcatttttc ccatttgcaa cttgatacaa atatttttag    180

cagcaaattt tcctactgcc agcttagttt acataaattt tgtctgttga catcttgcac    240

acaataaggt atggcgcata taatgcgata ttactaccat taatttacta cctagtcatt    300

aacgtctccc gccagagaac agttttgaat aggtagtcaa ttttaggtat tgaacctgct    360

gtaaatttat taaatcgatg aatttccccg aaatctgctc tagcagactt gggttatata    420

ccagtaggct caggtgcaaa acaacaaagc acaaatttta cccattaagg atataggcaa    480

tctgtcaaat agttgttatc tttcttaata cagaggaata atcaacaata tggggcaggt    540

actaactaaa gtcctatgcc tgtggggctt ctgtaaccga cataaccttt acgcgttgtc    600

ttttaggagt ctgttatgaa cggtaccagt aaaggagaag aactattcac tggagttgtc    660

ccaattcttg ttgaattaga tggtgatgtt aatgggcaca aattttctgt cagtggagag    720

ggtgaaggtg atgcaacata cggaaaactt acccttaaat ttatttgcac tactggaaaa    780

ctacctgttc catggccaac acttgtcact actttcgcgt atggtcttca atgctttgcg    840

agatacccag atcatatgaa acagcatgac tttttcaaga gtgccatgcc cgaaggttat    900

gtacaggaaa gaactatatt tttcaaagat gacgggaact acaagacacg tgctgaagtc    960

aagtttgaag gtgataccct tgttaataga atcgagttaa aaggtattga ttttaaagaa   1020

gatggaaaca ttcttggaca caaattggaa tacaactata actcacacaa tgtatacatc   1080

atggcagaca aacaaaagaa tggaatcaaa gttaacttca aaattagaca caacattgaa   1140

gatggaagcg ttcaactagc agaccattat caacaaaata ctccaattgg cgatggccct   1200

gtccttttac cagacaacca ttacctgtcc acacaatctg ccctttcgaa agatcccaac   1260

gaaaagagag accacatggt ccttcttgag tttgtaacag ctgctgggat tacacatggc   1320

atggatgaac tatacaaata agagctcgaa ttgatccttt ttgataatct catgaccaaa   1380

atcccttaac gtgagttttc gttccactga gcgtcagacc ccgtagaaaa gatcaaagga   1440

tcttcttgag atcctttttt tctgcgcgta atctgctgct tgcaaacaaa aaaaccaccg   1500

ctaccagcgg tggtttgttt gccggatcaa gagctaccaa ctctttttcc gaaggtaact   1560

ggcttcagca gagcgcagat accaaatact gtccttctag tgtagccgta gttaggccac   1620

cacttcaaga actctgtagc accgcctaca tacctcgctc tgctaatcct gttaccagtg   1680
```

-continued

```
gctgctgcca gtggcgataa gtcgtgtctt accgggttgg actcaagacg atagttaccg   1740
gataaggcgc agcggtcggg ctgaacgggg ggttcgtgca cacagcccag cttggagcga   1800
acgacctaca ccgaactgag atacctacag cgtgagctat gagaaagcgc cacgcttccc   1860
gaagggagaa aggcggacag gtatccggta agcggcaggg tcggaacagg agagcgcacg   1920
agggagcttc caggggggaaa cgcctggtat ctttatagtc ctgtcgggtt tcgccacctc   1980
tgacttgagc gtcgattttt gtgatgctcg tcaggggggc ggagcctatg gaaaaacgcc   2040
agcaacgcgg cctttttacg gttcctggcc ttttgctggc cttttgctca catgttcttt   2100
cctgcgttat cccctgattc tgtggataac cgtattaccg cctttgagtg agctgatacc   2160
gctcgccgca gccgaacgac cgagcgcagc gagtcagtga gcgaggaagc ggaagagcgc   2220
ctgatgcggt attttctcct tacgcatctg tgcggtattt cacaccgcat atggtgcact   2280
ctcagtacaa tctgctctga tgccgcatag ttaagccagt atacactccg ctatcgctac   2340
gtgactgggt catggctgcg ccccgacacc cgccaacacc cgctgacgcg ccctgacggg   2400
cttgtctgct cccggcatcc gcttacagac aagctgtgac cgtctccggg agctgcatgt   2460
gtcagaggtt ttcaccgtca tcaccgaaac gcgcgaggca gctgcggtaa agctcatcag   2520
cgtggtcgtg aagcgattca cagatgtctg cctgttcatc cgcgtccagc tcgttgagtt   2580
tctccagaag cgttaatgtc tggcttctga taaagcgggc ctgccaccat acccacgccg   2640
aaacaagcgc tcatgagccc gaagtggcga gcccgatctt ccccatcggt gatgtcggcg   2700
atataggcgc cagcaaccgc acctgtggcg ccggtgatgc ccgaagaact ccagcatgag   2760
atccccgcgc tggaggatca tccagccggc gtcccggaaa acgattccga agcccaacct   2820
ttcatagaag gcggcggtgg aatcgaaatc tcgtgatggc aggttgggcg tcgcttggtc   2880
ggtcatttcg aaccccagag tcccgctcag aagaactcgt caagaaggcg atagaaggcg   2940
atgcgctgcg aatcgggagc ggcgataccg taaagcacga ggaagcggtc agcccattcg   3000
ccgccaagct cttcagcaat atcacgggta gccaacgcta tgtcctgata gcggtccgcc   3060
acacccagcc ggccacagtc gatgaatcca gaaaagcggc cattttccac catgatattc   3120
ggcaagcagg catcgccatg ggtcacgacg agatcatcgc cgtcgggcat gcgcgccttg   3180
agcctggcga acagttcggc tggcgcgagc ccctgatgct cttcgtccag atcatcctga   3240
tcgacaagac cggcttccat ccgagtacgt gctcgctcga tgcgatgttt cgcttggtgg   3300
tcgaatgggc aggtagccgg atcaagcgta tgcagccgcc gcattgcatc agccatgatg   3360
gatactttct cggcaggagc aaggtgagat gacaggagat cctgccccgg cacttcgccc   3420
aatagcagcc agtcccttcc cgcttcagtg acaacgtcga gcacagctgc gcaaggaacg   3480
cccgtcgtgg ccagccacga tagccgcgct gcctcgtcct gcagttcatt cagggcaccg   3540
gacaggtcgg tcttgacaaa aagaaccggg cgcccctgcg ctgacagccg gaacacggcg   3600
gcatcagagc agccgattgt ctgttgtgcc cagtcatagc cgaatagcct ctccacccaa   3660
gcggccggag aacctgcgtg caatccatct tgttcaatca tgcgaaacga tcctcatcct   3720
gtctcttgat cagatcttga tcccctgcgc catcagatcc ttggcggcaa gaaagccatc   3780
cagtttactt tgcagggctt cccaacctta ccagagggcg ccccagctgg caattccggt   3840
tcgcttgctg tccataaaac cgcccagtct agctatcgcc atgtaagccc actgcaagct   3900
acctgctttc tctttgcgct tgcgttttcc cttgtccaga tagcccagta gctgacattc   3960
atccggggtc agcaccgttt ctgcggactg gctttctacg tgttccgctt cctttagcag   4020
cccttgcgcc ctgagtgctt gcggcagcgt gaagctttct ctgagctgta acagcctgac   4080
```

cgcaacaaac gagaggatcg agaccatccg ctccagatta tccggctcct ccatgcgttg 4140
cctctcggct cctgctccgg ttttccatgc cttatggaac tcctcgatcc gccagcgatg 4200
ggtataaatg tcgatgacgc gcaaggcttg ggctagcgac tcgaccggtt cgctggtcag 4260
caacaaccat ttcaacgggg tctcaccctt gggcgggtta atctcctcgg ccagcaccgc 4320
gttgagcgtg atattcccct gttttagcgt gatgcgccca ctgcgcatag aaattgcatc 4380
aacgcatata gcgctagcag cacgccatag tgactggcga tgctgtcgga atggacgata 4440
tctagactta tatagacact aatatagaca atagtttata ctgctatcta tacaagtata 4500
gacattatct aatcatggca gacaaaactc tagccacttt tcgtattgac tccgaagaat 4560
gggagtcttt taaaaacctt gctagttctg aaagttccaa cgcctcagca ctgttaacag 4620
aatttgttcg ttggtatttg gcaggtaaca ggtttaatac tcccacttct cacactccca 4680
cccatctaga cacatccctc gaacagcgta tagacaatat tgaacaacgt ctagataaag 4740
tcacaactaa taatctagac aatatagatg aatttataga caagcgtata gaagataatc 4800
tagcaacacg tctagacaaa cttcaatcgc aactggagga actgcgggga aaatcgaaag 4860
cccggtagtt caggcagaag gacaagctac cgggcaagac agaaagaata tagacaatag 4920
tatagacaat ctagacaaat tggaggcaac ccgcgatcgc accctcaata agctaaaaat 4980
gggtaggcag tcagccgccg ggaaagccat cgacgcgttt atcaaagagt tgctttcttc 5040
aggagacaac ataagctgaa gttatcaaaa ttctgtcctt acgtcgaaag cctgatttta 5100
ccgtgcaacg attgataagc ttggctaaac tagcactggc tttcaacaga aagcatacga 5160
agaatcaata gatatagcca ccaattccac aaaatgcaga taacgtgtag agtattggaa 5220
tgcttaatct gtaagggtta tgaaggttaa cggcaacgga cgagccaaaa tactcacctc 5280
cgacgaactc aggcgactgt ttagcgacgg attcaccaca ccgcgcgatc gcgttttgtt 5340
tggcatctgt ctattcaccg gttgccgcgt tagtgaagct ctagcactcc aaacaacgga 5400
cattaaaggc gaaacactaa cctttaggaa gtctaccacc aaagggaaac tcaaaacccg 5460
cgtggttgac atccagccag gactagccgc actcatggct gactatcacc ccaaaccggg 5520
aaccctgttc cctggcatga ggggagtcag cgataggctc acgcgatacg cggcggataa 5580
aatcttgcgc gatgcagcca aagaatcggg gctagaaggc atcagtaccc acagtttccg 5640
ccgtactgcc ctcaaccaaa tgtctagcgc cggtatcccg ttgcgacaca ttcaagagat 5700
atccggtcac aatgaccttg gcacactgca acgctatctt gaagttacac ccgaacagcg 5760
acgcaaagct gtatccgtga ttggcttcta atgtacgcca acgctgttta gacccctatg 5820
ggtgctaaaa aaagacgcag cctaaacaca cgctctacac ttgaggatac ttttaaagta 5880
tccatcggtt ctagaactct gcacacgttc cggactttgg aaacgttata cctttccctg 5940
tgttgcagaa tgctgcaata tttcttcgac aagttaactt gtgactggtt taatattttc 6000
tcaaattgcc ccaaaacaac acgcctaaat ccttagacgt ttctgtggaa acctattagg 6060
tttttatcgc cgttgtttta gtggtaaacc caaagggttt gtatattctt gtatgaagtt 6120
cgactctgag ggttaagaag aatggctcgc cgaatttttt acaagtggaa accgattaaa 6180
ggttaagggt caatcgggac gatgaatatt ttctaattgt gaccttctcc atctaataag 6240
ctttctttgg ggttaaggtc gaagaaagta ctacgcatga tctgcatacg atctctattg 6300
ccaaaaagcc gcgaccctat aggctctcgg tcatgctgca ctagttcgtg tcgatcacta 6360
tactggttgc cgcagcattt cacgctaaaa aaaaattctt aaaaatgtcc ttcatatctc 6420

-continued

```
gccagagtgg caacctatta caaaacggtt gcctacccga ccggctcgat tttcgctgaa   6480
gtggcactgt gacagtttga aatggtactt ccgccgtgct gctgacatcg ttgttagggt   6540
gaattgttcg cggtagatgt tgcaccgatt catgaacacc ttgtcaccca ctttgaataa   6600
tcgaccgtca aattcagtcg cgtcaatttg gtaagtgttg ggctgtctct ttttggctcc   6660
aggggcaatg ccatcagaaa acacaaccgc gtcacccata acttgataac cgatatcagt   6720
tttggttcca gtgaaagccc aaaattcaga cgcgtcatta ttccgagcgt gccggagttg   6780
attgtactca attttggctt ggcaaagttg acggcgattc atgcccagct gcttttgatg   6840
tcgtcgcact gtgcgcttgt gaatacccaa ctcacagctg acagcttttt gagatgtacc   6900
atagtggatg aaactttttg agacgaatat ccgcgacgaa ctaatgtgaa gtacacaagg   6960
tacttccccc tctggcgatt taagagagga ttgccttgtg tccttcacta gctcgttcgg   7020
gtgtggcgct ccaaaaagtt ttctgtactc tggtttaagt tgtctgttgg ccgcatagcg   7080
gctcttttgt tgaaagcttt gtgtgactat gccagtggtc agtgagcgta aatcgcttaa   7140
cacttggact aaaggcacta ctgcaacatc accccatctt tttaaattta ggttgtaaca   7200
aacttgaaac ataccgccca agtagacggt tatcattcct gctttaattt tgtagcggcg   7260
gaatgctcct attttttttc catcctgtaa ccaacggtaa acagacttat cactacaatc   7320
taagaacgtc tgtactacag gcaatggcaa tgttaaatga ccagacccat ccttatcaag   7380
cgctcgacac aaataccaca accgcgcaca aggttctcga ccaatgcgag tgtgtaccct   7440
gaccgtgtaa gtgccaagaa ttatttcagt ttgtagttcc cttgtaagca gggttagtga   7500
tacatttgta tttaagcttt ctgggctgat catttggaaa tgtctcagtc cagtacctat   7560
tgaatgttat ttgcttaacc tgaagctaaa taaaacttgt taactacacc cattaattga   7620
taaattcaaa gcacgttttt tctgtttggt gtttggtgtg gtaacaattc tgtgtatgtg   7680
tgttttattt agcttcggtt aagtagcata acaacccccca agcactgaac ttttttttaat   7740
aggtaattta aactttgcct atcggcaaaa ttttcaatca attgtacgcc aaagtgttgc   7800
atgatcaacg tttgacttat ttttgtattt actaaatact gaatttcgcc gtgacgcttt   7860
ttacagatgg aaattcacgg caaaatgttt tttgctaact ttgctatgta aaacaagaaa   7920
cttggcactc ggttattact aaataaactg gtaaaaaaata accattagaa ccaaaaagaa   7980
cgaaaaccag tacacccttg ccagttttca agcttttgct atgacgactc taataatcgg   8040
gtttaacacc attccgcttt gagaaaatta tccttgtaca gcaagtaaca gtcaatgcta   8100
aaccgcaccg ctacaaatcc ttaagttttt ccagtagcga tttaccttct tggtaacgcc   8160
cgccttgata gcccaaaatt tctttaatca ccttactttc tgaaaaaccc gcttccagac   8220
aggcttttac cacttttgct agggtttcat ctcttggttc tgggagggat gaaacgggct   8280
gtaatgcttg ttctgaggtc ggttgagccg tttggagtgg ctgaaaactg gttacagact   8340
gtaaccgggg cataaccatt ttgtaactgc ttacatctgg taactgacac ggcatatcat   8400
ccaccatgca gcgatatttc cccgacttta accactccac aagggcaagg tcttttaagg   8460
acttggcgtg gctaactgca aacttaccca ggcgtaacat cctaaaacac ttacggacac   8520
cgccttcacc ctcgatacct aaggtcttga cattatcatc ttgagtcagc ccaataacaa   8580
aacgcttggg cttgcggccg cgcctggcgt gtttgatgag ccattcggtt gctatctcga   8640
cttcatctct cagcagtggc agttcttcag caattaaaac gctttctttt cctgctagtg   8700
ccttatcccc agactcaccc cgtagctcaa tccggcgctg caattcctcc aggtcagcag   8760
ccatgcccga ctgtatagcc tcaaagtcac cacggcggcc aatgacattt aaccccgtcc   8820
```

-continued

```
actcgtccgg tgcagcgtca gcgtcataga ctgtcacctc acccccgact tgataagcaa   8880
gccattgggc tatggtgctt ttgccagttc ccgtatcccc aactattaaa cagtgcttac   8940
cagacagagc ttgcatcaag tcggtgatga ttccctctgg ttcgaccgca agggtgacgg   9000
cggtagtgtc aatgatagcc gcgccgtaag tgccagcata gggcaattgg tcgtaaactt   9060
tgaccaagtt gtatacagac tgtctacacc acttcaccac tgttaacgct gtttgcaaag   9120
cgtaagacgt ggcatcaaat aaaaatatgc tggcactaaa agttaatcgc cccaatcccc   9180
acagtaaaaa cctgcctagc tgttgacgac taggcaagtg catttcaatc cagtcatttg   9240
ccataaatca ccccgtcttt aaagccttgc agttgagcgc gacaggtatt taactgtgct   9300
tgtaactctg tttgctggtt ttgataccac agactgacgg cggcggccgc cagtcctaaa   9360
aatagaaact ggcgatcgct cattattgac ttactccctg ttgattagcg tggtagtgag   9420
tcatagccgc attgaccgct tcttgggctt ggggtgttct gccaagattg ggttttgtag   9480
ggtcatcgtt ggctacgact aaggacgctt gttcggctat cgcttgcggg acaccaactt   9540
tagttaactc tgtcaaggat acttggtaaa gtcgctcgtt cattagccga ttctccggta   9600
cataaaactg ttgctggcag tcccttcatt ggcgacgagt tcttcagccg gagtatcagc   9660
gataatgtca gcccagccgg tgacattatt attaataatg ttttgttcgg caattgcacc   9720
caagccagga cgcgccgttt caaactcaga gatgacttgc tgctctttct cggtgagtgg   9780
tctatctgtc atgataatta tgtccttcat tatgtaggcg attccagtgg gtgtttacga   9840
ggcagtccac aggaatcagt gcgattcacc tttaaggtga atcgtcatca aaaaatcact   9900
cggtagcaac gacccgaacc gaccaggatt gatttcccgg ttctcagttc gcaggctttt   9960
gagcgcgtca ccttgaccat tgggtaactg ccatcagccg ataagctaaa cgggctgtat  10020
agcggtaaag catcccacac agtcgggctg gcatcaactt tgcaggaata gctcacgtca  10080
ctcatctcac tcgcgcctgg gttggatggc agcgaaggca gattacgacg cagttttta   10140
ctggcacttt tacccgcatt aaaaacgggt acagtgccat tgttgacggt ctgtacttcg  10200
gtcatatact cggtgtacac ttaatacact ctatactatt actgccgatt agtacatttg  10260
tcaatcactc tttgcacaag gtgtatgata tggactcagg agtacaccaa acgtcatgcc  10320
aaccaataaa gggagaatag cagtcactct agaagctgaa atttaccaat ggattgctaa  10380
ccgagcgtct gaggaaggaa gaccgttggc taatcttgcc gctttcttac tcacacgagt  10440
tgttaaagaa caaatggaac aagaagccaa ggacaaccaa gacaagcagg gggcagcatg  10500
agcgaagaca gactagccag aatagaagct gcgttagaca gccaagttgc agtgaatgcc  10560
gacctccgca catcggttac agaactccgc gcaaccgcag aagcattgtt gcaaacagtt  10620
caaatccatc agcagaactt tgaaattctt accgctaggc aattacaaac cgaagcacgg  10680
cttgatgagt accaacgtac cactagcgcg gcactcgaca gaattggcgc ggtcttagac  10740
tacctcgtta ggcagcaaaa cggttgaggt gagggatgag cgatgactat ctagacggat  10800
atcccgcaag aggccctttc gtcttcaaga attcccgttt gactggcgat gctgctactg  10860
aaactaacaa ctacatcgac tacgcaatta acgccctcag ctaattttgc ttagtctagg  10920
cccggatggg taagtggttt tcagcttaag tgttgggttc tacttacttc tccgggtctt  10980
gctctatcta aaaacattgg tttaacaagg agtattaggc aaatgccagt tactgtcgct  11040
gcctctcgct tgggaaccgc tgcgtttgac caatcacccg tcgaactgcg cgctaactat  11100
tctcgacctg caggtcgatc gacttttttg ctgaggtact gagtacacag ctaataaaat  11160
```

-continued

```
tgggcaatct ccgcgcctct atgacttgaa ggagagtgta ggggtatagg ggaaagatat  11220
cttttatcta catcacataa ataaaaaatt taatttgtcg ctctggctgc atatattgat  11280
gtatttttag ccataagttt tttagtgcca tgtaattata gtgattttta gcgatcgcag  11340
agcatttttc cctggattta tcgcgatctc aaaaaaaatt tgcccgaagt atgacagatt  11400
gtcatatttg gtgtcgattt tatttaaaat gaaataagaa aaataaaact acaggttagg  11460
agaacgccat gaattcttat actgtcggta cctatttagc ggagcggctt gtccagattg  11520
gtctcaagca tcacttcgca gtcgcgggcg actacaacct cgtccttctt gacaacctgc  11580
ttttgaacaa aaacatggag caggtttatt gctgtaacga actgaactgc ggtttcagtg  11640
cagaaggtta tgctcgtgcc aaaggcgcag cagcagccgt cgttacctac agcgtcggtg  11700
cgctttccgc atttgatgct atcggtggcg cctatgcaga aaaccttccg gttatcctga  11760
tctccggtgc tccgaacaac aatgatcacg ctgctggtca cgtgttgcat cacgctcttg  11820
gcaaaaccga ctatcactat cagttggaaa tggccaagaa catcacggcc gcagctgaag  11880
cgatttacac cccagaagaa gctccggcta aaatcgatca cgtgattaaa actgctcttc  11940
gtgagaagaa gccggtttat ctcgaaatcg cttgcaacat tgcttccatg ccctgcgccg  12000
ctcctggacc ggcaagcgca ttgttcaatg acgaagccag cgacgaagct tctttgaatg  12060
cagcggttga agaaaccctg aaattcatcg ccaaccgcga caaagttgcc gtcctcgtcg  12120
gcagcaagct gcgcgcagct ggtgctgaag aagctgctgt caaatttgct gatgctctcg  12180
gtggcgcagt tgctaccatg gctgctgcaa aaagcttctt cccagaagaa aacccgcatt  12240
acatcggtac ctcatggggt gaagtcagct atccgggcgt tgaaaagacg atgaaagaag  12300
ccgatgcggt tatcgctctg gctcctgtct tcaacgacta ctccaccact ggttggacgg  12360
atattcctga tcctaagaaa ctggttctcg ctgaaccgcg ttctgtcgtc gttaacggcg  12420
ttcgcttccc cagcgttcat ctgaaagact atctgacccg tttggctcag aaagtttcca  12480
agaaaaccgg tgctttggac ttcttcaaat ccctcaatgc aggtgaactg aagaaagccg  12540
ctccggctga tccgagtgct ccgttggtca acgcagaaat cgcccgtcag gtcgaagctc  12600
ttctgacccc gaacacgacg gttattgctg aaaccggtga ctcttggttc aatgctcagc  12660
gcatgaagct cccgaacggt gctcgcgttg aatatgaaat gcagtggggt cacatcggtt  12720
ggtccgttcc tgccgccttc ggttatgccg tcggtgctcc ggaacgtcgc aacatcctca  12780
tggttggtga tggttccttc cagctgacgg ctcaggaagt cgctcagatg gttcgcctga  12840
aactgccggt tatcatcttc ttgatcaata actatggtta caccatcgaa gttatgatcc  12900
atgatggtcc gtacaacaac atcaagaact gggattatgc cggtctgatg gaagtgttca  12960
acggtaacgg tggttatgac agcggtgctg gtaaaggcct gaaggctaaa accggtggcg  13020
aactggcaga agctatcaag gttgctctgg caaacaccga cggcccaacc ctgatcgaat  13080
gcttcatcgg tcgtgaagac tgcactgaag aattggtcaa atggggtaag cgcgttgctg  13140
ccgccaacag ccgtaagcct gttaacaagc tcctctagtt tttggggatc aattcgagct  13200
ctctggataa aactaataaa ctctattacc catgattaaa gcctacgctg ccctggaagc  13260
caacggaaaa ctccaaccct ttgaatacga ccccggtgcc ctgggtgcta atgaggtgga  13320
gattgaggtg cagtattgtg ggtgtgcca cagtgatttg tccatgatta ataacgaatg  13380
gggcatttcc aattaccccc tagtgccggg tcatgaggtg gtgggtactg tggccgccat  13440
gggcgaaggg gtgaaccatg ttgaggtggg ggatttagtg gggctgggtt ggcattcggg  13500
ctactgcatg acctgccata gttgtttatc tggctaccac aacctttgtg ccacggcgga  13560
```

```
atcgaccatt gtgggccact acggtggctt tggcgatcgg gttcgggcca agggagtcag  13620

cgtggtgaaa ttacctaaag gcattgacct agccagtgcc gggccccttt tctgtggagg  13680

aattaccgtt ttcagtccta tggtggaact gagtttaaag cccactgcaa aagtggcagt  13740

gatcggcatt gggggcttgg gccatttagc ggtgcaattt ctccgggcct ggggctgtga  13800

agtgactgcc tttacctcca gtgccaggaa gcaaacggaa gtgttggaat tgggcgctca  13860

ccacatacta gattccacca atccagaggc gatcgccagt gcggaaggca aatttgacta  13920

tattatctcc actgtgaacc tgaagcttga ctggaactta tacatcagca ccctggcgcc  13980

ccagggacat ttccactttg ttggggtggt gttggagcct ttggatctaa atctttttcc  14040

ccttttgatg ggacaacgct ccgtttctgc ctccccagtg ggtagtcccg ccaccattgc  14100

caccatgttg gactttgctg tgcgccatga cattaaaccc gtggtggaac aatttagctt  14160

tgatcagatc aacgaggcga tcgcccatct agaaagcggc aaagcccatt atcgggtagt  14220

gctcagccat agtaaaaatt agctctgcaa aggttgcttc tgggtccgtg gaatggtcaa  14280

acggagtcga tctcagtttt gatacgctct atctggaaag cttgacattc gatctgca    14338
```

<210> SEQ ID NO 2
<211> LENGTH: 14278
<212> TYPE: DNA
<213> ORGANISM: Artificial Sequence
<220> FEATURE:
<223> OTHER INFORMATION: plasmid TK122

<400> SEQUENCE: 2

```
aattcttata ctgtcggtac ctatttagcg gagcggcttg tccagattgg tctcaagcat     60

cacttcgcag tcgcgggcga ctacaacctc gtccttcttg acaacctgct tttgaacaaa    120

aacatggagc aggtttattg ctgtaacgaa ctgaactgcg gtttcagtgc agaaggttat    180

gctcgtgcca aaggcgcagc agcagccgtc gttacctaca gcgtcggtgc gctttccgca    240

tttgatgcta tcggtggcgc ctatgcagaa aaccttccgg ttatcctgat ctccggtgct    300

ccgaacaaca atgatcacgc tgctggtcac gtgttgcatc acgctcttgg caaaaccgac    360

tatcactatc agttggaaat ggccaagaac atcacggccg cagctgaagc gatttacacc    420

ccagaagaag ctccggctaa aatcgatcac gtgattaaaa ctgctcttcg tgagaagaag    480

ccggtttatc tcgaaatcgc ttgcaacatt gcttccatgc cctgcgccgc tcctggaccg    540

gcaagcgcat tgttcaatga cgaagccagc gacgaagctt ctttgaatgc agcggttgaa    600

gaaaccctga aattcatcgc caaccgcgac aaagttgccg tcctcgtcgg cagcaagctg    660

cgcgcagctg gtgctgaaga agctgctgtc aaatttgctg atgctctcgg tggcgcagtt    720

gctaccatgg ctgctgcaaa aagcttcttc ccagaagaaa acccgcatta catcggtacc    780

tcatggggtg aagtcagcta tccgggcgtt gaaaagacga tgaaagaagc cgatgcggtt    840

atcgctctgg ctcctgtctt caacgactac tccaccactg gttggacgga tattcctgat    900

cctaagaaac tggttctcgc tgaaccgcgt tctgtcgtcg ttaacggcgt tcgcttcccc    960

agcgttcatc tgaaagacta tctgacccgt ttggctcaga aagtttccaa gaaaaccggt   1020

gctttggact tcttcaaatc cctcaatgca ggtgaactga agaaagccgc tccggctgat   1080

ccgagtgctc cgttggtcaa cgcagaaatc gcccgtcagg tcgaagctct tctgaccccg   1140

aacacgacgg ttattgctga aaccggtgac tcttggttca atgctcagcg catgaagctc   1200

ccgaacggtg ctcgcgttga atatgaaatg cagtggggtc acatcggttg gtccgttcct   1260
```

-continued

```
gccgccttcg gttatgccgt cggtgctccg gaacgtcgca acatcctcat ggttggtgat   1320
ggttccttcc agctgacggc tcaggaagtc gctcagatgg ttcgcctgaa actgccggtt   1380
atcatcttct tgatcaataa ctatggttac accatcgaag ttatgatcca tgatggtccg   1440
tacaacaaca tcaagaactg ggattatgcc ggtctgatgg aagtgttcaa cggtaacggt   1500
ggttatgaca gcggtgctgg taaaggcctg aaggctaaaa ccggtggcga actggcagaa   1560
gctatcaagg ttgctctggc aaacaccgac ggcccaaccc tgatcgaatg cttcatcggt   1620
cgtgaagact gcactgaaga attggtcaaa tggggtaagc gcgttgctgc cgccaacagc   1680
cgtaagcctg ttaacaagct cctctagttt ttggggatca attcgagctc tctggataaa   1740
actaataaac tctattaccc atgattaaag cctacgctgc cctggaagcc aacggaaaac   1800
tccaaccctt tgaatacgac cccggtgccc tgggtgctaa tgaggtggag attgaggtgc   1860
agtattgtgg ggtgtgccac agtgatttgt ccatgattaa taacgaatgg ggcatttcca   1920
attacccct agtgccgggt catgaggtgg tgggtactgt ggccgccatg ggcgaagggg   1980
tgaaccatgt tgaggtgggg gatttagtgg ggctgggttg gcattcgggc tactgcatga   2040
cctgccatag ttgtttatct ggctaccaca acctttgtgc cacggcggaa tcgaccattg   2100
tgggccacta cggtggcttt ggcgatcggg ttcgggccaa gggagtcagc gtggtgaaat   2160
tacctaaagg cattgaccta gccagtgccg ggcccctttt ctgtggagga attaccgttt   2220
tcagtcctat ggtggaactg agtttaaagc ccactgcaaa agtggcagtg atcggcattg   2280
gggcttggg ccatttagcg gtgcaatttc tccgggcctg ggctgtgaa gtgactgcct   2340
ttacctccag tgccaggaag caaacggaag tgttggaatt gggcgctcac cacatactag   2400
attccaccaa tccagaggcg atcgccagtg cggaaggcaa atttgactat attatctcca   2460
ctgtgaacct gaagcttgac tggaacttat acatcagcac cctggcgccc cagggacatt   2520
tccactttgt tggggtggtg ttggagcctt tggatctaaa tctttttccc cttttgatgg   2580
gacaacgctc cgtttctgcc tccccagtgg gtagtcccgc caccattgcc accatgttgg   2640
actttgctgt gcgccatgac attaaacccg tggtggaaca atttagcttt gatcagatca   2700
acgaggcgat cgcccatcta gaaagcggca aagcccatta tcgggtagtg ctcagccata   2760
gtaaaaatta gctctgcaaa ggttgcttct gggtccgtgg aatggtcaaa cggagtcgat   2820
ctcagttttg atacgctcta tctggaaagc ttgacattcg atctgcaggc cccccggggg   2880
gctcgactct agaggatccg ataacatcac cgtcgttatc gtcgctttag aataacgttc   2940
ccaaaatagc tcatttccaa ctggcaactc acaaccaaaa accgcatttt tagtaaatat   3000
actcagcaat ttgttcaacc tgagcatttt tcccatttgc aacttgatac aaatattttt   3060
agcagcaaat tttcctactg ccagcttagt ttacataaat tttgtctgtt gacatcttgc   3120
acacaataag gtatggcgca tataatgcga tattactacc attaatttac tacctagtca   3180
ttaacgtctc ccgccagaga acagttttga ataggtagtc aattttaggt attgaacctg   3240
ctgtaaattt attaaatcga tgaatttccc cgaaatctgc tctagcagac ttgggttata   3300
taccagtagg ctcaggtgca aaacaacaaa gcacaaattt tacccattaa ggatataggc   3360
aatctgtcaa atagttgtta tctttcttaa tacagaggaa taatcaacaa tatggggcag   3420
gtactaacta aagtcctatg cctgtggggc ttctgtaacc gacataacct ttacgcgttg   3480
tcttttagga gtctgttatg aacggtacca gtaaaggaga agaactattc actggagttg   3540
tcccaattct tgttgaatta gatggtgatg ttaatgggca caaattttct gtcagtggag   3600
agggtgaagg tgatgcaaca tacggaaaac ttacccttaa atttatttgc actactggaa   3660
```

-continued

```
aactacctgt tccatggcca acacttgtca ctactttcgc gtatggtctt caatgctttg   3720
cgagataccc agatcatatg aaacagcatg actttttcaa gagtgccatg cccgaaggtt   3780
atgtacagga aagaactata tttttcaaag atgacgggaa ctacaagaca cgtgctgaag   3840
tcaagtttga aggtgatacc cttgttaata gaatcgagtt aaaaggtatt gattttaaag   3900
aagatggaaa cattcttgga cacaaattgg aatacaacta taactcacac aatgtataca   3960
tcatggcaga caaacaaaag aatggaatca aagttaactt caaaattaga cacaacattg   4020
aagatggaag cgttcaacta gcagaccatt atcaacaaaa tactccaatt ggcgatggcc   4080
ctgtcctttt accagacaac cattacctgt ccacacaatc tgccctttcg aaagatccca   4140
acgaaaagag agaccacatg gtccttcttg agtttgtaac agctgctggg attacacatg   4200
gcatggatga actatacaaa taagagctcg aattgatcct tttgataat ctcatgacca   4260
aaatccctta acgtgagttt tcgttccact gagcgtcaga ccccgtagaa aagatcaaag   4320
gatcttcttg agatcctttt tttctgcgcg taatctgctg cttgcaaaca aaaaaaccac   4380
cgctaccagc ggtggtttgt ttgccggatc aagagctacc aactcttttt ccgaaggtaa   4440
ctggcttcag cagagcgcag ataccaaata ctgtccttct agtgtagccg tagttaggcc   4500
accacttcaa gaactctgta gcaccgccta catacctcgc tctgctaatc ctgttaccag   4560
tggctgctgc cagtggcgat aagtcgtgtc ttaccgggtt ggactcaaga cgatagttac   4620
cggataaggc gcagcggtcg ggctgaacgg ggggttcgtg cacacagccc agcttggagc   4680
gaacgaccta caccgaactg agatacctac agcgtgagct atgagaaagc gccacgcttc   4740
ccgaagggag aaaggcggac aggtatccgg taagcggcag ggtcggaaca ggagagcgca   4800
cgagggagct tccaggggga aacgcctggt atctttatag tcctgtcggg tttcgccacc   4860
tctgacttga gcgtcgattt ttgtgatgct cgtcaggggg gcggagccta tggaaaaacg   4920
ccagcaacgc ggccttttta cggttcctgg ccttttgctg gccttttgct cacatgttct   4980
ttcctgcgtt atcccctgat tctgtggata accgtattac cgcctttgag tgagctgata   5040
ccgctcgccg cagccgaacg accgagcgca gcgagtcagt gagcgaggaa gcggaagagc   5100
gcctgatgcg gtattttctc cttacgcatc tgtgcggtat ttcacaccgc atatggtgca   5160
ctctcagtac aatctgctct gatgccgcat agttaagcca gtatacactc cgctatcgct   5220
acgtgactgg gtcatggctg cgccccgaca cccgccaaca cccgctgacg cgccctgacg   5280
ggcttgtctg ctcccggcat ccgcttacag acaagctgtg accgtctccg ggagctgcat   5340
gtgtcagagg ttttcaccgt catcaccgaa acgcgcgagg cagctgcggt aaagctcatc   5400
agcgtggtcg tgaagcgatt cacagatgtc tgcctgttca tccgcgtcca gctcgttgag   5460
tttctccaga agcgttaatg tctggcttct gataaagcgg gcctgccacc atacccacgc   5520
cgaaacaagc gctcatgagc ccgaagtggc gagcccgatc ttccccatcg gtgatgtcgg   5580
cgatataggc gccagcaacc gcacctgtgg cgccggtgat gcccgaagaa ctccagcatg   5640
agatccccgc gctggaggat catccagccg gcgtcccgga aaacgattcc gaagcccaac   5700
ctttcataga aggcggcggt ggaatcgaaa tctcgtgatg gcaggttggg cgtcgcttgg   5760
tcggtcattt cgaaccccag agtcccgctc agaagaactc gtcaagaagg cgatagaagg   5820
cgatgcgctg cgaatcggga gcggcgatac cgtaaagcac gaggaagcgg tcagcccatt   5880
cgccgccaag ctcttcagca atatcacggg tagccaacgc tatgtcctga tagcggtccg   5940
ccacacccag ccggccacag tcgatgaatc cagaaaagcg gccattttcc accatgatat   6000
```

-continued

```
tcggcaagca ggcatcgcca tgggtcacga cgagatcatc gccgtcgggc atgcgcgcct   6060
tgagcctggc gaacagttcg gctggcgcga gcccctgatg ctcttcgtcc agatcatcct   6120
gatcgacaag accggcttcc atccgagtac gtgctcgctc gatgcgatgt ttcgcttggt   6180
ggtcgaatgg gcaggtagcc ggatcaagcg tatgcagccg ccgcattgca tcagccatga   6240
tggatacttt ctcggcagga gcaaggtgag atgacaggag atcctgcccc ggcacttcgc   6300
ccaatagcag ccagtccctt cccgcttcag tgacaacgtc gagcacagct gcgcaaggaa   6360
cgcccgtcgt ggccagccac gatagccgcg ctgcctcgtc ctgcagttca ttcagggcac   6420
cggacaggtc ggtcttgaca aaaagaaccg ggcgcccctg cgctgacagc cggaacacgg   6480
cggcatcaga gcagccgatt gtctgttgtg cccagtcata gccgaatagc ctctccaccc   6540
aagcggccgg agaacctgcg tgcaatccat cttgttcaat catgcgaaac gatcctcatc   6600
ctgtctcttg atcagatctt gatcccctgc gccatcagat ccttggcggc aagaaagcca   6660
tccagtttac tttgcagggc ttcccaacct taccagaggg cgccccagct ggcaattccg   6720
gttcgcttgc tgtccataaa accgcccagt ctagctatcg ccatgtaagc ccactgcaag   6780
ctacctgctt tctctttgcg cttgcgtttt cccttgtcca gatagcccag tagctgacat   6840
tcatccgggg tcagcaccgt ttctgcggac tggctttcta cgtgttccgc ttcctttagc   6900
agcccttgcg ccctgagtgc ttgcggcagc gtgaagcttt ctctgagctg taacagcctg   6960
accgcaacaa acgagaggat cgagaccatc cgctccagat tatccggctc ctccatgcgt   7020
tgcctctcgg ctcctgctcc ggttttccat gccttatgga actcctcgat ccgccagcga   7080
tgggtataaa tgtcgatgac gcgcaaggct tgggctagcg actcgaccgg ttcgctggtc   7140
agcaacaacc atttcaacgg ggtctcaccc ttgggcgggt taatctcctc ggccagcacc   7200
gcgttgagcg tgatattccc ctgttttagc gtgatgcgcc cactgcgcat agaaattgca   7260
tcaacgcata tagcgctagc agcacgccat agtgactggc gatgctgtcg gaatggacga   7320
tatctagact tatatagaca ctaatataga caatagttta tactgctatc tatacaagta   7380
tagacattat ctaatcatgg cagacaaaac tctagccact tttcgtattg actccgaaga   7440
atgggagtct tttaaaaacc ttgctagttc tgaaagttcc aacgcctcag cactgttaac   7500
agaatttgtt cgttggtatt tggcaggtaa caggtttaat actcccactt ctcacactcc   7560
cacccatcta gacacatccc tcgaacagcg tatagacaat attgaacaac gtctagataa   7620
agtcacaact aataatctag acaatataga tgaatttata gacaagcgta tagaagataa   7680
tctagcaaca cgtctagaca aacttcaatc gcaactggag gaactgcggg gaaaatcgaa   7740
agcccggtag ttcaggcaga aggacaagct accgggcaag acagaaagaa tatagacaat   7800
agtatagaca atctagacaa attggaggca acccgcgatc gcaccctcaa taagctaaaa   7860
atgggtaggc agtcagccgc cgggaaagcc atcgacgcgt ttatcaaaga gttgctttct   7920
tcaggagaca acataagctg aagttatcaa aattctgtcc ttacgtcgaa agcctgattt   7980
taccgtgcaa cgattgataa gcttggctaa actagcactg gctttcaaca gaaagcatac   8040
gaagaatcaa tagatatagc caccaattcc acaaaatgca gataacgtgt agagtattgg   8100
aatgcttaat ctgtaagggt tatgaaggtt aacggcaacg gacgagccaa aatactcacc   8160
tccgacgaac tcaggcgact gtttagcgac ggattcacca caccgcgcga tcgcgttttg   8220
tttggcatct gtctattcac cggttgccgc gttagtgaag ctctagcact ccaaacaacg   8280
gacattaaag gcgaaacact aacctttagg aagtctacca ccaaagggaa actcaaaacc   8340
cgcgtggttg acatccagcc aggactagcc gcactcatgg ctgactatca ccccaaaccg   8400
```

-continued

```
ggaaccctgt tccctggcat gaggggagtc agcgataggc tcacgcgata cgcggcggat   8460
aaaatcttgc gcgatgcagc caaaagaatc gggctagaag gcatcagtac ccacagtttc   8520
cgccgtactg ccctcaacca aatgtctagc gccggtatcc cgttgcgaca cattcaagag   8580
atatccggtc acaatgacct tggcacactg caacgctatc ttgaagttac acccgaacag   8640
cgacgcaaag ctgtatccgt gattggcttc taatgtacgc caacgctgtt tagacccccta   8700
tgggtgctaa aaaaagacgc agcctaaaca cacgctctac acttgaggat acttttaaag   8760
tatccatcgg ttctagaact ctgcacacgt tccggacttt ggaaacgtta tacctttccc   8820
tgtgttgcag aatgctgcaa tatttcttcg acaagttaac ttgtgactgg tttaatattt   8880
tctcaaattg ccccaaaaca acacgcctaa atccttagac gtttctgtgg aaacctatta   8940
ggtttttatc gccgttgttt tagtggtaaa cccaaagggt ttgtatattc ttgtatgaag   9000
ttcgactctg agggttaaga agaatggctc gccgaatttt ttacaagtgg aaaccgatta   9060
aaggttaagg gtcaatcggg acgatgaata ttttctaatt gtgaccttct ccatctaata   9120
agctttcttt ggggttaagg tcgaagaaag tactacgcat gatctgcata cgatctctat   9180
tgccaaaaag ccgcgaccct ataggctctc ggtcatgctg cactagttcg tgtcgatcac   9240
tatactggtt gccgcagcat ttcacgctaa aaaaaaattc ttaaaaatgt ccttcatatc   9300
tcgccagagt ggcaacctat tacaaaacgg ttgcctaccc gaccggctcg attttcgctg   9360
aagtggcact gtgacagttt gaaatggtac ttccgccgtg ctgctgacat cgttgttagg   9420
gtgaattgtt cgcggtagat gttgcaccga ttcatgaaca ccttgtcacc cactttgaat   9480
aatcgaccgt caaattcagt cgcgtcaatt tggtaagtgt tgggctgtct ctttttggct   9540
ccaggggcaa tgccatcaga aaacacaacc gcgtcaccca taacttgata accgatatca   9600
gttttggttc cagtgaaagc ccaaaattca gacgcgtcat tattccgagc gtgccggagt   9660
tgattgtact caattttggc ttggcaaagt tgacggcgat tcatgcccag ctgcttttga   9720
tgtcgtcgca ctgtgcgctt gtgaataccc aactcacagc tgacagcttt ttgagatgta   9780
ccatagtgga tgaaactttt tgagacgaat atccgcgacg aactaatgtg aagtacacaa   9840
ggtacttccc cctctggcga tttaagagag gattgccttg tgtccttcac tagctcgttc   9900
gggtgtggcg ctccaaaaag ttttctgtac tctggtttaa gttgtctgtt ggccgcatag   9960
cggctctttt gttgaaagct ttgtgtgact atgccagtgg tcagtgagcg taaatcgctt  10020
aacacttgga ctaaaggcac tactgcaaca tcaccccatc tttttaaatt taggttgtaa  10080
caaacttgaa acataccgcc caagtagacg gttatcattc ctgctttaat tttgtagcgg  10140
cggaatgctc ctattttttt tccatcctgt aaccaacggt aaacagactt atcactacaa  10200
tctaagaacg tctgtactac aggcaatggc aatgttaaat gaccagaccc atccttatca  10260
agcgctcgac acaaatacca caaccgcgca caaggttctc gaccaatgcg agtgtgtacc  10320
ctgaccgtgt aagtgccaag aattatttca gtttgtagtt cccttgtaag cagggttagt  10380
gatacatttg tatttaagct ttctgggctg atcatttgga aatgtctcag tccagtacct  10440
attgaatgtt atttgcttaa cctgaagcta aataaaactt gttaactaca cccattaatt  10500
gataaattca aagcacgttt tttctgtttg gtgtttggtg tggtaacaat tctgtgtatg  10560
tgtgttttat ttagcttcgg ttaagtagca taacaacccc caagcactga acttttttta  10620
ataggtaatt taaactttgc ctatcggcaa aattttcaat caattgtacg ccaaagtgtt  10680
gcatgatcaa cgtttgactt atttttgtat ttactaaata ctgaatttcg ccgtgacgct  10740
```

-continued

```
ttttacagat ggaaattcac ggcaaaatgt tttttgctaa ctttgctatg taaaacaaga  10800
aacttggcac tcggttatta ctaaataaac tggtaaaaaa taaccattag aaccaaaaag  10860
aacgaaaacc agtacaccct tgccagtttt caagcttttg ctatgacgac tctaataatc  10920
gggtttaaca ccattccgct ttgagaaaat tatccttgta cagcaagtaa cagtcaatgc  10980
taaaccgcac cgctacaaat ccttaagttt ttccagtagc gatttacctt cttggtaacg  11040
cccgccttga tagcccaaaa tttctttaat caccttactt tctgaaaaac ccgcttccag  11100
acaggctttt accacttttg ctagggtttc atctcttggt tctgggaggg atgaaacggg  11160
ctgtaatgct tgttctgagg tcggttgagc cgtttggagt ggctgaaaac tggttacaga  11220
ctgtaaccgg ggcataacca ttttgtaact gcttacatct ggtaactgac acggcatatc  11280
atccaccatg cagcgatatt tccccgactt taaccactcc acaagggcaa ggtcttttaa  11340
ggacttggcg tggctaactg caaacttacc caggcgtaac atcctaaaac acttacggac  11400
accgccttca ccctcgatac ctaaggtctt gacattatca tcttgagtca gcccaataac  11460
aaaacgcttg ggcttgcggc cgcgcctggc gtgtttgatg agccattcgg ttgctatctc  11520
gacttcatct ctcagcagtg gcagttcttc agcaattaaa acgctttctt ttcctgctag  11580
tgccttatcc ccagactcac cccgtagctc aatccggcgc tgcaattcct ccaggtcagc  11640
agccatgccc gactgtatag cctcaaagtc accacggcgg ccaatgacat ttaaccccgt  11700
ccactcgtcc ggtgcagcgt cagcgtcata gactgtcacc tcacccccga cttgataagc  11760
aagccattgg gctatggtgc ttttgccagt tcccgtatcc ccaactatta aacagtgctt  11820
accagacaga gcttgcatca agtcggtgat gattccctct ggttcgaccg caagggtgac  11880
ggcggtagtg tcaatgatag ccgcgccgta agtgccagca tagggcaatt ggtcgtaaac  11940
tttgaccaag ttgtatacag actgtctaca ccacttcacc actgttaacg ctgtttgcaa  12000
agcgtaagac gtggcatcaa ataaaaatat gctggcacta aaagttaatc gccccaatcc  12060
ccacagtaaa aacctgccta gctgttgacg actaggcaag tgcatttcaa tccagtcatt  12120
tgccataaat caccccgtct ttaaagcctt gcagttgagc gcgacaggta tttaactgtg  12180
cttgtaactc tgtttgctgg ttttgatacc acagactgac ggcggcggcc gccagtccta  12240
aaaatagaaa ctggcgatcg ctcattattg acttactccc tgttgattag cgtggtagtg  12300
agtcatagcc gcattgaccg cttcttgggc ttggggtgtt ctgccaagat tgggttttgt  12360
agggtcatcg ttggctacga ctaaggacgc ttgttcggct atcgcttgcg ggacaccaac  12420
tttagttaac tctgtcaagg atacttggta aagtcgctcg ttcattagcc gattctccgg  12480
tacataaaac tgttgctggc agtcccttca ttggcgacga gttcttcagc cggagtatca  12540
gcgataatgt cagcccagcc ggtgacatta ttattaataa tgttttgttc ggcaattgca  12600
cccaagccag gacgcgccgt ttcaaactca gagatgactt gctgctcttt ctcggtgagt  12660
ggtctatctg tcatgataat tatgtccttc attatgtagg cgattccagt gggtgtttac  12720
gaggcagtcc acaggaatca gtgcgattca cctttaaggt gaatcgtcat caaaaaatca  12780
ctcggtagca acgacccgaa ccgaccagga ttgatttccc ggttctcagt tcgcaggctt  12840
ttgagcgcgt caccttgacc attgggtaac tgccatcagc cgataagcta aacgggctgt  12900
atagcggtaa agcatcccac acagtcgggc tggcatcaac tttgcaggaa tagctcacgt  12960
cactcatctc actcgcgcct gggttggatg gcagcgaagg cagattacga cgcagttttt  13020
tactggcact tttacccgca ttaaaaacgg gtacagtgcc attgttgacg gtctgtactt  13080
cggtcatata ctcggtgtac acttaataca ctctatacta ttactgccga ttagtacatt  13140
```

```
tgtcaatcac tctttgcaca aggtgtatga tatggactca ggagtacacc aaacgtcatg    13200

ccaaccaata aagggagaat agcagtcact ctagaagctg aaatttacca atggattgct    13260

aaccgagcgt ctgaggaagg aagaccgttg gctaatcttg ccgctttctt actcacacga    13320

gttgttaaag aacaaatgga acaagaagcc aaggacaacc aagacaagca gggggcagca    13380

tgagcgaaga cagactagcc agaatagaag ctgcgttaga cagccaagtt gcagtgaatg    13440

ccgacctccg cacatcggtt acagaactcc gcgcaaccgc agaagcattg ttgcaaacag    13500

ttcaaatcca tcagcagaac tttgaaattc ttaccgctag gcaattacaa accgaagcac    13560

ggcttgatga gtaccaacgt accactagcg cggcactcga cagaattggc gcggtcttag    13620

actacctcgt taggcagcaa aacggttgag gtgagggatg agcgatgact atctagacgg    13680

atatcccgca agaggcccTt tcgtcttcaa gaattgtcga cctccttaat ccgattcctg    13740

caaatggtct gcaacttccc gatacaaatt catcacatga ttatccgcca agctgtagta    13800

aacattacgg ccgacccggc gatactttac caggcgctgc gatcgtaaaa ttcgtaattg    13860

atgggaaact gccgattcac tcactttcat cgccgctgct aaatcacaga cacagagttc    13920

ttggcgggcc aatgccgaca ttaaacgcaa ccgactcgga tcagctagtg cactgaaaaa    13980

ctccgccatt tgctgggcct ggtccaatga catcacctct ggttgaacct gtcgtacctg    14040

ctcaagatga acaagaggtt gatcacaaag gggcatctct tcgttctggc aggattgtga    14100

cttTgacaac gaggacttac tcatagaggt tggcgttagg agctagggaa aaatttaaac    14160

tggatttaga aaatgatttt catcctaaca tctttaatat ctgagcatat cttcaggtgt    14220

ttcaagattt gtgctacggt tcaaggaggt ttttctttaa atcacgttgg ccgccatg     14278
```

<210> SEQ ID NO 3
<211> LENGTH: 118
<212> TYPE: DNA
<213> ORGANISM: Artificial Sequence
<220> FEATURE:
<223> OTHER INFORMATION: Putative promoter region of the ziaA gene,
      showing 2 possible start codon (ATG) sites

<400> SEQUENCE: 3

```
gatttcaaaa tagacagaat aataatcatt ctaacatctg aatatatatt cagatattga      60

gataactatg ttaaacttca aaggagttat tcttcagcga cttactgaaa cggctatg      118
```

<210> SEQ ID NO 4
<211> LENGTH: 14360
<212> TYPE: DNA
<213> ORGANISM: Artificial Sequence
<220> FEATURE:
<223> OTHER INFORMATION: plasmid TK187

<400> SEQUENCE: 4

```
ggccccccgg ggggctcgac tctagaggat ccgataacat caccgtcgtt atcgtcgctt      60

tagaataacg ttcccaaaat agctcatttc caactggcaa ctcacaacca aaaaccgcat     120

ttttagtaaa tatactcagc aatttgttca acctgagcat ttttcccatt tgcaacttga     180

tacaaatatt tttagcagca aattttccta ctgccagctt agtttacata aatttTgtct     240

gttgacatct tgcacacaat aaggtatggc gcatataatg cgatattact accattaatt     300

tactacctag tcattaacgt ctcccgccag agaacagttt tgaataggta gtcaatttta     360

ggtattgaac ctgctgtaaa tttattaaat cgatgaattt ccccgaaatc tgctctagca     420

gacttgggtt atataccagt aggctcaggt gcaaaacaac aaagcacaaa ttttacccat     480
```

-continued

```
taaggatata ggcaatctgt caaatagttg ttatctttct taatacagag gaataatcaa    540
caatatgggg caggtactaa ctaaagtcct atgcctgtgg ggcttctgta accgacataa    600
cctttacgcg ttgtctttta ggagtctgtt atgaacggta ccagtaaagg agaagaacta    660
ttcactggag ttgtcccaat tcttgttgaa ttagatggtg atgttaatgg gcacaaattt    720
tctgtcagtg gagagggtga aggtgatgca acatacggaa aacttaccct taaatttatt    780
tgcactactg gaaaactacc tgttccatgg ccaacacttg tcactacttt cgcgtatggt    840
cttcaatgct ttgcgagata cccagatcat atgaaacagc atgacttttt caagagtgcc    900
atgcccgaag gttatgtaca ggaaagaact atatttttca aagatgacgg gaactacaag    960
acacgtgctg aagtcaagtt tgaaggtgat acccttgtta atagaatcga gttaaaaggt   1020
attgatttta aagaagatgg aaacattctt ggacacaaat tggaatacaa ctataactca   1080
cacaatgtat acatcatggc agacaaacaa aagaatggaa tcaaagttaa cttcaaaatt   1140
agacacaaca ttgaagatgg aagcgttcaa ctagcagacc attatcaaca aaatactcca   1200
attggcgatg gccctgtcct tttaccagac aaccattacc tgtccacaca atctgccctt   1260
tcgaaagatc ccaacgaaaa gagagaccac atggtccttc ttgagtttgt aacagctgct   1320
gggattacac atggcatgga tgaactatac aaataagagc tcgaattgat ccttttttgat   1380
aatctcatga ccaaaatccc ttaacgtgag ttttcgttcc actgagcgtc agaccccgta   1440
gaaaagatca aaggatcttc ttgagatcct ttttttctgc gcgtaatctg ctgcttgcaa   1500
acaaaaaaac caccgctacc agcggtggtt tgtttgccgg atcaagagct accaactctt   1560
tttccgaagg taactggctt cagcagagcg cagataccaa atactgtcct tctagtgtag   1620
ccgtagttag gccaccactt caagaactct gtagcaccgc ctacatacct cgctctgcta   1680
atcctgttac cagtggctgc tgccagtggc gataagtcgt gtcttaccgg gttggactca   1740
agacgatagt taccggataa ggcgcagcgg tcgggctgaa cggggggttc gtgcacacag   1800
cccagcttgg agcgaacgac ctacaccgaa ctgagatacc tacagcgtga gctatgagaa   1860
agcgccacgc ttcccgaagg gagaaaggcg gacaggtatc cggtaagcgg cagggtcgga   1920
acaggagagc gcacgaggga gcttccaggg ggaaacgcct ggtatcttta tagtcctgtc   1980
gggtttcgcc acctctgact tgagcgtcga tttttgtgat gctcgtcagg ggggcggagc   2040
ctatggaaaa acgccagcaa cgcggccttt ttacggttcc tggccttttg ctggcctttt   2100
gctcacatgt tctttcctgc gttatcccct gattctgtgg ataaccgtat taccgccttt   2160
gagtgagctg ataccgctcg ccgcagccga acgaccgagc gcagcgagtc agtgagcgag   2220
gaagcggaag agcgcctgat gcggtatttt ctccttacgc atctgtgcgg tatttcacac   2280
cgcatatggt gcactctcag tacaatctgc tctgatgccg catagttaag ccagtataca   2340
ctccgctatc gctacgtgac tgggtcatgg ctgcgccccg acacccgcca acacccgctg   2400
acgcgccctg acgggcttgt ctgctcccgg catccgctta cagacaagct gtgaccgtct   2460
ccgggagctg catgtgtcag aggttttcac cgtcatcacc gaaacgcgcg aggcagctgc   2520
ggtaaagctc atcagcgtgg tcgtgaagcg attcacagat gtctgcctgt tcatccgcgt   2580
ccagctcgtt gagtttctcc agaagcgtta atgtctggct tctgataaag cgggcctgcc   2640
accataccca cgccgaaaca agcgctcatg agcccgaagt ggcgagcccg atcttcccca   2700
tcggtgatgt cggcgatata ggcgccagca accgcacctg tggcgccggt gatgccgaa    2760
gaactccagc atgagatccc cgcgctggag gatcatccag ccggcgtccc ggaaaacgat   2820
```

-continued tccgaagccc aacctttcat agaaggcggc ggtggaatcg aaatctcgtg atggcaggtt 2880
gggcgtcgct tggtcggtca tttcgaaccc cagagtcccg ctcagaagaa ctcgtcaaga 2940
aggcgataga aggcgatgcg ctgcgaatcg ggagcggcga taccgtaaag cacgaggaag 3000
cggtcagccc attcgccgcc aagctcttca gcaatatcac gggtagccaa cgctatgtcc 3060
tgatagcggt ccgccacacc cagccggcca cagtcgatga atccagaaaa gcggccattt 3120
tccaccatga tattcggcaa gcaggcatcg ccatgggtca cgacgagatc atcgccgtcg 3180
ggcatgcgcg ccttgagcct ggcgaacagt tcggctggcg cgagcccctg atgctcttcg 3240
tccagatcat cctgatcgac aagaccggct tccatccgag tacgtgctcg ctcgatgcga 3300
tgtttcgctt ggtggtcgaa tgggcaggta gccggatcaa gcgtatgcag ccgccgcatt 3360
gcatcagcca tgatggatac tttctcggca ggagcaaggt gagatgacag gagatcctgc 3420
cccggcactt cgcccaatag cagccagtcc cttcccgctt cagtgacaac gtcgagcaca 3480
gctgcgcaag gaacgcccgt cgtggccagc cacgatagcc gcgctgcctc gtcctgcagt 3540
tcattcaggg caccggacag gtcggtcttg acaaaaagaa ccgggcgccc ctgcgctgac 3600
agccggaaca cggcggcatc agagcagccg attgtctgtt gtgcccagtc atagccgaat 3660
agcctctcca cccaagcggc cggagaacct gcgtgcaatc catcttgttc aatcatgcga 3720
aacgatcctc atcctgtctc ttgatcagat cttgatcccc tgcgccatca gatccttggc 3780
ggcaagaaag ccatccagtt tactttgcag ggcttcccaa ccttaccaga gggcgcccca 3840
gctggcaatt ccggttcgct tgctgtccat aaaaccgccc agtctagcta tcgccatgta 3900
agcccactgc aagctacctg ctttctcttt gcgcttgcgt tttcccttgt ccagatagcc 3960
cagtagctga cattcatccg gggtcagcac cgtttctgcg gactggcttt ctacgtgttc 4020
cgcttccttt agcagccctt gcgccctgag tgcttgcggc agcgtgaagc tttctctgag 4080
ctgtaacagc ctgaccgcaa caaacgagag gatcgagacc atccgctcca gattatccgg 4140
ctcctccatg cgttgcctct cggctcctgc tccggttttc catgccttat ggaactcctc 4200
gatccgccag cgatgggtat aaatgtcgat gacgcgcaag gcttgggcta gcgactcgac 4260
cggttcgctg gtcagcaaca accatttcaa cggggtctca cccttgggcg ggttaatctc 4320
ctcggccagc accgcgttga gcgtgatatt cccctgtttt agcgtgatgc gcccactgcg 4380
catagaaatt gcatcaacgc atatagcgct agcagcacgc catagtgact ggcgatgctg 4440
tcggaatgga cgatatctag acttatatag acactaatat agacaatagt ttatactgct 4500
atctatacaa gtatagacat tatctaatca tggcagacaa aactctagcc acttttcgta 4560
ttgactccga agaatgggag tcttttaaaa accttgctag ttctgaaagt tccaacgcct 4620
cagcactgtt aacagaattt gttcgttggt atttggcagg taacaggttt aatactccca 4680
cttctcacac tcccacccat ctagacacat ccctcgaaca gcgtatagac aatattgaac 4740
aacgtctaga taaagtcaca actaataatc tagacaatat agatgaattt atagacaagc 4800
gtatagaaga taatctagca acacgtctag acaaacttca atcgcaactg gaggaactgc 4860
ggggaaaatc gaaagcccgg tagttcaggc agaaggacaa gctaccgggc aagacagaaa 4920
gaatatagac aatagtatag acaatctaga caaattggag gcaacccgcg atcgcaccct 4980
caataagcta aaaatgggta ggcagtcagc cgcccgggaaa gccatcgacg cgtttatcaa 5040
agagttgctt tcttcaggag acaacataag ctgaagttat caaaattctg tccttacgtc 5100
gaaagcctga ttttaccgtg caacgattga taagcttggc taaactagca ctggctttca 5160
acagaaagca tacgaagaat caatagatat agccaccaat tccacaaaat gcagataacg 5220

-continued

```
tgtagagtat tggaatgctt aatctgtaag ggttatgaag gttaacggca acggacgagc   5280
caaaatactc acctccgacg aactcaggcg actgtttagc gacggattca ccacaccgcg   5340
cgatcgcgtt ttgtttggca tctgtctatt caccggttgc cgcgttagtg aagctctagc   5400
actccaaaca acggacatta aaggcgaaac actaaccttt aggaagtcta ccaccaaagg   5460
gaaactcaaa acccgcgtgg ttgacatcca gccaggacta gccgcactca tggctgacta   5520
tcaccccaaa ccgggaaccc tgttccctgg catgagggga gtcagcgata ggctcacgcg   5580
atacgcggcg gataaaatct tgcgcgatgc agccaaaaga atcgggctag aaggcatcag   5640
tacccacagt ttccgccgta ctgccctcaa ccaaatgtct agcgccggta tcccgttgcg   5700
acacattcaa gagatatccg gtcacaatga ccttggcaca ctgcaacgct atcttgaagt   5760
tacacccgaa cagcgacgca aagctgtatc cgtgattggc ttctaatgta cgccaacgct   5820
gtttagaccc ctatgggtgc taaaaaaaga cgcagcctaa acacacgctc tacacttgag   5880
gatactttta aagtatccat cggttctaga actctgcaca cgttccggac tttggaaacg   5940
ttatacccttt ccctgtgttg cagaatgctg caatatttct tcgacaagtt aacttgtgac   6000
tggtttaata ttttctcaaa ttgccccaaa acaacacgcc taaatcctta gacgtttctg   6060
tggaaaccta ttaggttttt atcgccgttg ttttagtggt aaacccaaag ggtttgtata   6120
ttcttgtatg aagttcgact ctgagggtta agaagaatgg ctcgccgaat tttttacaag   6180
tggaaaccga ttaaaggtta agggtcaatc gggacgatga atattttcta attgtgacct   6240
tctccatcta ataagctttc tttggggtta aggtcgaaga aagtactacg catgatctgc   6300
atacgatctc tattgccaaa aagccgcgac cctataggct ctcggtcatg ctgcactagt   6360
tcgtgtcgat cactatactg gttgccgcag catttcacgc taaaaaaaaa ttcttaaaaa   6420
tgtccttcat atctcgccag agtggcaacc tattacaaaa cggttgccta cccgaccggc   6480
tcgattttcg ctgaagtggc actgtgacag tttgaaatgg tacttccgcc gtgctgctga   6540
catcgttgtt agggtgaatt gttcgcggta gatgttgcac cgattcatga acaccttgtc   6600
acccactttg aataatcgac cgtcaaattc agtcgcgtca atttggtaag tgttgggctg   6660
tctctttttg gctccagggg caatgccatc agaaaacaca accgcgtcac ccataacttg   6720
ataaccgata tcagttttgg ttccagtgaa agcccaaaat tcagacgcgt cattattccg   6780
agcgtgccgg agttgattgt actcaatttt ggcttggcaa agttgacggc gattcatgcc   6840
cagctgcttt tgatgtcgtc gcactgtgcg cttgtgaata cccaactcac agctgacagc   6900
tttttgagat gtaccatagt ggatgaaact ttttgagacg aatatccgcg acgaactaat   6960
gtgaagtaca caaggtactt ccccctctgg cgatttaaga gaggattgcc ttgtgtcctt   7020
cactagctcg ttcgggtgtg gcgctccaaa aagttttctg tactctggtt taagttgtct   7080
gttggccgca tagcggctct tttgttgaaa gctttgtgtg actatgccag tggtcagtga   7140
gcgtaaatcg cttaacactt ggactaaagg cactactgca acatcacccc atctttttaa   7200
atttaggttg taacaaactt gaaacatacc gcccaagtag acggttatca ttcctgcttt   7260
aattttgtag cggcggaatg ctcctatttt ttttccatcc tgtaaccaac ggtaaacaga   7320
cttatcacta caatctaaga acgtctgtac tacaggcaat ggcaatgtta aatgaccaga   7380
cccatcctta tcaagcgctc gacacaaata ccacaaccgc gcacaaggtt ctcgaccaat   7440
gcgagtgtgt accctgaccg tgtaagtgcc aagaattatt tcagtttgta gttcccttgt   7500
aagcagggtt agtgatacat ttgtatttaa gctttctggg ctgatcattt ggaaatgtct   7560
```

-continued

```
cagtccagta cctattgaat gttatttgct taacctgaag ctaaataaaa cttgttaact   7620
acacccatta attgataaat tcaaagcacg ttttttctgt ttggtgtttg gtgtggtaac   7680
aattctgtgt atgtgtgttt tatttagctt cggttaagta gcataacaac ccccaagcac   7740
tgaacttttt ttaataggta atttaaactt tgcctatcgg caaaattttc aatcaattgt   7800
acgccaaagt gttgcatgat caacgtttga cttatttttg tatttactaa atactgaatt   7860
tcgccgtgac gctttttaca gatggaaatt cacggcaaaa tgttttttgc taactttgct   7920
atgtaaaaca agaaacttgg cactcggtta ttactaaata aactggtaaa aaataaccat   7980
tagaaccaaa aagaacgaaa accagtacac ccttgccagt tttcaagctt ttgctatgac   8040
gactctaata atcgggttta acaccattcc gctttgagaa aattatcctt gtacagcaag   8100
taacagtcaa tgctaaaccg caccgctaca aatccttaag tttttccagt agcgatttac   8160
cttcttggta acgcccgcct tgatagccca aaatttcttt aatcacctta ctttctgaaa   8220
aacccgcttc cagacaggct tttaccactt ttgctagggt ttcatctctt ggttctggga   8280
gggatgaaac gggctgtaat gcttgttctg aggtcggttg agccgtttgg agtggctgaa   8340
aactggttac agactgtaac cggggcataa ccattttgta actgcttaca tctggtaact   8400
gacacggcat atcatccacc atgcagcgat atttccccga ctttaaccac tccacaaggg   8460
caaggtcttt taaggacttg gcgtggctaa ctgcaaactt acccaggcgt aacatcctaa   8520
aacacttacg gacaccgcct tcaccctcga tacctaaggt cttgacatta tcatcttgag   8580
tcagcccaat aacaaaacgc ttgggcttgc ggccgcgcct ggcgtgtttg atgagccatt   8640
cggttgctat ctcgacttca tctctcagca gtggcagttc ttcagcaatt aaaacgcttt   8700
cttttcctgc tagtgcctta tccccagact caccccgtag ctcaatccgg cgctgcaatt   8760
cctccaggtc agcagccatg cccgactgta tagcctcaaa gtcaccacgg cggccaatga   8820
catttaaccc cgtccactcg tccggtgcag cgtcagcgtc atagactgtc acctcacccc   8880
cgacttgata agcaagccat tgggctatgg tgcttttgcc agttcccgta tccccaacta   8940
ttaaacagtg cttaccagac agagcttgca tcaagtcggt gatgattccc tctggttcga   9000
ccgcaagggt gacggcggta gtgtcaatga tagccgcgcc gtaagtgcca gcatagggca   9060
attggtcgta aactttgacc aagttgtata cagactgtct acaccacttc accactgtta   9120
acgctgtttg caaagcgtaa gacgtggcat caaataaaaa tatgctggca ctaaaagtta   9180
atcgccccaa tccccacagt aaaaacctgc ctagctgttg acgactaggc aagtgcattt   9240
caatccagtc atttgccata aatcaccccg tctttaaagc cttgcagttg agcgcgacag   9300
gtatttaact gtgcttgtaa ctctgtttgc tggttttgat accacagact gacggcggcg   9360
gccgccagtc ctaaaaatag aaactggcga tcgctcatta ttgacttact ccctgttgat   9420
tagcgtggta gtgagtcata gccgcattga ccgcttcttg ggcttggggt gttctgccaa   9480
gattgggttt tgtagggtca tcgttggcta cgactaagga cgcttgttcg gctatcgctt   9540
gcgggacacc aactttagtt aactctgtca aggatacttg gtaaagtcgc tcgttcatta   9600
gccgattctc cggtacataa aactgttgct ggcagtccct tcattggcga cgagttcttc   9660
agccggagta tcagcgataa tgtcagccca gccggtgaca ttattattaa taatgttttg   9720
ttcggcaatt gcacccaagc caggacgcgc cgtttcaaac tcagagatga cttgctgctc   9780
tttctcggtg agtggtctat ctgtcatgat aattatgtcc ttcattatgt aggcgattcc   9840
agtgggtgtt tacgaggcag tccacaggaa tcagtgcgat tcacctttaa ggtgaatcgt   9900
catcaaaaaa tcactcggta gcaacgaccc gaaccgacca ggattgattt cccggttctc   9960
```

```
agttcgcagg cttttgagcg cgtcaccttg accattgggt aactgccatc agccgataag  10020
ctaaacgggc tgtatagcgg taaagcatcc cacacagtcg ggctggcatc aactttgcag  10080
gaatagctca cgtcactcat ctcactcgcg cctgggttgg atggcagcga aggcagatta  10140
cgacgcagtt ttttactggc acttttaccc gcattaaaaa cgggtacagt gccattgttg  10200
acggtctgta cttcggtcat atactcggtg tacacttaat acactctata ctattactgc  10260
cgattagtac atttgtcaat cactctttgc acaaggtgta tgatatggac tcaggagtac  10320
accaaacgtc atgccaacca ataaagggag aatagcagtc actctagaag ctgaaattta  10380
ccaatggatt gctaaccgag cgtctgagga aggaagaccg ttggctaatc ttgccgcttt  10440
cttactcaca cgagttgtta aagaacaaat ggaacaagaa gccaaggaca accaagacaa  10500
gcagggggca gcatgagcga agacagacta gccagaatag aagctgcgtt agacagccaa  10560
gttgcagtga atgccgacct ccgcacatcg gttacagaac tccgcgcaac cgcagaagca  10620
ttgttgcaaa cagttcaaat ccatcagcag aactttgaaa ttcttaccgc taggcaatta  10680
caaaccgaag cacggcttga tgagtaccaa cgtaccacta gcgcggcact cgacagaatt  10740
ggcgcggtct tagactacct cgttaggcag caaaacggtt gaggtgaggg atgagcgatg  10800
actatctaga cggatatccc gcaagaggcc ctttcgtctt caagaattaa ttgtcgacga  10860
tataaagttc aggagcaatt taccccgcca gccctttttt ccttctcatc tccactatta  10920
gacgaggcat cctccaccta cagattaagt attcgcttct ttcagatgct cggatacttc  10980
ttggtaaagg ctcataacat ggttgtccgc caaactgtaa tatatattcc gaccttcacg  11040
atagtattta accaaccgtt gcgatcgcaa aattcgcagt tggtgcgata ccgcagactc  11100
acccattttt acggctgcgg ctaaatcaca aacacacaat tctcgattaa ctaaagcaga  11160
catcaatcgc aaacgacttg gatcggctaa cgcattaaaa aactctgcca tctgttgcgc  11220
tttttcaaca gaaataattt ctggttgcac ctggcgcacc cgatcaagat gaaccaaatg  11280
agcatcacaa ctgggcgtgt cttcagactg aagagactcc gctttgggca atgttggttt  11340
tttcataagt agagatagtg ttgggagtag aggatgaatt caaaatagac agaataataa  11400
tcattctaac atctgaatat atattcagat attgagataa ctatgttaaa cttcaaagga  11460
gttattcttc agcgacttac tgaaacggct atgaattctt atactgtcgg tacctattta  11520
gcggagcggc ttgtccagat tggtctcaag catcacttcg cagtcgcggg cgactacaac  11580
ctcgtccttc ttgacaacct gcttttgaac aaaaacatgg agcaggttta ttgctgtaac  11640
gaactgaact gcggtttcag tgcagaaggt tatgctcgtg ccaaaggcgc agcagcagcc  11700
gtcgttacct acagcgtcgg tgcgctttcc gcatttgatg ctatcggtgg cgcctatgca  11760
gaaaaccttc cggttatcct gatctccggt gctccgaaca acaatgatca cgctgctggt  11820
cacgtgttgc atcacgctct tggcaaaacc gactatcact atcagttgga aatggccaag  11880
aacatcacgg ccgcagctga agcgatttac accccagaag aagctccggc taaaatcgat  11940
cacgtgatta aaactgctct tcgtgagaag aagccggttt atctcgaaat cgcttgcaac  12000
attgcttcca tgccctgcgc cgctcctgga ccggcaagcg cattgttcaa tgacgaagcc  12060
agcgacgaag cttctttgaa tgcagcggtt gaagaaaccc tgaaattcat cgccaaccgc  12120
gacaaagttg ccgtcctcgt cggcagcaag ctgcgcgcag ctggtgctga agaagctgct  12180
gtcaaatttg ctgatgctct cggtggcgca gttgctacca tggctgctgc aaaaagcttc  12240
ttcccagaag aaaacccgca ttacatcggt acctcatggg gtgaagtcag ctatccgggc  12300
```

-continued

```
gttgaaaaga cgatgaaaga agccgatgcg gttatcgctc tggctcctgt cttcaacgac  12360
tactccacca ctggttggac ggatattcct gatcctaaga aactggttct cgctgaaccg  12420
cgttctgtcg tcgttaacgg cgttcgcttc cccagcgttc atctgaaaga ctatctgacc  12480
cgtttggctc agaaagtttc caagaaaacc ggtgctttgg acttcttcaa atccctcaat  12540
gcaggtgaac tgaagaaagc cgctccggct gatccgagtg ctccgttggt caacgcagaa  12600
atcgcccgtc aggtcgaagc tcttctgacc ccgaacacga cggttattgc tgaaaccggt  12660
gactcttggt tcaatgctca gcgcatgaag ctcccgaacg gtgctcgcgt tgaatatgaa  12720
atgcagtggg gtcacatcgg ttggtccgtt cctgccgcct tcggttatgc cgtcggtgct  12780
ccggaacgtc gcaacatcct catggttggt gatggttcct tccagctgac ggctcaggaa  12840
gtcgctcaga tggttcgcct gaaactgccg gttatcatct tcttgatcaa taactatggt  12900
tacaccatcg aagttatgat ccatgatggt ccgtacaaca acatcaagaa ctgggattat  12960
gccggtctga tggaagtgtt caacggtaac ggtggttatg acagcggtgc tggtaaaggc  13020
ctgaaggcta aaaccggtgg cgaactggca gaagctatca aggttgctct ggcaaacacc  13080
gacggcccaa ccctgatcga atgcttcatc ggtcgtgaag actgcactga agaattggtc  13140
aaatggggta agcgcgttgc tgccgccaac agccgtaagc ctgttaacaa gctcctctag  13200
tttttgggga tcaattcgag ctctctggat aaaactaata aactctatta cccatgatta  13260
aagcctacgc tgccctggaa gccaacggaa aactccaacc ctttgaatac gaccccggtg  13320
ccctgggtgc taatgaggtg gagattgagg tgcagtattg tggggtgtgc cacagtgatt  13380
tgtccatgat taataacgaa tggggcattt ccaattaccc cctagtgccg ggtcatgagg  13440
tggtgggtac tgtggccgcc atgggcgaag gggtgaacca tgttgaggtg gggggattag  13500
tggggctggg ttggcattcg ggctactgca tgacctgcca tagttgttta tctggctacc  13560
acaacctttg tgccacggcg gaatcgacca ttgtgggcca ctacggtggc tttggcgatc  13620
gggttcgggc caagggagtc agcgtggtga aattacctaa aggcattgac ctagccagtg  13680
ccgggcccct tttctgtgga ggaattaccg ttttcagtcc tatggtggaa ctgagtttaa  13740
agcccactgc aaaagtggca gtgatcggca ttgggggctt gggccattta gcggtgcaat  13800
ttctccgggc ctggggctgt gaagtgactg cctttacctc cagtgccagg aagcaaacgg  13860
aagtgttgga attgggcgct caccacatac tagattccac caatccagag gcgatcgcca  13920
gtgcggaagg caaatttgac tatattatct ccactgtgaa cctgaagctt gactggaact  13980
tatacatcag caccctggcg ccccagggac atttccactt tgttggggtg gtgttggagc  14040
ctttggatct aaatcttttt cccctttttga tgggacaacg ctccgtttct gcctccccag  14100
tgggtagtcc cgccaccatt gccaccatgt tggactttgc tgtgcgccat gacattaaac  14160
ccgtggtgga acaatttagc tttgatcaga tcaacgaggc gatcgcccat ctagaaagcg  14220
gcaaagccca ttatcgggta gtgctcagcc atagtaaaaa ttagctctgc aaaggttgct  14280
tctgggtccg tggaatggtc aaacggagtc gatctcagtt ttgatacgct ctatctggaa  14340
agcttgacat tcgatctgca                                              14360
```

<210> SEQ ID NO 5
<211> LENGTH: 14683
<212> TYPE: DNA
<213> ORGANISM: Artificial Sequence
<220> FEATURE:
<223> OTHER INFORMATION: plasmid TK261

<400> SEQUENCE: 5

-continued

```
gaaggctaaa accggtggcg aactggcaga agctatcaag gttgctctgg caaacaccga     60
cggcccaacc ctgatcgaat gcttcatcgg tcgtgaagac tgcactgaag aattggtcaa    120
atggggtaag cgcgttgctg ccgccaacag ccgtaagcct gttaacaagc tcctctagtt    180
tcaagtttca tcccgacccc ctcagggtcg ggattttttt attgagctca ctagtcgatc    240
gacattgcca taagtaaagg catcccctgc gtgataagat taccttcagt ttatggagga    300
ctgaccatat gattaaagcc tacgctgccc tggaagccaa cggaaaactc caaccctttg    360
aatacgaccc cggtgccctg ggtgctaatg aggtggagat tgaggtgcag tattgtgggg    420
tgtgccacag tgatttgtcc atgattaata acgaatgggg catttccaat taccccctag    480
tgccgggtca tgaggtggtg ggtactgtgg ccgccatggg cgaaggggtg aaccatgttg    540
aggtgggggga tttagtgggg ctgggttggc attcgggcta ctgcatgacc tgccatagtt    600
gtttatctgg ctaccacaac ctttgtgcca cggcggaatc gaccattgtg ggccactacg    660
gtggctttgg cgatcgggtt cgggccaagg gagtcagcgt ggtgaaatta cctaaaggca    720
ttgacctagc cagtgccggg ccccttttct gtggaggaat taccgttttc agtcctatgg    780
tggaactgag tttaaagccc actgcaaaag tggcagtgat cggcattggg ggcttgggcc    840
atttagcggt gcaatttctc cgggcctggg gctgtgaagt gactgccttt acctccagtg    900
ccaggaagca aacggaagtg ttggaattgg gcgctcacca catactagat tccaccaatc    960
cagaggcgat cgccagtgcg gaaggcaaat ttgactatat tatctccact gtgaacctga   1020
agcttgactg gaacttatac atcagcaccc tggcgcccca gggacatttc cactttgttg   1080
ggtggtgtt ggagcctttg gatctaaatc tttttcccct tttgatggga caacgctccg   1140
tttctgcctc cccagtgggt agtcccgcca ccattgccac catgttggac tttgctgtgc   1200
gccatgacat taaacccgtg gtggaacaat ttagctttga tcagatcaac gaggcgatcg   1260
cccatctaga aagcggcaaa gcccattatc gggtagtgct cagccatagt aaaaattagc   1320
tctgcaaagg ttgcttctgg gtccgtggaa cgctcggttg ccgccgggcg ttttttattc   1380
ctgcaggccc cccgggggc tcgactctag aggatccgat aacatcaccg tcgttatcgt   1440
cgctttagaa taacgttccc aaaatagctc atttccaact ggcaactcac aaccaaaaac   1500
cgcattttta gtaaatatac tcagcaattt gttcaacctg agcatttttc ccatttgcaa   1560
cttgatacaa atatttttag cagcaaattt tcctactgcc agcttagttt acataaattt   1620
tgtctgttga catcttgcac acaataaggt atggcgcata taatgcgata ttactaccat   1680
taatttacta cctagtcatt aacgtctccc gccagagaac agttttgaat aggtagtcaa   1740
ttttaggtat tgaacctgct gtaaatttat taaatcgatg aatttccccg aaatctgctc   1800
tagcagactt gggttatata ccagtaggct caggtgcaaa acaacaaagc acaaatttta   1860
cccattaagg atataggcaa tctgtcaaat agttgttatc tttcttaata cagaggaata   1920
atcaacaata tggggcaggt actaactaaa gtcctatgcc tgtggggctt ctgtaaccga   1980
cataaccttt acgcgttgtc ttttaggagt ctgttatgaa cggtaccagt aaaggagaag   2040
aactattcac tggagttgtc ccaattcttg ttgaattaga tggtgatgtt aatgggcaca   2100
aattttctgt cagtggagag ggtgaaggtg atgcaacata cggaaaactt acccttaaat   2160
ttatttgcac tactggaaaa ctacctgttc catggccaac acttgtcact actttcgcgt   2220
atggtcttca atgctttgcg agatacccag atcatatgaa acagcatgac tttttcaaga   2280
gtgccatgcc cgaaggttat gtacaggaaa gaactatatt tttcaaagat gacgggaact   2340
```

-continued

```
acaagacacg tgctgaagtc aagtttgaag gtgataccct tgttaataga atcgagttaa   2400
aaggtattga ttttaaagaa gatggaaaca ttcttggaca caaattggaa tacaactata   2460
actcacacaa tgtatacatc atggcagaca aacaaaagaa tggaatcaaa gttaacttca   2520
aaattagaca caacattgaa gatggaagcg ttcaactagc agaccattat caacaaaata   2580
ctccaattgg cgatggccct gtccttttac cagacaacca ttacctgtcc acacaatctg   2640
ccctttcgaa agatcccaac gaaaagagag accacatggt ccttcttgag tttgtaacag   2700
ctgctgggat tacacatggc atggatgaac tatacaaata agagctcgaa ttgatccttt   2760
ttgataatct catgaccaaa atcccttaac gtgagttttc gttccactga gcgtcagacc   2820
ccgtagaaaa gatcaaagga tcttcttgag atcctttttt tctgcgcgta atctgctgct   2880
tgcaaacaaa aaaaccaccg ctaccagcgg tggtttgttt gccggatcaa gagctaccaa   2940
ctctttttcc gaaggtaact ggcttcagca gagcgcagat accaaatact gtccttctag   3000
tgtagccgta gttaggccac cacttcaaga actctgtagc accgcctaca tacctcgctc   3060
tgctaatcct gttaccagtg gctgctgcca gtggcgataa gtcgtgtctt accgggttgg   3120
actcaagacg atagttaccg gataaggcgc agcggtcggg ctgaacgggg ggttcgtgca   3180
cacagcccag cttggagcga acgacctaca ccgaactgag atacctacag cgtgagctat   3240
gagaaagcgc cacgcttccc gaagggagaa aggcggacag gtatccggta agcggcaggg   3300
tcggaacagg agagcgcacg agggagcttc caggggggaaa cgcctggtat ctttatagtc   3360
ctgtcgggtt tcgccacctc tgacttgagc gtcgattttt gtgatgctcg tcaggggggc   3420
ggagcctatg gaaaaacgcc agcaacgcgg cctttttacg gttcctggcc ttttgctggc   3480
cttttgctca catgttcttt cctgcgttat cccctgattc tgtggataac cgtattaccg   3540
cctttgagtg agctgatacc gctcgccgca gccgaacgac cgagcgcagc gagtcagtga   3600
gcgaggaagc ggaagagcgc ctgatgcggt attttctcct tacgcatctg tgcggtattt   3660
cacaccgcat atggtgcact ctcagtacaa tctgctctga tgccgcatag ttaagccagt   3720
atacactccg ctatcgctac gtgactgggt catggctgcg ccccgacacc cgccaacacc   3780
cgctgacgcg ccctgacggg cttgtctgct cccggcatcc gcttacagac aagctgtgac   3840
cgtctccggg agctgcatgt gtcagaggtt ttcaccgtca tcaccgaaac gcgcgaggca   3900
gctgcggtaa agctcatcag cgtggtcgtg aagcgattca cagatgtctg cctgttcatc   3960
cgcgtccagc tcgttgagtt tctccagaag cgttaatgtc tggcttctga taaagcgggc   4020
ctgccaccat acccacgccg aaacaagcgc tcatgagccc gaagtggcga gcccgatctt   4080
ccccatcggt gatgtcggcg atataggcgc cagcaaccgc acctgtggcg ccggtgatgc   4140
ccgaagaact ccagcatgag atccccgcgc tggaggatca tccagccggc gtcccggaaa   4200
acgattccga agcccaacct ttcatagaag gcggcggtgg aatcgaaatc tcgtgatggc   4260
aggttgggcg tcgcttggtc ggtcatttcg aaccccagag tcccgctcag aagaactcgt   4320
caagaaggcg atagaaggcg atgcgctgcg aatcgggagc ggcgataccg taaagcacga   4380
ggaagcggtc agcccattcg ccgccaagct cttcagcaat atcacgggta gccaacgcta   4440
tgtcctgata gcggtccgcc acacccagcc ggccacagtc gatgaatcca gaaaagcggc   4500
cattttccac catgatattc ggcaagcagg catcgccatg ggtcacgacg agatcatcgc   4560
cgtcgggcat gcgcgccttg agcctggcga acagttcggc tggcgcgagc ccctgatgct   4620
cttcgtccag atcatcctga tcgacaagac cggcttccat ccgagtacgt gctcgctcga   4680
tgcgatgttt cgcttggtgg tcgaatgggc aggtagccgg atcaagcgta tgcagccgcc   4740
```

-continued

```
gcattgcatc agccatgatg gatactttct cggcaggagc aaggtgagat gacaggagat   4800
cctgccccgg cacttcgccc aatagcagcc agtcccttcc cgcttcagtg acaacgtcga   4860
gcacagctgc gcaaggaacg cccgtcgtgg ccagccacga tagccgcgct gcctcgtcct   4920
gcagttcatt cagggcaccg gacaggtcgg tcttgacaaa aagaaccggg cgcccctgcg   4980
ctgacagccg gaacacggcg gcatcagagc agccgattgt ctgttgtgcc cagtcatagc   5040
cgaatagcct ctccacccaa gcggccggag aacctgcgtg caatccatct tgttcaatca   5100
tgcgaaacga tcctcatcct gtctcttgat cagatcttga tcccctgcgc catcagatcc   5160
ttggcggcaa gaaagccatc cagtttactt tgcagggctt cccaacctta ccagagggcg   5220
ccccagctgg caattccggt tcgcttgctg tccataaaac cgcccagtct agctatcgcc   5280
atgtaagccc actgcaagct acctgctttc tctttgcgct tgcgttttcc cttgtccaga   5340
tagcccagta gctgacattc atccggggtc agcaccgttt ctgcggactg gctttctacg   5400
tgttccgctt cctttagcag cccttgcgcc ctgagtgctt gcggcagcgt gaagctttct   5460
ctgagctgta acagcctgac cgcaacaaac gagaggatcg agaccatccg ctccagatta   5520
tccggctcct ccatgcgttg cctctcggct cctgctccgg ttttccatgc cttatggaac   5580
tcctcgatcc gccagcgatg ggtataaatg tcgatgacgc gcaaggcttg ggctagcgac   5640
tcgaccggtt cgctggtcag caacaaccat ttcaacgggg tctcaccctt gggcgggtta   5700
atctcctcgg ccagcaccgc gttgagcgtg atattcccct gttttagcgt gatgcgccca   5760
ctgcgcatag aaattgcatc aacgcatata gcgctagcag cacgccatag tgactggcga   5820
tgctgtcgga atggacgata tctagactta tatagacact aatatagaca atagtttata   5880
ctgctatcta tacaagtata gacattatct aatcatggca gacaaaactc tagccacttt   5940
tcgtattgac tccgaagaat gggagtcttt taaaaacctt gctagttctg aaagttccaa   6000
cgcctcagca ctgttaacag aatttgttcg ttggtatttg gcaggtaaca ggtttaatac   6060
tcccacttct cacactccca cccatctaga cacatccctc gaacagcgta tagacaatat   6120
tgaacaacgt ctagataaag tcacaactaa taatctagac aatatagatg aatttataga   6180
caagcgtata gaagataatc tagcaacacg tctagacaaa cttcaatcgc aactggagga   6240
actgcgggga aaatcgaaag cccggtagtt caggcagaag gacaagctac cgggcaagac   6300
agaaagaata tagacaatag tatagacaat ctagacaaat tggaggcaac ccgcgatcgc   6360
accctcaata agctaaaaat gggtaggcag tcagccgccg ggaaagccat cgacgcgttt   6420
atcaaagagt tgctttcttc aggagacaac ataagctgaa gttatcaaaa ttctgtcctt   6480
acgtcgaaag cctgatttta ccgtgcaacg attgataagc ttggctaaac tagcactggc   6540
tttcaacaga aagcatacga agaatcaata gatatagcca ccaattccac aaaatgcaga   6600
taacgtgtag agtattggaa tgcttaatct gtaagggtta tgaaggttaa cggcaacgga   6660
cgagccaaaa tactcacctc cgacgaactc aggcgactgt ttagcgacgg attcaccaca   6720
ccgcgcgatc gcgttttgtt tggcatctgt ctattcaccg gttgccgcgt tagtgaagct   6780
ctagcactcc aaacaacgga cattaaaggc gaaacactaa cctttaggaa gtctaccacc   6840
aaagggaaac tcaaaacccg cgtggttgac atccagccag gactagccgc actcatggct   6900
gactatcacc ccaaaccggg aaccctgttc cctggcatga ggggagtcag cgataggctc   6960
acgcgatacg cggcggataa aatcttgcgc gatgcagcca aaagaatcgg gctagaaggc   7020
atcagtaccc acagtttccg ccgtactgcc ctcaaccaaa tgtctagcgc cggtatcccg   7080
```

-continued

```
ttgcgacaca ttcaagagat atccggtcac aatgaccttg gcacactgca acgctatctt   7140
gaagttacac ccgaacagcg acgcaaagct gtatccgtga ttggcttcta atgtacgcca   7200
acgctgttta gacccctatg ggtgctaaaa aaagacgcag cctaaacaca cgctctacac   7260
ttgaggatac ttttaaagta tccatcggtt ctagaactct gcacacgttc cggactttgg   7320
aaacgttata cctttccctg tgttgcagaa tgctgcaata tttcttcgac aagttaactt   7380
gtgactggtt taatattttc tcaaattgcc ccaaaacaac acgcctaaat ccttagacgt   7440
ttctgtggaa acctattagg tttttatcgc cgttgtttta gtggtaaacc caaagggttt   7500
gtatattctt gtatgaagtt cgactctgag ggttaagaag aatggctcgc cgaatttttt   7560
acaagtggaa accgattaaa ggttaagggt caatcgggac gatgaatatt ttctaattgt   7620
gaccttctcc atctaataag ctttctttgg ggttaaggtc gaagaaagta ctacgcatga   7680
tctgcatacg atctctattg ccaaaaagcc gcgaccctat aggctctcgg tcatgctgca   7740
ctagttcgtg tcgatcacta tactggttgc cgcagcattt cacgctaaaa aaaaattctt   7800
aaaaatgtcc ttcatatctc gccagagtgg caacctatta caaaacggtt gcctacccga   7860
ccggctcgat tttcgctgaa gtggcactgt gacagtttga aatggtactt ccgccgtgct   7920
gctgacatcg ttgttagggt gaattgttcg cggtagatgt tgcaccgatt catgaacacc   7980
ttgtcaccca ctttgaataa tcgaccgtca aattcagtcg cgtcaatttg gtaagtgttg   8040
ggctgtctct ttttggctcc aggggcaatg ccatcagaaa acacaaccgc gtcacccata   8100
acttgataac cgatatcagt tttggttcca gtgaaagccc aaaattcaga cgcgtcatta   8160
ttccgagcgt gccggagttg attgtactca attttggctt ggcaaagttg acggcgattc   8220
atgcccagct gcttttgatg tcgtcgcact gtgcgcttgt gaatacccaa ctcacagctg   8280
acagcttttt gagatgtacc atagtggatg aaactttttg agacgaatat ccgcgacgaa   8340
ctaatgtgaa gtacacaagg tacttccccc tctggcgatt taagagagga ttgccttgtg   8400
tccttcacta gctcgttcgg gtgtggcgct ccaaaaagtt ttctgtactc tggtttaagt   8460
tgtctgttgg ccgcatagcg gctcttttgt tgaaagcttt gtgtgactat gccagtggtc   8520
agtgagcgta aatcgcttaa cacttggact aaaggcacta ctgcaacatc accccatctt   8580
tttaaattta ggttgtaaca aacttgaaac ataccgccca agtagacggt tatcattcct   8640
gctttaattt tgtagcggcg gaatgctcct atttttttc catcctgtaa ccaacggtaa   8700
acagacttat cactacaatc taagaacgtc tgtactacag gcaatggcaa tgttaaatga   8760
ccagacccat ccttatcaag cgctcgacac aaataccaca accgcgcaca aggttctcga   8820
ccaatgcgag tgtgtaccct gaccgtgtaa gtgccaagaa ttatttcagt ttgtagttcc   8880
cttgtaagca gggttagtga tacatttgta tttaagcttt ctgggctgat catttggaaa   8940
tgtctcagtc cagtacctat tgaatgttat ttgcttaacc tgaagctaaa taaaacttgt   9000
taactacacc cattaattga taaattcaaa gcacgttttt tctgtttggt gtttggtgtg   9060
gtaacaattc tgtgtatgtg tgttttattt agcttcggtt aagtagcata acaaccccca   9120
agcactgaac tttttttaat aggtaattta aactttgcct atcggcaaaa ttttcaatca   9180
attgtacgcc aaagtgttgc atgatcaacg tttgacttat ttttgtattt actaaatact   9240
gaatttcgcc gtgacgcttt ttacagatgg aaattcacgg caaaatgttt tttgctaact   9300
ttgctatgta aaacaagaaa cttggcactc ggttattact aaataaactg gtaaaaaata   9360
accattagaa ccaaaaagaa cgaaaaccag tacacccttg ccagttttca agcttttgct   9420
atgacgactc taataatcgg gtttaacacc attccgcttt gagaaaatta tccttgtaca   9480
```

```
gcaagtaaca gtcaatgcta aaccgcaccg ctacaaatcc ttaagttttt ccagtagcga   9540
tttaccttct tggtaacgcc cgccttgata gcccaaaatt tctttaatca ccttactttc   9600
tgaaaaaccc gcttccagac aggcttttac cacttttgct agggtttcat ctcttggttc   9660
tgggagggat gaaacgggct gtaatgcttg ttctgaggtc ggttgagccg tttggagtgg   9720
ctgaaaactg gttacagact gtaaccgggg cataaccatt ttgtaactgc ttacatctgg   9780
taactgacac ggcatatcat ccaccatgca gcgatatttc cccgacttta accactccac   9840
aagggcaagg tcttttaagg acttggcgtg gctaactgca aacttaccca ggcgtaacat   9900
cctaaaacac ttacggacac cgccttcacc ctcgatacct aaggtcttga cattatcatc   9960
ttgagtcagc ccaataacaa aacgcttggg cttgcggccg cgcctggcgt gtttgatgag  10020
ccattcggtt gctatctcga cttcatctct cagcagtggc agttcttcag caattaaaac  10080
gctttctttt cctgctagtg ccttatcccc agactcaccc cgtagctcaa tccggcgctg  10140
caattcctcc aggtcagcag ccatgcccga ctgtatagcc tcaaagtcac cacggcggcc  10200
aatgacattt aaccccgtcc actcgtccgg tgcagcgtca gcgtcataga ctgtcacctc  10260
acccccgact tgataagcaa gccattgggc tatggtgctt ttgccagttc ccgtatcccc  10320
aactattaaa cagtgcttac cagacagagc ttgcatcaag tcggtgatga ttccctctgg  10380
ttcgaccgca agggtgacgg cggtagtgtc aatgatagcc gcgccgtaag tgccagcata  10440
gggcaattgg tcgtaaactt tgaccaagtt gtatacagac tgtctacacc acttcaccac  10500
tgttaacgct gtttgcaaag cgtaagacgt ggcatcaaat aaaaatatgc tggcactaaa  10560
agttaatcgc cccaatcccc acagtaaaaa cctgcctagc tgttgacgac taggcaagtg  10620
catttcaatc cagtcatttg ccataaatca ccccgtcttt aaagccttgc agttgagcgc  10680
gacaggtatt taactgtgct tgtaactctg tttgctggtt ttgataccac agactgacgg  10740
cggcggccgc cagtcctaaa aatagaaact ggcgatcgct cattattgac ttactccctg  10800
ttgattagcg tggtagtgag tcatagccgc attgaccgct tcttgggctt ggggtgttct  10860
gccaagattg ggttttgtag ggtcatcgtt ggctacgact aaggacgctt gttcggctat  10920
cgcttgcggg acaccaactt tagttaactc tgtcaaggat acttggtaaa gtcgctcgtt  10980
cattagccga ttctccggta cataaaactg ttgctggcag tcccttcatt ggcgacgagt  11040
tcttcagccg gagtatcagc gataatgtca gcccagccgg tgacattatt attaataatg  11100
ttttgttcgg caattgcacc caagccagga cgcgccgttt caaactcaga gatgacttgc  11160
tgctctttct cggtgagtgg tctatctgtc atgataatta tgtccttcat tatgtaggcg  11220
attccagtgg gtgtttacga ggcagtccac aggaatcagt gcgattcacc tttaaggtga  11280
atcgtcatca aaaaatcact cggtagcaac gacccgaacc gaccaggatt gatttcccgg  11340
ttctcagttc gcaggctttt gagcgcgtca ccttgaccat tgggtaactg ccatcagccg  11400
ataagctaaa cgggctgtat agcggtaaag catcccacac agtcgggctg gcatcaactt  11460
tgcaggaata gctcacgtca ctcatctcac tcgcgcctgg gttggatggc agcgaaggca  11520
gattacgacg cagtttttta ctggcacttt tacccgcatt aaaaacgggt acagtgccat  11580
tgttgacggt ctgtacttcg gtcatatact cggtgtacac ttaatacact ctatactatt  11640
actgccgatt agtacatttg tcaatcactc tttgcacaag gtgtatgata tggactcagg  11700
agtacaccaa acgtcatgcc aaccaataaa gggagaatag cagtcactct agaagctgaa  11760
atttaccaat ggattgctaa ccgagcgtct gaggaaggaa gaccgttggc taatcttgcc  11820
```

-continued

```
gctttcttac tcacacgagt tgttaaagaa caaatggaac aagaagccaa ggacaaccaa  11880
gacaagcagg gggcagcatg agcgaagaca gactagccag aatagaagct gcgttagaca  11940
gccaagttgc agtgaatgcc gacctccgca catcggttac agaactccgc gcaaccgcag  12000
aagcattgtt gcaaacagtt caaatccatc agcagaactt tgaaattctt accgctaggc  12060
aattacaaac cgaagcacgg cttgatgagt accaacgtac cactagcgcg gcactcgaca  12120
gaattggcgc ggtcttagac tacctcgtta ggcagcaaaa cggttgaggt gagggatgag  12180
cgatgactat ctagacggat atcccgcaag aggccctttc gtcttcaaga attcccgttt  12240
gactggcgat gctgctactg aaactaacaa ctacatcgac tacgcaatta acgccctcag  12300
ctaattttgc ttagtctagg cccggatggg taagtggttt tcagcttaag tgttgggttc  12360
tacttacttc tccgggtctt gctctatcta aaaacattgg tttaacaagg agtattaggc  12420
aaatgccagt tactgtcgct gcctctcgct tgggaaccgc tgcgtttgac caatcacccg  12480
tcgaactgcg cgctaactat tctcgacctg caggtcgacg atataaagtt caggagcaat  12540
ttaccccgcc agccctttt tccttctcat ctccactatt agacgaggca tcctccacct  12600
acagattaag tattcgcttc tttcagatgc tcggatactt cttggtaaag gctcataaca  12660
tggttgtccg ccaaactgta atatatattc cgaccttcac gatagtattt aaccaaccgt  12720
tgcgatcgca aaattcgcag ttggtgcgat accgcagact cacccatttt tacggctgcg  12780
gctaaatcac aaacacacaa ttctcgatta actaaagcag acatcaatcg caaacgactt  12840
ggatcggcta acgcattaaa aaactctgcc atctgttgcg ctttttcaac agaaataatt  12900
tctggttgca cctggcgcac ccgatcaaga tgaaccaaat gagcatcaca actgggcgtg  12960
tcttcagact gaagagactc cgctttgggc aatgttggtt ttttcataag tagagatagt  13020
gttgggagta gaggatgaat tcaaaataga cagaataata atcattctaa catctgaata  13080
tatattcaga tattgagata actatgttaa acttcaaagg agttattctt cagcgactta  13140
ctgaaacggc tatgaattct tatactgtcg gtacctattt agcggagcgg cttgtccaga  13200
ttggtctcaa gcatcacttc gcagtcgcgg gcgactacaa cctcgtcctt cttgacaacc  13260
tgcttttgaa caaaaacatg gagcaggttt attgctgtaa cgaactgaac tgcggtttca  13320
gtgcagaagg ttatgctcgt gccaaaggcg cagcagcagc cgtcgttacc tacagcgtcg  13380
gtgcgctttc cgcatttgat gctatcggtg gcgcctatgc agaaaacctt ccggttatcc  13440
tgatctccgg tgctccgaac aacaatgatc acgctgctgg tcacgtgttg catcacgctc  13500
ttggcaaaac cgactatcac tatcagttgg aaatggccaa gaacatcacg gccgcagctg  13560
aagcgattta caccccagaa gaagctccgg ctaaaatcga tcacgtgatt aaaactgctc  13620
ttcgtgagaa gaagccggtt tatctcgaaa tcgcttgcaa cattgcttcc atgccctgcg  13680
ccgctcctgg accggcaagc gcattgttca atgacgaagc cagcgacgaa gcttctttga  13740
atgcagcggt tgaagaaacc ctgaaattca tcgccaaccg cgacaaagtt gccgtcctcg  13800
tcggcagcaa gctgcgcgca gctggtgctg aagaagctgc tgtcaaattt gctgatgctc  13860
tcggtggcgc agttgctacc atggctgctg caaaaagctt cttcccagaa gaaaacccgc  13920
attacatcgg tacctcatgg ggtgaagtca gctatccggg cgttgaaaag acgatgaaag  13980
aagccgatgc ggttatcgct ctggctcctg tcttcaacga ctactccacc actggttgga  14040
cggatattcc tgatcctaag aaactggttc tcgctgaacc gcgttctgtc gtcgttaacg  14100
gcgttcgctt ccccagcgtt catctgaaag actatctgac ccgtttggct cagaaagttt  14160
ccaagaaaac cggtgctttg gacttcttca aatccctcaa tgcaggtgaa ctgaagaaag  14220
```

ccgctccggc tgatccgagt gctccgttgg tcaacgcaga aatcgcccgt caggtcgaag 14280
ctcttctgac cccgaacacg acggttattg ctgaaaccgg tgactcttgg ttcaatgctc 14340
agcgcatgaa gctcccgaac ggtgctcgcg ttgaatatga aatgcagtgg ggtcacatcg 14400
gttggtccgt tcctgccgcc ttcggttatg ccgtcggtgc tccggaacgt cgcaacatcc 14460
tcatggttgg tgatggttcc ttccagctga cggctcagga agtcgctcag atggttcgcc 14520
tgaaactgcc ggttatcatc ttcttgatca ataactatgg ttacaccatc gaagttatga 14580
tccatgatgg tccgtacaac aacatcaaga actgggatta tgccggtctg atggaagtgt 14640
tcaacggtaa cggtggttat gacagcggtg ctggtaaagg cct 14683

<210> SEQ ID NO 6
<211> LENGTH: 13537
<212> TYPE: DNA
<213> ORGANISM: Artificial Sequence
<220> FEATURE:
<223> OTHER INFORMATION: plasmid TK336

<400> SEQUENCE: 6
ttatactgtc ggtacctatt tagcggagcg gcttgtccag attggtttaa agcatcactt 60
cgcagtcgcg ggcgactaca acttagtcct tcttgacaac ctgcttttga acaaaaacat 120
ggagcaggtt tattgctgta acgaactgaa ctgcggtttc agtgcagaag gttatgctcg 180
tgccaaaggc gcagcagcag ccgtcgttac ctacagcgtc ggtgcgcttt ccgcatttga 240
tgctatcggt ggcgcctatg cagaaaacct tccggttatc ctgatctccg gtgctccgaa 300
caacaatgat cacgctgctg gtcacgtgtt gcatcacgct cttggcaaaa ccgactatca 360
ctatcagttg gaaatggcca agaacatcac tgccgcagct gaagcgattt acaccccaga 420
agaagctccg gctaaaatcg atcacgtgat taaaactgct cttcgtgaga agaagccggt 480
ttatttagaa atcgcttgca acattgcttc catgccctgc gccgctcctg gaccggcaag 540
cgcattgttc aatgacgaag ccagcgacga agcttctttg aatgcagcgg ttgaagaaac 600
cctgaaattc atcgccaacc gcgacaaagt tgccgtctta gtcggcagca agctgcgcgc 660
agctggtgct gaagaagctg ctgtcaaatt tgctgatgct ttaggtggcg cagttgctac 720
catggctgct gcaaaaagct tcttcccaga agaaaacccg cattacatcg gtacctcatg 780
gggtgaagtc agctatccgg gcgttgaaaa gactatgaaa gaagccgatg cggttatcgc 840
tctggctcct gtcttcaacg actactccac cactggttgg actgatattc ctgatcctaa 900
gaaactggtt ttagctgaac cgcgttctgt cgtcgttaac ggcgttcgct tccccagcgt 960
tcatctgaaa gactatctga cccgtttggc tcagaaagtt tccaagaaaa ccggtgcttt 1020
ggacttcttc aaatccttaa atgcaggtga actgaagaaa gccgctccgg ctgatccgag 1080
tgctccgttg gtcaacgcag aaatcgcccg tcaggtcgaa gctcttctga ccccgaacac 1140
tactgttatt gctgaaaccg gtgactcttg gttcaatgct caacgcatga agttaccgaa 1200
cggtgctcgc gttgaatatg aaatgcagtg gggtcacatc ggttggtccg ttcctgccgc 1260
cttcggttat gccgtcggtg ctccggaacg tcgcaacatc ttaatggttg gtgatggttc 1320
cttccagctg actgctcagg aagtcgctca gatggttcgc ctgaaactgc cggttatcat 1380
cttcttgatc aataactatg gttacaccat cgaagttatg atccatgatg gtccgtacaa 1440
caacatcaag aactgggatt atgccggtct gatggaagtg ttcaacggta acggtggtta 1500
tgacagcggt gctggtaaag gcctgaaggc taaaaccggt ggcgaactgg cagaagctat 1560

-continued

```
caaggttgct ctggcaaaca ccgacggccc aaccctgatc gaatgcttca tcggtcgtga   1620
agactgcact gaagaattgg tcaaatgggg taagcgcgtt gctgccgcca acagccgtaa   1680
gcctgttaac aagttattat agacgtcgga aataaaaaac gcccggcggc aaccgagcgt   1740
ctcgagataa catcaccgtc gttatcgtcg ctttagaata acgttcccaa aatagctcat   1800
ttccaactgg caactcacaa ccaaaaaccg catttttagt aaatatactc agcaatttgt   1860
tcaacctgag catttttccc atttgcaact tgatacaaat atttttagca gcaaattttc   1920
ctactgccag cttagtttac ataaattttg tctgttgaca tcttgcacac aataaggtat   1980
ggcgcatata atgcgatatt actaccatta atttactacc tagtcattaa cgtctcccgc   2040
cagagaacag ttttgaatag gtagtcaatt ttaggtattg aacctgctgt aaatttatta   2100
aatcgatgaa tttccccgaa atctgctcta gcagacttgg gttatatacc agtaggctca   2160
ggtgcaaaac aacaaagcac aaattttacc cattaaggat ataggcaatc tgtcaaatag   2220
ttgttatctt tcttaataca gaggaataat caacaatatg gggcaggtac taactaaagt   2280
cctatgcctg tggggcttct gtaaccgaca taacctttac gcgttgtctt ttaggagtct   2340
gttatgcata ttaaagccta cgctgccctg gaagccaacg gaaaattaca accctttgaa   2400
tacgaccccg gtgccctggg tgctaatgag gtggagattg aggtgcagta ttgtggggtg   2460
tgccacagtg atttgtccat gattaataac gaatggggca tttccaatta cccccctagtg  2520
ccgggtcatg aggtggtggg tactgtggcc gccatgggcg aaggggtgaa ccatgttgag   2580
gtgggggatt tagtggggct gggttggcat tctggctact gcatgacctg ccatagttgt   2640
ttatctggct accacaacct ttgtgccact gcggaatcta ccattgtggg ccactacggt   2700
ggctttggcg atcgggttcg ggccaaggga gtcagcgtgg tgaaattacc taaaggcatt   2760
gacctagcca gtgccgggcc ccttttctgt ggaggaatta ccgttttcag tcctatggtg   2820
gaactgagtt taaagcccac tgcaaaagtg gcagtgatcg gcattggggg cttgggccat   2880
ttagcggtgc aatttttacg ggcctggggc tgtgaagtga ctgcctttac ctccagtgcc   2940
cgcaagcaaa ctgaagtgtt ggaattgggc gctcaccaca tactagattc caccaatcca   3000
gaggcgatcg ccagtgcgga aggcaaattt gactatatta tctccactgt gaacctgaag   3060
cttgactgga acttatacat cagcaccctg gcgccccagg gacatttcca ctttgttggg   3120
gtggtgttgg agcctttgga tctaaatctt tttcccccttt tgatgggaca acgctccgtt  3180
tctgcctccc cagtgggtag tcccgccacc attgccacca tgttggactt tgctgtgcgc   3240
catgacatta aacccgtggt ggaacaattt agctttgatc agatcaacga ggcgatcgcc   3300
catctagaaa gcggcaaagc ccattatcgg gtagtgttaa gccatagtaa aaattaggat   3360
ccggaaataa aaaacgcccg gcggcaaccg agcgtgagct cgaattgatc ctttttgata   3420
atctcatgac caaaatccct taacgtgagt tttcgttcca ctgagcgtca gaccccgtag   3480
aaaagatcaa aggatcttct tgagatcctt tttttctgcg cgtaatctgc tgcttgcaaa   3540
caaaaaaacc accgctacca gcggtggttt gtttgccgga tcaagagcta ccaactcttt   3600
ttccgaaggt aactggcttc agcagagcgc agataccaaa tactgtcctt ctagtgtagc   3660
cgtagttagg ccaccacttc aagaactctg tagcaccgcc tacatacctc gctctgctaa   3720
tcctgttacc agtggctgct gccagtggcg ataagtcgtg tcttaccggg ttggactcaa   3780
gacgatagtt accggataag gcgcagcggt cgggctgaac ggggggttcg tgcacacagc   3840
ccagcttgga gcgaacgacc tacaccgaac tgagatacct acagcgtgag ctatgagaaa   3900
gcgccacgct tcccgaaggg agaaaggcgg acaggtatcc ggtaagcggc agggtcggaa   3960
```

-continued

```
caggagagcg cacgagggag cttccagggg gaaacgcctg gtatctttat agtcctgtcg   4020
ggtttcgcca cctctgactt gagcgtcgat ttttgtgatg ctcgtcaggg gggcggagcc   4080
tatggaaaaa cgccagcaac gcggcctttt tacggttcct ggccttttgc tggccttttg   4140
ctcacatgtt ctttcctgcg ttatcccctg attctgtgga taaccgtatt accgcctttg   4200
agtgagctga taccgctcgc cgcagccgaa cgaccgagcg cagcgagtca gtgagcgagg   4260
aagcggaaga gcgcctgatg cggtattttc tccttacgca tctgtgcggt atttcacacc   4320
gcatatggtg cactctcagt acaatctgct ctgatgccgc atagttaagc cagtatacac   4380
tccgctatcg ctacgtgact gggtcatggc tgcgccccga cacccgccaa cacccgctga   4440
cgcgccctga cgggcttgtc tgctcccggc atccgcttac agacaagctg tgaccgtctc   4500
cgggagctgc atgtgtcaga ggttttcacc gtcatcaccg aaacgcgcga ggcagctgcg   4560
gtaaagctca tcagcgtggt cgtgaagcga ttcacagatg tctgcctgtt catccgcgtc   4620
cagctcgttg agtttctcca gaagcgttaa tgtctggctt ctgataaagc gggcctgcca   4680
ccatacccac gccgaaacaa gcgctcatga gcccgaagtg gcgagcccga tcttccccat   4740
cggtgatgtc ggcgatatag gcgccagcaa ccgcacctgt ggcgccggtg atgcccgaag   4800
aactccagca tgagatcccc gcgctggagg atcatccagc cggcgtcccg gaaaacgatt   4860
ccgaagccca acctttcata gaaggcggcg gtggaatcga aatctcgtga tggcaggttg   4920
ggcgtcgctt ggtcggtcat ttcgaacccc agagtcccgc tcagaagaac tcgtcaagaa   4980
ggcgatagaa ggcgatgcgc tgcgaatcgg gagcggcgat accgtaaagc acgaggaagc   5040
ggtcagccca ttcgccgcca agctcttcag caatatcacg ggtagccaac gctatgtcct   5100
gatagcggtc cgccacaccc agccggccac agtcgatgaa tccagaaaag cggccatttt   5160
ccaccatgat attcggcaag caggcatcgc catgggtcac gacgagatca tcgccgtcgg   5220
gcatgcgcgc cttgagcctg gcgaacagtt cggctggcgc gagcccctga tgctcttcgt   5280
ccagatcatc ctgatcgaca agaccggctt ccatccgagt acgtgctcgc tcgatgcgat   5340
gtttcgcttg gtggtcgaat gggcaggtag ccggatcaag cgtatgcagc cgccgcattg   5400
catcagccat gatggatact ttctcggcag gagcaaggtg agatgacagg agatcctgcc   5460
ccggcacttc gcccaatagc agccagtccc ttcccgcttc agtgacaacg tcgagcacag   5520
ctgcgcaagg aacgcccgtc gtggccagcc acgatagccg cgctgcctcg tcctgcagtt   5580
cattcagggc accggacagg tcggtcttga caaaaagaac cgggcgcccc tgcgctgaca   5640
gccggaacac ggcggcatca gagcagccga ttgtctgttg tgcccagtca tagccgaata   5700
gcctctccac ccaagcggcc ggagaacctg cgtgcaatcc atcttgttca atcatgcgaa   5760
acgatcctca tcctgtctct tgatcagatc ttgatcccct gcgccatcag atccttggcg   5820
gcaagaaagc catccagttt actttgcagg gcttcccaac cttaccagag ggcgccccag   5880
ctggcaattc cggttcgctt gctgtccata aaaccgccca gtctagctat cgccatgtaa   5940
gcccactgca agctacctgc tttctctttg cgcttgcgtt ttcccttgtc cagatagccc   6000
agtagctgac attcatccgg ggtcagcacc gtttctgcgg actggctttc tacgtgttcc   6060
gcttccttta gcagcccttg cgccctgagt gcttgcggca gcgtgaagct ttctctgagc   6120
tgtaacagcc tgaccgcaac aaacgagagg atcgagacca tccgctccag attatccggc   6180
tcctccatgc gttgcctctc ggctcctgct ccggttttcc atgccttatg gaactcctcg   6240
atccgccagc gatgggtata aatgtcgatg acgcgcaagg cttgggctag cgactcgacc   6300
```

-continued

```
ggttcgctgg tcagcaacaa ccatttcaac ggggtctcac ccttgggcgg gttaatctcc   6360
tcggccagca ccgcgttgag cgtgatattc ccctgtttta gcgtgatgcg cccactgcgc   6420
atagaaattg catcaacgca tatagcgcta gcagcacgcc atagtgactg gcgatgctgt   6480
cggaatggac gatatctaga cttatataga cactaatata gacaatagtt tatactgcta   6540
tctatacaag tatagacatt atctaatcat ggcagacaaa actctagcca cttttcgtat   6600
tgactccgaa gaatgggagt cttttaaaaa ccttgctagt tctgaaagtt ccaacgcctc   6660
agcactgtta acagaatttg ttcgttggta tttggcaggt aacaggttta atactcccac   6720
ttctcacact cccacccatc tagacacatc cctcgaacag cgtatagaca atattgaaca   6780
acgtctagat aaagtcacaa ctaataatct agacaatata gatgaattta tagacaagcg   6840
tatagaagat aatctagcaa cacgtctaga caaacttcaa tcgcaactgg aggaactgcg   6900
gggaaaatcg aaagcccggt agttcaggca gaaggacaag ctaccgggca agacagaaag   6960
aatatagaca atagtataga caatctagac aaattggagg caacccgcga tcgcaccctc   7020
aataagctaa aaatgggtag gcagtcagcc gccgggaaag ccatcgacgc gtttatcaaa   7080
gagttgcttt cttcaggaga caacataagc tgaagttatc aaaattctgt ccttacgtcg   7140
aaagcctgat ttaccgtgc aacgattgat aagcttggct aaactagcac tggctttcaa   7200
cagaaagcat acgaagaatc aatagatata gccaccaatt ccacaaaatg cagataacgt   7260
gtagagtatt ggaatgctta atctgtaagg gttatgaagg ttaacggcaa cggacgagcc   7320
aaaatactca cctccgacga actcaggcga ctgtttagcg acggattcac cacaccgcgc   7380
gatcgcgttt tgtttggcat ctgtctattc accggttgcc gcgttagtga agctctagca   7440
ctccaaacaa cggacattaa aggcgaaaca ctaaccttta ggaagtctac caccaaaggg   7500
aaactcaaaa cccgcgtggt tgacatccag ccaggactag ccgcactcat ggctgactat   7560
caccccaaac cgggaaccct gttccctggc atgaggggag tcagcgatag gctcacgcga   7620
tacgcggcgg ataaaatctt gcgcgatgca gccaaaagaa tcgggctaga aggcatcagt   7680
acccacagtt tccgccgtac tgccctcaac caaatgtcta gcgccggtat cccgttgcga   7740
cacattcaag agatatccgg tcacaatgac cttggcacac tgcaacgcta tcttgaagtt   7800
acacccgaac agcgacgcaa agctgtatcc gtgattggct tctaatgtac gccaacgctg   7860
tttagacccc tatgggtgct aaaaaaagac gcagcctaaa cacacgctct acacttgagg   7920
atacttttaa agtatccatc ggttctagaa ctctgcacac gttccggact ttggaaacgt   7980
tatacctttc cctgtgttgc agaatgctgc aatatttctt cgacaagtta acttgtgact   8040
ggtttaatat tttctcaaat tgccccaaaa caacacgcct aaatccttag acgtttctgt   8100
ggaaacctat taggttttta tcgccgttgt tttagtggta aacccaaagg gtttgtatat   8160
tcttgtatga agttcgactc tgagggttaa gaagaatggc tcgccgaatt ttttacaagt   8220
ggaaaccgat taaaggttaa gggtcaatcg ggacgatgaa tattttctaa ttgtgacctt   8280
ctccatctaa taagctttct ttggggttaa ggtcgaagaa agtactacgc atgatctgca   8340
tacgatctct attgccaaaa agccgcgacc ctataggctc tcggtcatgc tgcactagtt   8400
cgtgtcgatc actatactgg ttgccgcagc atttcacgct aaaaaaaaat tcttaaaaat   8460
gtccttcata tctcgccaga gtggcaacct attacaaaac ggttgcctac ccgaccggct   8520
cgattttcgc tgaagtggca ctgtgacagt ttgaaatggt acttccgccg tgctgctgac   8580
atcgttgtta gggtgaattg ttcgcggtag atgttgcacc gattcatgaa caccttgtca   8640
cccactttga ataatcgacc gtcaaattca gtcgcgtcaa tttggtaagt gttgggctgt   8700
```

-continued

```
ctctttttgg ctccaggggc aatgccatca gaaaacacaa ccgcgtcacc cataacttga   8760
taaccgatat cagttttggt tccagtgaaa gcccaaaatt cagacgcgtc attattccga   8820
gcgtgccgga gttgattgta ctcaattttg gcttggcaaa gttgacggcg attcatgccc   8880
agctgctttt gatgtcgtcg cactgtgcgc ttgtgaatac ccaactcaca gctgacagct   8940
ttttgagatg taccatagtg gatgaaactt tttgagacga atatccgcga cgaactaatg   9000
tgaagtacac aaggtacttc cccctctggc gatttaagag aggattgcct tgtgtccttc   9060
actagctcgt tcgggtgtgg cgctccaaaa agttttctgt actctggttt aagttgtctg   9120
ttggccgcat agcggctctt ttgttgaaag ctttgtgtga ctatgccagt ggtcagtgag   9180
cgtaaatcgc ttaacacttg gactaaaggc actactgcaa catcacccca tctttttaaa   9240
tttaggttgt aacaaacttg aaacataccg cccaagtaga cggttatcat tcctgcttta   9300
attttgtagc ggcggaatgc tcctattttt tttccatcct gtaaccaacg gtaaacagac   9360
ttatcactac aatctaagaa cgtctgtact acaggcaatg gcaatgttaa atgaccagac   9420
ccatccttat caagcgctcg acacaaatac cacaaccgcg cacaaggttc tcgaccaatg   9480
cgagtgtgta ccctgaccgt gtaagtgcca agaattattt cagtttgtag ttcccttgta   9540
agcagggtta gtgatacatt tgtatttaag ctttctgggc tgatcatttg gaaatgtctc   9600
agtccagtac ctattgaatg ttatttgctt aacctgaagc taaataaaac ttgttaacta   9660
cacccattaa ttgataaatt caaagcacgt tttttctgtt tggtgtttgg tgtggtaaca   9720
attctgtgta tgtgtgtttt atttagcttc ggttaagtag cataacaacc cccaagcact   9780
gaactttttt taataggtaa tttaaacttt gcctatcggc aaaattttca atcaattgta   9840
cgccaaagtg ttgcatgatc aacgtttgac ttatttttgt atttactaaa tactgaattt   9900
cgccgtgacg ctttttacag atggaaattc acggcaaaat gtttttttgct aactttgcta   9960
tgtaaaacaa gaaacttggc actcggttat tactaaataa actggtaaaa aataaccatt  10020
agaaccaaaa agaacgaaaa ccagtacacc cttgccagtt ttcaagcttt tgctatgacg  10080
actctaataa tcgggtttaa caccattccg ctttgagaaa attatccttg tacagcaagt  10140
aacagtcaat gctaaaccgc accgctacaa atccttaagt tttccagta gcgatttacc  10200
ttcttggtaa cgcccgcctt gatagcccaa aatttcttta atcaccttac tttctgaaaa  10260
acccgcttcc agacaggctt ttaccacttt tgctagggtt tcatctcttg gttctgggag  10320
ggatgaaacg ggctgtaatg cttgttctga ggtcggttga gccgtttgga gtggctgaaa  10380
actggttaca gactgtaacc ggggcataac cattttgtaa ctgcttacat ctggtaactg  10440
acacggcata tcatccacca tgcagcgata tttccccgac tttaaccact ccacaagggc  10500
aaggtctttt aaggacttgg cgtggctaac tgcaaactta cccaggcgta acatcctaaa  10560
acacttacgg acaccgcctt caccctcgat acctaaggtc ttgacattat catcttgagt  10620
cagcccaata acaaaacgct tggcttgcg gccgcgcctg gcgtgtttga tgagccattc  10680
ggttgctatc tcgacttcat ctctcagcag tggcagttct tcagcaatta aaacgctttc  10740
ttttcctgct agtgccttat ccccagactc accccgtagc tcaatccggc gctgcaattc  10800
ctccaggtca gcagccatgc ccgactgtat agcctcaaag tcaccacggc ggccaatgac  10860
atttaacccc gtccactcgt ccggtgcagc gtcagcgtca tagactgtca cctcaccccc  10920
gacttgataa gcaagccatt gggctatggt gcttttgcca gttcccgtat ccccaactat  10980
taaacagtgc ttaccagaca gagcttgcat caagtcggtg atgattccct ctggttcgac  11040
```

-continued

```
cgcaagggtg acggcggtag tgtcaatgat agccgcgccg taagtgccag catagggcaa  11100
ttggtcgtaa actttgacca agttgtatac agactgtcta caccacttca ccactgttaa  11160
cgctgtttgc aaagcgtaag acgtggcatc aaataaaaat atgctggcac taaaagttaa  11220
tcgccccaat ccccacagta aaaacctgcc tagctgttga cgactaggca agtgcatttc  11280
aatccagtca tttgccataa atcaccccgt ctttaaagcc ttgcagttga gcgcgacagg  11340
tatttaactg tgcttgtaac tctgtttgct ggttttgata ccacagactg acggcggcgg  11400
ccgccagtcc taaaaataga aactggcgat cgctcattat tgacttactc cctgttgatt  11460
agcgtggtag tgagtcatag ccgcattgac cgcttcttgg gcttggggtg ttctgccaag  11520
attgggtttt gtagggtcat cgttggctac gactaaggac gcttgttcgg ctatcgcttg  11580
cgggacacca actttagtta actctgtcaa ggatacttgg taaagtcgct cgttcattag  11640
ccgattctcc ggtacataaa actgttgctg gcagtccctt cattggcgac gagttcttca  11700
gccggagtat cagcgataat gtcagcccag ccggtgacat tattattaat aatgttttgt  11760
tcggcaattg cacccaagcc aggacgcgcc gtttcaaact cagagatgac ttgctgctct  11820
ttctcggtga gtggtctatc tgtcatgata attatgtcct tcattatgta ggcgattcca  11880
gtgggtgttt acgaggcagt ccacaggaat cagtgcgatt cacctttaag gtgaatcgtc  11940
atcaaaaaat cactcggtag caacgacccg aaccgaccag gattgatttc ccggttctca  12000
gttcgcaggc ttttgagcgc gtcaccttga ccattgggta actgccatca gccgataagc  12060
taaacgggct gtatagcggt aaagcatccc acacagtcgg gctggcatca actttgcagg  12120
aatagctcac gtcactcatc tcactcgcgc ctgggttgga tggcagcgaa ggcagattac  12180
gacgcagttt tttactggca cttttacccg cattaaaaac gggtacagtg ccattgttga  12240
cggtctgtac ttcggtcata tactcggtgt acacttaata cactctatac tattactgcc  12300
gattagtaca tttgtcaatc actctttgca caaggtgtat gatatggact caggagtaca  12360
ccaaacgtca tgccaaccaa taaagggaga atagcagtca ctctagaagc tgaaatttac  12420
caatggattg ctaaccgagc gtctgaggaa ggaagaccgt tggctaatct tgccgctttc  12480
ttactcacac gagttgttaa agaacaaatg gaacaagaag ccaaggacaa ccaagacaag  12540
cagggggcag catgagcgaa gacagactag ccagaataga agctgcgtta gacagccaag  12600
ttgcagtgaa tgccgacctc cgcacatcgg ttacagaact ccgcgcaacc gcagaagcat  12660
tgttgcaaac agttcaaatc catcagcaga actttgaaat tcttaccgct aggcaattac  12720
aaaccgaagc acggcttgat gagtaccaac gtaccactag cgcggcactc gacagaattg  12780
gcgcggtctt agactacctc gttaggcagc aaaacggttg aggtgaggga tgagcgatga  12840
ctatctagac ggatatcccg caagaggccc tttcgtcttc aagaattaat tgtcgacgat  12900
ataaagttca ggagcaattt accccgccag cccttttttc cttctcatct ccactattag  12960
acgaggcatc ctccacctac agattaagta ttcgcttctt tcagatgctc ggatacttct  13020
tggtaaaggc tcataacatg gttgtccgcc aaactgtaat atatattccg accttcacga  13080
tagtatttaa ccaaccgttg cgatcgcaaa attcgcagtt ggtgcgatac cgcagactca  13140
cccattttta cggctgcggc taaatcacaa acacacaatt ctcgattaac taaagcagac  13200
atcaatcgca aacgacttgg atcggctaac gcattaaaaa actctgccat ctgttgcgct  13260
ttttcaacag aaataatttc tggttgcacc tggcgcaccc gatcaagatg aaccaaatga  13320
gcatcacaac tgggcgtgtc ttcagactga agagactccg ctttgggcaa tgttggtttt  13380
ttcataagta gagatagtgt tgggagtaga ggatgaattc aaaatagaca gaataataat  13440
```

cattctaaca tctgaatata tattcagata ttgagataac tatgttaaac ttcaaaggag 13500
ttattcttca gcgacttact gaaacggcta tgaattc 13537

<210> SEQ ID NO 7
<211> LENGTH: 12928
<212> TYPE: DNA
<213> ORGANISM: Artificial Sequence
<220> FEATURE:
<223> OTHER INFORMATION: plasmid TK414

<400> SEQUENCE: 7
ttatactgtc ggtacctatt tagcggagcg gcttgtccag attggtttaa agcatcactt 60
cgcagtcgcg ggcgactaca acttagtcct tcttgacaac ctgcttttga acaaaaacat 120
ggagcaggtt tattgctgta acgaactgaa ctgcggtttc agtgcagaag gttatgctcg 180
tgccaaaggc gcagcagcag ccgtcgttac ctacagcgtc ggtgcgcttt ccgcatttga 240
tgctatcggt ggcgcctatg cagaaaacct tccggttatc ctgatctccg gtgctccgaa 300
caacaatgat cacgctgctg gtcacgtgtt gcatcacgct cttggcaaaa ccgactatca 360
ctatcagttg gaaatggcca agaacatcac tgccgcagct gaagcgattt acaccccaga 420
agaagctccg gctaaaatcg atcacgtgat taaaactgct cttcgtgaga agaagccggt 480
ttatttagaa atcgcttgca acattgcttc catgccctgc gccgctcctg gaccggcaag 540
cgcattgttc aatgacgaag ccagcgacga agcttctttg aatgcagcgg ttgaagaaac 600
cctgaaattc atcgccaacc gcgacaaagt tgccgtctta gtcggcagca agctgcgcgc 660
agctggtgct gaagaagctg ctgtcaaatt tgctgatgct ttaggtggcg cagttgctac 720
catggctgct gcaaaaagct tcttcccaga agaaaacccg cattacatcg gtacctcatg 780 ggtgaagtc agctatccgg gcgttgaaaa gactatgaaa gaagccgatg cggttatcgc 840
tctggctcct gtcttcaacg actactccac cactggttgg actgatattc ctgatcctaa 900
gaaactggtt ttagctgaac cgcgttctgt cgtcgttaac ggcgttcgct tccccagcgt 960
tcatctgaaa gactatctga cccgtttggc tcagaaagtt tccaagaaaa ccggtgcttt 1020
ggacttcttc aaatccttaa atgcaggtga actgaagaaa gccgctccgg ctgatccgag 1080
tgctccgttg gtcaacgcag aaatcgcccg tcaggtcgaa gctcttctga ccccgaacac 1140
tactgttatt gctgaaaccg gtgactcttg gttcaatgct caacgcatga agttaccgaa 1200
cggtgctcgc gttgaatatg aaatgcagtg gggtcacatc ggttggtccg ttcctgccgc 1260
cttcggttat gccgtcggtg ctccggaacg tcgcaacatc ttaatggttg gtgatggttc 1320
cttccagctg actgctcagg aagtcgctca gatggttcgc ctgaaactgc cggttatcat 1380
cttcttgatc aataactatg gttacaccat cgaagttatg atccatgatg gtccgtacaa 1440
caacatcaag aactgggatt atgccggtct gatggaagtg ttcaacggta acggtggtta 1500
tgacagcggt gctggtaaag gcctgaaggc taaaaccggt ggcgaactgg cagaagctat 1560
caaggttgct ctggcaaaca ccgacggccc aaccctgatc gaatgcttca tcggtcgtga 1620
agactgcact gaagaattgg tcaaatgggg taagcgcgtt gctgccgcca acagccgtaa 1680
gcctgttaac aagttattat agacgtctct ggataaaact aataaactct attacccatg 1740
attaaagcct acgctgccct ggaagccaac ggaaaattac aacccctttga atacgacccc 1800 ggtgccctgg gtgctaatga ggtggagatt gaggtgcagt attgtggggt gtgccacagt 1860
gatttgtcca tgattaataa cgaatggggc atttccaatt acccccctagt gccgggtcat 1920

-continued

```
gaggtggtgg gtactgtggc cgccatgggc gaaggggtga accatgttga ggtgggggat   1980
ttagtggggc tgggttggca ttctggctac tgcatgacct gccatagttg tttatctggc   2040
taccacaacc tttgtgccac tgcggaatct accattgtgg gccactacgg tggctttggc   2100
gatcgggttc gggccaaggg agtcagcgtg gtgaaattac ctaaaggcat tgacctagcc   2160
agtgccgggc cccttttctg tggaggaatt accgttttca gtcctatggt ggaactgagt   2220
ttaaagccca ctgcaaaagt ggcagtgatc ggcattgggg gcttgggcca tttagcggtg   2280
caatttttac gggcctgggg ctgtgaagtg actgccttta cctccagtgc ccgcaagcaa   2340
actgaagtgt tggaattggg cgctcaccac atactagatt ccaccaatcc agaggcgatc   2400
gccagtgcgg aaggcaaatt tgactatatt atctccactg tgaacctgaa gcttgactgg   2460
aacttataca tcagcaccct ggcgccccag ggacatttcc actttgttgg ggtggtgttg   2520
gagcctttgg atctaaatct tttcccctt ttgatgggac aacgctccgt ttctgcctcc   2580
ccagtgggta gtcccgccac cattgccacc atgttggact ttgctgtgcg ccatgacatt   2640
aaacccgtgg tggaacaatt tagctttgat cagatcaacg aggcgatcgc ccatctagaa   2700
agcggcaaag cccattatcg ggtagtgtta agccatagta aaaattagga tccggaaata   2760
aaaaacgccc ggcggcaacc gagcgtgagc tcgaattgat ccttttgat aatctcatga   2820
ccaaaatccc ttaacgtgag ttttcgttcc actgagcgtc agaccccgta gaaaagatca   2880
aaggatcttc ttgagatcct ttttttctgc gcgtaatctg ctgcttgcaa acaaaaaaac   2940
caccgctacc agcggtggtt tgtttgccgg atcaagagct accaactctt tttccgaagg   3000
taactggctt cagcagagcg cagataccaa atactgtcct tctagtgtag ccgtagttag   3060
gccaccactt caagaactct gtagcaccgc ctacatacct cgctctgcta atcctgttac   3120
cagtggctgc tgccagtggc gataagtcgt gtcttaccgg gttggactca agacgatagt   3180
taccggataa ggcgcagcgg tcgggctgaa cggggggttc gtgcacacag cccagcttgg   3240
agcgaacgac ctacaccgaa ctgagatacc tacagcgtga gctatgagaa agcgccacgc   3300
ttcccgaagg gagaaaggcg gacaggtatc cggtaagcgg cagggtcgga acaggagagc   3360
gcacgaggga gcttccaggg ggaaacgcct ggtatcttta tagtcctgtc gggtttcgcc   3420
acctctgact tgagcgtcga tttttgtgat gctcgtcagg ggggcggagc ctatggaaaa   3480
acgccagcaa cgcggccttt ttacggttcc tggccttttg ctggcctttt gctcacatgt   3540
tctttcctgc gttatcccct gattctgtgg ataaccgtat taccgccttt gagtgagctg   3600
ataccgctcg ccgcagccga acgaccgagc gcagcgagtc agtgagcgag gaagcggaag   3660
agcgcctgat gcggtatttt ctccttacgc atctgtgcgg tatttcacac cgcatatggt   3720
gcactctcag tacaatctgc tctgatgccg catagttaag ccagtataca ctccgctatc   3780
gctacgtgac tgggtcatgg ctgcgccccg acacccgcca acacccgctg acgcgccctg   3840
acgggcttgt ctgctcccgg catccgctta cagacaagct gtgaccgtct ccgggagctg   3900
catgtgtcag aggttttcac cgtcatcacc gaaacgcgcg aggcagctgc ggtaaagctc   3960
atcagcgtgg tcgtgaagcg attcacagat gtctgcctgt tcatccgcgt ccagctcgtt   4020
gagtttctcc agaagcgtta atgtctggct tctgataaag cgggcctgcc accataccca   4080
cgccgaaaca agcgctcatg agcccgaagt ggcgagcccg atcttcccca tcggtgatgt   4140
cggcgatata ggcgccagca accgcacctg tggcgccggt gatgcccgaa gaactccagc   4200
atgagatccc cgcgctggag gatcatccag ccggcgtccc ggaaaacgat tccgaagccc   4260
aacctttcat agaaggcggc ggtggaatcg aaatctcgtg atggcaggtt gggcgtcgct   4320
```

-continued

```
tggtcggtca tttcgaaccc cagagtcccg ctcagaagaa ctcgtcaaga aggcgataga   4380
aggcgatgcg ctgcgaatcg ggagcggcga taccgtaaag cacgaggaag cggtcagccc   4440
attcgccgcc aagctcttca gcaatatcac gggtagccaa cgctatgtcc tgatagcggt   4500
ccgccacacc cagccggcca cagtcgatga atccagaaaa gcggccattt tccaccatga   4560
tattcggcaa gcaggcatcg ccatgggtca cgacgagatc atcgccgtcg ggcatgcgcg   4620
ccttgagcct ggcgaacagt tcggctggcg cgagcccctg atgctcttcg tccagatcat   4680
cctgatcgac aagaccggct tccatccgag tacgtgctcg ctcgatgcga tgtttcgctt   4740
ggtggtcgaa tgggcaggta gccggatcaa gcgtatgcag ccgccgcatt gcatcagcca   4800
tgatggatac tttctcggca ggagcaaggt gagatgacag gagatcctgc cccggcactt   4860
cgcccaatag cagccagtcc cttcccgctt cagtgacaac gtcgagcaca gctgcgcaag   4920
gaacgcccgt cgtggccagc cacgatagcc gcgctgcctc gtcctgcagt tcattcaggg   4980
caccggacag gtcggtcttg acaaaaagaa ccgggcgccc ctgcgctgac agccggaaca   5040
cggcggcatc agagcagccg attgtctgtt gtgcccagtc atagccgaat agcctctcca   5100
cccaagcggc cggagaacct gcgtgcaatc catcttgttc aatcatgcga aacgatcctc   5160
atcctgtctc ttgatcagat cttgatcccc tgcgccatca gatccttggc ggcaagaaag   5220
ccatccagtt tactttgcag ggcttcccaa ccttaccaga gggcgcccca gctggcaatt   5280
ccggttcgct tgctgtccat aaaaccgccc agtctagcta tcgccatgta agcccactgc   5340
aagctacctg ctttctcttt gcgcttgcgt tttcccttgt ccagatagcc cagtagctga   5400
cattcatccg gggtcagcac cgtttctgcg gactggcttt ctacgtgttc cgcttccttt   5460
agcagccctt gcgccctgag tgcttgcggc agcgtgaagc tttctctgag ctgtaacagc   5520
ctgaccgcaa caaacgagag gatcgagacc atccgctcca gattatccgg ctcctccatg   5580
cgttgcctct cggctcctgc tccggttttc catgccttat ggaactcctc gatccgccag   5640
cgatgggtat aaatgtcgat gacgcgcaag gcttgggcta gcgactcgac cggttcgctg   5700
gtcagcaaca accatttcaa cggggtctca cccttgggcg ggttaatctc ctcggccagc   5760
accgcgttga gcgtgatatt cccctgtttt agcgtgatgc gcccactgcg catagaaatt   5820
gcatcaacgc atatagcgct agcagcacgc catagtgact ggcgatgctg tcggaatgga   5880
cgatatctag acttatatag acactaatat agacaatagt ttatactgct atctatacaa   5940
gtatagacat tatctaatca tggcagacaa aactctagcc acttttcgta ttgactccga   6000
agaatgggag tcttttaaaa accttgctag ttctgaaagt tccaacgcct cagcactgtt   6060
aacagaattt gttcgttggt atttggcagg taacaggttt aatactccca cttctcacac   6120
tcccacccat ctagacacat ccctcgaaca gcgtatagac aatattgaac aacgtctaga   6180
taaagtcaca actaataatc tagacaatat agatgaattt atagacaagc gtatagaaga   6240
taatctagca acacgtctag acaaacttca atcgcaactg gaggaactgc ggggaaaatc   6300
gaaagcccgg tagttcaggc agaaggacaa gctaccgggc aagacagaaa gaatatagac   6360
aatagtatag acaatctaga caaattggag gcaacccgcg atcgcaccct caataagcta   6420
aaaatgggta ggcagtcagc cgccgggaaa gccatcgacg cgtttatcaa agagttgctt   6480
tcttcaggag acaacataag ctgaagttat caaaattctg tccttacgtc gaaagcctga   6540
ttttaccgtg caacgattga taagcttggc taaactagca ctggctttca acagaaagca   6600
tacgaagaat caatagatat agccaccaat tccacaaaat gcagataacg tgtagagtat   6660
```

-continued

```
tggaatgctt aatctgtaag ggttatgaag gttaacggca acggacgagc caaaatactc   6720
acctccgacg aactcaggcg actgtttagc gacggattca ccacaccgcg cgatcgcgtt   6780
ttgtttggca tctgtctatt caccggttgc cgcgttagtg aagctctagc actccaaaca   6840
acggacatta aaggcgaaac actaaccttt aggaagtcta ccaccaaagg gaaactcaaa   6900
acccgcgtgg ttgacatcca gccaggacta gccgcactca tggctgacta tcaccccaaa   6960
ccgggaaccc tgttccctgg catgagggga gtcagcgata ggctcacgcg atacgcggcg   7020
gataaaatct tgcgcgatgc agccaaaaga atcgggctag aaggcatcag tacccacagt   7080
ttccgccgta ctgccctcaa ccaaatgtct agcgccggta tcccgttgcg acacattcaa   7140
gagatatccg gtcacaatga ccttggcaca ctgcaacgct atcttgaagt tacacccgaa   7200
cagcgacgca aagctgtatc cgtgattggc ttctaatgta cgccaacgct gtttagaccc   7260
ctatgggtgc taaaaaaaga cgcagcctaa acacacgctc tacacttgag gatactttta   7320
aagtatccat cggttctaga actctgcaca cgttccggac tttggaaacg ttataccttt   7380
ccctgtgttg cagaatgctg caatatttct tcgacaagtt aacttgtgac tggtttaata   7440
ttttctcaaa ttgccccaaa acaacacgcc taaatcctta gacgtttctg tggaaaccta   7500
ttaggttttt atcgccgttg ttttagtggt aaacccaaag ggtttgtata ttcttgtatg   7560
aagttcgact ctgagggtta agaagaatgg ctcgccgaat tttttacaag tggaaaccga   7620
ttaaaggtta agggtcaatc gggacgatga atattttcta attgtgacct tctccatcta   7680
ataagctttc tttggggtta aggtcgaaga aagtactacg catgatctgc atacgatctc   7740
tattgccaaa aagccgcgac cctataggct ctcggtcatg ctgcactagt tcgtgtcgat   7800
cactatactg gttgccgcag catttcacgc taaaaaaaaa ttcttaaaaa tgtccttcat   7860
atctcgccag agtggcaacc tattacaaaa cggttgccta cccgaccggc tcgattttcg   7920
ctgaagtggc actgtgacag tttgaaatgg tacttccgcc gtgctgctga catcgttgtt   7980
agggtgaatt gttcgcggta gatgttgcac cgattcatga acaccttgtc acccactttg   8040
aataatcgac cgtcaaattc agtcgcgtca atttggtaag tgttgggctg tctctttttg   8100
gctccagggg caatgccatc agaaaacaca accgcgtcac ccataacttg ataaccgata   8160
tcagttttgg ttccagtgaa agcccaaaat tcagacgcgt cattattccg agcgtgccgg   8220
agttgattgt actcaatttt ggcttggcaa agttgacggc gattcatgcc cagctgcttt   8280
tgatgtcgtc gcactgtgcg cttgtgaata cccaactcac agctgacagc tttttgagat   8340
gtaccatagt ggatgaaact ttttgagacg aatatccgcg acgaactaat gtgaagtaca   8400
caaggtactt ccccctctgg cgatttaaga gaggattgcc ttgtgtcctt cactagctcg   8460
ttcgggtgtg gcgctccaaa aagttttctg tactctggtt taagttgtct gttggccgca   8520
tagcggctct tttgttgaaa gctttgtgtg actatgccag tggtcagtga gcgtaaatcg   8580
cttaacactt ggactaaagg cactactgca acatcacccc atctttttaa atttaggttg   8640
taacaaactt gaaacatacc gcccaagtag acggttatca ttcctgcttt aattttgtag   8700
cggcggaatg ctcctatttt ttttccatcc tgtaaccaac ggtaaacaga cttatcacta   8760
caatctaaga acgtctgtac tacaggcaat ggcaatgtta aatgaccaga cccatcctta   8820
tcaagcgctc gacacaaata ccacaaccgc gcacaaggtt ctcgaccaat gcgagtgtgt   8880
accctgaccg tgtaagtgcc aagaattatt tcagtttgta gttcccttgt aagcagggtt   8940
agtgatacat ttgtatttaa gctttctggg ctgatcattt ggaaatgtct cagtccagta   9000
cctattgaat gttatttgct taacctgaag ctaaataaaa cttgttaact acacccatta   9060
```

attgataaat tcaaagcacg ttttttctgt ttggtgtttg gtgtggtaac aattctgtgt 9120
atgtgtgttt tatttagctt cggttaagta gcataacaac ccccaagcac tgaacttttt 9180
ttaataggta atttaaactt tgcctatcgg caaaattttc aatcaattgt acgccaaagt 9240
gttgcatgat caacgtttga cttatttttg tatttactaa atactgaatt tcgccgtgac 9300
gctttttaca gatggaaatt cacggcaaaa tgtttttttgc taactttgct atgtaaaaca 9360
agaaacttgg cactcggtta ttactaaata aactggtaaa aaataaccat tagaaccaaa 9420
aagaacgaaa accagtacac ccttgccagt tttcaagctt ttgctatgac gactctaata 9480
atcgggttta acaccattcc gctttgagaa aattatcctt gtacagcaag taacagtcaa 9540
tgctaaaccg caccgctaca aatccttaag tttttccagt agcgatttac cttcttggta 9600
acgcccgcct tgatagccca aaatttcttt aatcacctta ctttctgaaa aacccgcttc 9660
cagacaggct tttaccactt ttgctagggt ttcatctctt ggttctggga gggatgaaac 9720
gggctgtaat gcttgttctg aggtcggttg agccgtttgg agtggctgaa aactggttac 9780
agactgtaac cggggcataa ccattttgta actgcttaca tctggtaact gacacggcat 9840
atcatccacc atgcagcgat atttccccga ctttaaccac tccacaaggg caaggtcttt 9900
taaggacttg gcgtggctaa ctgcaaactt acccaggcgt aacatcctaa aacacttacg 9960
gacaccgcct tcaccctcga tacctaaggt cttgacatta tcatcttgag tcagcccaat 10020
aacaaaacgc ttgggcttgc ggccgcgcct ggcgtgtttg atgagccatt cggttgctat 10080
ctcgacttca tctctcagca gtggcagttc ttcagcaatt aaaacgcttt cttttcctgc 10140
tagtgcctta tccccagact caccccgtag ctcaatccgg cgctgcaatt cctccaggtc 10200
agcagccatg cccgactgta tagcctcaaa gtcaccacgg cggccaatga catttaaccc 10260
cgtccactcg tccggtgcag cgtcagcgtc atagactgtc acctcacccc cgacttgata 10320
agcaagccat tgggctatgg tgcttttgcc agttcccgta tccccaacta ttaaacagtg 10380
cttaccagac agagcttgca tcaagtcggt gatgattccc tctggttcga ccgcaagggt 10440
gacggcggta gtgtcaatga tagccgcgcc gtaagtgcca gcatagggca attggtcgta 10500
aactttgacc aagttgtata cagactgtct acaccacttc accactgtta acgctgtttg 10560
caaagcgtaa gacgtggcat caaataaaaa tatgctggca ctaaaagtta atcgccccaa 10620
tccccacagt aaaaacctgc ctagctgttg acgactaggc aagtgcattt caatccagtc 10680
atttgccata aatcaccccg tctttaaagc cttgcagttg agcgcgacag gtatttaact 10740
gtgcttgtaa ctctgtttgc tggttttgat accacagact gacggcggcg gccgccagtc 10800
ctaaaaatag aaactggcga tcgctcatta ttgacttact ccctgttgat tagcgtggta 10860
gtgagtcata gccgcattga ccgcttcttg ggcttggggt gttctgccaa gattgggttt 10920
tgtagggtca tcgttggcta cgactaagga cgcttgttcg gctatcgctt gcgggacacc 10980
aactttagtt aactctgtca aggatacttg gtaaagtcgc tcgttcatta gccgattctc 11040
cggtacataa aactgttgct ggcagtccct tcattggcga cgagttcttc agccggagta 11100
tcagcgataa tgtcagccca gccggtgaca ttattattaa taatgttttg ttcggcaatt 11160
gcacccaagc caggacgcgc cgtttcaaac tcagagatga cttgctgctc tttctcggtg 11220
agtggtctat ctgtcatgat aattatgtcc ttcattatgt aggcgattcc agtgggtgtt 11280
tacgaggcag tccacaggaa tcagtgcgat tcacctttaa ggtgaatcgt catcaaaaaa 11340
tcactcggta gcaacgaccc gaaccgacca ggattgattt cccggttctc agttcgcagg 11400

-continued

```
cttttgagcg cgtcaccttg accattgggt aactgccatc agccgataag ctaaacgggc  11460

tgtatagcgg taaagcatcc cacacagtcg ggctggcatc aactttgcag gaatagctca  11520

cgtcactcat ctcactcgcg cctgggttgg atggcagcga aggcagatta cgacgcagtt  11580

ttttactggc acttttaccc gcattaaaaa cgggtacagt gccattgttg acggtctgta  11640

cttcggtcat atactcggtg tacacttaat acactctata ctattactgc cgattagtac  11700

atttgtcaat cactctttgc acaaggtgta tgatatggac tcaggagtac accaaacgtc  11760

atgccaacca ataaagggag aatagcagtc actctagaag ctgaaattta ccaatggatt  11820

gctaaccgag cgtctgagga aggaagaccg ttggctaatc ttgccgcttt cttactcaca  11880

cgagttgtta aagaacaaat ggaacaagaa gccaaggaca accaagacaa gcagggggca  11940

gcatgagcga agacagacta gccagaatag aagctgcgtt agacagccaa gttgcagtga  12000

atgccgacct ccgcacatcg gttacagaac tccgcgcaac cgcagaagca ttgttgcaaa  12060

cagttcaaat ccatcagcag aactttgaaa ttcttaccgc taggcaatta caaaccgaag  12120

cacggcttga tgagtaccaa cgtaccacta gcgcggcact cgacagaatt ggcgcggtct  12180

tagactacct cgttaggcag caaaacggtt gaggtgaggg atgagcgatg actatctaga  12240

cggatatccc gcaagaggcc ctttcgtctt caagaattaa ttgtcgacga tataaagttc  12300

aggagcaatt taccccgcca gccctttttt ccttctcatc tccactatta gacgaggcat  12360

cctccaccta cagattaagt attcgcttct ttcagatgct cggatacttc ttggtaaagg  12420

ctcataacat ggttgtccgc caaactgtaa tatatattcc gaccttcacg atagtattta  12480

accaaccgtt gcgatcgcaa aattcgcagt tggtgcgata ccgcagactc acccattttt  12540

acggctgcgg ctaaatcaca aacacacaat tctcgattaa ctaaagcaga catcaatcgc  12600

aaacgacttg gatcggctaa cgcattaaaa aactctgcca tctgttgcgc tttttcaaca  12660

gaaataattt ctggttgcac ctggcgcacc cgatcaagat gaaccaaatg agcatcacaa  12720

ctgggcgtgt cttcagactg aagagactcc gctttgggca atgttggttt tttcataagt  12780

agagatagtg ttgggagtag aggatgaatt caaaatagac agaataataa tcattctaac  12840

atctgaatat atattcagat attgagataa ctatgttaaa cttcaaagga gttattcttc  12900

agcgacttac tgaaacggct atgaattc                                    12928
```

```
<210> SEQ ID NO 8
<211> LENGTH: 13282
<212> TYPE: DNA
<213> ORGANISM: Artificial Sequence
<220> FEATURE:
<223> OTHER INFORMATION: plasmid TK346

<400> SEQUENCE: 8

ttatactgtc ggtacctatt tagcggagcg gcttgtccag attggtttaa agcatcactt     60

cgcagtcgcg ggcgactaca acttagtcct tcttgacaac ctgcttttga acaaaaacat    120

ggagcaggtt tattgctgta acgaactgaa ctgcggtttc agtgcagaag gttatgctcg    180

tgccaaaggc gcagcagcag ccgtcgttac ctacagcgtc ggtgcgcttt ccgcatttga    240

tgctatcggt ggcgcctatg cagaaaacct tccggttatc ctgatctccg gtgctccgaa    300

caacaatgat cacgctgctg gtcacgtgtt gcatcacgct cttggcaaaa ccgactatca    360

ctatcagttg gaaatggcca agaacatcac tgccgcagct gaagcgattt acaccccaga    420

agaagctccg gctaaaatcg atcacgtgat taaaactgct cttcgtgaga agaagccggt    480

ttatttagaa atcgcttgca acattgcttc catgccctgc gccgctcctg gaccggcaag    540
```

-continued

```
cgcattgttc aatgacgaag ccagcgacga agcttctttg aatgcagcgg ttgaagaaac    600
cctgaaattc atcgccaacc gcgacaaagt tgccgtctta gtcggcagca agctgcgcgc    660
agctggtgct gaagaagctg ctgtcaaatt tgctgatgct ttaggtggcg cagttgctac    720
catggctgct gcaaaaagct tcttcccaga agaaaacccg cattacatcg gtacctcatg    780
gggtgaagtc agctatccgg gcgttgaaaa gactatgaaa gaagccgatg cggttatcgc    840
tctggctcct gtcttcaacg actactccac cactggttgg actgatattc ctgatcctaa    900
gaaactggtt ttagctgaac cgcgttctgt cgtcgttaac ggcgttcgct tccccagcgt    960
tcatctgaaa gactatctga cccgtttggc tcagaaagtt tccaagaaaa ccggtgcttt   1020
ggacttcttc aaatccttaa atgcaggtga actgaagaaa gccgctccgg ctgatccgag   1080
tgctccgttg gtcaacgcag aaatcgcccg tcaggtcgaa gctcttctga ccccgaacac   1140
tactgttatt gctgaaaccg gtgactcttg gttcaatgct caacgcatga agttaccgaa   1200
cggtgctcgc gttgaatatg aaatgcagtg gggtcacatc ggttggtccg ttcctgccgc   1260
cttcggttat gccgtcggtg ctccggaacg tcgcaacatc ttaatggttg gtgatggttc   1320
cttccagctg actgctcagg aagtcgctca gatggttcgc ctgaaactgc cggttatcat   1380
cttcttgatc aataactatg gttacaccat cgaagttatg atccatgatg gtccgtacaa   1440
caacatcaag aactgggatt atgccggtct gatggaagtg ttcaacggta acggtggtta   1500
tgacagcggt gctggtaaag gcctgaaggc taaaaccggt ggcgaactgg cagaagctat   1560
caaggttgct ctggcaaaca ccgacggccc aaccctgatc gaatgcttca tcggtcgtga   1620
agactgcact gaagaattgg tcaaatgggg taagcgcgtt gctgccgcca acagccgtaa   1680
gcctgttaac aagttattat agacgtcgga aataaaaaac gcccggcggc aaccgagcgt   1740
ctcgagataa catcaccgtc gttatcgtcg ctttagaata acgttcccaa aatagctcat   1800
ttccaactgg caactcacaa ccaaaaaccg catttttagt aaatatactc agcaatttgt   1860
tcaacctgag catttttccc atttgcaact tgatacaaat atttttagca gcaaattttc   1920
ctactgccag cttagtttac ataaattttg tctgttgaca tcttgcacac aataaggtat   1980
ggcgcatata atgcgatatt actaccatta atttactacc tagtcattaa cgtctcccgc   2040
cagagaacag ttttgaatag gtagtcaatt ttaggtattg aacctgctgt aaatttatta   2100
aatcgatgaa tttccccgaa atctgctcta gcagacttgg gttatatacc agtaggctca   2160
ggtgcaaaac aacaaagcac aaattttacc cattaaggat ataggcaatc tgtcaaatag   2220
ttgttatctt tcttaataca gaggaataat caacaatatg gggcaggtac taactaaagt   2280
cctatgcctg tggggcttct gtaaccgaca taacctttac gcgttgtctt ttaggagtct   2340
gttatgcata ttaaagccta cgctgccctg gaagccaacg gaaaattaca accctttgaa   2400
tacgaccccg gtgccctggg tgctaatgag gtggagattg aggtgcagta ttgtggggtg   2460
tgccacagtg atttgtccat gattaataac gaatggggca tttccaatta ccccctagtg   2520
ccgggtcatg aggtggtggg tactgtggcc gccatgggcg aaggggtgaa ccatgttgag   2580
gtgggggatt tagtggggct gggttggcat tctggctact gcatgacctg ccatagttgt   2640
ttatctggct accacaacct ttgtgccact gcggaatcta ccattgtggg ccactacggt   2700
ggctttggcg atcgggttcg ggccaaggga gtcagcgtgg tgaaattacc taaaggcatt   2760
gacctagcca gtgccgggcc ccttttctgt ggaggaatta ccgttttcag tcctatggtg   2820
gaactgagtt taaagcccac tgcaaaagtg gcagtgatcg gcattggggg cttgggccat   2880
```

-continued

```
ttagcggtgc aatttttacg ggcctggggc tgtgaagtga ctgcctttac ctccagtgcc   2940
cgcaagcaaa ctgaagtgtt ggaattgggc gctcaccaca tactagattc caccaatcca   3000
gaggcgatcg ccagtgcgga aggcaaattt gactatatta tctccactgt gaacctgaag   3060
cttgactgga acttatacat cagcaccctg gcgccccagg gacatttcca ctttgttggg   3120
gtggtgttgg agcctttgga tctaaatctt tttcccottt tgatgggaca acgctccgtt   3180
tctgcctccc cagtgggtag tcccgccacc attgccacca tgttggactt tgctgtgcgc   3240
catgacatta aacccgtggt ggaacaattt agctttgatc agatcaacga ggcgatcgcc   3300
catctagaaa gcggcaaagc ccattatcgg gtagtgttaa gccatagtaa aaattaggat   3360
ccggaaataa aaaacgcccg gcggcaaccg agcgtgagct cgaattgatc ctttttgata   3420
atctcatgac caaaatccct taacgtgagt tttcgttcca ctgagcgtca gaccccgtag   3480
aaaagatcaa aggatcttct tgagatcctt tttttctgcg cgtaatctgc tgcttgcaaa   3540
caaaaaaacc accgctacca gcggtggttt gtttgccgga tcaagagcta ccaactcttt   3600
ttccgaaggt aactggcttc agcagagcgc agataccaaa tactgtcctt ctagtgtagc   3660
cgtagttagg ccaccacttc aagaactctg tagcaccgcc tacatacctc gctctgctaa   3720
tcctgttacc agtggctgct gccagtggcg ataagtcgtg tcttaccggg ttggactcaa   3780
gacgatagtt accggataag gcgcagcggt cgggctgaac ggggggttcg tgcacacagc   3840
ccagcttgga gcgaacgacc tacaccgaac tgagatacct acagcgtgag ctatgagaaa   3900
gcgccacgct tcccgaaggg agaaaggcgg acaggtatcc ggtaagcggc agggtcggaa   3960
caggagagcg cacgagggag cttccagggg gaaacgcctg gtatctttat agtcctgtcg   4020
ggtttcgcca cctctgactt gagcgtcgat ttttgtgatg ctcgtcaggg gggcggagcc   4080
tatggaaaaa cgccagcaac gcggcctttt tacggttcct ggccttttgc tggccttttg   4140
ctcacatgtt ctttcctgcg ttatcccctg attctgtgga taaccgtatt accgcctttg   4200
agtgagctga taccgctcgc cgcagccgaa cgaccgagcg cagcgagtca gtgagcgagg   4260
aagcggaaga gcgcctgatg cggtattttc tccttacgca tctgtgcggt atttcacacc   4320
gcatatggtg cactctcagt acaatctgct ctgatgccgc atagttaagc cagtatacac   4380
tccgctatcg ctacgtgact gggtcatggc tgcgccccga cacccgccaa cacccgctga   4440
cgcgccctga cgggcttgtc tgctcccggc atccgcttac agacaagctg tgaccgtctc   4500
cgggagctgc atgtgtcaga ggttttcacc gtcatcaccg aaacgcgcga ggcagctgcg   4560
gtaaagctca tcagcgtggt cgtgaagcga ttcacagatg tctgcctgtt catccgcgtc   4620
cagctcgttg agtttctcca gaagcgttaa tgtctggctt ctgataaagc gggcctgcca   4680
ccatacccac gccgaaacaa gcgctcatga gcccgaagtg gcgagcccga tcttccccat   4740
cggtgatgtc ggcgatatag gcgccagcaa ccgcacctgt ggcgccggtg atgcccgaag   4800
aactccagca tgagatcccc gcgctggagg atcatccagc cggcgtcccg gaaaacgatt   4860
ccgaagccca acctttcata gaaggcggcg gtggaatcga aatctcgtga tggcaggttg   4920
ggcgtcgctt ggtcggtcat ttcgaacccc agagtcccgc tcagaagaac tcgtcaagaa   4980
ggcgatagaa ggcgatgcgc tgcgaatcgg gagcggcgat accgtaaagc acgaggaagc   5040
ggtcagccca ttcgccgcca agctcttcag caatatcacg ggtagccaac gctatgtcct   5100
gatagcggtc cgccacaccc agccggccac agtcgatgaa tccagaaaag cggccatttt   5160
ccaccatgat attcggcaag caggcatcgc catgggtcac gacgagatca tcgccgtcgg   5220
gcatgcgcgc cttgagcctg gcgaacagtt cggctggcgc gagcccctga tgctcttcgt   5280
```

-continued

```
ccagatcatc ctgatcgaca agaccggctt ccatccgagt acgtgctcgc tcgatgcgat   5340
gtttcgcttg gtggtcgaat gggcaggtag ccggatcaag cgtatgcagc cgccgcattg   5400
catcagccat gatggatact ttctcggcag gagcaaggtg agatgacagg agatcctgcc   5460
ccggcacttc gcccaatagc agccagtccc ttcccgcttc agtgacaacg tcgagcacag   5520
ctgcgcaagg aacgcccgtc gtggccagcc acgatagccg cgctgcctcg tcctgcagtt   5580
cattcagggc accggacagg tcggtcttga caaaaagaac cgggcgcccc tgcgctgaca   5640
gccggaacac ggcggcatca gagcagccga ttgtctgttg tgcccagtca tagccgaata   5700
gcctctccac ccaagcggcc ggagaacctg cgtgcaatcc atcttgttca atcatgcgaa   5760
acgatcctca tcctgtctct tgatcagatc ttgatcccct gcgccatcag atccttggcg   5820
gcaagaaagc catccagttt actttgcagg gcttcccaac cttaccagag ggcgccccag   5880
ctggcaattc cggttcgctt gctgtccata aaaccgccca gtctagctat cgccatgtaa   5940
gcccactgca agctacctgc tttctctttg cgcttgcgtt ttcccttgtc cagatagccc   6000
agtagctgac attcatccgg ggtcagcacc gtttctgcgg actggctttc tacgtgttcc   6060
gcttccttta gcagcccttg cgccctgagt gcttgcggca gcgtgaagct ttctctgagc   6120
tgtaacagcc tgaccgcaac aaacgagagg atcgagacca tccgctccag attatccggc   6180
tcctccatgc gttgcctctc ggctcctgct ccggttttcc atgccttatg gaactcctcg   6240
atccgccagc gatgggtata aatgtcgatg acgcgcaagg cttgggctag cgactcgacc   6300
ggttcgctgg tcagcaacaa ccatttcaac ggggtctcac ccttgggcgg gttaatctcc   6360
tcggccagca ccgcgttgag cgtgatattc ccctgtttta gcgtgatgcg cccactgcgc   6420
atagaaattg catcaacgca tatagcgcta gcagcacgcc atagtgactg gcgatgctgt   6480
cggaatggac gatatctaga cttatataga cactaatata gacaatagtt tatactgcta   6540
tctatacaag tatagacatt atctaatcat ggcagacaaa actctagcca cttttcgtat   6600
tgactccgaa gaatgggagt cttttaaaaa ccttgctagt tctgaaagtt ccaacgcctc   6660
agcactgtta acagaatttg ttcgttggta tttggcaggt aacaggttta atactcccac   6720
ttctcacact cccacccatc tagacacatc cctcgaacag cgtatagaca atattgaaca   6780
acgtctagat aaagtcacaa ctaataatct agacaatata gatgaattta tagacaagcg   6840
tatagaagat aatctagcaa cacgtctaga caaacttcaa tcgcaactgg aggaactgcg   6900
gggaaaatcg aaagcccggt agttcaggca gaaggacaag ctaccgggca agacagaaag   6960
aatatagaca atagtataga caatctagac aaattggagg caacccgcga tcgcaccctc   7020
aataagctaa aaatgggtag gcagtcagcc gccgggaaag ccatcgacgc gtttatcaaa   7080
gagttgcttt cttcaggaga caacataagc tgaagttatc aaaattctgt ccttacgtcg   7140
aaagcctgat tttaccgtgc aacgattgat aagcttggct aaactagcac tggctttcaa   7200
cagaaagcat acgaagaatc aatagatata gccaccaatt ccacaaaatg cagataacgt   7260
gtagagtatt ggaatgctta atctgtaagg gttatgaagg ttaacggcaa cggacgagcc   7320
aaaatactca cctccgacga actcaggcga ctgtttagcg acggattcac cacaccgcgc   7380
gatcgcgttt tgtttggcat ctgtctattc accggttgcc gcgttagtga agctctagca   7440
ctccaaacaa cggacattaa aggcgaaaca ctaaccttta ggaagtctac caccaaaggg   7500
aaactcaaaa cccgcgtggt tgacatccag ccaggactag ccgcactcat ggctgactat   7560
caccccaaac cgggaaccct gttccctggc atgaggggag tcagcgatag gctcacgcga   7620
```

-continued

```
tacgcggcgg ataaaatctt gcgcgatgca gccaaaagaa tcgggctaga aggcatcagt   7680
acccacagtt tccgccgtac tgccctcaac caaatgtcta gcgccggtat cccgttgcga   7740
cacattcaag agatatccgg tcacaatgac cttggcacac tgcaacgcta tcttgaagtt   7800
acacccgaac agcgacgcaa agctgtatcc gtgattggct tctaatgtac gccaacgctg   7860
tttagacccc tatgggtgct aaaaaaagac gcagcctaaa cacacgctct acacttgagg   7920
atacttttaa agtatccatc ggttctagaa ctctgcacac gttccggact ttggaaacgt   7980
tataccttc cctgtgttgc agaatgctgc aatatttctt cgacaagtta acttgtgact   8040
ggtttaatat tttctcaaat tgccccaaaa caacacgcct aaatccttag acgtttctgt   8100
ggaaacctat taggttttta tcgccgttgt tttagtggta aacccaaagg gtttgtatat   8160
tcttgtatga agttcgactc tgagggttaa gaagaatggc tcgccgaatt ttttacaagt   8220
ggaaaccgat taaaggttaa gggtcaatcg ggacgatgaa tattttctaa ttgtgacctt   8280
ctccatctaa taagctttct ttggggttaa ggtcgaagaa agtactacgc atgatctgca   8340
tacgatctct attgccaaaa agccgcgacc ctataggctc tcggtcatgc tgcactagtt   8400
cgtgtcgatc actatactgg ttgccgcagc atttcacgct aaaaaaaaat tcttaaaaat   8460
gtccttcata tctcgccaga gtggcaacct attacaaaac ggttgcctac ccgaccggct   8520
cgattttcgc tgaagtggca ctgtgacagt ttgaaatggt acttccgccg tgctgctgac   8580
atcgttgtta gggtgaattg ttcgcggtag atgttgcacc gattcatgaa caccttgtca   8640
cccactttga ataatcgacc gtcaaattca gtcgcgtcaa tttggtaagt gttgggctgt   8700
ctctttttgg ctccaggggc aatgccatca gaaaacacaa ccgcgtcacc cataacttga   8760
taaccgatat cagttttggt tccagtgaaa gcccaaaatt cagacgcgtc attattccga   8820
gcgtgccgga gttgattgta ctcaattttg gcttggcaaa gttgacggcg attcatgccc   8880
agctgctttt gatgtcgtcg cactgtgcgc ttgtgaatac ccaactcaca gctgacagct   8940
ttttgagatg taccatagtg gatgaaactt tttgagacga atatccgcga cgaactaatg   9000
tgaagtacac aaggtacttc cccctctggc gatttaagag aggattgcct tgtgtccttc   9060
actagctcgt tcgggtgtgg cgctccaaaa agttttctgt actctggttt aagttgtctg   9120
ttggccgcat agcggctctt ttgttgaaag ctttgtgtga ctatgccagt ggtcagtgag   9180
cgtaaatcgc ttaacacttg gactaaaggc actactgcaa catcacccca tctttttaaa   9240
tttaggttgt aacaaacttg aaacataccg cccaagtaga cggttatcat tcctgcttta   9300
attttgtagc ggcggaatgc tcctattttt tttccatcct gtaaccaacg gtaaacagac   9360
ttatcactac aatctaagaa cgtctgtact acaggcaatg gcaatgttaa atgaccagac   9420
ccatccttat caagcgctcg acacaaatac cacaaccgcg cacaaggttc tcgaccaatg   9480
cgagtgtgta ccctgaccgt gtaagtgcca agaattattt cagtttgtag ttcccttgta   9540
agcagggtta gtgatacatt tgtatttaag ctttctgggc tgatcatttg gaaatgtctc   9600
agtccagtac ctattgaatg ttatttgctt aacctgaagc taaataaaac ttgttaacta   9660
cacccattaa ttgataaatt caaagcacgt tttttctgtt tggtgtttgg tgtggtaaca   9720
attctgtgta tgtgtgtttt atttagcttc ggttaagtag cataacaacc cccaagcact   9780
gaactttttt taataggtaa tttaaacttt gcctatcggc aaaattttca atcaattgta   9840
cgccaaagtg ttgcatgatc aacgtttgac ttatttttgt atttactaaa tactgaattt   9900
cgccgtgacg ctttttacag atggaaattc acggcaaaat gttttttgct aactttgcta   9960
tgtaaaacaa gaaacttggc actcggttat tactaaataa actggtaaaa aataaccatt  10020
```

agaaccaaaa agaacgaaaa ccagtacacc cttgccagtt ttcaagcttt tgctatgacg 10080
actctaataa tcgggtttaa caccattccg ctttgagaaa attatccttg tacagcaagt 10140
aacagtcaat gctaaaccgc accgctacaa atccttaagt tttccagta gcgatttacc 10200
ttcttggtaa cgcccgcctt gatagcccaa aatttcttta atcaccttac tttctgaaaa 10260
acccgcttcc agacaggctt ttaccacttt tgctagggtt tcatctcttg gttctgggag 10320
ggatgaaacg ggctgtaatg cttgttctga ggtcggttga gccgtttgga gtggctgaaa 10380
actggttaca gactgtaacc ggggcataac cattttgtaa ctgcttacat ctggtaactg 10440
acacggcata tcatccacca tgcagcgata tttccccgac tttaaccact ccacaagggc 10500
aaggtctttt aaggacttgg cgtggctaac tgcaaactta cccaggcgta acatcctaaa 10560
acacttacgg acaccgcctt caccctcgat acctaaggtc ttgacattat catcttgagt 10620
cagcccaata acaaaacgct tgggcttgcg gccgcgcctg gcgtgtttga tgagccattc 10680
ggttgctatc tcgacttcat ctctcagcag tggcagttct tcagcaatta aaacgctttc 10740
ttttcctgct agtgccttat ccccagactc accccgtagc tcaatccggc gctgcaattc 10800
ctccaggtca gcagccatgc ccgactgtat agcctcaaag tcaccacggc ggccaatgac 10860
atttaacccc gtccactcgt ccggtgcagc gtcagcgtca tagactgtca cctcaccccc 10920
gacttgataa gcaagccatt gggctatggt gcttttgcca gttcccgtat ccccaactat 10980
taaacagtgc ttaccagaca gagcttgcat caagtcggtg atgattccct ctggttcgac 11040
cgcaagggtg acggcggtag tgtcaatgat agccgcgccg taagtgccag catagggcaa 11100
ttggtcgtaa actttgacca agttgtatac agactgtcta caccacttca ccactgttaa 11160
cgctgtttgc aaagcgtaag acgtggcatc aaataaaaat atgctggcac taaaagttaa 11220
tcgccccaat ccccacagta aaaacctgcc tagctgttga cgactaggca agtgcatttc 11280
aatccagtca tttgccataa atcaccccgt ctttaaagcc ttgcagttga gcgcgacagg 11340
tatttaactg tgcttgtaac tctgtttgct ggttttgata ccacagactg acggcggcgg 11400
ccgccagtcc taaaaataga aactggcgat cgctcattat tgacttactc cctgttgatt 11460
agcgtggtag tgagtcatag ccgcattgac cgcttcttgg gcttggggtg ttctgccaag 11520
attgggtttt gtagggtcat cgttggctac gactaaggac gcttgttcgg ctatcgcttg 11580
cgggacacca actttagtta actctgtcaa ggatacttgg taaagtcgct cgttcattag 11640
ccgattctcc ggtacataaa actgttgctg gcagtccctt cattggcgac gagttcttca 11700
gccggagtat cagcgataat gtcagcccag ccggtgacat tattattaat aatgttttgt 11760
tcggcaattg cacccaagcc aggacgcgcc gtttcaaact cagagatgac ttgctgctct 11820
ttctcggtga gtggtctatc tgtcatgata attatgtcct tcattatgta ggcgattcca 11880
gtgggtgttt acgaggcagt ccacaggaat cagtgcgatt cacctttaag gtgaatcgtc 11940
atcaaaaaat cactcggtag caacgacccg aaccgaccag gattgatttc ccggttctca 12000
gttcgcaggc ttttgagcgc gtcaccttga ccattgggta actgccatca gccgataagc 12060
taaacgggct gtatagcggt aaagcatccc acacagtcgg gctggcatca actttgcagg 12120
aatagctcac gtcactcatc tcactcgcgc ctgggttgga tggcagcgaa ggcagattac 12180
gacgcagttt tttactggca cttttacccg cattaaaaac gggtacagtg ccattgttga 12240
cggtctgtac ttcggtcata tactcggtgt acacttaata cactctatac tattactgcc 12300
gattagtaca tttgtcaatc actctttgca caaggtgtat gatatggact caggagtaca 12360
ccaaacgtca tgccaaccaa taaagggaga atagcagtca ctctagaagc tgaaatttac 12420
caatggattg ctaaccgagc gtctgaggaa ggaagaccgt tggctaatct tgccgctttc 12480
ttactcacac gagttgttaa agaacaaatg gaacaagaag ccaaggacaa ccaagacaag 12540
cagggggcag catgagcgaa gacagactag ccagaataga agctgcgtta gacagccaag 12600
ttgcagtgaa tgccgacctc cgcacatcgg ttacagaact ccgcgcaacc gcagaagcat 12660
tgttgcaaac agttcaaatc catcagcaga actttgaaat tcttaccgct aggcaattac 12720
aaaccgaagc acggcttgat gagtaccaac gtaccactag cgcggcactc gacagaattg 12780
gcgcggtctt agactacctc gttaggcagc aaaacggttg aggtgaggga tgagcgatga 12840
ctatctagac ggatatcccg caagaggccc tttcgtcttc aagaattaat tgtcgacccc 12900
tgccaaattc aatgcacata tcactgccta tcttttgggg agcactgttc taattatcgg 12960
ttaattattc atcgtgactt ttacatccgg ctgagaagct aattaagagt tgctaagaat 13020
agggttggag gaacgcaaaa ggacaagggg acaagaggac aaggagacac ggggaaaagg 13080
ggagtaataa accactaact agtgtacggg cgggttttaa ccgcaatttc tctgatgatt 13140
acgaatatat ctaaataaac ccacccctac taaccaataa ccaatcctag tcccctattt 13200
actcacacaa gcttgacatt aacattaatg tcaaggttta gcttaaggga gtcagtagta 13260
ttaatttggc tctcatgaat tc 13282

<210> SEQ ID NO 9
<211> LENGTH: 14109
<212> TYPE: DNA
<213> ORGANISM: Artificial Sequence
<220> FEATURE:
<223> OTHER INFORMATION: plasmid TK348

<400> SEQUENCE: 9
gatccgataa catcaccgtc gttatcgtcg ctttagaata acgttcccaa aatagctcat 60
ttccaactgg caactcacaa ccaaaaaccg catttttagt aaatatactc agcaatttgt 120
tcaacctgag catttttccc atttgcaact tgatacaaat atttttagca gcaaattttc 180
ctactgccag cttagtttac ataaattttg tctgttgaca tcttgcacac aataaggtat 240
ggcgcatata atgcgatatt actaccatta atttactacc tagtcattaa cgtctcccgc 300
cagagaacag ttttgaatag gtagtcaatt ttaggtattg aacctgctgt aaatttatta 360
aatcgatgaa tttccccgaa atctgctcta gcagacttgg gttatatacc agtaggctca 420
ggtgcaaaac aacaaagcac aaattttacc cattaaggat ataggcaatc tgtcaaatag 480
ttgttatctt tcttaataca gaggaataat caacaatatg gggcaggtac taactaaagt 540
cctatgcctg tggggcttct gtaaccgaca taacctttac gcgttgtctt ttaggagtct 600
gttatgaacg gtaccagtaa aggagaagaa ctattcactg gagttgtccc aattcttgtt 660
gaattagatg gtgatgttaa tgggcacaaa ttttctgtca gtggagaggg tgaaggtgat 720
gcaacatacg gaaaacttac ccttaaattt atttgcacta ctggaaaact acctgttcca 780
tggccaacac ttgtcactac tttcgcgtat ggtcttcaat gctttgcgag atacccagat 840
catatgaaac agcatgactt tttcaagagt gccatgcccg aaggttatgt acaggaaaga 900
actatatttt tcaaagatga cgggaactac aagacacgtg ctgaagtcaa gtttgaaggt 960
gatacccttg ttaatagaat cgagttaaaa ggtattgatt ttaaagaaga tggaaacatt 1020
cttggacaca aattggaata caactataac tcacacaatg tatacatcat ggcagacaaa 1080
caaaagaatg gaatcaaagt taacttcaaa attagacaca acattgaaga tggaagcgtt 1140

-continued

```
caactagcag accattatca acaaaatact ccaattggcg atggccctgt ccttttacca   1200
gacaaccatt acctgtccac acaatctgcc ctttcgaaag atcccaacga aaagagagac   1260
cacatggtcc ttcttgagtt tgtaacagct gctgggatta cacatggcat ggatgaacta   1320
tacaaataag agctcgaatt gatccttttt gataatctca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagctatga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgcct gatgcggtat   2220
tttctcctta cgcatctgtg cggtatttca caccgcatat ggtgcactct cagtacaatc   2280
tgctctgatg ccgcatagtt aagccagtat acactccgct atcgctacgt gactgggtca   2340
tggctgcgcc ccgacacccg ccaacacccg ctgacgcgcc ctgacgggct tgtctgctcc   2400
cggcatccgc ttacagacaa gctgtgaccg tctccgggag ctgcatgtgt cagaggtttt   2460
caccgtcatc accgaaacgc gcgaggcagc tgcggtaaag ctcatcagcg tggtcgtgaa   2520
gcgattcaca gatgtctgcc tgttcatccg cgtccagctc gttgagtttc tccagaagcg   2580
ttaatgtctg gcttctgata aagcgggcct gccaccatac ccacgccgaa acaagcgctc   2640
atgagcccga agtggcgagc ccgatcttcc ccatcggtga tgtcggcgat ataggcgcca   2700
gcaaccgcac ctgtggcgcc ggtgatgccc gaagaactcc agcatgagat ccccgcgctg   2760
gaggatcatc cagccggcgt cccggaaaac gattccgaag cccaaccttt catagaaggc   2820
ggcggtggaa tcgaaatctc gtgatggcag gttgggcgtc gcttggtcgg tcatttcgaa   2880
ccccagagtc ccgctcagaa gaactcgtca agaaggcgat agaaggcgat gcgctgcgaa   2940
tcgggagcgg cgataccgta aagcacgagg aagcggtcag cccattcgcc gccaagctct   3000
tcagcaatat cacgggtagc caacgctatg tcctgatagc ggtccgccac acccagccgg   3060
ccacagtcga tgaatccaga aaagcggcca ttttccacca tgatattcgg caagcaggca   3120
tcgccatggg tcacgacgag atcatcgccg tcgggcatgc gcgccttgag cctggcgaac   3180
agttcggctg gcgcgagccc ctgatgctct tcgtccagat catcctgatc gacaagaccg   3240
gcttccatcc gagtacgtgc tcgctcgatg cgatgtttcg cttggtggtc gaatgggcag   3300
gtagccggat caagcgtatg cagccgccgc attgcatcag ccatgatgga tactttctcg   3360
gcaggagcaa ggtgagatga caggagatcc tgccccggca cttcgcccaa tagcagccag   3420
tcccttcccg cttcagtgac aacgtcgagc acagctgcgc aaggaacgcc cgtcgtggcc   3480
```

-continued

```
agccacgata gccgcgctgc ctcgtcctgc agttcattca gggcaccgga caggtcggtc   3540
ttgacaaaaa gaaccgggcg cccctgcgct gacagccgga acacggcggc atcagagcag   3600
ccgattgtct gttgtgccca gtcatagccg aatagcctct ccacccaagc ggccggagaa   3660
cctgcgtgca atccatcttg ttcaatcatg cgaaacgatc ctcatcctgt ctcttgatca   3720
gatcttgatc ccctgcgcca tcagatcctt ggcggcaaga aagccatcca gtttactttg   3780
cagggcttcc caaccttacc agagggcgcc ccagctggca attccggttc gcttgctgtc   3840
cataaaaccg cccagtctag ctatcgccat gtaagcccac tgcaagctac ctgctttctc   3900
tttgcgcttg cgttttccct tgtccagata gcccagtagc tgacattcat ccggggtcag   3960
caccgtttct gcggactggc tttctacgtg ttccgcttcc tttagcagcc cttgcgccct   4020
gagtgcttgc ggcagcgtga agctttctct gagctgtaac agcctgaccg caacaaacga   4080
gaggatcgag accatccgct ccagattatc cggctcctcc atgcgttgcc tctcggctcc   4140
tgctccggtt ttccatgcct tatggaactc ctcgatccgc cagcgatggg tataaatgtc   4200
gatgacgcgc aaggcttggg ctagcgactc gaccggttcg ctggtcagca acaaccattt   4260
caacggggtc tcacccttgg gcgggttaat ctcctcggcc agcaccgcgt tgagcgtgat   4320
attcccctgt tttagcgtga tgcgcccact gcgcatagaa attgcatcaa cgcatatagc   4380
gctagcagca cgccatagtg actggcgatg ctgtcggaat ggacgatatc tagacttata   4440
tagacactaa tatagacaat agtttatact gctatctata caagtataga cattatctaa   4500
tcatggcaga caaaactcta gccacttttc gtattgactc cgaagaatgg gagtctttta   4560
aaaaccttgc tagttctgaa agttccaacg cctcagcact gttaacagaa tttgttcgtt   4620
ggtatttggc aggtaacagg tttaatactc ccacttctca cactcccacc catctagaca   4680
catccctcga acagcgtata gacaatattg aacaacgtct agataaagtc acaactaata   4740
atctagacaa tatagatgaa tttatagaca agcgtataga agataatcta gcaacacgtc   4800
tagacaaact tcaatcgcaa ctggaggaac tgcgggggaaa atcgaaagcc cggtagttca   4860
ggcagaagga caagctaccg ggcaagacag aaagaatata gacaatagta tagacaatct   4920
agacaaattg gaggcaaccc gcgatcgcac cctcaataag ctaaaaatgg gtaggcagtc   4980
agccgccggg aaagccatcg acgcgtttat caaagagttg ctttcttcag gagacaacat   5040
aagctgaagt tatcaaaatt ctgtccttac gtcgaaagcc tgattttacc gtgcaacgat   5100
tgataagctt ggctaaacta gcactggctt tcaacagaaa gcatacgaag aatcaataga   5160
tatagccacc aattccacaa aatgcagata acgtgtagag tattggaatg cttaatctgt   5220
aagggttatg aaggttaacg gcaacggacg agccaaaata ctcacctccg acgaactcag   5280
gcgactgttt agcgacggat tcaccacacc gcgcgatcgc gttttgtttg gcatctgtct   5340
attcaccggt tgccgcgtta gtgaagctct agcactccaa acaacggaca ttaaaggcga   5400
aacactaacc tttaggaagt ctaccaccaa agggaaactc aaaacccgcg tggttgacat   5460
ccagccagga ctagccgcac tcatggctga ctatcacccc aaaccgggaa ccctgttccc   5520
tggcatgagg ggagtcagcg ataggctcac gcgatacgcg gcggataaaa tcttgcgcga   5580
tgcagccaaa agaatcgggc tagaaggcat cagtacccac agtttccgcc gtactgccct   5640
caaccaaatg tctagcgccg gtatcccgtt gcgacacatt caagagatat ccggtcacaa   5700
tgaccttggc acactgcaac gctatcttga agttacaccc gaacagcgac gcaaagctgt   5760
atccgtgatt ggcttctaat gtacgccaac gctgtttaga cccctatggg tgctaaaaaa   5820
agacgcagcc taaacacacg ctctacactt gaggatactt ttaaagtatc catcggttct   5880
```

```
agaactctgc acacgttccg gactttggaa acgttatacc tttccctgtg ttgcagaatg   5940
ctgcaatatt tcttcgacaa gttaacttgt gactggttta atattttctc aaattgcccc   6000
aaaacaacac gcctaaatcc ttagacgttt ctgtggaaac ctattaggtt tttatcgccg   6060
ttgttttagt ggtaaaccca aagggtttgt atattcttgt atgaagttcg actctgaggg   6120
ttaagaagaa tggctcgccg aattttttac aagtggaaac cgattaaagg ttaagggtca   6180
atcgggacga tgaatatttt ctaattgtga ccttctccat ctaataagct ttctttgggg   6240
ttaaggtcga agaaagtact acgcatgatc tgcatacgat ctctattgcc aaaaagccgc   6300
gaccctatag gctctcggtc atgctgcact agttcgtgtc gatcactata ctggttgccg   6360
cagcatttca cgctaaaaaa aaattcttaa aaatgtcctt catatctcgc cagagtggca   6420
acctattaca aaacggttgc ctacccgacc ggctcgattt tcgctgaagt ggcactgtga   6480
cagtttgaaa tggtacttcc gccgtgctgc tgacatcgtt gttagggtga attgttcgcg   6540
gtagatgttg caccgattca tgaacacctt gtcacccact ttgaataatc gaccgtcaaa   6600
ttcagtcgcg tcaatttggt aagtgttggg ctgtctcttt ttggctccag gggcaatgcc   6660
atcagaaaac acaaccgcgt cacccataac ttgataaccg atatcagttt tggttccagt   6720
gaaagcccaa aattcagacg cgtcattatt ccgagcgtgc cggagttgat tgtactcaat   6780
tttggcttgg caaagttgac ggcgattcat gcccagctgc ttttgatgtc gtcgcactgt   6840
gcgcttgtga atacccaact cacagctgac agctttttga gatgtaccat agtggatgaa   6900
actttttgag acgaatatcc gcgacgaact aatgtgaagt acacaaggta cttccccctc   6960
tggcgattta agagaggatt gccttgtgtc cttcactagc tcgttcgggt gtggcgctcc   7020
aaaaagtttt ctgtactctg gtttaagttg tctgttggcc gcatagcggc tcttttgttg   7080
aaagctttgt gtgactatgc cagtggtcag tgagcgtaaa tcgcttaaca cttggactaa   7140
aggcactact gcaacatcac cccatctttt taaatttagg ttgtaacaaa cttgaaacat   7200
accgcccaag tagacggtta tcattcctgc tttaattttg tagcggcgga atgctcctat   7260
tttttttcca tcctgtaacc aacggtaaac agacttatca ctacaatcta agaacgtctg   7320
tactacaggc aatggcaatg ttaaatgacc agacccatcc ttatcaagcg ctcgacacaa   7380
ataccacaac cgcgcacaag gttctcgacc aatgcgagtg tgtaccctga ccgtgtaagt   7440
gccaagaatt atttcagttt gtagttccct tgtaagcagg gttagtgata catttgtatt   7500
taagctttct gggctgatca tttggaaatg tctcagtcca gtacctattg aatgttattt   7560
gcttaacctg aagctaaata aaacttgtta actacaccca ttaattgata aattcaaagc   7620
acgtttttttc tgtttggtgt ttggtgtggt aacaattctg tgtatgtgtg ttttatttag   7680
cttcggttaa gtagcataac aacccccaag cactgaactt tttttaatag gtaatttaaa   7740
ctttgcctat cggcaaaatt ttcaatcaat tgtacgccaa agtgttgcat gatcaacgtt   7800
tgacttattt ttgtatttac taaatactga atttcgccgt gacgcttttt acagatggaa   7860
attcacggca aaatgttttt tgctaacttt gctatgtaaa acaagaaact tggcactcgg   7920
ttattactaa ataaactggt aaaaaataac cattagaacc aaaaagaacg aaaaccagta   7980
caccccttgcc agttttcaag cttttgctat gacgactcta ataatcgggt ttaacaccat   8040
tccgctttga gaaaattatc cttgtacagc aagtaacagt caatgctaaa ccgcaccgct   8100
acaaatcctt aagtttttcc agtagcgatt taccttcttg gtaacgcccg ccttgatagc   8160
ccaaaatttc tttaatcacc ttactttctg aaaaacccgc ttccagacag gcttttacca   8220
```

```
cttttgctag ggtttcatct cttggttctg ggagggatga aacgggctgt aatgcttgtt   8280
ctgaggtcgg ttgagccgtt tggagtggct gaaaactggt tacagactgt aaccggggca   8340
taaccatttt gtaactgctt acatctggta actgacacgg catatcatcc accatgcagc   8400
gatatttccc cgactttaac cactccacaa gggcaaggtc ttttaaggac ttggcgtggc   8460
taactgcaaa cttacccagg cgtaacatcc taaaacactt acggacaccg ccttcaccct   8520
cgatacctaa ggtcttgaca ttatcatctt gagtcagccc aataacaaaa cgcttgggct   8580
tgcggccgcg cctggcgtgt ttgatgagcc attcggttgc tatctcgact tcatctctca   8640
gcagtggcag ttcttcagca attaaaacgc tttcttttcc tgctagtgcc ttatccccag   8700
actcaccccg tagctcaatc cggcgctgca attcctccag gtcagcagcc atgcccgact   8760
gtatagcctc aaagtcacca cggcggccaa tgacatttaa ccccgtccac tcgtccggtg   8820
cagcgtcagc gtcatagact gtcacctcac ccccgacttg ataagcaagc cattgggcta   8880
tggtgctttt gccagttccc gtatccccaa ctattaaaca gtgcttacca gacagagctt   8940
gcatcaagtc ggtgatgatt ccctctggtt cgaccgcaag ggtgacggcg gtagtgtcaa   9000
tgatagccgc gccgtaagtg ccagcatagg gcaattggtc gtaaactttg accaagttgt   9060
atacagactg tctacaccac ttcaccactg ttaacgctgt ttgcaaagcg taagacgtgg   9120
catcaaataa aaatatgctg gcactaaaag ttaatcgccc caatccccac agtaaaaacc   9180
tgcctagctg ttgacgacta ggcaagtgca tttcaatcca gtcatttgcc ataaatcacc   9240
ccgtctttaa agccttgcag ttgagcgcga caggtattta actgtgcttg taactctgtt   9300
tgctggtttt gataccacag actgacggcg gcggccgcca gtcctaaaaa tagaaactgg   9360
cgatcgctca ttattgactt actccctgtt gattagcgtg gtagtgagtc atagccgcat   9420
tgaccgcttc ttgggcttgg ggtgttctgc caagattggg ttttgtaggg tcatcgttgg   9480
ctacgactaa ggacgcttgt tcggctatcg cttgcgggac accaacttta gttaactctg   9540
tcaaggatac ttggtaaagt cgctcgttca ttagccgatt ctccggtaca taaaactgtt   9600
gctggcagtc ccttcattgg cgacgagttc ttcagccgga gtatcagcga taatgtcagc   9660
ccagccggtg acattattat taataatgtt ttgttcggca attgcaccca agccaggacg   9720
cgccgtttca aactcagaga tgacttgctg ctctttctcg gtgagtggtc tatctgtcat   9780
gataattatg tccttcatta tgtaggcgat tccagtgggt gtttacgagg cagtccacag   9840
gaatcagtgc gattcacctt taaggtgaat cgtcatcaaa aaatcactcg gtagcaacga   9900
cccgaaccga ccaggattga tttcccggtt ctcagttcgc aggcttttga gcgcgtcacc   9960
ttgaccattg ggtaactgcc atcagccgat aagctaaacg ggctgtatag cggtaaagca  10020
tcccacacag tcgggctggc atcaactttg caggaatagc tcacgtcact catctcactc  10080
gcgcctgggt tggatggcag cgaaggcaga ttacgacgca gtttttttact ggcactttta  10140
cccgcattaa aaacgggtac agtgccattg ttgacggtct gtacttcggt catatactcg  10200
gtgtacactt aatacactct atactattac tgccgattag tacatttgtc aatcactctt  10260
tgcacaaggt gtatgatatg gactcaggag tacaccaaac gtcatgccaa ccaataaagg  10320
gagaatagca gtcactctag aagctgaaat ttaccaatgg attgctaacc gagcgtctga  10380
ggaaggaaga ccgttggcta atcttgccgc tttcttactc acacgagttg ttaaagaaca  10440
aatggaacaa gaagccaagg acaaccaaga caagcagggg gcagcatgag cgaagacaga  10500
ctagccagaa tagaagctgc gttagacagc caagttgcag tgaatgccga cctccgcaca  10560
tcggttacag aactccgcgc aaccgcagaa gcattgttgc aaacagttca aatccatcag  10620
```

cagaactttg aaattcttac cgctaggcaa ttacaaaccg aagcacggct tgatgagtac 10680
caacgtacca ctagcgcggc actcgacaga attggcgcgg tcttagacta cctcgttagg 10740
cagcaaaacg gttgaggtga gggatgagcg atgactatct agacggatat cccgcaagag 10800
gccctttcgt cttcaagaat taattgtcga cacccaagta catagccgac actttaaaag 10860
gtgttgctac acagacaaag cctgcaaagg caggcttggt tatgatagcc tcaggctacc 10920
ctacgggaaa ctgccctgta ggcttaagtg aagtttattg agttctagag tgattttgag 10980
agcgatcgca actcaatttc atcttaattt catttctcag tgaaacatta gtagaagagc 11040
cttttaaatc caataccttc gccaaaatcc aacaccctag aagggtgtcg ctatacaaac 11100
caaggctgcc tccgcagcct gtaaggattt cagcccacgg aagtgggctt tgtttgtgta 11160
gccccaggct tccagcctgt gggcgtttgt actcaaggaa ttttgaagcg tgatgaattc 11220
ttatactgtc ggtacctatt tagcggagcg gcttgtccag attggtctca agcatcactt 11280
cgcagtcgcg ggcgactaca acctcgtcct tcttgacaac ctgcttttga acaaaaacat 11340
ggagcaggtt tattgctgta acgaactgaa ctgcggtttc agtgcagaag gttatgctcg 11400
tgccaaaggc gcagcagcag ccgtcgttac ctacagcgtc ggtgcgcttt ccgcatttga 11460
tgctatcggt ggcgcctatg cagaaaacct tccggttatc ctgatctccg gtgctccgaa 11520
caacaatgat cacgctgctg gtcacgtgtt gcatcacgct cttggcaaaa ccgactatca 11580
ctatcagttg gaaatggcca agaacatcac ggccgcagct gaagcgattt acaccccaga 11640
agaagctccg gctaaaatcg atcacgtgat taaaactgct cttcgtgaga agaagccggt 11700
ttatctcgaa atcgcttgca acattgcttc catgccctgc gccgctcctg gaccggcaag 11760
cgcattgttc aatgacgaag ccagcgacga agcttctttg aatgcagcgg ttgaagaaac 11820
cctgaaattc atcgccaacc gcgacaaagt tgccgtcctc gtcggcagca agctgcgcgc 11880
agctggtgct gaagaagctg ctgtcaaatt tgctgatgct ctcggtggcg cagttgctac 11940
catggctgct gcaaaaagct tcttcccaga agaaaacccg cattacatcg gtacctcatg 12000
ggtgaagtc agctatccgg gcgttgaaaa gacgatgaaa gaagccgatg cggttatcgc 12060
tctggctcct gtcttcaacg actactccac cactggttgg acggatattc ctgatcctaa 12120
gaaactggtt ctcgctgaac cgcgttctgt cgtcgttaac ggcgttcgct tccccagcgt 12180
tcatctgaaa gactatctga cccgtttggc tcagaaagtt tccaagaaaa ccggtgcttt 12240
ggacttcttc aaatccctca atgcaggtga actgaagaaa gccgctccgg ctgatccgag 12300
tgctccgttg gtcaacgcag aaatcgcccg tcaggtcgaa gctcttctga ccccgaacac 12360
gacggttatt gctgaaaccg gtgactcttg gttcaatgct cagcgcatga agctcccgaa 12420
cggtgctcgc gttgaatatg aaatgcagtg gggtcacatc ggttggtccg ttcctgccgc 12480
cttcggttat gccgtcggtg ctccggaacg tcgcaacatc ctcatggttg gtgatggttc 12540
cttccagctg acggctcagg aagtcgctca gatggttcgc ctgaaactgc cggttatcat 12600
cttcttgatc aataactatg gttacaccat cgaagttatg atccatgatg gtccgtacaa 12660
caacatcaag aactgggatt atgccggtct gatggaagtg ttcaacggta acggtggtta 12720
tgacagcggt gctggtaaag gcctgaaggc taaaaccggt ggcgaactgg cagaagctat 12780
caaggttgct ctggcaaaca ccgacggccc aaccctgatc gaatgcttca tcggtcgtga 12840
agactgcact gaagaattgg tcaaatgggg taagcgcgtt gctgccgcca acagccgtaa 12900
gcctgttaac aagctcctct agtttttggg gatcaattcg agctctctgg ataaaactaa 12960

```
taaactctat tacccatgat taaagcctac gctgccctgg aagccaacgg aaaactccaa  13020
ccctttgaat acgaccccgg tgccctgggt gctaatgagg tggagattga ggtgcagtat  13080
tgtggggtgt gccacagtga tttgtccatg attaataacg aatggggcat ttccaattac  13140
cccctagtgc cgggtcatga ggtggtgggt actgtggccg ccatgggcga aggggtgaac  13200
catgttgagg tgggggattt agtggggctg ggttggcatt cgggctactg catgacctgc  13260
catagttgtt tatctggcta ccacaacctt tgtgccacgg cggaatcgac cattgtgggc  13320
cactacggtg gctttggcga tcgggttcgg gccaagggag tcagcgtggt gaaattacct  13380
aaaggcattg acctagccag tgccgggccc cttttctgtg gaggaattac cgttttcagt  13440
cctatggtgg aactgagttt aaagcccact gcaaaagtgg cagtgatcgg cattgggggc  13500
ttgggccatt tagcggtgca atttctccgg gcctggggct gtgaagtgac tgcctttacc  13560
tccagtgcca ggaagcaaac ggaagtgttg gaattgggcg ctcaccacat actagattcc  13620
accaatccag aggcgatcgc cagtgcggaa ggcaaatttg actatattat ctccactgtg  13680
aacctgaagc ttgactggaa cttatacatc agcaccctgg cgccccaggg acatttccac  13740
tttgttgggg tggtgttgga gcctttggat ctaaatcttt ttcccctttt gatgggacaa  13800
cgctccgttt ctgcctcccc agtgggtagt cccgccacca ttgccaccat gttggacttt  13860
gctgtgcgcc atgacattaa acccgtggtg gaacaattta gctttgatca gatcaacgag  13920
gcgatcgccc atctagaaag cggcaaagcc cattatcggg tagtgctcag ccatagtaaa  13980
aattagctct gcaaaggttg cttctgggtc cgtggaatgg tcaaacggag tcgatctcag  14040
ttttgatacg ctctatctgg aaagcttgac attcgatctg caggcccccc gggggggctcg  14100
actctagag                                                         14109
```

<210> SEQ ID NO 10
<211> LENGTH: 14132
<212> TYPE: DNA
<213> ORGANISM: Artificial Sequence
<220> FEATURE:
<223> OTHER INFORMATION: plasmid TK351

<400> SEQUENCE: 10

```
gatccgataa catcaccgtc gttatcgtcg ctttagaata acgttcccaa aatagctcat     60
ttccaactgg caactcacaa ccaaaaaccg catttttagt aaatatactc agcaatttgt    120
tcaacctgag catttttccc atttgcaact tgatacaaat atttttagca gcaaattttc    180
ctactgccag cttagtttac ataaattttg tctgttgaca tcttgcacac aataaggtat    240
ggcgcatata atgcgatatt actaccatta atttactacc tagtcattaa cgtctcccgc    300
cagagaacag ttttgaatag gtagtcaatt ttaggtattg aacctgctgt aaatttatta    360
aatcgatgaa tttccccgaa atctgctcta gcagacttgg gttatatacc agtaggctca    420
ggtgcaaaac aacaaagcac aaattttacc cattaaggat ataggcaatc tgtcaaatag    480
ttgttatctt tcttaataca gaggaataat caacaatatg gggcaggtac taactaaagt    540
cctatgcctg tggggcttct gtaaccgaca taacctttac gcgttgtctt ttaggagtct    600
gttatgaacg gtaccagtaa aggagaagaa ctattcactg gagttgtccc aattcttgtt    660
gaattagatg gtgatgttaa tgggcacaaa ttttctgtca gtggagaggg tgaaggtgat    720
gcaacatacg gaaaacttac ccttaaattt atttgcacta ctggaaaact acctgttcca    780
tggccaacac ttgtcactac tttcgcgtat ggtcttcaat gctttgcgag atacccagat    840
catatgaaac agcatgactt tttcaagagt gccatgcccg aaggttatgt acaggaaaga    900
```

-continued

```
actatatttt tcaaagatga cgggaactac aagacacgtg ctgaagtcaa gtttgaaggt    960
gataccettg ttaatagaat cgagttaaaa ggtattgatt ttaaagaaga tggaaacatt   1020
cttggacaca aattggaata caactataac tcacacaatg tatacatcat ggcagacaaa   1080
caaaagaatg gaatcaaagt taacttcaaa attagacaca acattgaaga tggaagcgtt   1140
caactagcag accattatca acaaaatact ccaattggcg atggccctgt ccttttacca   1200
gacaaccatt acctgtccac acaatctgcc ctttcgaaag atcccaacga aaagagagac   1260
cacatggtcc ttcttgagtt tgtaacagct gctgggatta cacatggcat ggatgaacta   1320
tacaaataag agctcgaatt gatccttttt gataatctca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagctatga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgcct gatgcggtat   2220
tttctcctta cgcatctgtg cggtatttca caccgcatat ggtgcactct cagtacaatc   2280
tgctctgatg ccgcatagtt aagccagtat acactccgct atcgctacgt gactgggtca   2340
tggctgcgcc ccgacacccg ccaacacccg ctgacgcgcc ctgacgggct tgtctgctcc   2400
cggcatccgc ttacagacaa gctgtgaccg tctccgggag ctgcatgtgt cagaggtttt   2460
caccgtcatc accgaaacgc gcgaggcagc tgcggtaaag ctcatcagcg tggtcgtgaa   2520
gcgattcaca gatgtctgcc tgttcatccg cgtccagctc gttgagtttc tccagaagcg   2580
ttaatgtctg gcttctgata aagcgggcct gccaccatac ccacgccgaa acaagcgctc   2640
atgagcccga agtggcgagc ccgatcttcc ccatcggtga tgtcggcgat ataggcgcca   2700
gcaaccgcac ctgtggcgcc ggtgatgccc gaagaactcc agcatgagat ccccgcgctg   2760
gaggatcatc cagccggcgt cccggaaaac gattccgaag cccaaccttt catagaaggc   2820
ggcggtggaa tcgaaatctc gtgatggcag gttgggcgtc gcttggtcgg tcatttcgaa   2880
ccccagagtc ccgctcagaa gaactcgtca agaaggcgat agaaggcgat gcgctgcgaa   2940
tcgggagcgg cgataccgta aagcacgagg aagcggtcag cccattcgcc gccaagctct   3000
tcagcaatat cacgggtagc caacgctatg tcctgatagc ggtccgccac acccagccgg   3060
ccacagtcga tgaatccaga aaagcggcca ttttccacca tgatattcgg caagcaggca   3120
tcgccatggg tcacgacgag atcatcgccg tcgggcatgc gcgccttgag cctggcgaac   3180
agttcggctg gcgcgagccc ctgatgctct tcgtccagat catcctgatc gacaagaccg   3240
```

-continued

```
gcttccatcc gagtacgtgc tcgctcgatg cgatgtttcg cttggtggtc gaatgggcag   3300
gtagccggat caagcgtatg cagccgccgc attgcatcag ccatgatgga tactttctcg   3360
gcaggagcaa ggtgagatga caggagatcc tgccccggca cttcgcccaa tagcagccag   3420
tcccttcccg cttcagtgac aacgtcgagc acagctgcgc aaggaacgcc cgtcgtggcc   3480
agccacgata gccgcgctgc ctcgtcctgc agttcattca gggcaccgga caggtcggtc   3540
ttgacaaaaa gaaccgggcg cccctgcgct gacagccgga acacggcggc atcagagcag   3600
ccgattgtct gttgtgccca gtcatagccg aatagcctct ccacccaagc ggccggagaa   3660
cctgcgtgca atccatcttg ttcaatcatg cgaaacgatc ctcatcctgt ctcttgatca   3720
gatcttgatc ccctgcgcca tcagatcctt ggcggcaaga aagccatcca gtttactttg   3780
cagggcttcc caaccttacc agagggcgcc ccagctggca attccggttc gcttgctgtc   3840
cataaaaccg cccagtctag ctatcgccat gtaagcccac tgcaagctac ctgctttctc   3900
tttgcgcttg cgttttccct tgtccagata gcccagtagc tgacattcat ccggggtcag   3960
caccgtttct gcggactggc tttctacgtg ttccgcttcc tttagcagcc cttgcgccct   4020
gagtgcttgc ggcagcgtga agctttctct gagctgtaac agcctgaccg caacaaacga   4080
gaggatcgag accatccgct ccagattatc cggctcctcc atgcgttgcc tctcggctcc   4140
tgctccggtt ttccatgcct tatggaactc ctcgatccgc cagcgatggg tataaatgtc   4200
gatgacgcgc aaggcttggg ctagcgactc gaccggttcg ctggtcagca acaaccattt   4260
caacggggtc tcacccttgg gcgggttaat ctcctcggcc agcaccgcgt tgagcgtgat   4320
attcccctgt tttagcgtga tgcgcccact gcgcatagaa attgcatcaa cgcatatagc   4380
gctagcagca cgccatagtg actggcgatg ctgtcggaat ggacgatatc tagacttata   4440
tagacactaa tatagacaat agtttatact gctatctata caagtataga cattatctaa   4500
tcatggcaga caaaactcta gccacttttc gtattgactc cgaagaatgg gagtctttta   4560
aaaaccttgc tagttctgaa agttccaacg cctcagcact gttaacagaa tttgttcgtt   4620
ggtatttggc aggtaacagg tttaatactc ccacttctca cactcccacc catctagaca   4680
catccctcga acagcgtata gacaatattg aacaacgtct agataaagtc acaactaata   4740
atctagacaa tatagatgaa tttatagaca agcgtataga agataatcta gcaacacgtc   4800
tagacaaact tcaatcgcaa ctggaggaac tgcggggaaa atcgaaagcc cggtagttca   4860
ggcagaagga caagctaccg ggcaagacag aaagaatata gacaatagta tagacaatct   4920
agacaaattg gaggcaaccc gcgatcgcac cctcaataag ctaaaaatgg gtaggcagtc   4980
agccgccggg aaagccatcg acgcgtttat caaagagttg ctttcttcag gagacaacat   5040
aagctgaagt tatcaaaatt ctgtccttac gtcgaaagcc tgattttacc gtgcaacgat   5100
tgataagctt ggctaaacta gcactggctt tcaacagaaa gcatacgaag aatcaataga   5160
tatagccacc aattccacaa aatgcagata acgtgtagag tattggaatg cttaatctgt   5220
aagggttatg aaggttaacg gcaacggacg agccaaaata ctcacctccg acgaactcag   5280
gcgactgttt agcgacggat tcaccacacc gcgcgatcgc gttttgtttg gcatctgtct   5340
attcaccggt tgccgcgtta gtgaagctct agcactccaa acaacggaca ttaaaggcga   5400
aacactaacc tttaggaagt ctaccaccaa agggaaactc aaaacccgcg tggttgacat   5460
ccagccagga ctagccgcac tcatggctga ctatcacccc aaaccgggaa ccctgttccc   5520
tggcatgagg ggagtcagcg ataggctcac gcgatacgcg gcggataaaa tcttgcgcga   5580
tgcagccaaa agaatcgggc tagaaggcat cagtacccac agtttccgcc gtactgccct   5640
```

caaccaaatg tctagcgccg gtatcccgtt gcgacacatt caagagatat ccggtcacaa 5700
tgaccttggc acactgcaac gctatcttga agttacaccc gaacagcgac gcaaagctgt 5760
atccgtgatt ggcttctaat gtacgccaac gctgtttaga cccctatggg tgctaaaaaa 5820
agacgcagcc taaacacacg ctctacactt gaggatactt ttaaagtatc catcggttct 5880
agaactctgc acacgttccg gactttggaa acgttatacc tttccctgtg ttgcagaatg 5940
ctgcaatatt tcttcgacaa gttaacttgt gactggttta atattttctc aaattgcccc 6000
aaaacaacac gcctaaatcc ttagacgttt ctgtggaaac ctattaggtt tttatcgccg 6060
ttgttttagt ggtaaaccca aagggtttgt atattcttgt atgaagttcg actctgaggg 6120
ttaagaagaa tggctcgccg aattttttac aagtggaaac cgattaaagg ttaagggtca 6180
atcgggacga tgaatatttt ctaattgtga ccttctccat ctaataagct ttctttgggg 6240
ttaaggtcga agaaagtact acgcatgatc tgcatacgat ctctattgcc aaaaagccgc 6300
gaccctatag gctctcggtc atgctgcact agttcgtgtc gatcactata ctggttgccg 6360
cagcatttca cgctaaaaaa aaattcttaa aaatgtcctt catatctcgc cagagtggca 6420
acctattaca aaacggttgc ctacccgacc ggctcgattt tcgctgaagt ggcactgtga 6480
cagtttgaaa tggtacttcc gccgtgctgc tgacatcgtt gttagggtga attgttcgcg 6540
gtagatgttg caccgattca tgaacacctt gtcacccact ttgaataatc gaccgtcaaa 6600
ttcagtcgcg tcaatttggt aagtgttggg ctgtctcttt ttggctccag ggggcaatgcc 6660 atcagaaaac acaaccgcgt cacccataac ttgataaccg atatcagttt tggttccagt 6720
gaaagcccaa aattcagacg cgtcattatt ccgagcgtgc cggagttgat tgtactcaat 6780
tttggcttgg caaagttgac ggcgattcat gcccagctgc ttttgatgtc gtcgcactgt 6840
gcgcttgtga atacccaact cacagctgac agctttttga gatgtaccat agtggatgaa 6900
actttttgag acgaatatcc gcgacgaact aatgtgaagt acacaaggta cttccccctc 6960
tggcgattta agagaggatt gccttgtgtc cttcactagc tcgttcgggt gtggcgctcc 7020
aaaaagtttt ctgtactctg gtttaagttg tctgttggcc gcatagcggc tcttttgttg 7080
aaagctttgt gtgactatgc cagtggtcag tgagcgtaaa tcgcttaaca cttggactaa 7140
aggcactact gcaacatcac cccatctttt taaatttagg ttgtaacaaa cttgaaacat 7200
accgcccaag tagacggtta tcattcctgc tttaattttg tagcggcgga atgctcctat 7260
tttttttcca tcctgtaacc aacggtaaac agacttatca ctacaatcta agaacgtctg 7320
tactacaggc aatggcaatg ttaaatgacc agacccatcc ttatcaagcg ctcgacacaa 7380
ataccacaac cgcgcacaag gttctcgacc aatgcgagtg tgtaccctga ccgtgtaagt 7440
gccaagaatt atttcagttt gtagttccct tgtaagcagg gttagtgata catttgtatt 7500
taagctttct gggctgatca tttggaaatg tctcagtcca gtacctattg aatgttattt 7560
gcttaacctg aagctaaata aaacttgtta actacaccca ttaattgata aattcaaagc 7620 acgtttttc tgtttggtgt ttggtgtggt aacaattctg tgtatgtgtg ttttatttag 7680
cttcggttaa gtagcataac aacccccaag cactgaactt tttttaatag gtaatttaaa 7740
ctttgcctat cggcaaaatt ttcaatcaat tgtacgccaa agtgttgcat gatcaacgtt 7800
tgacttattt ttgtatttac taaatactga atttcgccgt gacgcttttt acagatggaa 7860
attcacggca aaatgttttt tgctaacttt gctatgtaaa acaagaaact tggcactcgg 7920
ttattactaa ataaactggt aaaaaataac cattagaacc aaaaagaacg aaaaccagta 7980

-continued

```
caccccttgcc agttttcaag cttttgctat gacgactcta ataatcgggt ttaacaccat   8040
tccgctttga gaaaattatc cttgtacagc aagtaacagt caatgctaaa ccgcaccgct   8100
acaaatcctt aagtttttcc agtagcgatt taccttcttg gtaacgcccg ccttgatagc   8160
ccaaaatttc tttaatcacc ttactttctg aaaaacccgc ttccagacag gcttttacca   8220
cttttgctag ggtttcatct cttggttctg ggagggatga aacgggctgt aatgcttgtt   8280
ctgaggtcgg ttgagccgtt tggagtggct gaaaactggt tacagactgt aaccggggca   8340
taaccatttt gtaactgctt acatctggta actgacacgg catatcatcc accatgcagc   8400
gatatttccc cgactttaac cactccacaa gggcaaggtc ttttaaggac ttggcgtggc   8460
taactgcaaa cttacccagg cgtaacatcc taaaacactt acggacaccg ccttcaccct   8520
cgatacctaa ggtcttgaca ttatcatctt gagtcagccc aataacaaaa cgcttgggct   8580
tgcggccgcg cctggcgtgt ttgatgagcc attcggttgc tatctcgact tcatctctca   8640
gcagtggcag ttcttcagca attaaaacgc tttcttttcc tgctagtgcc ttatccccag   8700
actcaccccg tagctcaatc cggcgctgca attcctccag gtcagcagcc atgcccgact   8760
gtatagcctc aaagtcacca cggcggccaa tgacatttaa ccccgtccac tcgtccggtg   8820
cagcgtcagc gtcatagact gtcacctcac ccccgacttg ataagcaagc cattgggcta   8880
tggtgctttt gccagttccc gtatccccaa ctattaaaca gtgcttacca gacagagctt   8940
gcatcaagtc ggtgatgatt ccctctggtt cgaccgcaag ggtgacggcg gtagtgtcaa   9000
tgatagccgc gccgtaagtg ccagcatagg gcaattggtc gtaaactttg accaagttgt   9060
atacagactg tctacaccac ttcaccactg ttaacgctgt ttgcaaagcg taagacgtgg   9120
catcaaataa aaatatgctg gcactaaaag ttaatcgccc caatccccac agtaaaaacc   9180
tgcctagctg ttgacgacta ggcaagtgca tttcaatcca gtcatttgcc ataaatcacc   9240
ccgtctttaa agccttgcag ttgagcgcga caggtattta actgtgcttg taactctgtt   9300
tgctggtttt gataccacag actgacggcg gcggccgcca gtcctaaaaa tagaaactgg   9360
cgatcgctca ttattgactt actccctgtt gattagcgtg gtagtgagtc atagccgcat   9420
tgaccgcttc ttgggcttgg ggtgttctgc caagattggg ttttgtaggg tcatcgttgg   9480
ctacgactaa ggacgcttgt tcggctatcg cttgcgggac accaacttta gttaactctg   9540
tcaaggatac ttggtaaagt cgctcgttca ttagccgatt ctccggtaca taaaactgtt   9600
gctggcagtc ccttcattgg cgacgagttc ttcagccgga gtatcagcga taatgtcagc   9660
ccagccggtg acattattat taataatgtt ttgttcggca attgcaccca agccaggacg   9720
cgccgtttca aactcagaga tgacttgctg ctctttctcg gtgagtggtc tatctgtcat   9780
gataattatg tccttcatta tgtaggcgat tccagtgggt gtttacgagg cagtccacag   9840
gaatcagtgc gattcacctt taaggtgaat cgtcatcaaa aaatcactcg gtagcaacga   9900
cccgaaccga ccaggattga tttcccggtt ctcagttcgc aggcttttga gcgcgtcacc   9960
ttgaccattg ggtaactgcc atcagccgat aagctaaacg ggctgtatag cggtaaagca  10020
tcccacacag tcgggctggc atcaactttg caggaatagc tcacgtcact catctcactc  10080
gcgcctgggt tggatggcag cgaaggcaga ttacgacgca gtttttttact ggcactttta  10140
cccgcattaa aaacgggtac agtgccattg ttgacggtct gtacttcggt catatactcg  10200
gtgtacactt aatacactct atactattac tgccgattag tacatttgtc aatcactctt  10260
tgcacaaggt gtatgatatg gactcaggag tacaccaaac gtcatgccaa ccaataaagg  10320
gagaatagca gtcactctag aagctgaaat ttaccaatgg attgctaacc gagcgtctga  10380
```

-continued

```
ggaaggaaga ccgttggcta atcttgccgc tttcttactc acacgagttg ttaaagaaca  10440
aatggaacaa gaagccaagg acaaccaaga caagcagggg gcagcatgag cgaagacaga  10500
ctagccagaa tagaagctgc gttagacagc caagttgcag tgaatgccga cctccgcaca  10560
tcggttacag aactccgcgc aaccgcagaa gcattgttgc aaacagttca aatccatcag  10620
cagaactttg aaattcttac cgctaggcaa ttacaaaccg aagcacggct tgatgagtac  10680
caacgtacca ctagcgcggc actcgacaga attggcgcgg tcttagacta cctcgttagg  10740
cagcaaaacg gttgaggtga gggatgagcg atgactatct agacggatat cccgcaagag  10800
gccctttcgt cttcaagaat taattgtcga ccaagtcata tttgagggtt caatggagcg  10860
cttagttgct attttaatga cggctctcac ctcagctttg ggaatgatcc ctttagtcat  10920
tggtacgggc gcaggtaagg aaatcttgca acctttagca gtagtagtgc tgggagggtt  10980
gtttacttct acagcattaa cattacttgt attgcctgca ttgtactcta agttcggtaa  11040
ttacttaata cctaagcaaa ctttgtcaga agttgaaaag gtgaatagag tgggaacagt  11100
actggagtgg taaacaaaat tgacatatga aatttcatac tgatttcatt ttattttgag  11160
aaactggggt aaaggctagc caatgcacaa gcactgcgat caaactacaa tctttcactt  11220
gcctaaagtt ttaaaatgaa ttcttatact gtcggtacct atttagcgga gcggcttgtc  11280
cagattggtc tcaagcatca cttcgcagtc gcgggcgact acaacctcgt ccttcttgac  11340
aacctgcttt tgaacaaaaa catggagcag gtttattgct gtaacgaact gaactgcggt  11400
ttcagtgcag aaggttatgc tcgtgccaaa ggcgcagcag cagccgtcgt tacctacagc  11460
gtcggtgcgc tttccgcatt tgatgctatc ggtggcgcct atgcagaaaa ccttccggtt  11520
atcctgatct ccggtgctcc gaacaacaat gatcacgctg ctggtcacgt gttgcatcac  11580
gctcttggca aaaccgacta tcactatcag ttggaaatgg ccaagaacat cacggccgca  11640
gctgaagcga tttacacccc agaagaagct ccggctaaaa tcgatcacgt gattaaaact  11700
gctcttcgtg agaagaagcc ggtttatctc gaaatcgctt gcaacattgc ttccatgccc  11760
tgcgccgctc ctggaccggc aagcgcattg ttcaatgacg aagccagcga cgaagcttct  11820
ttgaatgcag cggttgaaga aaccctgaaa ttcatcgcca accgcgacaa agttgccgtc  11880
ctcgtcggca gcaagctgcg cgcagctggt gctgaagaag ctgctgtcaa atttgctgat  11940
gctctcggtg gcgcagttgc taccatggct gctgcaaaaa gcttcttccc agaagaaaac  12000
ccgcattaca tcggtacctc atggggtgaa gtcagctatc cgggcgttga aaagacgatg  12060
aaagaagccg atgcggttat cgctctggct cctgtcttca acgactactc caccactggt  12120
tggacggata ttcctgatcc taagaaactg gttctcgctg aaccgcgttc tgtcgtcgtt  12180
aacggcgttc gcttccccag cgttcatctg aaagactatc tgacccgttt ggctcagaaa  12240
gtttccaaga aaaccggtgc tttggacttc ttcaaatccc tcaatgcagg tgaactgaag  12300
aaagccgctc cggctgatcc gagtgctccg ttggtcaacg cagaaatcgc ccgtcaggtc  12360
gaagctcttc tgaccccgaa cacgacggtt attgctgaaa ccggtgactc ttggttcaat  12420
gctcagcgca tgaagctccc gaacggtgct cgcgttgaat atgaaatgca gtggggtcac  12480
atcggttggt ccgttcctgc cgccttcggt tatgccgtcg gtgctccgga acgtcgcaac  12540
atcctcatgg ttggtgatgg ttccttccag ctgacggctc aggaagtcgc tcagatggtt  12600
cgcctgaaac tgccggttat catcttcttg atcaataact atggttacac catcgaagtt  12660
atgatccatg atggtccgta caacaacatc aagaactggg attatgccgg tctgatggaa  12720
```

gtgttcaacg gtaacggtgg ttatgacagc ggtgctggta aaggcctgaa ggctaaaacc 12780
ggtggcgaac tggcagaagc tatcaaggtt gctctggcaa acaccgacgg cccaaccctg 12840
atcgaatgct tcatcggtcg tgaagactgc actgaagaat tggtcaaatg ggtaagcgc 12900 gttgctgccg ccaacagccg taagcctgtt aacaagctcc tctagttttt ggggatcaat 12960
tcgagctctc tggataaaac taataaactc tattacccat gattaaagcc tacgctgccc 13020
tggaagccaa cggaaaactc caaccctttg aatacgaccc cggtgccctg ggtgctaatg 13080
aggtggagat tgaggtgcag tattgtgggg tgtgccacag tgatttgtcc atgattaata 13140
acgaatgggg catttccaat taccccctag tgccgggtca tgaggtggtg ggtactgtgg 13200
ccgccatggg cgaaggggtg aaccatgttg aggtgggggga tttagtgggg ctgggttggc 13260
attcgggcta ctgcatgacc tgccatagtt gtttatctgg ctaccacaac ctttgtgcca 13320
cggcggaatc gaccattgtg ggccactacg gtggctttgg cgatcgggtt cgggccaagg 13380
gagtcagcgt ggtgaaatta cctaaaggca ttgacctagc cagtgccggg ccccttttct 13440
gtggaggaat taccgttttc agtcctatgg tggaactgag tttaaagccc actgcaaaag 13500
tggcagtgat cggcattggg ggcttgggcc atttagcggt gcaatttctc cgggcctggg 13560
gctgtgaagt gactgccttt acctccagtg ccaggaagca aacggaagtg ttggaattgg 13620
gcgctcacca catactagat tccaccaatc cagaggcgat cgccagtgcg gaaggcaaat 13680
ttgactatat tatctccact gtgaacctga agcttgactg gaacttatac atcagcaccc 13740
tggcgcccca gggacatttc cactttgttg gggtggtgtt ggagcctttg gatctaaatc 13800
tttttcccct tttgatggga caacgctccg tttctgcctc cccagtgggt agtcccgcca 13860
ccattgccac catgttggac tttgctgtgc gccatgacat taaacccgtg gtggaacaat 13920
ttagctttga tcagatcaac gaggcgatcg cccatctaga aagcggcaaa gcccattatc 13980
gggtagtgct cagccatagt aaaaattagc tctgcaaagg ttgcttctgg gtccgtggaa 14040
tggtcaaacg gagtcgatct cagttttgat acgctctatc tggaaagctt gacattcgat 14100
ctgcaggccc cccgggggc tcgactctag ag 14132

<210> SEQ ID NO 11
<211> LENGTH: 13983
<212> TYPE: DNA
<213> ORGANISM: Artificial Sequence
<220> FEATURE:
<223> OTHER INFORMATION: plasmid TK380

<400> SEQUENCE: 11
gatccgataa catcaccgtc gttatcgtcg ctttagaata acgttcccaa aatagctcat 60
ttccaactgg caactcacaa ccaaaaaccg catttttagt aaatatactc agcaatttgt 120
tcaacctgag catttttccc atttgcaact tgatacaaat atttttagca gcaaattttc 180
ctactgccag cttagtttac ataaattttg tctgttgaca tcttgcacac aataaggtat 240
ggcgcatata atgcgatatt actaccatta atttactacc tagtcattaa cgtctcccgc 300
cagagaacag ttttgaatag gtagtcaatt ttaggtattg aacctgctgt aaatttatta 360
aatcgatgaa tttccccgaa atctgctcta gcagacttgg gttatatacc agtaggctca 420
ggtgcaaaac aacaaagcac aaattttacc cattaaggat ataggcaatc tgtcaaatag 480
ttgttatctt tcttaataca gaggaataat caacaatatg gggcaggtac taactaaagt 540
cctatgcctg tggggcttct gtaaccgaca taacctttac gcgttgtctt ttaggagtct 600
gttatgaacg gtaccagtaa aggagaagaa ctattcactg gagttgtccc aattcttgtt 660

-continued

```
gaattagatg gtgatgttaa tgggcacaaa ttttctgtca gtggagaggg tgaaggtgat    720
gcaacatacg gaaaacttac ccttaaattt atttgcacta ctggaaaact acctgttcca    780
tggccaacac ttgtcactac tttcgcgtat ggtcttcaat gctttgcgag atacccagat    840
catatgaaac agcatgactt tttcaagagt gccatgcccg aaggttatgt acaggaaaga    900
actatatttt tcaaagatga cgggaactac aagacacgtg ctgaagtcaa gtttgaaggt    960
gatacccttg ttaatagaat cgagttaaaa ggtattgatt ttaaagaaga tggaaacatt   1020
cttggacaca aattggaata caactataac tcacacaatg tatacatcat ggcagacaaa   1080
caaaagaatg gaatcaaagt taacttcaaa attagacaca acattgaaga tggaagcgtt   1140
caactagcag accattatca acaaaatact ccaattggcg atggccctgt ccttttacca   1200
gacaaccatt acctgtccac acaatctgcc ctttcgaaag atcccaacga aaagagagac   1260
cacatggtcc ttcttgagtt tgtaacagct gctgggatta cacatggcat ggatgaacta   1320
tacaaataag agctcgaatt gatccttttt gataatctca tgaccaaaat cccttaacgt   1380
gagttttcgt tccactgagc gtcagacccc gtagaaaaga tcaaaggatc ttcttgagat   1440
cctttttttc tgcgcgtaat ctgctgcttg caaacaaaaa aaccaccgct accagcggtg   1500
gtttgtttgc cggatcaaga gctaccaact ctttttccga aggtaactgg cttcagcaga   1560
gcgcagatac caaatactgt ccttctagtg tagccgtagt taggccacca cttcaagaac   1620
tctgtagcac cgcctacata cctcgctctg ctaatcctgt taccagtggc tgctgccagt   1680
ggcgataagt cgtgtcttac cgggttggac tcaagacgat agttaccgga taaggcgcag   1740
cggtcgggct gaacgggggg ttcgtgcaca cagcccagct tggagcgaac gacctacacc   1800
gaactgagat acctacagcg tgagctatga gaaagcgcca cgcttcccga agggagaaag   1860
gcggacaggt atccggtaag cggcagggtc ggaacaggag agcgcacgag ggagcttcca   1920
gggggaaacg cctggtatct ttatagtcct gtcgggtttc gccacctctg acttgagcgt   1980
cgatttttgt gatgctcgtc aggggggcgg agcctatgga aaaacgccag caacgcggcc   2040
tttttacggt tcctggcctt ttgctggcct tttgctcaca tgttctttcc tgcgttatcc   2100
cctgattctg tggataaccg tattaccgcc tttgagtgag ctgataccgc tcgccgcagc   2160
cgaacgaccg agcgcagcga gtcagtgagc gaggaagcgg aagagcgcct gatgcggtat   2220
tttctcctta cgcatctgtg cggtatttca caccgcatat ggtgcactct cagtacaatc   2280
tgctctgatg ccgcatagtt aagccagtat acactccgct atcgctacgt gactgggtca   2340
tggctgcgcc ccgacacccg ccaacacccg ctgacgcgcc ctgacgggct tgtctgctcc   2400
cggcatccgc ttacagacaa gctgtgaccg tctccgggag ctgcatgtgt cagaggtttt   2460
caccgtcatc accgaaacgc gcgaggcagc tgcggtaaag ctcatcagcg tggtcgtgaa   2520
gcgattcaca gatgtctgcc tgttcatccg cgtccagctc gttgagtttc tccagaagcg   2580
ttaatgtctg gcttctgata aagcgggcct gccaccatac ccacgccgaa acaagcgctc   2640
atgagcccga agtggcgagc ccgatcttcc ccatcggtga tgtcggcgat ataggcgcca   2700
gcaaccgcac ctgtggcgcc ggtgatgccc gaagaactcc agcatgagat ccccgcgctg   2760
gaggatcatc cagccggcgt cccggaaaac gattccgaag cccaaccttt catagaaggc   2820
ggcggtggaa tcgaaatctc gtgatggcag gttgggcgtc gcttggtcgg tcatttcgaa   2880
ccccagagtc ccgctcagaa gaactcgtca agaaggcgat agaaggcgat gcgctgcgaa   2940
tcgggagcgg cgataccgta aagcacgagg aagcggtcag cccattcgcc gccaagctct   3000
```

-continued

```
tcagcaatat cacgggtagc caacgctatg tcctgatagc ggtccgccac acccagccgg   3060
ccacagtcga tgaatccaga aaagcggcca ttttccacca tgatattcgg caagcaggca   3120
tcgccatggg tcacgacgag atcatcgccg tcgggcatgc gcgccttgag cctggcgaac   3180
agttcggctg gcgcgagccc ctgatgctct tcgtccagat catcctgatc gacaagaccg   3240
gcttccatcc gagtacgtgc tcgctcgatg cgatgtttcg cttggtggtc gaatgggcag   3300
gtagccggat caagcgtatg cagccgccgc attgcatcag ccatgatgga tactttctcg   3360
gcaggagcaa ggtgagatga caggagatcc tgccccggca cttcgcccaa tagcagccag   3420
tcccttcccg cttcagtgac aacgtcgagc acagctgcgc aaggaacgcc cgtcgtggcc   3480
agccacgata gccgcgctgc ctcgtcctgc agttcattca gggcaccgga caggtcggtc   3540
ttgacaaaaa gaaccgggcg cccctgcgct gacagccgga acacggcggc atcagagcag   3600
ccgattgtct gttgtgccca gtcatagccg aatagcctct ccacccaagc ggccggagaa   3660
cctgcgtgca atccatcttg ttcaatcatg cgaaacgatc ctcatcctgt ctcttgatca   3720
gatcttgatc ccctgcgcca tcagatcctt ggcggcaaga aagccatcca gtttactttg   3780
cagggcttcc caaccttacc agagggcgcc ccagctggca attccggttc gcttgctgtc   3840
cataaaaccg cccagtctag ctatcgccat gtaagcccac tgcaagctac ctgctttctc   3900
tttgcgcttg cgttttccct tgtccagata gcccagtagc tgacattcat ccggggtcag   3960
caccgtttct gcggactggc tttctacgtg ttccgcttcc tttagcagcc cttgcgccct   4020
gagtgcttgc ggcagcgtga agctttctct gagctgtaac agcctgaccg caacaaacga   4080
gaggatcgag accatccgct ccagattatc cggctcctcc atgcgttgcc tctcggctcc   4140
tgctccggtt ttccatgcct tatggaactc ctcgatccgc cagcgatggg tataaatgtc   4200
gatgacgcgc aaggcttggg ctagcgactc gaccggttcg ctggtcagca acaaccattt   4260
caacggggtc tcacccttgg gcgggttaat ctcctcggcc agcaccgcgt tgagcgtgat   4320
attcccctgt tttagcgtga tgcgcccact gcgcatagaa attgcatcaa cgcatatagc   4380
gctagcagca cgccatagtg actggcgatg ctgtcggaat ggacgatatc tagacttata   4440
tagacactaa tatagacaat agtttatact gctatctata caagtataga cattatctaa   4500
tcatggcaga caaaactcta gccacttttc gtattgactc cgaagaatgg gagtctttta   4560
aaaaccttgc tagttctgaa agttccaacg cctcagcact gttaacagaa tttgttcgtt   4620
ggtatttggc aggtaacagg tttaatactc ccacttctca cactcccacc catctagaca   4680
catccctcga acagcgtata gacaatattg aacaacgtct agataaagtc acaactaata   4740
atctagacaa tatagatgaa tttatagaca agcgtataga agataatcta gcaacacgtc   4800
tagacaaact tcaatcgcaa ctggaggaac tgcggggaaa atcgaaagcc cggtagttca   4860
ggcagaagga caagctaccg ggcaagacag aaagaatata gacaatagta tagacaatct   4920
agacaaattg gaggcaaccc gcgatcgcac cctcaataag ctaaaaatgg gtaggcagtc   4980
agccgccggg aaagccatcg acgcgtttat caaagagttg ctttcttcag gagacaacat   5040
aagctgaagt tatcaaaatt ctgtccttac gtcgaaagcc tgattttacc gtgcaacgat   5100
tgataagctt ggctaaacta gcactggctt tcaacagaaa gcatacgaag aatcaataga   5160
tatagccacc aattccacaa aatgcagata acgtgtagag tattggaatg cttaatctgt   5220
aagggttatg aaggttaacg gcaacggacg agccaaaata ctcacctccg acgaactcag   5280
gcgactgttt agcgacggat tcaccacacc gcgcgatcgc gttttgtttg gcatctgtct   5340
attcaccggt tgccgcgtta gtgaagctct agcactccaa acaacggaca ttaaaggcga   5400
```

aacactaacc tttaggaagt ctaccaccaa agggaaactc aaaacccgcg tggttgacat 5460
ccagccagga ctagccgcac tcatggctga ctatcacccc aaaccgggaa ccctgttccc 5520
tggcatgagg ggagtcagcg ataggctcac gcgatacgcg gcggataaaa tcttgcgcga 5580
tgcagccaaa agaatcgggc tagaaggcat cagtacccac agtttccgcc gtactgccct 5640
caaccaaatg tctagcgccg gtatcccgtt gcgacacatt caagagatat ccggtcacaa 5700
tgaccttggc acactgcaac gctatcttga agttacaccc gaacagcgac gcaaagctgt 5760
atccgtgatt ggcttctaat gtacgccaac gctgtttaga cccctatggg tgctaaaaaa 5820
agacgcagcc taaacacacg ctctacactt gaggatactt ttaaagtatc catcggttct 5880
agaactctgc acacgttccg gactttggaa acgttatacc tttccctgtg ttgcagaatg 5940
ctgcaatatt tcttcgacaa gttaacttgt gactggttta atatttctc aaattgcccc 6000
aaaacaacac gcctaaatcc ttagacgttt ctgtggaaac ctattaggtt tttatcgccg 6060
ttgttttagt ggtaaaccca aagggtttgt atattcttgt atgaagttcg actctgaggg 6120
ttaagaagaa tggctcgccg aatttttttac aagtggaaac cgattaaagg ttaagggtca 6180
atcgggacga tgaatatttt ctaattgtga ccttctccat ctaataagct ttctttgggg 6240
ttaaggtcga agaaagtact acgcatgatc tgcatacgat ctctattgcc aaaaagccgc 6300
gaccctatag gctctcggtc atgctgcact agttcgtgtc gatcactata ctggttgccg 6360
cagcatttca cgctaaaaaa aaattcttaa aaatgtcctt catatctcgc cagagtggca 6420
acctattaca aaacggttgc ctacccgacc ggctcgattt tcgctgaagt ggcactgtga 6480
cagtttgaaa tggtacttcc gccgtgctgc tgacatcgtt gttagggtga attgttcgcg 6540
gtagatgttg caccgattca tgaacacctt gtcacccact ttgaataatc gaccgtcaaa 6600
ttcagtcgcg tcaatttggt aagtgttggg ctgtctcttt ttggctccag gggcaatgcc 6660
atcagaaaac acaaccgcgt cacccataac ttgataaccg atatcagttt tggttccagt 6720
gaaagcccaa aattcagacg cgtcattatt ccgagcgtgc cggagttgat tgtactcaat 6780
tttggcttgg caaagttgac ggcgattcat gcccagctgc ttttgatgtc gtcgcactgt 6840
gcgcttgtga atacccaact cacagctgac agctttttga gatgtaccat agtggatgaa 6900
actttttgag acgaatatcc gcgacgaact aatgtgaagt acacaaggta cttccccctc 6960
tggcgattta agagaggatt gccttgtgtc cttcactagc tcgttcgggt gtggcgctcc 7020
aaaaagtttt ctgtactctg gtttaagttg tctgttggcc gcatagcggc tcttttgttg 7080
aaagctttgt gtgactatgc cagtggtcag tgagcgtaaa tcgcttaaca cttggactaa 7140
aggcactact gcaacatcac cccatctttt taaatttagg ttgtaacaaa cttgaaacat 7200
accgcccaag tagacggtta tcattcctgc tttaattttg tagcggcgga atgctcctat 7260
ttttttttcca tcctgtaacc aacggtaaac agacttatca ctacaatcta agaacgtctg 7320
tactacaggc aatggcaatg ttaaatgacc agacccatcc ttatcaagcg ctcgacacaa 7380
ataccacaac cgcgcacaag gttctcgacc aatgcgagtg tgtaccctga ccgtgtaagt 7440
gccaagaatt atttcagttt gtagttccct tgtaagcagg gttagtgata catttgtatt 7500
taagctttct gggctgatca tttggaaatg tctcagtcca gtacctattg aatgttattt 7560
gcttaacctg aagctaaata aaacttgtta actacaccca ttaattgata aattcaaagc 7620
acgttttttc tgtttggtgt ttggtgtggt aacaattctg tgtatgtgtg ttttatttag 7680
cttcggttaa gtagcataac aaccccccaag cactgaactt tttttaatag gtaatttaaa 7740

-continued

```
ctttgcctat cggcaaaatt ttcaatcaat tgtacgccaa agtgttgcat gatcaacgtt   7800
tgacttattt ttgtatttac taaatactga atttcgccgt gacgcttttt acagatggaa   7860
attcacggca aaatgttttt tgctaacttt gctatgtaaa acaagaaact tggcactcgg   7920
ttattactaa ataaactggt aaaaaataac cattagaacc aaaaagaacg aaaaccagta   7980
cacccttgcc agttttcaag cttttgctat gacgactcta ataatcgggt ttaacaccat   8040
tccgctttga gaaaattatc cttgtacagc aagtaacagt caatgctaaa ccgcaccgct   8100
acaaatcctt aagtttttcc agtagcgatt taccttcttg gtaacgcccg ccttgatagc   8160
ccaaaatttc tttaatcacc ttactttctg aaaaacccgc ttccagacag gcttttacca   8220
cttttgctag ggtttcatct cttggttctg ggagggatga aacgggctgt aatgcttgtt   8280
ctgaggtcgg ttgagccgtt tggagtggct gaaaactggt tacagactgt aaccggggca   8340
taaccatttt gtaactgctt acatctggta actgacacgg catatcatcc accatgcagc   8400
gatatttccc cgactttaac cactccacaa gggcaaggtc ttttaaggac ttggcgtggc   8460
taactgcaaa cttacccagg cgtaacatcc taaaacactt acggacaccg ccttcaccct   8520
cgatacctaa ggtcttgaca ttatcatctt gagtcagccc aataacaaaa cgcttgggct   8580
tgcggccgcg cctggcgtgt ttgatgagcc attcggttgc tatctcgact tcatctctca   8640
gcagtggcag ttcttcagca attaaaacgc tttcttttcc tgctagtgcc ttatccccag   8700
actcaccccg tagctcaatc cggcgctgca attcctccag gtcagcagcc atgcccgact   8760
gtatagcctc aaagtcacca cggcggccaa tgacatttaa ccccgtccac tcgtccggtg   8820
cagcgtcagc gtcatagact gtcacctcac ccccgacttg ataagcaagc cattgggcta   8880
tggtgctttt gccagttccc gtatccccaa ctattaaaca gtgcttacca gacagagctt   8940
gcatcaagtc ggtgatgatt ccctctggtt cgaccgcaag ggtgacggcg gtagtgtcaa   9000
tgatagccgc gccgtaagtg ccagcatagg gcaattggtc gtaaactttg accaagttgt   9060
atacagactg tctacaccac ttcaccactg ttaacgctgt ttgcaaagcg taagacgtgg   9120
catcaaataa aaatatgctg gcactaaaag ttaatcgccc caatccccac agtaaaaacc   9180
tgcctagctg ttgacgacta ggcaagtgca tttcaatcca gtcatttgcc ataaatcacc   9240
ccgtctttaa agccttgcag ttgagcgcga caggtattta actgtgcttg taactctgtt   9300
tgctggtttt gataccacag actgacggcg gcggccgcca gtcctaaaaa tagaaactgg   9360
cgatcgctca ttattgactt actccctgtt gattagcgtg gtagtgagtc atagccgcat   9420
tgaccgcttc ttgggcttgg ggtgttctgc caagattggg ttttgtaggg tcatcgttgg   9480
ctacgactaa ggacgcttgt tcggctatcg cttgcgggac accaacttta gttaactctg   9540
tcaaggatac ttggtaaagt cgctcgttca ttagccgatt ctccggtaca taaaactgtt   9600
gctggcagtc ccttcattgg cgacgagttc ttcagccgga gtatcagcga taatgtcagc   9660
ccagccggtg acattattat taataatgtt ttgttcggca attgcaccca agccaggacg   9720
cgccgtttca aactcagaga tgacttgctg ctctttctcg gtgagtggtc tatctgtcat   9780
gataattatg tccttcatta tgtaggcgat tccagtgggt gtttacgagg cagtccacag   9840
gaatcagtgc gattcacctt taaggtgaat cgtcatcaaa aaatcactcg gtagcaacga   9900
cccgaaccga ccaggattga tttcccggtt ctcagttcgc aggcttttga gcgcgtcacc   9960
ttgaccattg ggtaactgcc atcagccgat aagctaaacg ggctgtatag cggtaaagca  10020
tcccacacag tcgggctggc atcaactttg caggaatagc tcacgtcact catctcactc  10080
gcgcctgggt tggatggcag cgaaggcaga ttacgacgca gtttttact ggcactttta  10140
```

```
cccgcattaa aaacgggtac agtgccattg ttgacggtct gtacttcggt catatactcg  10200
gtgtacactt aatacactct atactattac tgccgattag tacatttgtc aatcactctt  10260
tgcacaaggt gtatgatatg gactcaggag tacaccaaac gtcatgccaa ccaataaagg  10320
gagaatagca gtcactctag aagctgaaat ttaccaatgg attgctaacc gagcgtctga  10380
ggaaggaaga ccgttggcta atcttgccgc tttcttactc acacgagttg ttaaagaaca  10440
aatggaacaa gaagccaagg acaaccaaga caagcagggg gcagcatgag cgaagacaga  10500
ctagccagaa tagaagctgc gttagacagc caagttgcag tgaatgccga cctccgcaca  10560
tcggttacag aactccgcgc aaccgcagaa gcattgttgc aaacagttca aatccatcag  10620
cagaactttg aaattcttac cgctaggcaa ttacaaaccg aagcacggct tgatgagtac  10680
caacgtacca ctagcgcggc actcgacaga attggcgcgg tcttagacta cctcgttagg  10740
cagcaaaacg gttgaggtga gggatgagcg atgactatct agacggatat cccgcaagag  10800
gccctttcgt cttcaagaat taattgtcga ccaattatga aaccgaggtt tatatcgaca  10860
accacaaaca accaacaccc tctacttcca acacttctgt ggaagagcag gaaaactatc  10920
gtcgttcaga cagtaattaa tggttagtgg ttaaaagcaa tgaacaattg gcaaccaaca  10980
acaaacaatt aaattatgac tagtgcagtt ttgctaaatg ggtaatttct cgacgttggt  11040
tagtagcgat tgtagcactg tactatacgt ttaaataaat caaaatatga attcttatac  11100
tgtcggtacc tatttagcgg agcggcttgt ccagattggt ctcaagcatc acttcgcagt  11160
cgcgggcgac tacaacctcg tccttcttga caacctgctt ttgaacaaaa acatggagca  11220
ggtttattgc tgtaacgaac tgaactgcgg tttcagtgca gaaggttatg ctcgtgccaa  11280
aggcgcagca gcagccgtcg ttacctacag cgtcggtgcg ctttccgcat ttgatgctat  11340
cggtggcgcc tatgcagaaa accttccggt tatcctgatc tccggtgctc cgaacaacaa  11400
tgatcacgct gctggtcacg tgttgcatca cgctcttggc aaaaccgact atcactatca  11460
gttggaaatg gccaagaaca tcacggccgc agctgaagcg atttacaccc cagaagaagc  11520
tccggctaaa atcgatcacg tgattaaaac tgctcttcgt gagaagaagc cggtttatct  11580
cgaaatcgct tgcaacattg cttccatgcc ctgcgccgct cctggaccgg caagcgcatt  11640
gttcaatgac gaagccagcg acgaagcttc tttgaatgca gcggttgaag aaaccctgaa  11700
attcatcgcc aaccgcgaca aagttgccgt cctcgtcggc agcaagctgc gcgcagctgg  11760
tgctgaagaa gctgctgtca aatttgctga tgctctcggt ggcgcagttg ctaccatggc  11820
tgctgcaaaa agcttcttcc cagaagaaaa cccgcattac atcggtacct catggggtga  11880
agtcagctat ccgggcgttg aaaagacgat gaaagaagcc gatgcggtta tcgctctggc  11940
tcctgtcttc aacgactact ccaccactgg ttggacggat attcctgatc ctaagaaact  12000
ggttctcgct gaaccgcgtt ctgtcgtcgt taacggcgtt cgcttcccca gcgttcatct  12060
gaaagactat ctgacccgtt tggctcagaa agtttccaag aaaaccggtg ctttggactt  12120
cttcaaatcc ctcaatgcag gtgaactgaa gaaagccgct ccggctgatc cgagtgctcc  12180
gttggtcaac gcagaaatcg cccgtcaggt cgaagctctt ctgaccccga acacgacggt  12240
tattgctgaa accggtgact cttggttcaa tgctcagcgc atgaagctcc cgaacggtgc  12300
tcgcgttgaa tatgaaatgc agtggggtca catcggttgg tccgttcctg ccgccttcgg  12360
ttatgccgtc ggtgctccgg aacgtcgcaa catcctcatg gttggtgatg gttccttcca  12420
gctgacggct caggaagtcg ctcagatggt tcgcctgaaa ctgccggtta tcatcttctt  12480
```

gatcaataac tatggttaca ccatcgaagt tatgatccat gatggtccgt acaacaacat 12540
caagaactgg gattatgccg gtctgatgga agtgttcaac ggtaacggtg gttatgacag 12600
cggtgctggt aaaggcctga aggctaaaac cggtggcgaa ctggcagaag ctatcaaggt 12660
tgctctggca aacaccgacg gcccaaccct gatcgaatgc ttcatcggtc gtgaagactg 12720
cactgaagaa ttggtcaaat ggggtaagcg cgttgctgcc gccaacagcc gtaagcctgt 12780
taacaagctc ctctagtttt tggggatcaa ttcgagctct ctggataaaa ctaataaact 12840
ctattaccca tgattaaagc ctacgctgcc ctggaagcca acggaaaact ccaacccttt 12900
gaatacgacc ccggtgccct gggtgctaat gaggtggaga ttgaggtgca gtattgtggg 12960
gtgtgccaca gtgatttgtc catgattaat aacgaatggg gcatttccaa ttacccccta 13020
gtgccgggtc atgaggtggt gggtactgtg gccgccatgg gcgaaggggt gaaccatgtt 13080
gaggtggggg atttagtggg gctgggttgg cattcgggct actgcatgac ctgccatagt 13140
tgtttatctg gctaccacaa cctttgtgcc acggcggaat cgaccattgt gggccactac 13200
ggtggctttg gcgatcgggt tcgggccaag ggagtcagcg tggtgaaatt acctaaaggc 13260
attgacctag ccagtgccgg gcccctttc tgtggaggaa ttaccgtttt cagtcctatg 13320
gtggaactga gtttaaagcc cactgcaaaa gtggcagtga tcggcattgg gggcttgggc 13380
catttagcgg tgcaatttct ccgggcctgg ggctgtgaag tgactgcctt tacctccagt 13440
gccaggaagc aaacggaagt gttggaattg ggcgctcacc acatactaga ttccaccaat 13500
ccagaggcga tcgccagtgc ggaaggcaaa tttgactata ttatctccac tgtgaacctg 13560
aagcttgact ggaacttata catcagcacc ctggcgcccc agggacattt ccactttgtt 13620
ggggtggtgt tggagccttt ggatctaaat cttttcccc ttttgatggg acaacgctcc 13680
gtttctgcct ccccagtggg tagtcccgcc accattgcca ccatgttgga ctttgctgtg 13740
cgccatgaca ttaaacccgt ggtggaacaa tttagctttg atcagatcaa cgaggcgatc 13800
gcccatctag aaagcggcaa agcccattat cgggtagtgc tcagccatag taaaaattag 13860
ctctgcaaag gttgcttctg ggtccgtgga atggtcaaac ggagtcgatc tcagttttga 13920
tacgctctat ctggaaagct tgacattcga tctgcaggcc ccccgggggg ctcgactcta 13980
gag 13983

<210> SEQ ID NO 12
<211> LENGTH: 6211
<212> TYPE: DNA
<213> ORGANISM: Artificial Sequence
<220> FEATURE:
<223> OTHER INFORMATION: plasmid TK148

<400> SEQUENCE: 12
tcgaggggga tccactagag gatctcaatg aatattggtt gacacgggcg tataagacat 60
gttatactgt tgaataacaa ggacggatct gatcaagaga caggatgagg atcgtttcgc 120
atgattgaac aagatggatt gcacgcaggt tctccggccg cttgggtgga gaggctattc 180
ggctatgact gggcacaaca gacaatcggc tgctctgatg ccgccgtgtt ccggctgtca 240
gcgcaggggc gcccggttct ttttgtcaag accgacctgt ccggtgccct gaatgaactg 300
caggacgagg cagcgcggct atcgtggctg gccacgacgg gcgttccttg cgcagctgtg 360
ctcgacgttg tcactgaagc gggaagggac tggctgctat tgggcgaagt gccggggcag 420
gatctcctgt catctcacct tgctcctgcc gagaaagtat ccatcatggc tgatgcaatg 480
cggcggctgc atacgcttga tccggctacc tgcccattcg accaccaagc gaaacatcgc 540

```
atcgagcgag cacgtactcg gatggaagcc ggtcttgtcg atcaggatga tctggacgaa    600
gagcatcagg ggctcgcgcc agccgaactg ttcgccaggc tcaaggcgcg catgcccgac    660
ggcgaggatc tcgtcgtgac ccatggcgat gcctgcttgc cgaatatcat ggtggaaaat    720
ggccgctttt ctggattcat cgactgtggc cggctgggtg tggcggaccg ctatcaggac    780
atagcgttgg ctacccgtga tattgctgaa gagcttggcg gcgaatgggc tgaccgcttc    840
ctcgtgcttt acggtatcgc cgctcccgat tcgcagcgca tcgccttcta tcgccttctt    900
gacgagttct tctgagcggg actctggggt tcgaaatgac cgaccaagcg acgcccaacc    960
tgccatcacg agatttcgat tccaccgccg ccttctatga aaggttgggc ttcggaatcg   1020
ttttccggga cgccggctgg atgatcctcc agcgcgggga tctcatgctg gagttcttcg   1080
cccaccgggg atcctctagt tctagagcgg ccgcttcgtg tagtgtgtat tgaactaaat   1140
taaatatttt tcaaagtggg tagatgcttc tatccacttt gtttccatta tgtgagtcat   1200
tcacaaatct tgtccctata tttattttat gaaaatttca atgattactg atacatataa   1260
ttggcaacat ctggctgatc aatactttct acaagaaaac tatctccaag cagcacagtt   1320
atacgaacaa gcaatagcaa tagaaccaaa tactatttct tattattggc atttaggatt   1380
attattgcta ttacaaggac aagaagcaga agctcaaatg acttggatgc tgccaataac   1440
agaggcagat gaagagcatt tacaaatttg gacaaatgaa ctatttaaat ttttacaaac   1500
agaagctgaa aggcgggaaa atctgacgga atactctgta gcctggttaa ttcgccagca   1560
tatgagggaa attattccta gtgatattaa taatttactc caaattcttc tactttatct   1620
caaactagaa aaatttgaag taatgaatga attgcatgac tggggattaa ttgaaatttt   1680
aaatgaaaaa gaaagtgtaa atattgatgc taacttgttg agacaatttt tagaggaact   1740
tttaaatact attcctttac atccaatagt tttgagttta gtagaagctt gtttacctta   1800
tttctctgat acttatcaat gcttcgatat actacttacg gctactctga aaattggtca   1860
tactctacag caacctatac tagcatcatc tcttctcaag ttacatttgc gtttagagcc   1920
agaaaatgtc gaaattttgc gacatttagc tatttttat caagatgctc gcaattattc    1980
tcaaggaata gaaacagcta agttatgtta ttcgctatca gaaggtttag cggataaaat   2040
ttttgcactt catttactat taaggggttt aatgtcagca ggaggatatt ggaaagagat   2100
atgtgaaact tgccaggagc tagaaactgt atttcaacag tttatacaag cacaaccaat   2160
tgctttagaa gagggaagaa tcctgcggtt actgacacta gtgatggcgg ccgggagcat   2220
gcgacgtcgg gcccaattcg ccctatagtg agtcgtatta caattcactg gccgtcgttt   2280
tacaacgtcg tgactgggaa aaccctggcg ttacccaact taatcgcctt gcagcacatc   2340
ccccttcgc cagctggcgt aatagcgaag aggcccgcac cgatcgccct tcccaacagt    2400
tgcgcagcct gaatggcgaa tggacgcgcc ctgtagcggc gcattaagcg cggcgggtgt   2460
ggtggttacg cgcagcgtga ccgctacact tgccagcgcc ctagcgcccg ctcctttcgc   2520
tttcttccct tcctttctcg ccacgttcgc cggctttccc cgtcaagctc taaatcgggg   2580
gctcccttta gggttccgat ttagagcttt acggcacctc gaccgcaaaa aacttgattt   2640
gggtgatggt tcacgtagtg ggccatcgcc ctgatagacg gtttttcgcc ctttgacgtt   2700
ggagtccacg ttctttaata gtggactctt gttccaaact ggaacaacac tcaaccctat   2760
ctcggtctat tcttttgatt tataagggat tttgccgatt tcggcctatt ggttaaaaaa   2820
tgagctgatt taacaaatat ttaacgcgaa ttttaacaaa atattaacgt ttacaatttc   2880
```

```
gcctgatgcg gtattttctc cttacgcatc tgtgcggtat ttcacaccgc atacaggtgg   2940
cacttttcgg ggaaatgtgc gcggaacccc tatttgttta tttttctaaa tacattcaaa   3000
tatgtatccg ctcatgagac aataaccctg ataaatgctt caataatatt gaaaaaggaa   3060
gagtatgagt attcaacatt tccgtgtcgc ccttattccc ttttttgcgg cattttgcct   3120
tcctgttttt gctcacccag aaacgctggt gaaagtaaaa gatgctgaag atcagttggg   3180
tgcacgagtg ggttacatcg aactggatct caacagcggt aagatccttg agagttttcg   3240
ccccgaagaa cgttttccaa tgatgagcac ttttaaagtt ctgctatgtg gcgcggtatt   3300
atcccgtatt gacgccgggc aagagcaact cggtcgccgc atacactatt ctcagaatga   3360
cttggttgag tactcaccag tcacagaaaa gcatcttacg gatggcatga cagtaagaga   3420
attatgcagt gctgccataa ccatgagtga taacactgcg gccaacttac ttctgacaac   3480
gatcggagga ccgaaggagc taaccgcttt tttgcacaac atgggggatc atgtaactcg   3540
ccttgatcgt tgggaaccgg agctgaatga agccatacca aacgacgagc gtgacaccac   3600
gatgcctgta gcaatgccaa caacgttgcg caaactatta actggcgaac tacttactct   3660
agcttcccgg caacaattaa tagactggat ggaggcggat aaagttgcag gaccacttct   3720
gcgctcggcc cttccggctg gctggtttat tgctgataaa tctggagccg gtgagcgtgg   3780
gtctcgcggt atcattgcag cactggggcc agatggtaag ccctcccgta tcgtagttat   3840
ctacacgacg gggagtcagg caactatgga tgaacgaaat agacagatcg ctgagatagg   3900
tgcctcactg attaagcatt ggtaactgtc agaccaagtt tactcatata tactttagat   3960
tgatttaaaa cttcattttt aatttaaaag gatctaggtg aagatccttt ttgataatct   4020
catgaccaaa atcccttaac gtgagttttc gttccactga gcgtcagacc ccgtagaaaa   4080
gatcaaagga tcttcttgag atcctttttt tctgcgcgta atctgctgct tgcaaacaaa   4140
aaaaccaccg ctaccagcgg tggtttgttt gccggatcaa gagctaccaa ctctttttcc   4200
gaaggtaact ggcttcagca gagcgcagat accaaatact gtccttctag tgtagccgta   4260
gttaggccac cacttcaaga actctgtagc accgcctaca tacctcgctc tgctaatcct   4320
gttaccagtg gctgctgcca gtggcgataa gtcgtgtctt accgggttgg actcaagacg   4380
atagttaccg gataaggcgc agcggtcggg ctgaacgggg ggttcgtgca cacagcccag   4440
cttggagcga acgacctaca ccgaactgag atacctacag cgtgagctat gagaaagcgc   4500
cacgcttccc gaagggagaa aggcggacag gtatccggta agcggcaggg tcggaacagg   4560
agagcgcacg agggagcttc cagggggaaa cgcctggtat ctttatagtc ctgtcgggtt   4620
tcgccacctc tgacttgagc gtcgattttt gtgatgctcg tcaggggggc ggagcctatg   4680
gaaaaacgcc agcaacgcgg cctttttacg gttcctggcc ttttgctggc cttttgctca   4740
catgttcttt cctgcgttat cccctgattc tgtggataac cgtattaccg cctttgagtg   4800
agctgatacc gctcgccgca gccgaacgac cgagcgcagc gagtcagtga gcgaggaagc   4860
ggaagagcgc ccaatacgca aaccgcctct ccccgcgcgt tggccgattc attaatgcag   4920
ctggcacgac aggtttcccg actggaaagc gggcagtgag cgcaacgcaa ttaatgtgag   4980
ttagctcact cattaggcac cccaggcttt acactttatg cttccggctc gtatgttgtg   5040
tggaattgtg agcggataac aatttcacac aggaaacagc tatgaccatg attacgccaa   5100
gctatttagg tgacactata gaatactcaa gctatgcatg gagctggtag aagggaacat   5160
tatagttatg ggccatcag attacgaatc agaggaaata ggtgctcgtt taattacctt   5220
cttgaataac tgggtaatgt cgcgcaaatt agggcgagta actggttcta gcgcaggctt   5280
```

cattctgcca agtatggaag agggcgactc agaaaaaaga aacctgcgtg cccctgatgt 5340
ttcttttgtg cgggctgaca gactaaaaaa gagcaagcgc gactttgtag agttagttcc 5400
agatttgatg gtagaagtca aatcaaaatc agacagaatt aaaccgcttg aagaaaaaat 5460
tcagttattc ttacaacttg gctctacagt cgggatacta attgatcctg accagttgac 5520
agtaacagtt taccgactca accaagctcc agtagtattg cagaatggag acacactcac 5580
gttaccagat gtgctaccag gttgggaatt ggcaatatca gaactatggc cgcctgaatt 5640
tgaataacta gatatcacca gaaattaatt atgcgttact caaatatcaa tcttgtggta 5700
tggacaactt gtccgcaccg gacgggctaa aagcccatcc cacaagaaag ctatcatgca 5760
acattttaga cttgccacgc cactatcctc acgggaagca accgcacatc tatagagtga 5820
cagcgaccgt ttactgaacc atattgactt atctttcaaa ttcagtctgg aaatgcttat 5880
tagacaggtt ttcgcatcga aaagaaccac taacttacaa ccaaataaaa ttttttttgg 5940
tgggagtgat atgaaattga tcggtggtgg gtaagttatt tttagaacgc gataagcagt 6000
caccaccata aggagttaca gatatgaaaa ccgaactgaa agccaagttt ttacaacaca 6060
ttcttaataa aaagaaagaa gacgaaggtt tcaccctcat tgaattactg gtagtaatta 6120
ttattatcgg cattctgtca gctattgcac taccttcttt ccttaaccaa gctaataaag 6180
caaaacaatc tgaagcgaaa acctatgttg g 6211

<210> SEQ ID NO 13
<211> LENGTH: 5904
<212> TYPE: DNA
<213> ORGANISM: Artificial Sequence
<220> FEATURE:
<223> OTHER INFORMATION: plasmid TK149

<400> SEQUENCE: 13
taccatgttc aatcccgcca gtccaatcca ttattaaatg gtttcgcacc tttttaaaga 60
ggtgttgcac aacaatcggg ttaattggat ttttgacata ggttaattcg tatctaaact 120
ctcggtcagt atttttctgc tgacgtagta cataaatttg gtcaacctta tattttcgta 180
aatttacatc actggttagc ttaacccact ccatgaccac aagatacaaa ctattaggat 240
ttcttgcctt taaatcttct gctgcgcgtg aagaaccttc aagcatagtt ttgtcaaggt 300
acgtcttaca ctcgattgca acaactggta tgtcaaaaat gtgtgtctcg gtgttacctg 360
taactgtcac ctcagaatat gtacttggct cttcttttag aagaggaagt atctcaccag 420
tattttcatc ttgctctggg ggaggtgctg cttcaaatga tacttgaata gttgcaccaa 480
tgacaaaatc atgatccttc ttctcaatcc gcgcatacgg tcgcttgagc atttcagaat 540
attttggtgg cacaaagaag atatctttaa atgtatgtga cttaccaata agagcgtttt 600
ctccaaaatc tcctgtcaaa tctttaaata aataataaag aaattcctct aaaacactag 660
aatgaaggtt tgatcttgag tcaaattttt cagcataatg ctgctgatct aaaaaatctt 720
tgtatgtaga gagaagctct actctttcag caattattgc gtcatcctgc tcagtaggtt 780
ttgatgttgg gccgattaaa ttcatattgg ctaaatgcca tttattgtac tcagttctaa 840
tttcgttgag gtattttcta ctatcgacgt ctctatattt ggtacgatgg ttttccttct 900
gctcaaggtt agagccatga actagcggat tgtcgagggg gatccactag aggatctcaa 960
tgaatattgg ttgacacggg cgtataagac atgttatact gttgaataac aaggacggat 1020
ctgatcaaga gacaggatga ggatcgtttc gcatgattga acaagatgga ttgcacgcag 1080

-continued

```
gttctccggc cgcttgggtg gagaggctat tcggctatga ctgggcacaa cagacaatcg   1140
gctgctctga tgccgccgtg ttccggctgt cagcgcaggg gcgcccggtt ctttttgtca   1200
agaccgacct gtccggtgcc ctgaatgaac tgcaggacga ggcagcgcgg ctatcgtggc   1260
tggccacgac gggcgttcct tgcgcagctg tgctcgacgt tgtcactgaa gcgggaaggg   1320
actggctgct attgggcgaa gtgccggggc aggatctcct gtcatctcac cttgctcctg   1380
ccgagaaagt atccatcatg gctgatgcaa tgcggcggct gcatacgctt gatccggcta   1440
cctgcccatt cgaccaccaa gcgaaacatc gcatcgagcg agcacgtact cggatggaag   1500
ccggtcttgt cgatcaggat gatctggacg aagagcatca ggggctcgcg ccagccgaac   1560
tgttcgccag gctcaaggcg cgcatgcccg acggcgagga tctcgtcgtg acccatggcg   1620
atgcctgctt gccgaatatc atggtggaaa atggccgctt ttctggattc atcgactgtg   1680
gccggctggg tgtggcggac cgctatcagg acatagcgtt ggctacccgt gatattgctg   1740
aagagcttgg cggcgaatgg gctgaccgct tcctcgtgct ttacggtatc gccgctcccg   1800
attcgcagcg catcgccttc tatcgccttc ttgacgagtt cttctgagcg ggactctggg   1860
gttcgaaatg accgaccaag cgacgcccaa cctgccatca cgagatttcg attccaccgc   1920
cgccttctat gaaaggttgg gcttcggaat cgttttccgg gacgccggct ggatgatcct   1980
ccagcgcggg gatctcatgc tggagttctt cgcccaccgg ggatcctcta gttctagagc   2040
ggccgctgtg tgtgaaggct tatggggatt taagcggcga ttgttctggt cataactttt   2100
atttgataac tcgccattgc cactacgtcg tctggctcca tgttcttttg gtacatctga   2160
acttgattca ccccatttaa tatgtttaaa gcgttctaca agccgctcgg agtgttccat   2220
cgcaacatga ttataaagta tgtaactacc atgtctagcc caaacttgat aattgttttg   2280
aggttccaca atataaggtt gctcttcgtt accttcccgt gcattaagct ctggtaaatc   2340
tgatattgcg tcccatagag ttagagcagg tagtacctct gtgccatcaa aaacagatag   2400
ttgagattga cttatatgtt gtagttctag agagtgcgtc tttctaggag aggctaactc   2460
tttgcccatc ttattgccga cgataaaaat gcgctctcta atctgcggta caccatattc   2520
agcagcgttc aaaatccata cttccacaaa gtatccaagg tcttgaaagg tcttcctaat   2580
aatatctata accttttgtc cctctgcatt tttgcgtgac agtaatcctt ttacattttc   2640
cattacaaat gctttaggtt caagaaaatt tatccattga gcaaagttaa taaacaaact   2700
gtttctgggg tctttaggat ctttttgagc cggcccagca atactaaaac cttgacatgg   2760
aggcccgcca atcacaatgt ctggtttaaa gatacaaatt tccttaacac tactttccgt   2820
attaaaatta cggatgtcat gttgaataac tgtcatatcg ggcggttgc aacgcagcgt   2880
atcgcaagcc caagtatcaa tttcaacaga tagaggcaca gagaaaccag ccatttcaaa   2940
acccaaacca aagccaccag ctactagtga tggcggccgg gagcatgcga cgtcgggccc   3000
aattcgccct atagtgagtc gtattacaat tcactggccg tcgttttaca acgtcgtgac   3060
tgggaaaacc ctggcgttac ccaacttaat cgccttgcag cacatccccc tttcgccagc   3120
tggcgtaata gcgaagaggc ccgcaccgat cgcccttccc aacagttgcg cagcctgaat   3180
ggcgaatgga cgcgccctgt agcggcgcat taagcgcggc gggtgtggtg gttacgcgca   3240
gcgtgaccgc tacacttgcc agcgccctag cgcccgctcc tttcgctttc ttcccttcct   3300
ttctcgccac gttcgccggc tttccccgtc aagctctaaa tcgggggctc cctttagggt   3360
tccgatttag agctttacgg cacctcgacc gcaaaaaact tgatttgggt gatggttcac   3420
gtagtgggcc atcgccctga tagacggttt ttcgcccttt gacgttggag tccacgttct   3480
```

ttaatagtgg actcttgttc caaactggaa caacactcaa ccctatctcg gtctattctt 3540
ttgatttata agggattttg ccgatttcgg cctattggtt aaaaaatgag ctgatttaac 3600
aaatatttaa cgcgaatttt aacaaaatat taacgtttac aatttcgcct gatgcggtat 3660
tttctcctta cgcatctgtg cggtatttca caccgcatac aggtggcact tttcggggaa 3720
atgtgcgcgg aacccctatt tgtttatttt tctaaataca ttcaaatatg tatccgctca 3780
tgagacaata accctgataa atgcttcaat aatattgaaa aaggaagagt atgagtattc 3840
aacatttccg tgtcgccctt attccctttt ttgcggcatt ttgccttcct gtttttgctc 3900
acccagaaac gctggtgaaa gtaaaagatg ctgaagatca gttgggtgca cgagtgggtt 3960
acatcgaact ggatctcaac agcggtaaga tccttgagag ttttcgcccc gaagaacgtt 4020
ttccaatgat gagcactttt aaagttctgc tatgtggcgc ggtattatcc cgtattgacg 4080
ccgggcaaga gcaactcggt cgccgcatac actattctca gaatgacttg gttgagtact 4140
caccagtcac agaaaagcat cttacggatg gcatgacagt aagagaatta tgcagtgctg 4200
ccataaccat gagtgataac actgcggcca acttacttct gacaacgatc ggaggaccga 4260
aggagctaac cgcttttttg cacaacatgg gggatcatgt aactcgcctt gatcgttggg 4320
aaccggagct gaatgaagcc ataccaaacg acgagcgtga caccacgatg cctgtagcaa 4380
tgccaacaac gttgcgcaaa ctattaactg gcgaactact tactctagct tcccggcaac 4440
aattaataga ctggatggag gcggataaag ttgcaggacc acttctgcgc tcggcccttc 4500
cggctggctg gtttattgct gataaatctg gagccggtga gcgtgggtct cgcggtatca 4560
ttgcagcact ggggccagat ggtaagccct cccgtatcgt agttatctac acgacgggga 4620
gtcaggcaac tatggatgaa cgaaatagac agatcgctga gataggtgcc tcactgatta 4680
agcattggta actgtcagac caagtttact catatatact ttagattgat ttaaaacttc 4740
atttttaatt taaaaggatc taggtgaaga tcctttttga taatctcatg accaaaatcc 4800
cttaacgtga gttttcgttc cactgagcgt cagaccccgt agaaaagatc aaaggatctt 4860
cttgagatcc tttttttctg cgcgtaatct gctgcttgca aacaaaaaaa ccaccgctac 4920
cagcggtggt ttgtttgccg gatcaagagc taccaactct ttttccgaag gtaactggct 4980
tcagcagagc gcagatacca aatactgtcc ttctagtgta gccgtagtta ggccaccact 5040
tcaagaactc tgtagcaccg cctacatacc tcgctctgct aatcctgtta ccagtggctg 5100
ctgccagtgg cgataagtcg tgtcttaccg ggttggactc aagacgatag ttaccggata 5160
aggcgcagcg gtcgggctga acggggggtt cgtgcacaca gcccagcttg gagcgaacga 5220
cctacaccga actgagatac ctacagcgtg agctatgaga aagcgccacg cttcccgaag 5280
ggagaaaggc ggacaggtat ccggtaagcg gcagggtcgg aacaggagag cgcacgaggg 5340
agcttccagg gggaaacgcc tggtatcttt atagtcctgt cgggtttcgc cacctctgac 5400
ttgagcgtcg atttttgtga tgctcgtcag gggggcggag cctatggaaa aacgccagca 5460
acgcggcctt tttacggttc ctggcctttt gctggccttt tgctcacatg ttctttcctg 5520
cgttatcccc tgattctgtg gataaccgta ttaccgcctt tgagtgagct gataccgctc 5580
gccgcagccg aacgaccgag cgcagcgagt cagtgagcga ggaagcggaa gagcgcccaa 5640
tacgcaaacc gcctctcccc gcgcgttggc cgattcatta atgcagctgg cacgacaggt 5700
ttcccgactg gaaagcgggc agtgagcgca acgcaattaa tgtgagttag ctcactcatt 5760
aggcacccca ggctttacac tttatgcttc cggctcgtat gttgtgtgga attgtgagcg 5820

-continued gataacaatt tcacacagga aacagctatg accatgatta cgccaagcta tttaggtgac 5880
actatagaat actcaagcta tgca 5904

<210> SEQ ID NO 14
<211> LENGTH: 9703
<212> TYPE: DNA
<213> ORGANISM: Artificial Sequence
<220> FEATURE:
<223> OTHER INFORMATION: plasmid TK153

<400> SEQUENCE: 14
tcgactaaag agcaaggcgg acacgataac atcaccgtcg ttatcgtcgc tttagaataa 60
cgttcccaaa atagctcatt tccaactggc aactcacaac caaaaaccgc atttttagta 120
aatatactca gcaatttgtt caacctgagc atttttccca tttgcaactt gatacaaata 180
tttttagcag caaattttcc tactgccagc ttagtttaca taaattttgt ctgttgacat 240
cttgcacaca ataaggtatg gcgcatataa tgcgatatta ctaccattaa tttactacct 300
agtcattaac gtctcccgcc agagaacagt tttgaatagg tagtcaattt taggtattga 360
acctgctgta aatttattaa atcgatgaat ttccccgaaa tctgctctag cagacttggg 420
ttatatacca gtaggctcag gtgcaaaaca acaaagcaca aattttaccc attaaggata 480
taggcaatct gtcaaatagt tgttatcttt cttaatacag aggaataatc aacaatatgg 540
ggcaggtact aactaaagtc ctatgcctgt ggggcttctg taaccgacat aacctttacg 600
cgttgtcttt taggagtctg ttatgaattc ttatactgtc ggtacctatt tagcggagcg 660
gcttgtccag attggtctca agcatcactt cgcagtcgcg ggcgactaca acctcgtcct 720
tcttgacaac ctgcttttga acaaaaacat ggagcaggtt tattgctgta acgaactgaa 780
ctgcggtttc agtgcagaag gttatgctcg tgccaaaggc gcagcagcag ccgtcgttac 840
ctacagcgtc ggtgcgcttt ccgcatttga tgctatcggt ggcgcctatg cagaaaacct 900
tccggttatc ctgatctccg gtgctccgaa caacaatgat cacgctgctg gtcacgtgtt 960
gcatcacgct cttggcaaaa ccgactatca ctatcagttg gaaatggcca agaacatcac 1020
ggccgcagct gaagcgattt acaccccaga agaagctccg gctaaaatcg atcacgtgat 1080
taaaactgct cttcgtgaga agaagccggt ttatctcgaa atcgcttgca acattgcttc 1140
catgccctgc gccgctcctg gaccggcaag cgcattgttc aatgacgaag ccagcgacga 1200
agcttctttg aatgcagcgg ttgaagaaac cctgaaattc atcgccaacc gcgacaaagt 1260
tgccgtcctc gtcggcagca agctgcgcgc agctggtgct gaagaagctg ctgtcaaatt 1320
tgctgatgct ctcggtggcg cagttgctac catggctgct gcaaaaagct tcttcccaga 1380
agaaaacccg cattacatcg gtacctcatg ggtgaagtc agctatccgg gcgttgaaaa 1440
gacgatgaaa gaagccgatg cggttatcgc tctggctcct gtcttcaacg actactccac 1500
cactggttgg acggatattc ctgatcctaa gaaactggtt ctcgctgaac cgcgttctgt 1560
cgtcgttaac ggcgttcgct tccccagcgt tcatctgaaa gactatctga cccgtttggc 1620
tcagaaagtt tccaagaaaa ccggtgcttt ggacttcttc aaatccctca atgcaggtga 1680
actgaagaaa gccgctccgg ctgatccgag tgctccgttg gtcaacgcag aaatcgcccg 1740
tcaggtcgaa gctcttctga ccccgaacac gacggttatt gctgaaaccg gtgactcttg 1800
gttcaatgct cagcgcatga agctcccgaa cggtgctcgc gttgaatatg aaatgcagtg 1860
gggtcacatc ggttggtccg ttcctgccgc cttcggttat gccgtcggtg ctccggaacg 1920
tcgcaacatc ctcatggttg gtgatggttc cttccagctg acggctcagg aagtcgctca 1980

-continued

```
gatggttcgc ctgaaactgc cggttatcat cttcttgatc aataactatg gttacaccat   2040

cgaagttatg atccatgatg gtccgtacaa caacatcaag aactgggatt atgccggtct   2100

gatggaagtg ttcaacggta acggtggtta tgacagcggt gctggtaaag gcctgaaggc   2160

taaaaccggt ggcgaactgg cagaagctat caaggttgct ctggcaaaca ccgacggccc   2220

aaccctgatc gaatgcttca tcggtcgtga agactgcact gaagaattgg tcaaatgggg   2280

taagcgcgtt gctgccgcca acagccgtaa gcctgttaac aagctcctct agtttttggg   2340

gatcaattcg agctctctgg ataaaactaa taaactctat tacccatgat taaagcctac   2400

gctgccctgg aagccaacgg aaaactccaa ccctttgaat acgaccccgg tgccctgggt   2460

gctaatgagg tggagattga ggtgcagtat tgtggggtgt gccacagtga tttgtccatg   2520

attaataacg aatggggcat ttccaattac cccctagtgc cgggtcatga ggtggtgggt   2580

actgtggccg ccatgggcga aggggtgaac catgttgagg tgggggattt agtggggctg   2640

ggttggcatt cgggctactg catgacctgc catagttgtt tatctggcta ccacaacctt   2700

tgtgccacgg cggaatcgac cattgtgggc cactacggtg gctttggcga tcgggttcgg   2760

gccaagggag tcagcgtggt gaaattacct aaaggcattg acctagccag tgccgggccc   2820

cttttctgtg gaggaattac cgttttcagt cctatggtgg aactgagttt aaagcccact   2880

gcaaaagtgg cagtgatcgg cattgggggc ttgggccatt tagcggtgca atttctccgg   2940

gcctggggct gtgaagtgac tgcctttacc tccagtgcca ggaagcaaac ggaagtgttg   3000

gaattgggcg ctcaccacat actagattcc accaatccag aggcgatcgc cagtgcggaa   3060

ggcaaatttg actatattat ctccactgtg aacctgaagc ttgactggaa cttatacatc   3120

agcaccctgg cgccccaggg acatttccac tttgttgggg tggtgttgga gcctttggat   3180

ctaaatcttt ttcccctttt gatgggacaa cgctccgttt ctgcctcccc agtgggtagt   3240

cccgccacca ttgccaccat gttggacttt gctgtgcgcc atgacattaa acccgtggtg   3300

gaacaattta gctttgatca gatcaacgag gcgatcgccc atctagaaag cggcaaagcc   3360

cattatcggg tagtgctcag ccatagtaaa aattagctct gcaaaggttg cttctgggtc   3420

cgtggaatgg tcaaacggag tcgatctcag ttttgatacg ctctatctgg aaagcttgac   3480

attcgatctg cagcccgggg gatccactag aggatctcaa tgaatattgg ttgacacggg   3540

cgtataagac atgttatact gttgaataac aaggacggat ctgatcaaga gacaggatga   3600

ggatcgtttc gcatgattga acaagatgga ttgcacgcag gttctccggc cgcttgggtg   3660

gagaggctat tcggctatga ctgggcacaa cagacaatcg gctgctctga tgccgccgtg   3720

ttccggctgt cagcgcaggg gcgcccggtt ctttttgtca agaccgacct gtccggtgcc   3780

ctgaatgaac tgcaggacga ggcagcgcgg ctatcgtggc tggccacgac gggcgttcct   3840

tgcgcagctg tgctcgacgt tgtcactgaa gcgggaaggg actggctgct attgggcgaa   3900

gtgccggggc aggatctcct gtcatctcac cttgctcctg ccgagaaagt atccatcatg   3960

gctgatgcaa tgcggcggct gcatacgctt gatccggcta cctgcccatt cgaccaccaa   4020

gcgaaacatc gcatcgagcg agcacgtact cggatggaag ccggtcttgt cgatcaggat   4080

gatctggacg aagagcatca ggggctcgcg ccagccgaac tgttcgccag gctcaaggcg   4140

cgcatgcccg acggcgagga tctcgtcgtg acccatggcg atgcctgctt gccgaatatc   4200

atggtggaaa atggccgctt ttctggattc atcgactgtg gccggctggg tgtggcggac   4260

cgctatcagg acatagcgtt ggctacccgt gatattgctg aagagcttgg cggcgaatgg   4320
```

gctgaccgct tcctcgtgct ttacggtatc gccgctcccg attcgcagcg catcgccttc 4380
tatcgccttc ttgacgagtt cttctgagcg ggactctggg gttcgaaatg accgaccaag 4440
cgacgcccaa cctgccatca cgagatttcg attccaccgc cgccttctat gaaaggttgg 4500
gcttcggaat cgttttccgg gacgccggct ggatgatcct ccagcgcggg gatctcatgc 4560
tggagttctt cgcccaccgg ggatcctcta gttctagagc ggccgcttcg tgtagtgtgt 4620
attgaactaa attaaatatt tttcaaagtg ggtagatgct tctatccact ttgtttccat 4680
tatgtgagtc attcacaaat cttgtcccta tatttatttt atgaaaattt caatgattac 4740
tgatacatat aattggcaac atctggctga tcaatacttt ctacaagaaa actatctcca 4800
agcagcacag ttatacgaac aagcaatagc aatagaacca aatactattt cttattattg 4860
gcatttagga ttattattgc tattacaagg acaagaagca gaagctcaaa tgacttggat 4920
gctgccaata acagaggcag atgaagagca tttacaaatt tggacaaatg aactatttaa 4980
atttttacaa acagaagctg aaaggcggga aaatctgacg gaatactctg tagcctggtt 5040
aattcgccag catatgaggg aaattattcc tagtgatatt aataatttac tccaaattct 5100
tctactttat ctcaaactag aaaaatttga agtaatgaat gaattgcatg actggggatt 5160
aattgaaatt ttaaatgaaa aagaaagtgt aaatattgat gctaacttgt tgagacaatt 5220
tttagaggaa cttttaaata ctattccttt acatccaata gttttgagtt tagtagaagc 5280
ttgtttacct tatttctctg atacttatca atgcttcgat atactactta cggctactct 5340
gaaaattggt catactctac agcaacctat actagcatca tctcttctca agttacattt 5400
gcgtttagag ccagaaaatg tcgaaatttt gcgacattta gctatttttt atcaagatgc 5460
tcgcaattat tctcaaggaa tagaaacagc taagttatgt tattcgctat cagaaggttt 5520
agcggataaa atttttgcac ttcatttact attaaggggt ttaatgtcag caggaggata 5580
ttggaaagag atatgtgaaa cttgccagga gctagaaact gtatttcaac agtttataca 5640
agcacaacca attgctttag aagagggaag aatcctgcgg ttactgacac tagtgatggc 5700
ggccgggagc atgcgacgtc gggcccaatt cgccctatag tgagtcgtat tacaattcac 5760
tggccgtcgt tttacaacgt cgtgactggg aaaaccctgg cgttacccaa cttaatcgcc 5820
ttgcagcaca tccccctttc gccagctggc gtaatagcga agaggcccgc accgatcgcc 5880
cttcccaaca gttgcgcagc ctgaatggcg aatggacgcg ccctgtagcg gcgcattaag 5940
cgcggcgggt gtggtggtta cgcgcagcgt gaccgctaca cttgccagcg ccctagcgcc 6000
cgctcctttc gctttcttcc cttcctttct cgccacgttc gccggctttc cccgtcaagc 6060
tctaaatcgg gggctccctt tagggttccg atttagagct ttacggcacc tcgaccgcaa 6120
aaaacttgat ttgggtgatg gttcacgtag tgggccatcg ccctgataga cggtttttcg 6180
ccctttgacg ttggagtcca cgttctttaa tagtggactc ttgttccaaa ctggaacaac 6240
actcaaccct atctcggtct attcttttga tttataaggg attttgccga tttcggccta 6300
ttggttaaaa aatgagctga tttaacaaat atttaacgcg aattttaaca aaatattaac 6360
gtttacaatt tcgcctgatg cggtattttc tccttacgca tctgtgcggt atttcacacc 6420
gcatacaggt ggcacttttc ggggaaatgt gcgcggaacc cctatttgtt tatttttcta 6480
aatacattca aatatgtatc cgctcatgag acaataaccc tgataaatgc ttcaataata 6540
ttgaaaaagg aagagtatga gtattcaaca tttccgtgtc gcccttattc ccttttttgc 6600
ggcattttgc cttcctgttt ttgctcaccc agaaacgctg gtgaaagtaa aagatgctga 6660
agatcagttg ggtgcacgag tgggttacat cgaactggat ctcaacagcg gtaagatcct 6720

-continued

```
tgagagtttt cgccccgaag aacgttttcc aatgatgagc acttttaaag ttctgctatg   6780
tggcgcggta ttatcccgta ttgacgccgg gcaagagcaa ctcggtcgcc gcatacacta   6840
ttctcagaat gacttggttg agtactcacc agtcacagaa aagcatctta cggatggcat   6900
gacagtaaga gaattatgca gtgctgccat aaccatgagt gataacactg cggccaactt   6960
acttctgaca acgatcggag gaccgaagga gctaaccgct tttttgcaca acatggggga   7020
tcatgtaact cgccttgatc gttgggaacc ggagctgaat gaagccatac caaacgacga   7080
gcgtgacacc acgatgcctg tagcaatgcc aacaacgttg cgcaaactat taactggcga   7140
actacttact ctagcttccc ggcaacaatt aatagactgg atggaggcgg ataaagttgc   7200
aggaccactt ctgcgctcgg cccttccggc tggctggttt attgctgata aatctggagc   7260
cggtgagcgt gggtctcgcg gtatcattgc agcactgggg ccagatggta agccctcccg   7320
tatcgtagtt atctacacga cggggagtca ggcaactatg gatgaacgaa atagacagat   7380
cgctgagata ggtgcctcac tgattaagca ttggtaactg tcagaccaag tttactcata   7440
tatactttag attgatttaa aacttcattt ttaatttaaa aggatctagg tgaagatcct   7500
ttttgataat ctcatgacca aaatccctta acgtgagttt tcgttccact gagcgtcaga   7560
ccccgtagaa aagatcaaag gatcttcttg agatcctttt tttctgcgcg taatctgctg   7620
cttgcaaaca aaaaaaccac cgctaccagc ggtggtttgt ttgccggatc aagagctacc   7680
aactcttttt ccgaaggtaa ctggcttcag cagagcgcag ataccaaata ctgtccttct   7740
agtgtagccg tagttaggcc accacttcaa gaactctgta gcaccgccta catacctcgc   7800
tctgctaatc ctgttaccag tggctgctgc cagtggcgat aagtcgtgtc ttaccgggtt   7860
ggactcaaga cgatagttac cggataaggc gcagcggtcg ggctgaacgg ggggttcgtg   7920
cacacagccc agcttggagc gaacgaccta caccgaactg agatacctac agcgtgagct   7980
atgagaaagc gccacgcttc ccgaagggag aaaggcggac aggtatccgg taagcggcag   8040
ggtcggaaca ggagagcgca cgagggagct tccaggggga aacgcctggt atctttatag   8100
tcctgtcggg tttcgccacc tctgacttga gcgtcgattt ttgtgatgct cgtcaggggg   8160
gcggagccta tggaaaaacg ccagcaacgc ggccttttta cggttcctgg ccttttgctg   8220
gccttttgct cacatgttct ttcctgcgtt atcccctgat tctgtggata accgtattac   8280
cgcctttgag tgagctgata ccgctcgccg cagccgaacg accgagcgca gcgagtcagt   8340
gagcgaggaa gcggaagagc gcccaatacg caaaccgcct ctccccgcgc gttggccgat   8400
tcattaatgc agctggcacg acaggtttcc cgactggaaa gcgggcagtg agcgcaacgc   8460
aattaatgtg agttagctca ctcattaggc accccaggct ttacacttta tgcttccggc   8520
tcgtatgttg tgtggaattg tgagcggata acaatttcac acaggaaaca gctatgacca   8580
tgattacgcc aagctattta ggtgacacta tagaatactc aagctatgca tggagctggt   8640
agaagggaac attatagtta tggggccatc agattacgaa tcagaggaaa taggtgctcg   8700
tttaattacc ttcttgaata actgggtaat gtcgcgcaaa ttagggcgag taactggttc   8760
tagcgcaggc ttcattctgc caagtatgga agagggcgac tcagaaaaaa gaaacctgcg   8820
tgcccctgat gtttcttttg tgcgggctga cagactaaaa aagagcaagc gcgactttgt   8880
agagttagtt ccagatttga tggtagaagt caaatcaaaa tcagacagaa ttaaaccgct   8940
tgaagaaaaa attcagttat tcttacaact tggctctaca gtcgggatac taattgatcc   9000
tgaccagttg acagtaacag tttaccgact caaccaagct ccagtagtat tgcagaatgg   9060
```

-continued

```
agacacactc acgttaccag atgtgctacc aggttgggaa ttggcaatat cagaactatg   9120

gccgcctgaa tttgaataac tagatatcac cagaaattaa ttatgcgtta ctcaaatatc   9180

aatcttgtgg tatggacaac ttgtccgcac cggacgggct aaaagcccat cccacaagaa   9240

agctatcatg caacatttta gacttgccac gccactatcc tcacgggaag caaccgcaca   9300

tctatagagt gacagcgacc gtttactgaa ccatattgac ttatctttca aattcagtct   9360

ggaaatgctt attagacagg ttttcgcatc gaaaagaacc actaacttac aaccaaataa   9420

aatttttttt ggtgggagtg atatgaaatt gatcggtggt gggtaagtta tttttagaac   9480

gcgataagca gtcaccacca taaggagtta cagatatgaa aaccgaactg aaagccaagt   9540

ttttacaaca cattcttaat aaaaagaaag aagacgaagg tttcaccctc attgaattac   9600

tggtagtaat tattattatc ggcattctgt cagctattgc actaccttct ttccttaacc   9660

aagctaataa agcaaaacaa tctgaagcga aaacctatgt tgg                     9703


<210> SEQ ID NO 15
<211> LENGTH: 373
<212> TYPE: PRT
<213> ORGANISM: Anabaena PCC7119

<400> SEQUENCE: 15

Met Ile Ser Pro Glu Ser Leu Asn Thr Asn Val Ser Leu Thr Leu Leu
1               5                   10                  15

Thr Arg Glu Leu Gln Thr Glu Ile Ile Leu Gly Thr Tyr Thr Val Arg
            20                  25                  30

Val His Thr Arg Ile Gly Arg Glu Pro Cys Ala Arg Leu Trp Tyr Leu
        35                  40                  45

Cys Arg Ala Leu Asp Lys Asp Gly Ser Gly His Leu Thr Leu Pro Leu
    50                  55                  60

Pro Val Val Gln Thr Phe Leu Asp Cys Ser Asp Lys Ser Val Tyr Arg
65                  70                  75                  80

Trp Leu Gln Asp Gly Lys Lys Ile Gly Ala Phe Arg Arg Tyr Lys Ile
                85                  90                  95

Lys Ala Gly Met Ile Thr Val Tyr Leu Gly Gly Met Phe Gln Val Cys
            100                 105                 110

Tyr Asn Leu Asn Leu Lys Arg Trp Gly Asp Val Ala Val Val Pro Leu
        115                 120                 125

Val Gln Val Leu Ser Asp Leu Arg Ser Leu Thr Thr Gly Ile Val Thr
    130                 135                 140

Gln Ser Phe Gln Gln Lys Ser Arg Tyr Ala Ala Asn Arg Gln Leu Lys
145                 150                 155                 160

Pro Glu Tyr Arg Lys Leu Phe Gly Ala Pro His Pro Asn Glu Leu Val
                165                 170                 175

Lys Asp Thr Arg Gln Ser Ser Leu Lys Ser Pro Glu Gly Glu Val Pro
            180                 185                 190

Cys Val Leu His Ile Ser Ser Ser Arg Ile Phe Val Ser Lys Ser Phe
        195                 200                 205

Ile His Tyr Gly Thr Ser Gln Lys Ala Val Ser Cys Glu Leu Gly Ile
    210                 215                 220

His Lys Arg Thr Val Arg Arg His Gln Lys Gln Leu Gly Met Asn Arg
225                 230                 235                 240

Arg Gln Leu Cys Gln Ala Lys Ile Glu Tyr Asn Gln Leu Arg His Ala
                245                 250                 255

Arg Asn Asn Asp Ala Ser Glu Phe Trp Ala Phe Thr Gly Thr Lys Thr
```

```
            260                 265                 270

Asp Ile Gly Tyr Gln Val Met Gly Asp Ala Val Val Phe Ser Asp Gly
        275                 280                 285

Ile Ala Pro Gly Ala Lys Lys Arg Gln Pro Asn Thr Tyr Gln Ile Asp
    290                 295                 300

Ala Thr Glu Phe Asp Gly Arg Leu Phe Lys Val Gly Asp Lys Val Phe
305                 310                 315                 320

Met Asn Arg Cys Asn Ile Tyr Arg Glu Gln Phe Thr Leu Thr Thr Met
                325                 330                 335

Ser Ala Ala Arg Arg Lys Tyr His Phe Lys Leu Ser Gln Cys His Phe
            340                 345                 350

Ser Glu Asn Arg Ala Gly Arg Val Gly Asn Arg Phe Val Ile Gly Cys
        355                 360                 365

His Ser Gly Glu Ile
    370


<210> SEQ ID NO 16
<211> LENGTH: 183
<212> TYPE: PRT
<213> ORGANISM: Anabaena PCC7119

<400> SEQUENCE: 16

Met Lys Val Asn Gly Asn Gly Arg Ala Lys Ile Leu Thr Ser Asp Glu
1               5                   10                  15

Leu Arg Arg Leu Phe Ser Asp Gly Phe Thr Thr Pro Arg Asp Arg Val
            20                  25                  30

Leu Phe Gly Ile Cys Leu Phe Thr Gly Cys Arg Val Ser Glu Ala Leu
        35                  40                  45

Ala Leu Gln Thr Thr Asp Ile Lys Gly Glu Thr Leu Thr Phe Arg Lys
    50                  55                  60

Ser Thr Thr Lys Gly Lys Leu Lys Thr Arg Val Val Asp Ile Gln Pro
65                  70                  75                  80

Gly Leu Ala Ala Leu Met Ala Asp Tyr His Pro Lys Pro Gly Thr Leu
                85                  90                  95

Phe Pro Gly Met Arg Gly Val Ser Asp Arg Leu Thr Arg Tyr Ala Ala
            100                 105                 110

Asp Lys Ile Leu Arg Asp Ala Ala Lys Arg Ile Gly Leu Glu Gly Ile
        115                 120                 125

Ser Thr His Ser Phe Arg Arg Thr Ala Leu Asn Gln Met Ser Ser Ala
    130                 135                 140

Gly Ile Pro Leu Arg His Ile Gln Glu Ile Ser Gly His Asn Asp Leu
145                 150                 155                 160

Gly Thr Leu Gln Arg Tyr Leu Glu Val Thr Pro Glu Gln Arg Arg Lys
                165                 170                 175

Ala Val Ser Val Ile Gly Phe
            180


<210> SEQ ID NO 17
<211> LENGTH: 3718
<212> TYPE: DNA
<213> ORGANISM: Anabaena PCC7119

<400> SEQUENCE: 17

taccaagaag gtaaatcgct actggaaaaa cttaaggatt tgtagcggtg cgtttagcat      60

tgactgttac ttgctgtaca aggataattt tctcaaagcg gaatggtgtt aaacccgatt     120
```

-continued

```
attagagtcg tcatagcaaa agcttgaaaa ctggcaaggg tgtactggtt ttcgttcttt    180
ttggttctaa tggttatttt ttaccagttt atttagtaat aaccgagtgc caagtttctt    240
gttttacata gcaaagttag caaaaaacat tttgccgtga atttccatct gtaaaaagcg    300
tcacggcgaa attcagtatt tagtaaatac aaaaataagt caaacgttga tcatgcaaca    360
ctttggcgta caattgattg aaaattttgc cgataggcaa agtttaaatt acctattaaa    420
aaaagttcag tgcttggagg ttgttatgct acttaaccga agctaaataa aacacacata    480
cacagaattg ttaccacacc aaacaccaaa cagaaaaaac gtgctttgaa tttatcaatt    540
aatgggtgta gttaacaagt tttatttagc ttcaggttaa gcaaataaca ttcaataggt    600
actggactga gacatttcca aatgatcagc ccagaaagct taaatacaaa tgtatcacta    660
accctgctta caagggaact acaaactgaa ataattcttg gcacttacac ggtcagggta    720
cacactcgca ttggtcgaga accttgtgcg cggttgtggt atttgtgtcg agcgcttgat    780
aaggatgggt ctggtcattt aacattgcca ttgcctgtag tacagacgtt cttagattgt    840
agtgataagt ctgtttaccg ttggttacag gatggaaaaa aaataggagc attccgccgc    900
tacaaaatta aagcaggaat gataaccgtc tacttgggcg gtatgtttca agtttgttac    960
aacctaaatt taaaaagatg gggtgatgtt gcagtagtgc ctttagtcca agtgttaagc   1020
gatttacgct cactgaccac tggcatagtc acacaaagct ttcaacaaaa gagccgctat   1080
gcggccaaca gacaacttaa accagagtac agaaaacttt ttggagcgcc acacccgaac   1140
gagctagtga aggacacaag gcaatcctct cttaaatcgc cagaggggga agtaccttgt   1200
gtacttcaca ttagttcgtc gcggatattc gtctcaaaaa gtttcatcca ctatggtaca   1260
tctcaaaaag ctgtcagctg tgagttgggt attcacaagc gcacagtgcg acgacatcaa   1320
aagcagctgg gcatgaatcg ccgtcaactt tgccaagcca aaattgagta caatcaactc   1380
cggcacgctc ggaataatga cgcgtctgaa ttttgggctt tcactggaac caaaactgat   1440
atcggttatc aagttatggg tgacgcggtt gtgttttctg atggcattgc ccctggagcc   1500
aaaaagagac agcccaacac ttaccaaatt gacgcgactg aatttgacgg tcgattattc   1560
aaagtgggtg acaaggtgtt catgaatcgg tgcaacatct accgcgaaca attcacccta   1620
acaacgatgt cagcagcacg gcggaagtac catttcaaac tgtcacagtg ccacttcagc   1680
gaaaatcgag ccggtcgggt aggcaaccgt tttgtaatag gttgccactc tggcgagata   1740
tgaaggacat ttttaagaat tttttttag cgtgaaatgc tgcggcaacc agtatagtga    1800
tcgacacgaa ctagtgcagc atgaccgaga gcctataggg tcgcggcttt ttggcaatag   1860
agatcgtatg cagatcatgc gtagtacttt cttcgacctt aaccccaaag aaagcttatt   1920
agatggagaa ggtcacaatt agaaaatatt catcgtcccg attgaccctt aacctttaat   1980
cggtttccac ttgtaaaaaa ttcggcgagc cattcttctt aaccctcaga gtcgaacttc   2040
atacaagaat atacaaaccc tttgggttta ccactaaaac aacggcgata aaaacctaat   2100
aggtttccac agaaacgtct aaggatttag gcgtgttgtt ttggggcaat ttgagaaaat   2160
attaaaccag tcacaagtta acttgtcgaa gaaatattgc agcattctgc aacacaggga   2220
aaggtataac gtttccaaag tccggaacgt gtgcagagtt ctagaaccga tggatacttt   2280
aaaagtatcc tcaagtgtag agcgtgtgtt taggctgcgt cttttttag cacccatagg    2340
ggtctaaaca gcgttggcgt acattagaag ccaatcacgg atacagcttt gcgtcgctgt   2400
tcgggtgtaa cttcaagata gcgttgcagt gtgccaaggt cattgtgacc ggatatctct   2460
tgaatgtgtc gcaacgggat accggcgcta gacatttggt tgagggcagt acggcggaaa   2520
```

```
ctgtgggtac tgatgccttc tagcccgatt cttttggctg catcgcgcaa gattttatcc   2580
gccgcgtatc gcgtgagcct atcgctgact cccctcatgc cagggaacag ggttcccggt   2640
ttggggtgat agtcagccat gagtgcggct agtcctggct ggatgtcaac cacgcgggtt   2700
ttgagtttcc ctttggtggt agacttccta aaggttagtg tttcgccttt aatgtccgtt   2760
gtttggagtg ctagagcttc actaacgcgg caaccggtga atagacagat gccaaacaaa   2820
acgcgatcgc gcggtgtggt gaatccgtcg ctaaacagtc gcctgagttc gtcggaggtg   2880
agtattttgg ctcgtccgtt gccgttaacc ttcataaccc ttacagatta agcattccaa   2940
tactctacac gttatctgca ttttgtggaa ttggtggcta tatctattga ttcttcgtat   3000
gctttctgtt gaaagccagt gctagtttag ccaagcttat caatcgttgc acggtaaaat   3060
caggctttcg acgtaaggac agaattttga taacttcagc ttatgttgtc tcctgaagaa   3120
agcaactctt tgataaacgc gtcgatggct ttcccggcgg ctgactgcct acccattttt   3180
agcttattga gggtgcgatc gcgggttgcc tccaatttgt ctagattgtc tatactattg   3240
tctatattct ttctgtcttg cccggtagct tgtccttctg cctgaactac cgggctttcg   3300
attttccccg cagttcctcc agttgcgatt gaagtttgtc tagacgtgtt gctagattat   3360
cttctatacg cttgtctata aattcatcta tattgtctag attattagtt gtgactttat   3420
ctagacgttg ttcaatattg tctatacgct gttcgaggga tgtgtctaga tgggtgggag   3480
tgtgagaagt gggagtatta aacctgttac ctgccaaata ccaacgaaca aattctgtta   3540
acagtgctga ggcgttggaa ctttcagaac tagcaaggtt tttaaaagac tcccattctt   3600
cggagtcaat acgaaaagtg gctagagttt tgtctgccat gattagataa tgtctatact   3660
tgtatagata gcagtataaa ctattgtcta tattagtgtc tatataagtc tagatatc     3718
```

<210> SEQ ID NO 18
<211> LENGTH: 13729
<212> TYPE: DNA
<213> ORGANISM: Artificial Sequence
<220> FEATURE:
<223> OTHER INFORMATION: plasmid K230

<400> SEQUENCE: 18

```
gatccccggg taccagtaaa ggagaagaac tattcactgg agttgtccca attcttgttg     60
aattagatgg tgatgttaat gggcacaaat tttctgtcag tggagagggt gaaggtgatg    120
caacatacgg aaaacttacc cttaaattta tttgcactac tggaaaacta cctgttccat    180
ggccaacact tgtcactact ttcgcgtatg gtcttcaatg ctttgcgaga tacccagatc    240
atatgaaaca gcatgacttt ttcaagagtg ccatgcccga aggttatgta caggaaagaa    300
ctatattttt caaagatgac gggaactaca agacacgtgc tgaagtcaag tttgaaggtg    360
ataccettgt taatagaatc gagttaaaag gtattgattt taaagaagat ggaaacattc    420
ttggacacaa attggaatac aactataact cacacaatgt atacatcatg gcagacaaac    480
aaaagaatgg aatcaaagtt aacttcaaaa ttagacacaa cattgaagat ggaagcgttc    540
aactagcaga ccattatcaa caaaatactc caattggcga tggccctgtc cttttaccag    600
acaaccatta cctgtccaca caatctgccc tttcgaaaga tcccaacgaa aagagagacc    660
acatggtcct tcttgagttt gtaacagctg ctgggattac acatggcatg gatgaactat    720
acaaataaga gctcgaattg atcctttttg ataatctcat gaccaaaatc ccttaacgtg    780
agttttcgtt ccactgagcg tcagaccccg tagaaaagat caaaggatct tcttgagatc    840
```

-continued

```
cttttttct gcgcgtaatc tgctgcttgc aaacaaaaaa accaccgcta ccagcggtgg    900
tttgtttgcc ggatcaagag ctaccaactc tttttccgaa ggtaactggc ttcagcagag    960
cgcagatacc aaatactgtc cttctagtgt agccgtagtt aggccaccac ttcaagaact   1020
ctgtagcacc gcctacatac ctcgctctgc taatcctgtt accagtggct gctgccagtg   1080
gcgataagtc gtgtcttacc gggttggact caagacgata gttaccggat aaggcgcagc   1140
ggtcgggctg aacggggggt tcgtgcacac agcccagctt ggagcgaacg acctacaccg   1200
aactgagata cctacagcgt gagctatgag aaagcgccac gcttcccgaa gggagaaagg   1260
cggacaggta tccggtaagc ggcagggtcg gaacaggaga gcgcacgagg gagcttccag   1320
ggggaaacgc ctggtatctt tatagtcctg tcgggtttcg ccacctctga cttgagcgtc   1380
gatttttgtg atgctcgtca ggggggcgga gcctatggaa aaacgccagc aacgcggcct   1440
ttttacggtt cctggccttt tgctggcctt ttgctcacat gttctttcct gcgttatccc   1500
ctgattctgt ggataaccgt attaccgcct ttgagtgagc tgataccgct cgccgcagcc   1560
gaacgaccga gcgcagcgag tcagtgagcg aggaagcgga agagcgcctg atgcggtatt   1620
ttctccttac gcatctgtgc ggtatttcac accgcatatg gtgcactctc agtacaatct   1680
gctctgatgc cgcatagtta agccagtata cactccgcta tcgctacgtg actgggtcat   1740
ggctgcgccc cgacacccgc caacacccgc tgacgcgccc tgacgggctt gtctgctccc   1800
ggcatccgct tacagacaag ctgtgaccgt ctccgggagc tgcatgtgtc agaggttttc   1860
accgtcatca ccgaaacgcg cgaggcagct gcggtaaagc tcatcagcgt ggtcgtgaag   1920
cgattcacag atgtctgcct gttcatccgc gtccagctcg ttgagtttct ccagaagcgt   1980
taatgtctgg cttctgataa agcgggccatg ccaccatacc cacgccgaaa caagcgctca   2040
tgagcccgaa gtggcgagcc cgatcttccc catcggtgat gtcggcgata taggcgccag   2100
caaccgcacc tgtggcgccg gtgatgcccg aagaactcca gcatgagatc cccgcgctgg   2160
aggatcatcc agccggcgtc ccggaaaacg attccgaagc ccaacctttc atagaaggcg   2220
gcggtggaat cgaaatctcg tgatggcagg ttgggcgtcg cttggtcggt catttcgaac   2280
cccagagtcc cgctcagaag aactcgtcaa gaaggcgata gaaggcgatg cgctgcgaat   2340
cgggagcggc gataccgtaa agcacgagga agcggtcagc ccattcgccg ccaagctctt   2400
cagcaatatc acgggtagcc aacgctatgt cctgatagcg gtccgccaca cccagccggc   2460
cacagtcgat gaatccagaa aagcggccat tttccaccat gatattcggc aagcaggcat   2520
cgccatgggt cacgacgaga tcatcgccgt cgggcatgcg cgccttgagc ctggcgaaca   2580
gttcggctgg cgcgagcccc tgatgctctt cgtccagatc atcctgatcg acaagaccgg   2640
cttccatccg agtacgtgct cgctcgatgc gatgtttcgc ttggtggtcg aatgggcagg   2700
tagccggatc aagcgtatgc agccgccgca ttgcatcagc catgatggat actttctcgg   2760
caggagcaag gtgagatgac aggagatcct gccccggcac ttcgcccaat agcagccagt   2820
cccttcccgc ttcagtgaca acgtcgagca cagctgcgca aggaacgccc gtcgtggcca   2880
gccacgatag ccgcgctgcc tcgtcctgca gttcattcag ggcaccggac aggtcggtct   2940
tgacaaaaag aaccgggcgc ccctgcgctg acagccggaa cacggcggca tcagagcagc   3000
cgattgtctg ttgtgcccag tcatagccga atagcctctc cacccaagcg gccggagaac   3060
ctgcgtgcaa tccatcttgt tcaatcatgc gaaacgatcc tcatcctgtc tcttgatcag   3120
atcttgatcc cctgcgccat cagatccttg gcggcaagaa agccatccag tttactttgc   3180
agggcttccc aaccttacca gagggcgccc cagctggcaa ttccggttcg cttgctgtcc   3240
```

ataaaaccgc ccagtctagc tatcgccatg taagcccact gcaagctacc tgctttctct 3300
ttgcgcttgc gttttccctt gtccagatag cccagtagct gacattcatc cggggtcagc 3360
accgtttctg cggactggct ttctacgtgt tccgcttcct ttagcagccc ttgcgccctg 3420
agtgcttgcg gcagcgtgaa gctttctctg agctgtaaca gcctgaccgc aacaaacgag 3480
aggatcgaga ccatccgctc cagattatcc ggctcctcca tgcgttgcct ctcggctcct 3540
gctccggttt tccatgcctt atggaactcc tcgatccgcc agcgatgggt ataaatgtcg 3600
atgacgcgca aggcttgggc tagcgactcg accggttcgc tggtcagcaa caaccatttc 3660
aacggggtct caccccttggg cgggttaatc tcctcggcca gcaccgcgtt gagcgtgata 3720
ttcccctgtt ttagcgtgat gcgcccactg cgcatagaaa ttgcatcaac gcatatagcg 3780
ctagcagcac gccatagtga ctggcgatgc tgtcggaatg gacgatatct agacttatat 3840
agacactaat atagacaata gtttatactg ctatctatac aagtatagac attatctaat 3900
catggcagac aaaactctag ccacttttcg tattgactcc gaagaatggg agtcttttaa 3960
aaaccttgct agttctgaaa gttccaacgc ctcagcactg ttaacagaat ttgttcgttg 4020
gtatttggca ggtaacaggt ttaatactcc cacttctcac actcccaccc atctagacac 4080
atccctcgaa cagcgtatag acaatattga acaacgtcta gataaagtca caactaataa 4140
tctagacaat atagatgaat ttatagacaa gcgtatagaa gataatctag caacacgtct 4200
agacaaactt caatcgcaac tggaggaact gcggggaaaa tcgaaagccc ggtagttcag 4260
gcagaaggac aagctaccgg gcaagacaga aagaatatag acaatagtat agacaatcta 4320
gacaaattgg aggcaacccg cgatcgcacc ctcaataagc taaaaatggg taggcagtca 4380
gccgccggga aagccatcga cgcgtttatc aaagagttgc tttcttcagg agacaacata 4440
agctgaagtt atcaaaattc tgtccttacg tcgaaagcct gattttaccg tgcaacgatt 4500
gataagcttg gctaaactag cactggcttt caacagaaag catacgaaga atcaatagat 4560
atagccacca attccacaaa atgcagataa cgtgtagagt attggaatgc ttaatctgta 4620
agggttatga aggttaacgg caacggacga gccaaaatac tcacctccga cgaactcagg 4680
cgactgttta gcgacggatt caccacaccg cgcgatcgcg ttttgtttgg catctgtcta 4740
ttcaccggtt gccgcgttag tgaagctcta gcactccaaa caacggacat taaaggcgaa 4800
acactaacct ttaggaagtc taccaccaaa gggaaactca aaacccgcgt ggttgacatc 4860
cagccaggac tagccgcact catggctgac tatcacccca aaccgggaac cctgttccct 4920
ggcatgaggg gagtcagcga taggctcacg cgatacgcgg cggataaaat cttgcgcgat 4980
gcagccaaaa gaatcgggct agaaggcatc agtacccaca gtttccgccg tactgccctc 5040
aaccaaatgt ctagcgccgg tatcccgttg cgacacattc aagagatatc cggtcacaat 5100
gaccttggca cactgcaacg ctatcttgaa gttacacccg aacagcgacg caaagctgta 5160
tccgtgattg gcttctaatg tacgccaacg ctgtttagac ccctatgggt gctaaaaaaa 5220
gacgcagcct aaacacacgc tctacacttg aggatacttt taaagtatcc atcggttcta 5280
gaactctgca cacgttccgg actttggaaa cgttatacct ttccctgtgt tgcagaatgc 5340
tgcaatattt cttcgacaag ttaacttgtg actggtttaa tattttctca aattgcccca 5400
aaacaacacg cctaaatcct tagacgtttc tgtggaaacc tattaggttt ttatcgccgt 5460
tgttttagtg gtaaacccaa agggtttgta tattcttgta tgaagttcga ctctgagggt 5520
taagaagaat ggctcgccga attttttaca agtggaaacc gattaaaggt taagggtcaa 5580

-continued

```
tcgggacgat gaatattttc taattgtgac cttctccatc taataagctt tctttggggt   5640
taaggtcgaa gaaagtacta cgcatgatct gcatacgatc tctattgcca aaaagccgcg   5700
accctatagg ctctcggtca tgctgcacta gttcgtgtcg atcactatac tggttgccgc   5760
agcatttcac gctaaaaaaa aattcttaaa aatgtccttc atatctcgcc agagtggcaa   5820
cctattacaa aacggttgcc tacccgaccg gctcgatttt cgctgaagtg gcactgtgac   5880
agtttgaaat ggtacttccg ccgtgctgct gacatcgttg ttagggtgaa ttgttcgcgg   5940
tagatgttgc accgattcat gaacaccttg tcacccactt tgaataatcg accgtcaaat   6000
tcagtcgcgt caatttggta agtgttgggc tgtctctttt tggctccagg ggcaatgcca   6060
tcagaaaaca caaccgcgtc acccataact tgataaccga tatcagtttt ggttccagtg   6120
aaagcccaaa attcagacgc gtcattattc cgagcgtgcc ggagttgatt gtactcaatt   6180
ttggcttggc aaagttgacg gcgattcatg cccagctgct tttgatgtcg tcgcactgtg   6240
cgcttgtgaa tacccaactc acagctgaca gctttttgag atgtaccata gtggatgaaa   6300
ctttttgaga cgaatatccg cgacgaacta atgtgaagta cacaaggtac ttcccccctct   6360
ggcgatttaa gagaggattg ccttgtgtcc ttcactagct cgttcgggtg tggcgctcca   6420
aaaagtttc tgtactctgg tttaagttgt ctgttggccg catagcggct cttttgttga   6480
aagctttgtg tgactatgcc agtggtcagt gagcgtaaat cgcttaacac ttggactaaa   6540
ggcactactg caacatcacc ccatcttttt aaatttaggt tgtaacaaac ttgaaacata   6600
ccgcccaagt agacggttat cattcctgct ttaattttgt agcggcggaa tgctcctatt   6660
tttttccat cctgtaacca acggtaaaca gacttatcac tacaatctaa gaacgtctgt   6720
actacaggca atggcaatgt taaatgacca gacccatcct tatcaagcgc tcgacacaaa   6780
taccacaacc gcgcacaagg ttctcgacca atgcgagtgt gtaccctgac cgtgtaagtg   6840
ccaagaatta tttcagtttg tagttccctt gtaagcaggg ttagtgatac atttgtattt   6900
aagctttctg ggctgatcat ttggaaatgt ctcagtccag tacctattga atgttatttg   6960
cttaacctga agctaaataa aacttgttaa ctacacccat taattgataa attcaaagca   7020
cgttttttct gtttggtgtt tggtgtggta acaattctgt gtatgtgtgt tttatttagc   7080
ttcggttaag tagcataaca acccccaagc actgaacttt ttttaatagg taatttaaac   7140
tttgcctatc ggcaaaattt tcaatcaatt gtacgccaaa gtgttgcatg atcaacgttt   7200
gacttatttt tgtatttact aaatactgaa tttcgccgtg acgcttttta cagatggaaa   7260
ttcacggcaa aatgtttttt gctaactttg ctatgtaaaa caagaaactt ggcactcggt   7320
tattactaaa taaactggta aaaaataacc attagaacca aaaagaacga aaaccagtac   7380
acccttgcca gttttcaagc ttttgctatg acgactctaa taatcgggtt taacaccatt   7440
ccgctttgag aaaattatcc ttgtacagca agtaacagtc aatgctaaac cgcaccgcta   7500
caaatcctta agtttttcca gtagcgattt accttcttgg taacgcccgc cttgatagcc   7560
caaaatttct ttaatcacct tactttctga aaaacccgct tccagacagg cttttaccac   7620
ttttgctagg gtttcatctc ttggttctgg gagggatgaa acgggctgta atgcttgttc   7680
tgaggtcggt tgagccgttt ggagtggctg aaaactggtt acagactgta accggggcat   7740
aaccattttg taactgctta catctggtaa ctgacacggc atatcatcca ccatgcagcg   7800
atatttcccc gactttaacc actccacaag ggcaaggtct tttaaggact tggcgtggct   7860
aactgcaaac ttacccaggc gtaacatcct aaaacactta cggacaccgc cttcaccctc   7920
gatacctaag gtcttgacat tatcatcttg agtcagccca ataacaaaac gcttgggctt   7980
```

gcggccgcgc ctggcgtgtt tgatgagcca ttcggttgct atctcgactt catctctcag 8040
cagtggcagt tcttcagcaa ttaaaacgct ttcttttcct gctagtgcct tatccccaga 8100
ctcaccccgt agctcaatcc ggcgctgcaa ttcctccagg tcagcagcca tgcccgactg 8160
tatagcctca aagtcaccac ggcggccaat gacatttaac cccgtccact cgtccggtgc 8220
agcgtcagcg tcatagactg tcacctcacc cccgacttga taagcaagcc attgggctat 8280
ggtgcttttg ccagttcccg tatccccaac tattaaacag tgcttaccag acagagcttg 8340
catcaagtcg gtgatgattc cctctggttc gaccgcaagg gtgacggcgg tagtgtcaat 8400
gatagccgcg ccgtaagtgc cagcataggg caattggtcg taaactttga ccaagttgta 8460
tacagactgt ctacaccact tcaccactgt taacgctgtt tgcaaagcgt aagacgtggc 8520
atcaaataaa aatatgctgg cactaaaagt taatcgcccc aatccccaca gtaaaaacct 8580
gcctagctgt tgacgactag gcaagtgcat ttcaatccag tcatttgcca taaatcaccc 8640
cgtctttaaa gccttgcagt tgagcgcgac aggtatttaa ctgtgcttgt aactctgttt 8700
gctggttttg ataccacaga ctgacggcgg cggccgccag tcctaaaaat agaaactggc 8760
gatcgctcat tattgactta ctccctgttg attagcgtgg tagtgagtca tagccgcatt 8820
gaccgcttct tgggcttggg gtgttctgcc aagattgggt tttgtagggt catcgttggc 8880
tacgactaag gacgcttgtt cggctatcgc ttgcgggaca ccaactttag ttaactctgt 8940
caaggatact tggtaaagtc gctcgttcat tagccgattc tccggtacat aaaactgttg 9000
ctggcagtcc cttcattggc gacgagttct tcagccggag tatcagcgat aatgtcagcc 9060
cagccggtga cattattatt aataatgttt tgttcggcaa ttgcacccaa gccaggacgc 9120
gccgtttcaa actcagagat gacttgctgc tctttctcgg tgagtggtct atctgtcatg 9180
ataattatgt ccttcattat gtaggcgatt ccagtgggtg tttacgaggc agtccacagg 9240
aatcagtgcg attcaccttt aaggtgaatc gtcatcaaaa aatcactcgg tagcaacgac 9300
ccgaaccgac caggattgat ttcccggttc tcagttcgca ggcttttgag cgcgtcacct 9360
tgaccattgg gtaactgcca tcagccgata agctaaacgg gctgtatagc ggtaaagcat 9420
cccacacagt cgggctggca tcaactttgc aggaatagct cacgtcactc atctcactcg 9480
cgcctgggtt ggatggcagc gaaggcagat tacgacgcag tttttttactg gcacttttac 9540
ccgcattaaa aacgggtaca gtgccattgt tgacggtctg tacttcggtc atatactcgg 9600
tgtacactta atacactcta tactattact gccgattagt acatttgtca atcactcttt 9660
gcacaaggtg tatgatatgg actcaggagt acaccaaacg tcatgccaac caataaaggg 9720
agaatagcag tcactctaga agctgaaatt taccaatgga ttgctaaccg agcgtctgag 9780
gaaggaagac cgttggctaa tcttgccgct ttcttactca cacgagttgt taaagaacaa 9840
atggaacaag aagccaagga caaccaagac aagcaggggg cagcatgagc gaagacagac 9900
tagccagaat agaagctgcg ttagacagcc aagttgcagt gaatgccgac ctccgcacat 9960
cggttacaga actccgcgca accgcagaag cattgttgca aacagttcaa atccatcagc 10020
agaactttga aattcttacc gctaggcaat tacaaaccga agcacggctt gatgagtacc 10080
aacgtaccac tagcgcggca ctcgacagaa ttggcgcggt cttagactac ctcgttaggc 10140
agcaaaacgg ttgaggtgag ggatgagcga tgactatcta gacggatatc ccgcaagagg 10200
ccctttcgtc ttcaagaatt cccgtttgac tggcgatgct gctactgaaa ctaacaacta 10260
catcgactac gcaattaacg ccctcagcta attttgctta gtctaggccc ggatgggtaa 10320

-continued

```
gtggttttca gcttaagtgt tgggttctac ttacttctcc gggtcttgct ctatctaaaa  10380
acattggttt aacaaggagt attaggcaaa tgccagttac tgtcgctgcc tctcgcttgg  10440
gaaccgctgc gtttgaccaa tcacccgtcg aactgcgcgc taactattct cgacctgcag  10500
gtcgactttt ttgctgaggt actgagtaca cagctaataa aattgggcaa tctccgcgcc  10560
tctatgactt gaaggagagt gtaggggtat aggggaaaga tatcttttat ctacatcaca  10620
taaataaaaa atttaatttg tcgctctggc tgcatatatt gatgtatttt tagccataag  10680
tttttagtg ccatgtaatt atagtgattt ttagcgatcg cagagcattt ttccctggat  10740
ttatcgcgat ctcaaaaaaa atttgcccga agtatgacag attgtcatat ttggtgtcga  10800
ttttatttaa aatgaaataa gaaaaataaa actacaggtt aggagaacgc catgaattct  10860
tatactgtcg gtacctattt agcggagcgg cttgtccaga ttggtctcaa gcatcacttc  10920
gcagtcgcgg gcgactacaa cctcgtcctt cttgacaacc tgcttttgaa caaaaacatg  10980
gagcaggttt attgctgtaa cgaactgaac tgcggtttca gtgcagaagg ttatgctcgt  11040
gccaaaggcg cagcagcagc cgtcgttacc tacagcgtcg gtgcgctttc cgcatttgat  11100
gctatcggtg gcgcctatgc agaaaacctt ccggttatcc tgatctccgg tgctccgaac  11160
aacaatgatc acgctgctgg tcacgtgttg catcacgctc ttggcaaaac cgactatcac  11220
tatcagttgg aaatggccaa gaacatcacg gccgcagctg aagcgattta caccccagaa  11280
gaagctccgg ctaaaatcga tcacgtgatt aaaactgctc ttcgtgagaa gaagccggtt  11340
tatctcgaaa tcgcttgcaa cattgcttcc atgccctgcg ccgctcctgg accggcaagc  11400
gcattgttca atgacgaagc cagcgacgaa gcttctttga atgcagcggt tgaagaaacc  11460
ctgaaattca tcgccaaccg cgacaaagtt gccgtcctcg tcggcagcaa gctgcgcgca  11520
gctggtgctg aagaagctgc tgtcaaattt gctgatgctc tcggtggcgc agttgctacc  11580
atggctgctg caaaaagctt cttcccagaa gaaaacccgc attacatcgg tacctcatgg  11640
ggtgaagtca gctatccggg cgttgaaaag acgatgaaag aagccgatgc ggttatcgct  11700
ctggctcctg tcttcaacga ctactccacc actggttgga cggatattcc tgatcctaag  11760
aaactggttc tcgctgaacc gcgttctgtc gtcgttaacg gcgttcgctt ccccagcgtt  11820
catctgaaag actatctgac ccgtttggct cagaaagttt ccaagaaaac cggtgctttg  11880
gacttcttca aatccctcaa tgcaggtgaa ctgaagaaag ccgctccggc tgatccgagt  11940
gctccgttgg tcaacgcaga aatcgcccgt caggtcgaag ctcttctgac cccgaacacg  12000
acggttattg ctgaaaccgg tgactcttgg ttcaatgctc agcgcatgaa gctcccgaac  12060
ggtgctcgcg ttgaatatga aatgcagtgg ggtcacatcg gttggtccgt tcctgccgcc  12120
ttcggttatg ccgtcggtgc tccggaacgt cgcaacatcc tcatggttgg tgatggttcc  12180
ttccagctga cggctcagga agtcgctcag atggttcgcc tgaaactgcc ggttatcatc  12240
ttcttgatca ataactatgg ttacaccatc gaagttatga tccatgatgg tccgtacaac  12300
aacatcaaga actgggatta tgccggtctg atggaagtgt tcaacggtaa cggtggttat  12360
gacagcggtg ctggtaaagg cctgaaggct aaaaccggtg gcgaactggc agaagctatc  12420
aaggttgctc tggcaaacac cgacggccca accctgatcg aatgcttcat cggtcgtgaa  12480
gactgcactg aagaattggt caaatggggt aagcgcgttg ctgccgccaa cagccgtaag  12540
cctgttaaca agctcctcta gtttttgggg atcaattcga gctctctgga taaaactaat  12600
aaactctatt acccatgatt aaagcctacg ctgccctgga agccaacgga aaactccaac  12660
cctttgaata cgaccccggt gccctgggtg ctaatgaggt ggagattgag gtgcagtatt  12720
```

```
gtggggtgtg ccacagtgat ttgtccatga ttaataacga atggggcatt tccaattacc  12780
ccctagtgcc gggtcatgag gtggtgggta ctgtggccgc catgggcgaa ggggtgaacc  12840
atgttgaggt gggggattta gtggggctgg gttggcattc gggctactgc atgacctgcc  12900
atagttgttt atctggctac cacaaccttt gtgccacggc ggaatcgacc attgtgggcc  12960
actacggtgg ctttggcgat cgggttcggg ccaagggagt cagcgtggtg aaattaccta  13020
aaggcattga cctagccagt gccgggcccc ttttctgtgg aggaattacc gttttcagtc  13080
ctatggtgga actgagttta aagcccactg caaaagtggc agtgatcggc attgggggct  13140
tgggccattt agcggtgcaa tttctccggg cctggggctg tgaagtgact gcctttacct  13200
ccagtgccag gaagcaaacg gaagtgttgg aattgggcgc tcaccacata ctagattcca  13260
ccaatccaga ggcgatcgcc agtgcggaag gcaaatttga ctatattatc tccactgtga  13320
acctgaagct tgactggaac ttatacatca gcaccctggc gccccaggga catttccact  13380
ttgttggggt ggtgttggag cctttggatc taaatctttt tccccttttg atgggacaac  13440
gctccgtttc tgcctcccca gtgggtagtc ccgccaccat tgccaccatg ttggactttg  13500
ctgtgcgcca tgacattaaa cccgtggtgg aacaatttag ctttgatcag atcaacgagg  13560
cgatcgccca tctagaaagc ggcaaagccc attatcgggt agtgctcagc catagtaaaa  13620
attagctctg caaaggttgc ttctgggtcc gtggaatggt caaacggagt cgatctcagt  13680
tttgatacgc tctatctgga aagcttgaca ttcgatctgc agcccgggg              13729
```

```
<210> SEQ ID NO 19
<211> LENGTH: 8921
<212> TYPE: DNA
<213> ORGANISM: Artificial Sequence
<220> FEATURE:
<223> OTHER INFORMATION: plasmid K236Cm

<400> SEQUENCE: 19
```

```
tcgacgggtt gatgatgggt agtcgttccg gtgccatcga tccggggatc attgttcact     60
taatgcgaca atcagattac tctgctgaaa gattggacta tgttttaaat aaagcttccg    120
gcttacgcgg tatttctggg gtttccagcg atttacccca ggtcatagaa gccattaccc    180
aaggtaacta ccgcgcccaa ctggcgtggg atatgtacgt acatcggctg cgttctggga    240
ttggttccat gttggcgagt ctggggggtt tggatgtgtt ggtgtttacc gcaggcgtag    300
gggaaaaatc agcaggtatt cgccaagcag cttgtgaagc ctttgggttt ttagggttaa    360
aacttgaccc agaaaagaac caaaacaaac cagtagatat agatatcgcc actgctgatt    420
ctacagtacg ggtgttagta attcatactc aagaagattg ggcgatcgca caacaatgtt    480
ggcatttgtt aaaaaggtaa gcgggagagt gagcgtatca tgaatttacc tagtagtggc    540
cagatataac gtaaagtacg tttgacaatt tctggtgtca accacgaaag aattagcaac    600
aacaataagt aaatgttact caactcccca acgccatgag aaataatacc agaaacacta    660
caaacgatag cccaaaccca attaatgcag caatggcaac aacgttgcgc aaactattaa    720
ctggcgaact acttactcta gcttcccggc aacaattaat agactggatg gaggcggata    780
aagttgcagg accacttctg cgctcggccc ttccggctgg ctggtttatt gctgataaat    840
ctggagccgg tgagcgtggg tctcgcggta tcattgcagc actggggcca gatggtaagc    900
cctcccgtat cgtagttatc tacacgacgg ggagtcaggc aactatggat gaacgaaata    960
gacagatcgc tgagataggt gcctcactga ttaagcattg gtaactgtca gaccaagttt   1020
```

```
actcatatat actttagatt gatttaaaac ttcattttta atttaaaagg atctaggtga   1080
agatcctttt tgataatctc atgaccaaaa tcccttaacg tgagttttcg ttccactgag   1140
cgtcagaccc cgtagaaaag atcaaaggat cttcttgaga tccttttttt ctgcgcgtaa   1200
tctgctgctt gcaaacaaaa aaaccaccgc taccagcggt ggtttgtttg ccggatcaag   1260
agctaccaac tctttttccg aaggtaactg gcttcagcag agcgcagata ccaaatactg   1320
tccttctagt gtagccgtag ttaggccacc acttcaagaa ctctgtagca ccgcctacat   1380
acctcgctct gctaatcctg ttaccagtgg ctgctgccag tggcgataag tcgtgtctta   1440
ccgggttgga ctcaagacga tagttaccgg ataaggcgca gcggtcgggc tgaacggggg   1500
gttcgtgcac acagcccagc ttggagcgaa cgacctacac cgaactgaga tacctacagc   1560
gtgagcattg agaaagcgcc acgcttcccg aagggagaaa ggcggacagg tatccggtaa   1620
gcggcagggt cggaacagga gagcgcacga gggagcttcc agggggaaac gcctggtatc   1680
tttatagtcc tgtcgggttt cgccacctct gacttgagcg tcgatttttg tgatgctcgt   1740
caggggggcg gagcctatgg aaaaacgcca gcaacgcggc ctttttacgg ttcctggcct   1800
tttgctggcc ttttgctcac atgttctttc ctgcgttatc ccctgattct gtggataacc   1860
gtattaccgc ctttgagtga gctgataccg ctcgccgcag ccgaacgacc gagcgcagcg   1920
agtcagtgag cgaggaagcg gaagagcgcc tgatgcggta ttttctcctt acgcatctgt   1980
gcggtatttc acaccgcata tggtgcactc tcagtacaat ctgctctgat gccgcatagt   2040
taagccagta tacactccgc tatcgctacg tgactgggtc atggctgcgc cccgacaccc   2100
gccaacaccc gctgacgcgc cctgacgggc ttgtctgctc ccggcatccg cttacagaca   2160
agctgtgacc gtctccggga gctgcatgtg tcagaggttt tcaccgtcat caccgaaacg   2220
cgcgaggcag gctggctgtt ttacgcgtat gacaggctcc ggaagacggt tgttgcgcac   2280
gtattcggtg aacgcactat ggcgacgctg gggcgtctta tgagcctgct gtcacccttt   2340
gacgtggtga tatggatgac ggatggctgg ccgctgtatg aatcccgcct gaagggaaag   2400
ctgcacgtaa tcagcaagcg atatacgcag cgaattgagc ggcataacct gaatctgagg   2460
cagcacctgg cacggctggg acggaagtcg ctgtcgttct caaaatcggt ggagctgcat   2520
gacaaagtca tcgggcatta tctgaacata aaacactatc aataagttgg agtcattacc   2580
aaaaggttag gaatacggtt agccatttgc ctgcttttat atagttcata tgggattcac   2640
ctttatgttg ataagaaata aaagaaaatg ccaataggat atcggcattt tcttttgcgt   2700
ttttatttgt taactgttaa ttgtccttgt tcaaggatgc tgtctttgac aacagatgtt   2760
ttcttgcctt tgatgttcag caggaagctt ggcgcaaacg ttgattgttt gtctgcgtag   2820
aatcctctgt ttgtcatata gcttgtaatc acgacattgt ttcctttcgc ttgaggtaca   2880
gcgaagtgtg agtaagtaaa ggttacatcg ttaggatcaa gatccatttt taacacaagg   2940
ccagttttgt tcagcggctt gtatgggcca gttaaagaat tagaaacata accaagcatg   3000
taaatatcgt tagacgtaat gccgtcaatc gtcatttttg atccgcggga gtcagtgaac   3060
aggtaccatt tgccgttcat tttaaagacg ttcgcgcgtt caatttcatc tgttactgtg   3120
ttagatgcaa tcagcggttt catcactttt ttcagtgtgt aatcatcgtt tagctcaatc   3180
ataccgagag cgccgtttgc taactcagcc gtgcgttttt tatcgctttg cagaagtttt   3240
tgactttctt gacggaagaa tgatgtgctt ttgccatagt atgctttgtt aaataaagat   3300
tcttcgcctt ggtagccatc ttcagttcca gtgtttgctt caaatactaa gtatttgtgg   3360
cctttatctt ctacgtagtg aggatctctc agcgtatggt tgtcgcctga gctgtagttg   3420
```

-continued

```
ccttcatcga tgaactgctg tacattttga tacgtttttc cgtcaccgtc aaagattgat   3480
ttataatcct ctacaccgtt gatgttcaaa gagctgtctg atgctgatac gttaacttgt   3540
gcagttgtca gtgtttgttt gccgtaatgt ttaccggaga aatcagtgta gaataaacgg   3600
atttttccgt cagatgtaaa tgtggctgaa cctgaccatt cttgtgtttg gtcttttagg   3660
atagaatcat ttgcatcgaa tttgtcgctg tctttaaaga cgcggccagc gtttttccag   3720
ctgtcaatag aagtttcgcc gactttttga tagaacatgt aaatcgatgt gtcatccgca   3780
tttttaggat ctccggctaa tgcaaagacg atgtggtagc cgtgatagtt tgcgacagtg   3840
ccgtcagcgt tttgtaatgg ccagctgtcc caaacctcca ggccttttgc agaagagata   3900
tttttaattg tggacgaatc gaattcagga acttgatatt tttcattttt ttgctgttca   3960
gggatttgca gcatatcatg gcgtgtaata tgggaaatgc cgtatgtttc cttatatggc   4020
ttttggttcg tttctttcgc aaacgcttga gttgcgcctc ctgccagcag tgcggtagta   4080
aaggttaata ctgttgcttg ttttgcaaac tttttgatgt tcatcgttca tgtctccttt   4140
tttatgtact gtgttagcgg tctgcttctt ccagccctcc tgtttgaaga tggcaagtta   4200
gttacgcaca ataaaaaaag acctaaaata tgtaaggggt gacgccaaag tatacacttt   4260
gccctttaca cattttaggt cttgcctgct ttatcagtaa caaacccgcg cgatttactt   4320
ttcgacctca ttctattaga ctctcgtttg gattgcaact ggtctatttt cctcttttgt   4380
ttgatagaaa atcataaaag gatttgcaga ctacgggcct aaagaactaa aaaatctatc   4440
tgtttctttt cattctctgt atttttata gtttctgttg catgggcata aagttgcctt   4500
tttaatcaca attcagaaaa tatcataata tctcatttca ctaaataata gtgaacggca   4560
ggtatatgtg atgggttaaa aaggatcgat cctctagcta gagtcgacct gcatccctta   4620
acttacttat taaataattt atagctattg aaaagagata agaattgttc aaagctaata   4680
ttgtttaaat cgtcaattcc tgcatgtttt aaggaattgt taaattgatt ttttgtaaat   4740
attttcttgt attctttgtt aacccatttc ataacgaaat aattatactt ttgtttatct   4800
ttgtgtgata ttcttgattt ttttctactt aatctgataa gtgagctatt cactttaggt   4860
ttaggatgaa aaaaaataaa aaaggggacc tctagggtcc ccaattaatt agtaatataa   4920
tctattaaag gtcattcaaa aggtcatcca ccggatcagc ttagtaaagc cctcgctaga   4980
ttttaatgcg gatgttgcga ttacttcgcc aactattgcg ataacaagaa aaagccagcc   5040
tttcatgata tatctcccaa tttgtgtagg gcttattatg cacgcttaaa aataataaaa   5100
gcagacttga cctgatagtt tggctgtgag caattatgtg cttagtgcat ctaacgcttg   5160
agttaagccg cgccgcgaag cggcgtcggc ttgaacgaat tgttagacat tatttgccga   5220
ctaccttggt gatctcgcct ttcacgtagt ggacaaattc ttccaactga tctgcgcgcg   5280
aggccaagcg atcttcttct tgtccaagat aagcctgtct agcttcaagt atgacgggct   5340
gatactgggc cggcaggcgc tccattgccc agtcggcagc gacatccttc ggcgcgattt   5400
tgccggttac tgcgctgtac caaatgcggg acaacgtaag cactacattt cgctcatcgc   5460
cagcccagtc gggcggcgag ttccatagcg ttaaggtttc atttagcgcc tcaaatagat   5520
cctgttcagg aaccggatca aagagttcct ccgccgctgg acctaccaag gcaacgctat   5580
gttctcttgc ttttgtcagc aagatagcca gatcaatgtc gatcgtggct ggctcgaaga   5640
tacctgcaag aatgtcattg cgctgccatt ctccaaattg cagttcgcgc ttagctggat   5700
aacgccacgg aatgatgtcg tcgtgcacaa caatggtgac ttctacagcg cggagaatct   5760
```

-continued

```
cgctctctcc aggggaagcc gaagtttcca aaaggtcgtt gatcaaagct cgccgcgttg   5820
tttcatcaag ccttacggtc accgtaacca gcaaatcaat atcactgtgt ggcttcaggc   5880
cgccatccac tgcggagccg tacaaatgta cggccagcaa cgtcggttcg agatggcgct   5940
cgatgacgcc aactacctct gatagttgag tcgatacttc ggcgatcacc gcttccctca   6000
tgatgtttaa ctttgtttta gggcgactgc cctgctgcgt aacatcgttg ctgctccata   6060
acatcaaaca tcgacccacg gcgtaacgcg cttgctgctt ggatgcccga ggcatagact   6120
gtaccccaaa aaaacagtca taacaagcca tgaaaaccgc cactgcgccg ttaccaccgc   6180
tgcgttcggt caaggttctg gaccagttgc gtgagcgcat acgctacttg cattacagct   6240
tacgaaccga acaggcttat gtccactggg ttcgtgcctt catccgtttc cacggtgtgc   6300
gtcacccggc aaccttgggc agcagcgaag tcgaggcatt tctgtcctgg ctggcgaacg   6360
agcgcaaggt ttcggtctcc acgcatcgtc aggcattggc ggccttgctg ttcttctacg   6420
gcaaggtgct gtgcacggat ctgccctggc ttcaggagat cggaagacct cggccgtcgc   6480
ggcgcttgcc ggtggtgctg accccggatg aagtggttcg catcctcggt tttctggaag   6540
gcgagcatcg tttgttcgcc cagcttctgt atggaacggg catgcggatc agtgagggtt   6600
tgcaactgcg ggtcaaggat ctggatttcg atcacggcac gatcatcgtg cgggagggca   6660
agggctccaa ggatcgggcc ttgatgttac ccgagagctt ggcacccagc ctgcgcgagc   6720
aggggaattg atccggtgga tgaccttttg aatgaccttt aatagattat attactaatt   6780
aattggggac cctagaggtc cccttttttta ttttactgcg atgagtggca gggcggggcg   6840
taattttttt aaggcagtta ttggtgccct taaacgcctg gtgctacgcc tgaataagtg   6900
ataataagcg gatgaatggc agaaattcga tatctagatc tcgagctgga tacttcccgt   6960
ccgccagggg gacatgccgg cgatgctgaa ggtcgcgcgc attcccgatg aagaggccgg   7020
ttaccgcctg tttgaggata tagtaatctt tctaaatagc tttggattgg aggagtatgg   7080
ccactaatac taagttcagc taataaaaaa atttgctaaa gaactccagc tggatttcac   7140
tgatgagaat atcgtcggag ataaatataa taattccacg gactatagac tatactagtc   7200
acgaacaagt tcccatcctc cacgacgata gtattgaccg cgataatttg ctctacgata   7260
atgccgacca cgataacgtc cattacgata gtaatgcctg taataatgcc gattatgata   7320
gcgccgtctg tggtaatgcc gtctagcccg tcttcttccg tgataacgcc gtctatattg   7380
tcggtgagct attaatgttt ctttgtgttc accttcgact aagtttgttt ctgcttcaat   7440
agtttgctca ttcaaagcat tattgagagt attctcttta gcttcaacta atgtaggcgg   7500
atagatgaaa gctaataaca ggaacacgat tgaggatagc ttttggaaac ggttcacgtc   7560
tttgcttttc ctaaaatatc ggtaataagt ttaataaata cctgaaatta ggaaatgata   7620
tagctcacac ttcacaaacc tgaatcacgt aaatgtaatg aaagtactaa ttttgaatgc   7680
tggttcaagc agccaaaaga gttgtctata tgaaattccc gatgatgctc tcctgagtga   7740
agcaccccag ccgctttggg aagggaaagt taactggact caagacagaa gtgtggcgga   7800
aattgaggtc aaaacagcta gaggtgaaac gctccatgag tctatatatg gtgattcccg   7860
tcaagcacac gtcacctata tgctttatac cctcagtcgc ggccgccctg tgacggaaga   7920
tcacttcgca gaataaataa atcctggtgt ccctgttgat accgggaagc cctgggccaa   7980
cttttggcga aaatgagacg ttgatcggca cgtaagaggt tccaactttc accataatga   8040
aataagatca ctaccgggcg tattttttga gttatcgaga ttttcaggag ctaaggaagc   8100
taaaatggag aaaaaaatca ctggatatac caccgttgat atatcccaat ggcatcgtaa   8160
```

agaacatttt gaggcatttc agtcagttgc tcaatgtacc tataaccaga ccgttcagct 8220
ggatattacg gcctttttaa agaccgtaaa gaaaaataag cacaagtttt atccggcctt 8280
tattcacatt cttgcccgcc tgatgaatgc tcatccggaa ttccgtatgg caatgaaaga 8340
cggtgagctg gtgatatggg atagtgttca cccttgttac accgttttcc atgagcaaac 8400
tgaaacgttt tcatcgctct ggagtgaata ccacgacgat ttccggcagt ttctacacat 8460
atattcgcaa gatgtggcgt gttacggtga aaacctggcc tatttcccta aagggtttat 8520
tgagaatatg tttttcgtct cagccaatcc ctgggtgagt ttcaccagtt ttgatttaaa 8580
cgtggccaat atggacaact tcttcgcccc cgttttcacc atgggcaaat attatacgca 8640
aggcgacaag gtgctgatgc cgctggcgat tcaggttcat catgccgttt gtgatggctt 8700
ccatgtcggc agaatgctta atgaattaca acagtactgc gatgagtggc agggcggggc 8760
gtaatttttt taaggcagtt attggtgccc ttaaacgcct ggtgctacgc ctgaataagt 8820
gataataagc ggatgaatgg cagaaattcg atatctagat ctcgagctgg atacttcccg 8880
tccgccaggg ggacatgccg gcgatggcgg ccgcctgcag g 8921

<210> SEQ ID NO 20
<211> LENGTH: 12288
<212> TYPE: DNA
<213> ORGANISM: Artificial Sequence
<220> FEATURE:
<223> OTHER INFORMATION: plasmid K244

<400> SEQUENCE: 20
actttcttcg accttaaccc caaagaaagc ttattagatg gagaaggtca caattagaaa 60
atattcatcg tcccgattga cccttaacct ttaatcggtt tccacttgta aaaaattcgg 120
cgagccattc ttcttaaccc tcagagtcga acttcataca agaatataca aaccctttgg 180
gtttaccact aaaacaacgg cgataaaaac ctaataggtt tccacagaaa cgtctaagga 240
tttaggcgtg ttgttttggg gcaatttgag aaaatattaa accagtcaca agttaacttg 300
tcgaagaaat attgcagcat tctgcaacac agggaaaggt ataacgtttc caaagtccgg 360
aacgtgtgca gagttctaga accgatggat actttaaaag tatcctcaag tgtagagcgt 420
gtgtttaggc tgcgtctttt tttagcaccc ataggggtct aaacagcgtt ggcgtacatt 480
agaagccaat cacggataca gctttgcgtc gctgttcggg tgtaacttca agatagcgtt 540
gcagtgtgcc aaggtcattg tgaccggata tctcttgaat gtgtcgcaac gggataccgg 600
cgctagacat ttggttgagg gcagtacggc ggaaactgtg ggtactgatg ccttctagcc 660
cgattctttt ggctgcatcg cgcaagattt tatccgccgc gtatcgcgtg agcctatcgc 720
tgactcccct catgccaggg aacagggttc ccggtttggg gtgatagtca gccatgagtg 780
cggctagtcc tggctggatg tcaaccacgc gggttttgag tttccctttg gtggtagact 840
tcctaaaggt tagtgtttcg cctttaatgt ccgttgtttg gagtgctaga gcttcactaa 900
cgcggcaacc ggtgaataga cagatgccaa acaaaacgcg atcgcgcggt gtggtgaatc 960
cgtcgctaaa cagtcgcctg agttcgtcgg aggtgagtat tttggctcgt ccgttgccgt 1020
taaccttcat aaccccttaca gattaagcat tccaatactc tacacgttat ctgcattttg 1080
tggaattggt ggctatatct attgattctt cgtatgcttt ctgttgaaag ccagtgctag 1140
tttagccaag cttatcaatc gttgcacggt aaaatcaggc tttcgacgta aggacagaat 1200
tttgataact tcagcttatg ttgtctcctg aagaaagcaa ctctttgata aacgcgtcga 1260

-continued

```
tggctttccc ggcggctgac tgcctaccca tttttagctt attgagggtg cgatcgcggg   1320
ttgcctccaa tttgtctaga ttgtctatac tattgtctat attctttctg tcttgcccgg   1380
tagcttgtcc ttctgcctga actaccgggc tttcgatttt ccccgcagtt cctccagttg   1440
cgattgaagt ttgtctagac gtgttgctag attatcttct atacgcttgt ctataaattc   1500
atctatattg tctagattat tagttgtgac tttatctaga cgttgttcaa tattgtctat   1560
acgctgttcg agggatgtgt ctagatgggt gggagtgtga gaagtgggag tattaaacct   1620
gttacctgcc aaataccaac gaacaaattc tgttaacagt gctgaggcgt tggaactttc   1680
agaactagca aggtttttaa aagactccca ttcttcggag tcaatacgaa aagtggctag   1740
agttttgtct gccatgatta gataatgtct atacttgtat agatagcagt ataaactatt   1800
gtctatatta gtgtctatat aagtctagat atcgtccatt ccgacagcat cgccagtcac   1860
tatggcgtgc tgctagtggt tcccctcagc ttgcgactag atgttgaggc ctaacatttt   1920
attagagagc aggctagttg cttagataca tgatcttcag gccgttatct gtcagggcaa   1980
gcgaaaattg gccatttatg acgaccaatg ccccgcagaa gctcccatct ttgccgccat   2040
agacgccgcg cccccctttt ggggtgtaga acatcctttt gccagatgtg gaaaagaagt   2100
tcgttgtccc attgttggca atgacgtagt agccggcgaa agtgcgagac ccatttgcgc   2160
tatatataag cctacgattt ccgttgcgac tattgtcgta attggatgaa ctattatcgt   2220
agttgctctc agagttgtcg taatttgatg gactattgtc gtaattgctt atggagttgt   2280
cgtagttgct tggagaaatg tcgtagttgg atggggagta gtcataggga agacgagctt   2340
catccactaa aacaattggc aggtcagcaa gtgcctgccc cgatgccatc gcaagtacga   2400
ggcttagaac caccttcaac agatcgcgca tagtcttccc cagctctcta acgcttgagt   2460
taagccgcgc cgcgaagcgg cgtcggcttg aacgaattgt tagacattat ttgccgacta   2520
ccttggtgat ctcgcctttc acgtagtgaa caaattcttc caactgatct gcgcgcgagg   2580
ccaagcgatc ttcttgtcca agataagcct gcctagcttc aagtatgacg ggctgatact   2640
gggccggcag gcgctccatt gcccagtcgg cagcgacatc cttcggcgcg attttgccgg   2700
ttactgcgct gtaccaaatg cgggacaacg taagcactac atttcgctca tcgccagccc   2760
agtcgggcgg cgagttccat agcgttaagg tttcatttag cgcctcaaat agatcctgtt   2820
caggaaccgg atcaaagagt tcctccgccg ctggacctac caaggcaacg ctatgttctc   2880
ttgcttttgt cagcaagata gccagatcaa tgtcgatcgt ggctggctcg aagatacctg   2940
caagaatgtc attgcgctgc cattctccaa attgcagttc gcgcttagct ggataacgcc   3000
acggaatgat gtcgtcgtgc acaacaatgg tgacttctac agcgcggaga atctcgctct   3060
ctccagggga agccgaagtt tccaaaaggt cgttgatcaa agctcgccgc gttgtttcat   3120
caagccttac ggtcaccgta accagcaaat caatatcact gtgtggcttc aggccgccat   3180
ccactgcgga gccgtacaaa tgtacggcca gcaacgtcgg ttcgagatgg cgctcgatga   3240
cgccaactac ctctgatagt tgagtcgata cttcggcgat caccgcttcc ctcatgatgt   3300
ttaactcctg aattaagccg cgccgcgaag cggtgtcggc ttgaatgaat tgttaggcgt   3360
catcctgtgc tccaagcttg catgaatcaa cctatcatca atcggaacca tttattgaag   3420
cccagaagcg agatttgatt tgatttgctt aacgctggct catgccctgc ttattgaaga   3480
tgaggagcga tcgctgaacc atggcaaaag ccgcctcccg tctagcttga aggcgttgac   3540
atcactctgt acttaggtct actgagtccg aaactttcag ccaaaaacca agggaattac   3600
agtgcttttt ccatcactga tcatcacgag gatatcgccg acatcaccga tggggaagat   3660
```

-continued

```
cgggctcgcc acttcgggct catgagcgct tgtttcggcg tgggtatggt ggcaggcccg   3720
ctttatcaga agccagacat taacgcttct ggagaaactc aacgagctgg acgcggatga   3780
acaggcagac atctgtgaat cgcttcacga ccacgctgat gagctttacc gcagctgcct   3840
cgcgcgtttc ggtgatgacg gtgaaaacct ctgacacatg cagctcccgg agacggtcac   3900
agcttgtctg taagcggatg ccgggagcag acaagcccgt cagggcgcgt cagcgggtgt   3960
tggcgggtgt cggggcgcag ccatgaccca gtcacgtagc gatagcggag tgtatactgg   4020
cttaactatg cggcatcaga gcagattgta ctgagagtgc accatatgcg gtgtgaaata   4080
ccgcacagat gcgtaaggag aaaataccgc atcaggcgct cttccgcttc ctcgctcact   4140
gactcgctgc gctcggtcgt tcggctgcgg cgagcggtat cagctcactc aaaggcggta   4200
atacggttat ccacagaatc aggggataac gcaggaaaga acatgtgagc aaaaggccag   4260
caaaaggcca ggaaccgtaa aaaggccgcg ttgctggcgt ttttccatag gctccgcccc   4320
cctgacgagc atcacaaaaa tcgacgctca agtcagaggt ggcgaaaccc gacaggacta   4380
taaagatacc aggcgtttcc ccctggaagc tccctcgtgc gctctcctgt tccgaccctg   4440
ccgcttaccg gatacctgtc cgcctttctc ccttcgggaa gcgtggcgct ttctcaatgc   4500
tcacgctgta ggtatctcag ttcggtgtag gtcgttcgct ccaagctggg ctgtgtgcac   4560
gaaccccccg ttcagcccga ccgctgcgcc ttatccggta actatcgtct tgagtccaac   4620
ccggtaagac acgacttatc gccactggca gcagccactg gtaacaggat tagcagagcg   4680
aggtatgtag gcggtgctac agagttcttg aagtggtggc ctaactacgg ctacactaga   4740
aggacagtat ttggtatctg cgctctgctg aagccagtta ccttcggaaa aagagttggt   4800
agctcttgat ccggcaaaca aaccaccgct ggtagcggtg gtttttttgt ttgcaagcag   4860
cagattacgc gcagaaaaaa aggatctcaa gaagatcctt tgatcttttc tacggggtct   4920
gacgctcagt ggaacgaaaa ctcacgttaa gggattttgg tcatgagatt atcaaaaagg   4980
atctcgatcc cgcgaaatta atacgactca ctatagggag accacaacgg tttccctcta   5040
ccgggatccg gcgctgctaa caaagcccga aaggaagctg agttggactg ctgccaccgc   5100
tgagcaataa ctagcataac cccttggggc ctctaaacgg gtcttgaggg gttttttgct   5160
gaaaggagga actatatgcg ccggatcgag atccttttaa attaaaaatg aagttttaaa   5220
tcaatctaaa gtatatatga gtaaacttgg tctgacagtt accaatgctt aatcagtgag   5280
gcacctatct cagcgatctg tctatttcgt tcatccatag ttgcctgact ccccgtcgtg   5340
tagataacta cgatacggga gggcttacca tctggcccgg cagtaccggc ataaccaagc   5400
ctatgcctac agcatccagg gtgacggtgc cgaggatgac gatgagcgca ttgttagatt   5460
tcatacacgg tgcctgactg cgttagcaat ttaactgtga taaactaccg cattaaagct   5520
tatcgatgat aagctgtcaa acatgagaat tcttgaagac gaaagggcct cttgcgggat   5580
atccgtctag atagtcatcg ctcatccctc acctcaaccg ttttgctgcc taacgaggta   5640
gtctaagacc gcgccaattc tgtcgagtgc cgcgctagtg gtacgttggt actcatcaag   5700
ccgtgcttcg gtttgtaatt gcctagcggt aagaatttca aagttctgct gatggatttg   5760
aactgtttgc aacaatgctt ctgcggttgc gcggagttct gtaaccgatg tgcggaggtc   5820
ggcattcact gcaacttggc tgtctaacgc agcttctatt ctggctagtc tgtcttcgct   5880
catgctgccc cctgcttgtc ttggttgtcc ttggcttctt gttccatttg ttctttaaca   5940
actcgtgtga gtaagaaagc ggcaagatta gccaacggtc ttccttcctc agacgctcgg   6000
```

-continued

```
ttagcaatcc attggtaaat ttcagcttct agagtgactg ctattctccc tttattggtt   6060
ggcatgacgt ttggtgtact cctgagtcca tatcatacac cttgtgcaaa gagtgattga   6120
caaatgtact aatcggcagt aatagtatag agtgtattaa gtgtacaccg agtatatgac   6180
cgaagtacag accgtcaaca atggcactgt acccgttttt aatgcgggta aaagtgccag   6240
taaaaaactg cgtcgtaatc tgccttcgct gccatccaac ccaggcgcga gtgagatgag   6300
tgacgtgagc tattcctgca aagttgatgc cagcccgact gtgtgggatg ctttaccgct   6360
atacagcccg tttagcttat cggctgatgg cagttaccca atggtcaagg tgacgcgctc   6420
aaaagcctgc gaactgagaa ccgggaaatc aatcctggtc ggttcgggtc gttgctaccg   6480
agtgattttt tgatgacgat tcaccttaaa ggtgaatcgc actgattcct gtggactgcc   6540
tcgtaaacac ccactggaat cgcctacata atgaaggaca taattatcat gacagataga   6600
ccactcaccg agaaagagca gcaagtcatc tctgagtttg aaacggcgcg tcctggcttg   6660
ggtgcaattg ccgaacaaaa cattattaat aataatgtca ccggctgggc tgacattatc   6720
gctgatactc cggctgaaga actcgtcgcc aatgaaggga ctgccagcaa cagttttatg   6780
taccggagaa tcggctaatg aacgagcgac tttaccaagt atccttgaca gagttaacta   6840
aagttggtgt cccgcaagcg atagccgaac aagcgtcctt agtcgtagcc aacgatgacc   6900
ctacaaaacc caatcttggc agaacacccc aagcccaaga agcggtcaat gcggctatga   6960
ctcactacca cgctaatcaa cagggagtaa gtcaataatg agcgatcgcc agtttctatt   7020
tttaggactg gcggccgccg ccgtcagtct gtggtatcaa aaccagcaaa cagagttaca   7080
agcacagtta aatacctgtc gcgctcaact gcaaggcttt aaagacgggg tgatttatgg   7140
caaatgactg gattgaaatg cacttgccta gtcgtcaaca gctaggcagg tttttactgt   7200
ggggattggg gcgattaact tttagtgcca gcatattttt atttgatgcc acgtcttacg   7260
ctttgcaaac agcgttaaca gtggtgaagt ggtgtagaca gtctgtatac aacttggtca   7320
aagtttacga ccaattgccc tatgctggca cttacggcgc ggctatcatt gacactaccg   7380
ccgtcaccct tgcggtcgaa ccagagggaa tcatcaccga cttgatgcaa gctctgtctg   7440
gtaagcactg tttaatagtt ggggatacgg gaactggcaa aagcaccata gcccaatggc   7500
ttgcttatca agtcgggggt gaggtgacag tctatgacgc tgacgctgca ccggacgagt   7560
ggacggggtt aaatgtcatt ggccgccgtg gtgactttga ggctatacag tcgggcatgg   7620
ctgctgacct ggaggaattg cagcgccgga ttgagctacg gggtgagtct ggggataagg   7680
cactagcagg aaaagaaagc gttttaattg ctgaagaact gccactgctg agagatgaag   7740
tcgagatagc aaccgaatgg ctcatcaaac acgccaggcg cggccgcaag cccaagcgtt   7800
ttgttattgg gctgactcaa gatgataatg tcaagacctt aggtatcgag ggtgaaggcg   7860
gtgtccgtaa gtgttttagg atgttacgcc tgggtaagtt tgcagttagc cacgccaagt   7920
ccttaaaaga ccttgccctt gtggagtggt taaagtcggg gaaatatcgc tgcatggtgg   7980
atgatatgcc gtgtcagtta ccagatgtaa gcagttacaa aatggttatg ccccggttac   8040
agtctgtaac cagttttcag ccactccaaa cggctcaacc gacctcagaa caagcattac   8100
agcccgtttc atccctccca gaaccaagag atgaaaccct agcaaaagtg gtaaaagcct   8160
gtctggaagc gggtttttca gaaagtaagg tgattaaaga aattttgggc tatcaaggcg   8220
ggcgttacca agaaggtaaa tcgctactgg aaaaacttaa ggatttgtag cggtgcggtt   8280
tagcattgac tgttacttgc tgtacaagga taattttctc aaagcggaat ggtgttaaac   8340
ccgattatta gagtcgtcat agcaaaagct tgaaaactgg caagggtgta ctggttttcg   8400
```

-continued

```
ttctttttgg ttctaatggt tattttttac cagtttattt agtaataacc gagtgccaag   8460
tttcttgttt tacatagcaa agttagcaaa aaacattttg ccgtgaattt ccatctgtaa   8520
aaagcgtcac ggcgaaattc agtatttagt aaatacaaaa ataagtcaaa cgttgatcat   8580
gcaacacttt ggcgtacaat tgattgaaaa ttttgccgat aggcaaagtt taaattacct   8640
attaaaaaaa gttcagtgct tgggggttgt tatgctactt aaccgaagct aaataaaaca   8700
cacatacaca gaattgttac cacaccaaac accaaacaga aaaaacgtgc tttgaattta   8760
tcaattaatg ggtgtagtta acaagtttta tttagcttca ggttaagcaa ataacattca   8820
ataggtactg gactgagaca tttccaaatg atcagcccag aaagcttaaa tacaaatgta   8880
tcactaaccc tgcttacaag ggaactacaa actgaaataa ttcttggcac ttacacggtc   8940
agggtacaca ctcgcattgg tcgagaacct tgtgcgcggt tgtggtattt gtgtcgagcg   9000
cttgataagg atgggtctgg tcatttaaca ttgccattgc ctgtagtaca gacgttctta   9060
gattgtagtg ataagtctgt ttaccgttgg ttacaggatg gaaaaaaaat aggagcattc   9120
cgccgctaca aaattaaagc aggaatgata accgtctact tgggcggtat gtttcaagtt   9180
tgttacaacc taaatttaaa aagatggggt gatgttgcag tagtgccttt agtccaagtg   9240
ttaagcgatt tacgctcact gaccactggc atagtcacac aaagctttca acaaaagagc   9300
cgctatgcgg ccaacagaca acttaaacca gagtacagaa aactttttgg agcgccacac   9360
ccgaacgagc tagtgaagga cacaaggcaa tcctctctta aatcgccaga gggggaagta   9420
ccttgtgtac ttcacattag ttcgtcgcgg atattcgtct caaaaagttt catccactat   9480
ggtacatctc aaaaagctgt cagctgtgag ttgggtattc acaagcgcac agtgcgacga   9540
catcaaaagc agctgggcat gaatcgccgt caactttgcc aagccaaaat tgagtacaat   9600
caactccggc acgctcggaa taatgacgcg tctgaatttt gggctttcac tggaaccaaa   9660
actgatatcg gttatcaagt tatgggtgac gcggttgtgt tttctgatgg cattgcccct   9720
ggagccaaaa agagacagcc caacacttac caaattgacg cgactgaatt tgacggtcga   9780
ttattcaaag tgggtgacaa ggtgttcatg aatcggtgca acatctaccg cgaacaattc   9840
accctaacaa cgatgtcagc agcacggcgg aagtaccatt tcaaactgtc acagtgccac   9900
ttcagcgaaa atcgagccgg tcgggtaggc aaccgttttg taataggttg ccactctggc   9960
gagatatgaa ggacattttt aagaattttt ttttagcgtg aaatgctgcg gcaaccagta  10020
tagtgatcga cacgaactag tgcagcatga ccgagagcct atagggtcgc ggctttttgg  10080
caatagagat cgtatgcaga tcatgcgtag taacagacta acaagtaatg cttcctccat  10140
tgtggctaat gcttatcgtg ctttagttgc tgagcgtcca caaatattta atgctggtgg  10200
tgcttgtttc cacaaccgta accaagctgc ttgtatccgt gatttaggat ttattctgcg  10260
ttacgtcacc tattctgtat tagcaggtga tgctagtgtc atggacgatc gctgcttaaa  10320
tggtctgcgg gaaacatatc aagctttggg tactcctggc gatgcagtag catctggaat  10380
ccaaaaaatg aaagatgctg caattggcga tcgcggctca tattctcagt caaccgaaaa  10440
gtccgaggaa gcaatggggt gacggtaaag tctataacta aggcttaact gatgacctca  10500
aagtctgtct cgtgtccctc ctcatgaatt tggggaggga tttttagtac actattacaa  10560
ataaacgtca cgattaaagt tacaggaaag cctgatccct atgactattg aagcagcaat  10620
gggagaagaa gccattaagg aaaatttaga acagttcctg attgttctat cagtttcttt  10680
aggcgtagca accctctccc aaatttccag tttctttcgc caaattccct atacgttact  10740
```

```
tttggttatt gttggcttag gattagcatt tgttgacatc cgactcgtta atctttctcc  10800
cgaattaatc ttagaaatct ttttaccccc actcttattt gaagcagcgt ggaatattcg  10860
ctggcgtaat ctcaaaaaaa atttatttcc cgttgtttta cttgccatta ttggggttgt  10920
tatatcagtg gttgggattg gttttagtct caactatttt agtggcttat ccctccccat  10980
tgctttgtta gtcggtgcta ttttagcagc aaccgatcct gtttctgtta ttgctttatt  11040
ccgagaacta ggagtgggag aacgcttaac ggttctcatg gaaggagaaa gtttatttaa  11100
tgatggtgtt gcggttgttg cttttagtct attagtggga attcccctcg gaacgcaaga  11160
attttcggtc actaataccc tcattcaatt tgttaccttt acagggattg gcatcggtgc  11220
gggggcgtta attggctttg gaatttctta tttaacgcag cgttttgatt tgcccttagt  11280
ggaacaatct ctgactttaa tttctgctta cggaacttat ttaatcactg aagaattagg  11340
cggttctggt gtgattggtg tggtgacagt cgggctaatt ttagggaact ttggctctcg  11400
cattggcatg aatccgcgga ctcgtttatt agtttcagaa ttttgggagt tcattgcttt  11460
tttcgtcaat tcaattgtct ttctcctgat tggcgatcaa atcaatattc gcggtttagc  11520
cgataatgga cagttaattt taatcacaat tatcgcccta gtgatcattc gtgctatcag  11580
tatttatggc ttaggaacaa ttagtaattt aatcacgaaa caggatatta gttggcaaga  11640
agaaacggtt ttatggtggg gcggtttacg cggttcggtt tccattgcgt tggcgttaag  11700
tgtccctgtc atgttagatg ggagacaaga tattattgaa gcggtgtttg gcgttgtcct  11760
ttttaccttg ttagtccaag gattgacgat gcaaaccgtt attgagaagc taggcttaat  11820
cggcgatcgc gctcaacgtc gtacctatag cgaattaatc gcccgtcgca gtgcgctcga  11880
acgggtttta gcccacttaa atgcggttcc cccctccccc agtattgatg aagagtttaa  11940
agactaccaa agaggcttag tcaaaggaca actcgaaagc gtcaaccaag aaattacgaa  12000
gctacaacaa tcttatcccc agttacgatc tttagaacaa gaacaactgc gggaacaact  12060
tttagaagtg gaagcagaca cttacgctga gttgattcgg gcgggtaaac tcaataataa  12120
tctatctccc ttattgcaag aagtcctcgc caaaccagag tgagcggccg cttggcccag  12180
ggcttcccgg tatcaacagg gacaccagga tttatttatt ctgcgaagtg atcttccgtc  12240
acaggtattt attcgatgaa ttcgcgtgct ataattatac taatttta              12288
```

<210> SEQ ID NO 21
<211> LENGTH: 16301
<212> TYPE: DNA
<213> ORGANISM: Artificial Sequence
<220> FEATURE:
<223> OTHER INFORMATION: plasmid pRL528

<400> SEQUENCE: 21

```
aagtcacggt actctccgga ggcctttttc atatccggcg ggcctgacac ttccggatgc     60
agcacacgaa aacagaagtc accggaacac gccattctga gaaaactgtc actaatctgt    120
tttattccgc aaacagaaaa ccaccggata accggggtat aggaagtata aaccaccttt    180
ttgggtatag gaagtataaa ccaccttttt gctcctcatc cgaagtatct tacctgaaat    240
tccctcactc gtttaccgct caagccccaa ttttaactgc cggtccagcc taaaccgctc    300
taataaggtt cgatttggcg gtaaaatctc tagcctgata gctcgagatc tagatatcga    360
tgaattcgag ctcggtaccc tattcaatat ttaacttgat tactgtagaa gtataacaaa    420
gtataatcag gttctaactg ttgtcaatta gtctataaaa aatagggttc aaatcttaag    480
tgatagacga tagtgctttg tcctgataga atcttaagtt acctctttgt tacaagaaaa    540
```

```
atataaaatg acttcatttg agcttgagag tccaatagaa ataaagactg acccgactga    600
tcttgatcaa gagagtgatt cctttgtaca agaaatttct cgattcaata aagcacttga    660
gcaacgtttt agagataaga tgcgattgca tgaaagttta agtcgaaaaa tagttagttt    720
tcaagctaat aagtcaaaac ctcagtatcg ctggtttaaa tataaagaag ctttttcagt    780
tgatttggta aatcagttaa tattcgagta cgagaaaaaa tcatttgaga ggattcttga    840
ccccttcgca ggagcaggaa caatgctatt tgcctgtagt gatgccggta ttcaagcaga    900
tggtatagaa gtgttaccta ttggtcaaga gattattgaa gtaaggaaaa taatccagcg    960
acaattccgt cgagaagatt ttttgagatt gattgaatgg tacaaacaaa aaccttggaa   1020
tcagcataat aatagaaaat atcttaatcg tttaagaatt actgacggag cttatcctcc   1080
tgaaacagaa gcatcaatag agagattttt attttctata gaaaaagaga atattcttgt   1140
gaaacaagtt ctccgttttg ctctattgtg tattcttgaa tctatcagct atacccgtaa   1200
agatggacag tatctacgtt gggataaaag agcatttagg aaaagtggat cagataaatt   1260
tgataaaggt aaaattctgg atttcgatga agcaattact gagcaaataa aattaatttt   1320
gaatgattcc tttgacttaa taagtaatac attattttgt tatgggactc aaagaagtgg   1380
aattaattta tttaatgctt catgtcttaa aattctgcct gaatttgagc aagattttta   1440
cgactgtatc attacctctc caccctattg taatcgttat gactatacac gtacatacgc   1500
tctagaatta gctctattag gtgtgggaga aagagatata gtacaactta ggcaagatat   1560
gctgagttgt actgttgaaa acaaagaaaa gtctcttatt cacaattggc aggaagcatt   1620
acgcatactt gataaacaag aattgttaca aagtatcttg cgctttcttg agcgagagct   1680
tgaaagaaaa aaacttaata ataacggtat tcctcgtatg ataaaaggat atttctatga   1740
aatggcttgc gttattatag aatgctttag agttttaaaa aatggctcac ctttatttat   1800
ggtaaatgat aatgttcgct atgcaggtat tgatatttcg gttgatttaa ttctttctaa   1860
tattgcagaa gaaattggtt ttaatgtgga gaaaattctt gtcttaccta ctggcaaagg   1920
taacagtagc caacaaatgg ggacacatgg aagaaagaca cttcgcaaat gtgtgtatgt   1980
ttggagaaaa ccctagtgcc atatcaatat catattcaaa gcaatgatga tcttgtgact   2040
ccatatcaag aagtccgagc aggatttgtt gctttagctt tagaaagaaa tcgaaaagca   2100
acaccatttg ttgagcaggc aagagcatta aagatccgag taagccaaat tgaaaggggg   2160
gatcctctag aagctttaat gcggtagttt atcacagtta aattgctaac gcagtcaggc   2220
accgtgtatg aaatctaaca atgcgctcat cgtcatcctc ggcaccgtca ccctggatgc   2280
tgtaggcata ggcttggtta tgccggtact gccgggcctc ttgcgggata tcgtccattc   2340
cgacagcatc gccagtcact atggcgtgct gctagcgcta tatgcgttga tgcaatttct   2400
atgcgcaccc gttctcggag cactgtccga ccgctttggc cgccgcccag tcctgctcgc   2460
ttcgctactt ggagccacta tcgactacgc gatcatggcg accacacccg tcctgtggat   2520
cttctcaacg aagaaagaag aatcatcgct gaggtgaaaa ataaatactc aacggttact   2580
ggcggggatt tagcagataa atataaaggc ttagatgagt tggtatcacc gaaacatagc   2640
cgatttaagg attactgtgc gtactttgtt aatataatcc ctcgtaaacc tatcagatat   2700
aacagcccct ttactccttc caataaaggt agtggtactc tgtgtccttc gaaccctaac   2760
attagaatca ttgatggtgc gagtttctat gagcttgtca ctggcagacc agatgctctg   2820
caagaactcc atagtgctct ccctcacgca attgagtata ttttgagcga acgtcttggg   2880
```

-continued

```
cagcaaggtt tttccatccc tgataaagat agttttatta agtattttgg gctcgcttac   2940
ggctgataac catgatcaat gtttgacaaa gcacatgtaa acccatacag tagtaaccat   3000
gactaatgtt ggcatggtta ctaaatatgt taaaggaaga gttttcactt tcagaagttg   3060
cagacatttt gggcgtttca aaagaaactt taaggcgttg ggatactgct ggaaaattag   3120
tttctcaaag aaatgacgaa aacaactatc gattttataa aaaagagcaa cttaaaaatt   3180
ttgaacaagc tcagttttta tttaaaagcc agtggcctga tgagactaaa ataagcaata   3240
atgtttatac tgtattagag ttatttgctg gcgcaggggg gatggcttta ggtttagaaa   3300
aagccggttt aaaatctgtt ttactaaatg aaattgactc ccatgcttgt aagacgttac   3360
gaaaaaatag gcctgaatgg aatgtggttg aaggtgatgt gagccaagta gacttcaccc   3420
cttataggaa taccgttgat gtgctggctg gtggctttcc ttgccaggca ttctcttatg   3480
caggcaaaaa acttggtttt gaagatacac ggggcaccct tttctttgaa ttcgcccgag   3540
ccgctaaaga aatcaatccg aaagttcttt tagcagagaa tgttcgaggg ttgctaaatc   3600
atgatgctgg acgaacttta gaaacaataa aaaatattat cacagacttg ggctacactt   3660
tatttgagcc aagagtgctt aaggctattt tctacaaagt gccgcaaaaa cgcgagcgtt   3720
tgatcattgt agctgtaaga aatgatcttg ctgatggcat cgattatgag tggccttctt   3780
cttacaataa aatattaacc cttaaagatg cattaaaaaa gggagagctg tatgatagcg   3840
acgtgccaga atctgaagga caaaaatatc ccaaaagaaa agcagagatc ctaagtatgg   3900
ttcctcccgg tggctactgg agagatcttc ctgaagatat tcaaaaagaa tacatgctca   3960
agagttttta cttaggtggg ggcaaaactg gtatggctcg tcgtttgtca tgggatgaac   4020
caagcctaac attaacatgc gccccagcac agaaacaaac agagcgttgc cacccagaag   4080
aaacaagacc attaactgtg cgtgagtatg caagaataca gaccttcccc gatgaatggg   4140
tatttgaagg cccaatgtca gcgaaatata agcaaatagg aaacgctgtt cctgttaatc   4200
tgtcatttgc tgttggcaaa tctgtggtac atcttttaga taagataaat aaaagataga   4260
ccctgtaaat aattctgtgt aattgctgcc atattaaagg tgatcgctca ggcggtcacc   4320
gaactcgata ataaagcgac tcatcgccag ccgccagctc tggattggca tattccattt   4380
ttttgatgca tccttgatcg ccagagaaat gaccttccgc agcgagtcgt cagtcgggaa   4440
cactttacgc ttcttaatgg ccgcacggat cacgctgttc agcgattcga tagcgttcgt   4500
ggtgtagatg gccttgcgga tatcgggcga atagccgaag aacgtgttga tattttccca   4560
gtgcgcacgc cagcttttgc tgatttgcgg gtatttatcg tcccagacat tcgggaactg   4620
ctccggtgcc actagcgccg cctcttctgt tggcgcctga tacaccgttt ttaacccgcc   4680
agtgacggct ttgtagtcct tccacgatac gtatttcagg ctgttgcgca ccatatgaat   4740
gatgcacaac tggatgtgcg tctacggata cacgctgttt atcgcatccg gaaagccttt   4800
cagaccgtcc atgcaggcaa taaggatatc ctgaagcccc cgattcttaa gctctgtcag   4860
ccccccccagc cagaacttcg ccccttcgtt ctcggccagc cacatgccca gcaactcttt   4920
ctggcctcca gtattaatac cgagtgcaag gaacaccgct ttgttaatta cggtgccacc   4980
ttgacgaact ttcaccacga tacagtcaag gtaaacaatg ggatacagtg catccagagg   5040
tcgattttgc cattctgcaa cctgctcttt gaccgcatca gtgactttac atatcagcgt   5100
gggtgacaca tctgcgtcgt acatctcttt gaaggtggcg acaatttcgc gggtagtcat   5160
atctttggcg tagagggata aaatctggct gtccatctgc gtaatgcgcg tctggtgctt   5220
cttaatcaac tgcggttcga aggtgttttc acggtcacgc gacgtgttca gttcgatcct   5280
```

ctacgccgga cgcatcgtgg ccggcatcac cggcgccaca ggtgcggttg ctggcgccta 5340
tatcgccgac atcaccgatg gggaagatcg ggctcgccac ttcgggctca tgagcgcttg 5400
tttcggcgtg ggtatggtgg caggccccgt ggccggggga ctgttgggcg ccatctcctt 5460
gcatgcacca ttccttgcgg cggcggtgct caacggcctc aacctactac tgggctgctt 5520
cctaatgcag gagtcgcata agggagagcg tcgactctag agtcgacctg cagcaatggc 5580
aacaacgttg cgcaaactat taactggcga actacttact ctagcttccc ggcaacaatt 5640
aatagactgg atggaggcgg ataaagttgc aggaccactt ctgcgctcgg cccttccggc 5700
tggctggttt attgctgata aatctggagc cggtgagcgt ggatctcgcg gtatcattgc 5760
agcactgggg ccagatggta agccctcccg tatcgtagtt atctacacga cggggagtca 5820
ggcaactatg gatgaacgaa atagacagat cgctgagata ggtgcctcac tgattaagca 5880
ttggtaactg tcagaccaag tttactcata tatactttag attgatttaa aacttcattt 5940
ttaatttaaa aggatctagg tgaagatcct ttttgataat ctcatgacca aaatccctta 6000
acgtgagttt tcgttccact gagcgtcaga ccccgtacat cacgaatata gtttgcttga 6060
catcctgaca agaataatat tgtaattaga aaaattatta ttttcatatt tctttccaac 6120
aaaagtaaaa atacttatgc atttaaaata ctacctacat aatttacctg aatcacttat 6180
accatggatt cttattttaa tatttaacga caatgataac actcctttgt tatttatatt 6240
tatatcatca atacatgtat tgctatatcc atactctaaa ttaaccatat ctagatatat 6300
caaagaaaat acaaagttaa aaaaagaacc ctggtactta tgcaagttat ctgcattgtt 6360
ttatttatta atggcaatcc cagtaggatt gccaagtttc atatattaca ctctaaagag 6420
aaattaaatc cctaacaact cattaagttt gctcaactca tcatccccta tgtaagaaga 6480
aacaatacct gtgacaattg caatccccca gaaaccaaga ggcacaccaa caataaaact 6540
aaacattaat gccacaattt ttgccacacc tacatcgacc gcacttttct ccagcgtgac 6600
aaacaaaggt cgccagttac cagtttctat tgcattttta aaatcagaac caacatcata 6660
tagaaaagat actcgactgg tgattttaag cgactttgat atcttcgtta aattcttaga 6720
taactcatca taattaacag actctaacgc attaaaaata gcatcccgat caaccttact 6780
gaatttctta tccagtacat tcttatactt ttcaaatgct gccagagctt catcaacacc 6840
ttgaattttc tttcctttag acttttccgc taaatcctga gcaatttttg cgtatttttc 6900
tccatattgt tcggttatat attgataaaa tccaaccata gtttcaacag catcttttat 6960
ctggctcttt tcaagagcat cctgagcttc ttttaatttc tgctctgcct ctttaacctc 7020
agcggcctta ccatccctga cactaacagc attcttaatt tcattttcaa ctgcggagta 7080
ctcagcctgc ttagcttcaa gctgacgctg tagtttttc tgaacgtcac gccatcccgg 7140
aaatccggag accttcacgt caacactctt ctgagcgttt tcaagctctc ctgcaactct 7200
ggaaacagta gcttgcttac tctgtacatc actttcagcc ttcgccagtt cagctttcgc 7260
ctcagctaaa cgcttctctg cttccgccac cgcctgtttc tcttcattaa gagtttcatg 7320
ttcagcgacc tctgcatttt cacgagcctt ttcttcagct tccttctgtt tattcacatc 7380
accaatttta ctttgcaatg tatttttata agaattaagt ttgctaatat ctgcatcaag 7440
ctgatttgat ttttttgca actcatcaac atccctctca agatcagtga taccatgata 7500
agaatgatgc ttgaatactt ttttcatctc ctcgattttc ttctgttttt cactaatctg 7560
tgtagcaatt ttattcttct gcttttgttt ttcattaatt acattactca ccaccttcga 7620

```
actcttatcc atatcactga cctgagcatt cgttggtgca gtattaactg aagcagtgtt   7680
attgttgtta tttcctgagc tttctgcaaa aagtgatggc atatcactaa ttaaagaatt   7740
aagaactctg gagacccctc caaatggatt atcaaccaga gttgaattct cttctgtcat   7800
aacaatacca ttcatcaccg gaaggccatc attattaatg acaacatcac cccacggagt   7860
cagatatgac tcaccggttt tcatcacagt tgatgtagaa ccagatgaat ttgaatttcc   7920
ctgaccacca ttattaccat gcccagagcc accaccccag tgaaccccac tattactatt   7980
attatttcca ccttgctgat tcagattcgc ccctgttccc cccatagact caccagcagt   8040
tggtccatat ccacttagtt ctttagccat aaattcctct ttgataatta aaacaataaa   8100
ttaaaaacaa tatactgtac atataaccac tggttttatg tacagtaaaa acctactact   8160
cagcattgtc catgtcaaga gcatggattt tcatttttgc aataaggatc acactatggg   8220
gaggcaggca ttgagaacgt cgaaacagaa caccggagca aatcaggatg agatataaaa   8280
ctgttggatc atgaaaaaac ggagaacgat gtgagcaaat caccccgcca taaactgaac   8340
aaaacagaca aacgacttct cgacaccctt gttgctgccg gatatgagca tgacaaagcc   8400
cgtgacctca tccagaaaca ggtttacacg ctgacactgg ctgatcagcg tcatgtggtc   8460
agtgaaatca gtaatggtgt gaatcccacc caggcttact cggcggtata ccaggcaaga   8520
cgcattcgcc tcgcccgtaa atatctgaac ggtaaaaagg ttatggaaga aaccggggaa   8580
aatacgcccc catcagcgta aggatttctt ttgccgctcc agagactcca gtttttttacg   8640
caaatcctct ctttttggg catctctggt gccagccagc tctgctctca actcatcgat   8700
ctgaagttgt atcttcagtc tattactgaa cattttctgt ctggcattaa catccgcaac   8760
aatgccgttt tttgtcttct cggccttttg ttgaaaaaca ttgctgtccg catgactggc   8820
aaccgaagca gaaagaacac taaaaagcag gactggcaca catttttttca cgggattatt   8880
cctgactcat tgaccatcaa atcacattgg gagtaaaccg acgtatgata agagatactc   8940
ttcggagata taactccctg agtatcaaga ttaaaaacgc aaggagatgt ttatgagatc   9000
tgccgctgcc aggctgcttc tgatacctct gataacagca acaatagctc ttacaggatg   9060
cacaccaaag accagcctgg aacgacatac ccggcattat gtttatgctt cagatgatgg   9120
atttgatcct aacttctaca cccagaaagc agacaccata cgtatgatgc tcccgttctt   9180
tcagcagttc cgggatatgg ggatgaaaga caaagcagcc ggagtatcag cagaaacggc   9240
acagcaacgt gtaaaagaat tccactcaga aaaatttttt cactcactcc ggagcacaac   9300
agcctttgct ggcagaaaat acacaaacag cgatatgcct tcgccgaaaa aaatgaaact   9360
aatggcagac accatttctg cggtttatct cgatggatac gagggcagac agtaagggat   9420
ttaccataat cccttaattg tacgcaccgc tgaaatgcgt tcagcgcgat cacggctgct   9480
gacaggtaaa aatggcaaca aaccacccga aaagctgccg cgatcgcacc tgataaattt   9540
taaccgtatg catagctatt cagccatgtg aataacgctg gttttgcctg cgtaaacctc   9600
atgacactgt tttttttcca tcttttcagt tgatgacata cgcagacatc gcgggatgag   9660
gctgaggaat gagcgcgatc tggcaaagag gcaaaacaca gcaacaaaaa cgacacgcca   9720
gaatcgcgcc cggatgcgtt tttaacgcgt tccggtacca tctggcaacc tcccggaaca   9780
actcaccgtc acatacctat tgacgggcca cgccataccc gtgcttcccg ttcctgctct   9840
tcatgccagg accgcgcacg ctcccgttcc aggcgtgcct gcctttcctg ttcatccctt   9900
atctgctgtt cgtgataaat aaccgactca agtggtccac ctgcccggct aatctctgca   9960
cctgctgact caagtcgtcg cactgttccc tcagttgccc gttctcctgt cgtgtcagct  10020
```

-continued

```
cgaacatatg ctgcaaatcc gtgaaggcgc tctcccagtc tttcagccgc tgcatatagt  10080
cctgctgcaa ttgctctaag gcgttcagta agtgcatttc cagctctgtc atactcactt  10140
actccctgac cagtcttact gcgttcttct tctccaccgt ccagttgttt tccccccttca  10200
ccccggacgg caacactaga aatttcccgt tcctgccctc gtgatacgtc acaccccatg  10260
tttttcccg gagtttcgcc agcgtctctt cctggtccct gatagccagg atgttcgccg  10320
caatccggct ttcctgccac tgaatcagcc ccccatgacg ccagaaaaat cccgcccgtg  10380
acgcagagcg ccgtcagcga cgggtacagt atccgccctt tgaccagctt ccagagcagc  10440
tcttcctgcc gccgggccag ttcgttctct gtggcgctga actgcgcgtt cacggcactg  10500
ttcagcgtct ccagttgttc tttcaccgct gctgtgtgtg cgctgatagc gtctctgatt  10560
ttctgcccgt ttaagttcag ttccctgtct acagacgctt cgagcttcct gaactcgctg  10620
ttcagcatgt tctctgtaga gacggcacgc tctttcagtt tcttctcgaa gtctgtcccc  10680
atttgtaaaa gattgctcat acagcgcccc tttcagcctg agattacgcc caccctccgg  10740
gtcggcgata ctgatactgc tcctggttgt cctcacaacc tcaaaacctg ccgctgtaag  10800
cgcctcagtg acatcctgac gcgtttttag cgctccggca tggtaaagag cctccagtcc  10860
cctcgtaatc gcttctgcgg cctcctgttt cgctttcggc agattattcg gggtgacaag  10920
tgtccgcctg ttctccggtg cgttcgggtc gtgcagcccg taatggtgat tcaccagtgt  10980
ctgccaggca ttgattcgcg gacggtccgc tcggtcgtaa tagggctgga gccgtttcc  11040
gctcgccagc tccatattcg ggatgacaaa attcagctca agacgcccct tgtcctggtg  11100
ctccacccac aggatgctgt actgattttt ttcaagaccg ggcatcagta cccgctcaaa  11160
gctctccatc accctttcac gctctcccgg tggcagggtc tgctctgcaa aagacagaac  11220
ccccgaggtg tattttttcg caaacggcgt ggcatcgatg agttcccgca cctcttcggg  11280
agcaccccgc agaactctcg ccccttcccg gttacgctcc cggcccagca ggtaatcaac  11340
cggaccactg ccaccgcctt ttcccctggc atgaaactta actatcatcc cgttctccct  11400
gtttacggac ctcatccctc agctcactca gttcacgtcc gatggccatc agtgcagcca  11460
ccacatgaac ccggtcatgc cccgaccact gtccgctgtt tatcttccgg gctatctgat  11520
tcaggttatt gccgaccgaa gcgaactggc gcaacagcgg cggtgccagt gtcggaagac  11580
ctgacgtttt cgatggcggt gcccccaggc agaccttacg catccatgac gcaagttgtt  11640
ttccctcaca acgtgccagc agccgcgcat gttcctcatc cgtgacccgt atcgtgagca  11700
tcctttcgcg tttcaccggt atcattaaaa acctccgaca gactccccac acatggagaa  11760
acagaactgt gactaaacag gaaaaaaccg cccttaacat ggcccgcttc atcagaagcc  11820
agacgctgac cctgctggaa aaactgaatg aactggacgc cgacgaccag gctgacatct  11880
gcgaagcgct tcacgatcac gctgacgagc tttaccgcag ctgcctcgca cgcttcgggg  11940
ataacggtga aaacctctga cacatgcagc tcccggagac ggtcacagct ggcctgtgag  12000
cggatgccgg gagcagacaa gcccgtcagg gcgcgtcagc gggttttagc gggtgtcggg  12060
gcgcagccat gacccagtca cgtagcgata gcggagtgta tactggctta atcatttggc  12120
atcagtgagg attgtatgaa aagtgcacca tgccgggtgt gaaatgccgc acagatgcgt  12180
aaggagaaaa tgctcgtcca ggcgcttttc cgcttcctcg ctcactgact cgctccgctc  12240
ggtcgttcgg ctgcggcgag cggtatcagc tcactcaaag acggtaatgc ggttatccac  12300
agaatcaggg gataacacca aaagaaacat gtgagcaaaa aacaagaacc cggaaaaggc  12360
```

```
cacgcagctg gcgtttttcc ataggctccg cccccctgga cgagcatcac aaaaaaccga  12420
cgctcaagtc agaggtggcg aaacccgaca ggacttaaag ataccaggcg tttccccctg  12480
gtggctccct cgtgcgctct cctgttccga ccctgccgct taccggatac ctgtccgcct  12540
ttctcccttt gggaagcgtg gcgctttctc atagctcacg ctgttggtat ctcagttcgg  12600
tgtaggtcgt tcgctccaag ctgggctgtg tgcacgaacc ccccgttcag cccgaccgct  12660
gcgccttatc cggtaactat cgtcttgagt ccaacccggt aagacacgac ttaacgccac  12720
tggcagcagc cattggtaac tggatagtgg atttagatac gcagaactct tgaagttgaa  12780
gccttatagc ggctacactg gaaggacagc atttggtatc tgtgctccac taaagccagt  12840
tacccggtta agcagtcccc aactgactta accttcgact aaaccgcctc cccaggcggt  12900
tttttcgttt acaggcagca gattacgcgc agaaaaaaag gatctcaaga agatcctttg  12960
atcttttcta ctgaaccgcg atccccgtca gttcagaaga cgaagatggt gcaacggttc  13020
ctccttgtac aggggtctga cgctcagtgg aacgaaaact cacgttaagc aacgttttct  13080
acctctgacg cctcttttaa tggtctcaga tgtcctttgg tcaccagttc tgccagcgtg  13140
aaggaataat ggccgagcat attgatatgt ccgtggcaaa gcggggagag gcgtgcgata  13200
tcttcatcat tcagtgtttc accttgcgcc cggagatgat ccagggctgc ctgcatatac  13260
atagtgttcc ataacacgac ggcgttagtg accagcccca gtgcgcccag ttgatcttcc  13320
tgaccgtcgg tatatcgttt tcttatctca cctttttgac cgtgacagat ggctctggca  13380
acggcatggc ggctttctcc ccgattaagc tgggtcagaa tgcgccggcg gtaatcttca  13440
tcatcaatat aattaagcag atacagcgtt ttgttgatgc gccccacttc aatgattgcc  13500
tgagtcagtc cggaaggacg ttcacttttc agcaatgaac ggaccagcac tgaagcctgt  13560
actttgccca gtttcaggga gccagcggtc cggatcattt cgtcccactg aaggactatt  13620
tttcggggat ctgattgccc tctggcaata tcattcagca cgccatagtt ggcatcatgg  13680
cccattcgcc agaaaaccga agcaccggca tcagccaggc gtggagaaaa ctggtatccc  13740
agcagccaga aaaggccaaa gacaagttcg ctggtacctg ctgtatcggt cataatttcg  13800
gttggattca gcccggtctc ctgttccaga aggccttcca gcacaaagat agagtccctc  13860
agcgtccccg gtataacgat gccatgaaag ccggaatact gatcggacac aaagttgtac  13920
caggtgatcc ctctgttatt accaaagtat ttgcggttcg gtccggcatt gattgttctg  13980
actggcgtaa caaagcgcat tccatctgca gtccgcctca gcaatatcgg gatagagcgc  14040
agggtcagga aatccttgga tatcgttcag gtagcccacg ccgcgcttga gcgcatagcg  14100
ctgggtttcc ggttggaagc tgtcgattga aacacggtgc atctgatcgg acagggcgtc  14160
taagagcggc gcaatacgtc tgatctcatc ggccggcgat acaggcctcg cgtccggatg  14220
gctggcggcc ggtccgacat ccacgacgtc tgatccgact cgcagcattt cgatcgccgc  14280
ggtgacagcg ccggcggggt ctagccgccg gctctcatcg aagaaggagt cctcggtgag  14340
attcagaatg ccgaacaccg tcaccatggc gtcggcctcc gcagcgactt ccacgatggg  14400
gatcgggcga gcaaaaaggc agcaattatg agccccatac ctacaaagcc ccacgcatca  14460
agcttttgcc catgaagcaa ccaggcaatg gctgtaatta tgacgacgcc gagtcccgac  14520
cagactgcat aagcaacacc gacagggatg gatttcagaa ccagagaaca tgtcattgta  14580
ctggaaggcg cattacaact gcggctgggg gatgagtggc acaccgtttc tgccggggaa  14640
tccctgcgct tccatgcgga tatcccgcac gcttacgcca atcccggtaa ggccattgtg  14700
acactgcata atctgatcca ttatccgcgc ccggcggaca aataaaaaag cagggtataa  14760
```

taaatatacc ccgctttgac ttaacggatc gtcttacttt atttgtaaaa taaaaccaaa 14820
ataaatatgt gttcagctta acttattata tatcatcctt ataccaaccg ggatgatatg 14880
tttatactga acagaaaagc atgccattca gaatactatc ttctgttata tatggcggtt 14940
tatttattgt ttaattacac acactcaggc atatcactat gctatcgtga tgttttcact 15000
ggtgttgtta ctactgcctt tacggcattt tggtgttgtt caaaatgact gtcgcagcag 15060
tctttctggt gtcttaaata ctattattat aactgcatct ggtgttgtta atattattgt 15120
tactgcttac tttattatta ttgctgtcag tctttgctgt ttcttttttta ttaagggtat 15180 taccaaactg cgggggcatt atcgtacagt gatcctgaac cagtctgaaa cgaaattaca 15240
gattacggtt aaaatataaa aaaaagccac cattcctgcc ggatacggtg gcttaaatac 15300
agaattaatt aatttatttc agtatgttat cacacatcag ctgaagtgta ttaataaacc 15360
gtgctgcatg aaagccatca cagactgcat gatgaacctg tacagaaaca ggtaataata 15420
cgcggtcacc ttcctgctga aactttgcca tcgtaaaaac cggggcaaaa taatcatcat 15480
ttccggtgat gttcaggtta aatccgtcaa aactcaccca cggtaatgat gatatattca 15540
ggtgattctc cggtaaattt ccctgcggaa acaatctggt atcatgctga tattctgccg 15600
ttaccgcatt ataacctgcc ataaactcac tgagatccgg aaaataacgg caggacagtg 15660
cagagaatgt ttcggtttct ttatgaaaga cagtaaagac cgggtctgac tggtcccagt 15720
aaataagttc attgtctttc agtgccatcc ggaactccgg aaactgatta acagcccggg 15780
agatcaggta aatcatcagc ggataaaact tataacctgt ctccgccagt gcggtacgca 15840
aagcggtaat atcgagtttg gtggtcaggc tgaatccgca tttaatctgc tgacgataaa 15900
gggcaaagtg ttccctgcga ttccaggtat tcaggtcaat ccgggtaaaa ttcatggtta 15960
ttccttctga ttaatagtga aaaatattaa taatcagaag gcagtctggt tgtctcaatg 16020
ggtaacattc cgtcctccgt aagctgtttg gtattcagta ataataccct atacgggctt 16080
aatctgtatt aagcccggct ttatttattc cggccaatca tccgcaaaca catagcggat 16140
cagttctgcg gattcacggg gcggtgctct cagcacatcc gccattaaat caatctccat 16200
ctgacaggtt tgcagcttgt cttccgccgg tacatacgga tcatccgtca ggaaactatc 16260
gccgtattta tccatcgacc cctgtatttg tgccgaaaat a 16301

<210> SEQ ID NO 22
<211> LENGTH: 22
<212> TYPE: DNA
<213> ORGANISM: Artificial Sequence
<220> FEATURE:
<223> OTHER INFORMATION: Primer #417 (230spannA) for plasmid K230

<400> SEQUENCE: 22
ggtccgtgga atggtcaaac gg 22

<210> SEQ ID NO 23
<211> LENGTH: 22
<212> TYPE: DNA
<213> ORGANISM: Artificial Sequence
<220> FEATURE:
<223> OTHER INFORMATION: Primer #434 (230spannR) for plasmid K230

<400> SEQUENCE: 23
gaatgtcaag ctttccagat ag 22

<210> SEQ ID NO 24

<211> LENGTH: 20
<212> TYPE: DNA
<213> ORGANISM: Artificial Sequence
<220> FEATURE:
<223> OTHER INFORMATION: primer T394

<400> SEQUENCE: 24
acctacctcc acaggtgctg 20

<210> SEQ ID NO 25
<211> LENGTH: 20
<212> TYPE: DNA
<213> ORGANISM: Artificial Sequence
<220> FEATURE:
<223> OTHER INFORMATION: primer T395

<400> SEQUENCE: 25
gcttttcaac ttgcacgaca 20

<210> SEQ ID NO 26
<211> LENGTH: 20
<212> TYPE: DNA
<213> ORGANISM: Artificial Sequence
<220> FEATURE:
<223> OTHER INFORMATION: qRT-PCR, orf7041 forward primer

<400> SEQUENCE: 26
tggaaagagt ggggaaagtg 20

<210> SEQ ID NO 27
<211> LENGTH: 20
<212> TYPE: DNA
<213> ORGANISM: Artificial Sequence
<220> FEATURE:
<223> OTHER INFORMATION: qRT-PCR, orf7041 reverse primer

<400> SEQUENCE: 27
gccgcagctt ttaatacgtc 20

<210> SEQ ID NO 28
<211> LENGTH: 20
<212> TYPE: DNA
<213> ORGANISM: Artificial Sequence
<220> FEATURE:
<223> OTHER INFORMATION: qRT-PCR, orf5189 forward primer

<400> SEQUENCE: 28
tgcagggatg aaagataggg 20

<210> SEQ ID NO 29
<211> LENGTH: 20
<212> TYPE: DNA
<213> ORGANISM: Artificial Sequence
<220> FEATURE:
<223> OTHER INFORMATION: qRT-PCR, orf5189 reverse primer

<400> SEQUENCE: 29
tcgcacttct cacaccagac 20

<210> SEQ ID NO 30
<211> LENGTH: 32
<212> TYPE: DNA
<213> ORGANISM: Artificial Sequence
<220> FEATURE:
<223> OTHER INFORMATION: Porf7345 forward primer

<400> SEQUENCE: 30
gcgcagtcga cacccaagta catagccgac ac 32

<210> SEQ ID NO 31
<211> LENGTH: 37
<212> TYPE: DNA
<213> ORGANISM: Artificial Sequence
<220> FEATURE:
<223> OTHER INFORMATION: Porf7345 reverse primer

<400> SEQUENCE: 31
gcgcagaatt catcacgctt caaaattcct tgagtac 37

<210> SEQ ID NO 32
<211> LENGTH: 20
<212> TYPE: DNA
<213> ORGANISM: Artificial Sequence
<220> FEATURE:
<223> OTHER INFORMATION: orf5209 (=PziaA) forward primer

<400> SEQUENCE: 32
aggcgtggtt gaggtatctg 20

<210> SEQ ID NO 33
<211> LENGTH: 20
<212> TYPE: DNA
<213> ORGANISM: Artificial Sequence
<220> FEATURE:
<223> OTHER INFORMATION: orf5209 (=PziaA) reverse primer

<400> SEQUENCE: 33
ggctcgctca actactacgg 20

<210> SEQ ID NO 34
<211> LENGTH: 20
<212> TYPE: DNA
<213> ORGANISM: Artificial Sequence
<220> FEATURE:
<223> OTHER INFORMATION: Porf5203 forward primer

<400> SEQUENCE: 34
tctcgaacaa gtggcagatg 20

<210> SEQ ID NO 35
<211> LENGTH: 20
<212> TYPE: DNA
<213> ORGANISM: Artificial Sequence
<220> FEATURE:
<223> OTHER INFORMATION: Porf5203 reverse primer

<400> SEQUENCE: 35
gcctttgtaa cgcttggtgt 20

<210> SEQ ID NO 36
<211> LENGTH: 147
<212> TYPE: DNA
<213> ORGANISM: artificial sequence
<220> FEATURE:
<223> OTHER INFORMATION: Modified generalized PziaA promoter sequence
<220> FEATURE:
<221> NAME/KEY: misc_feature
<222> LOCATION: (1)..(61)
<223> OTHER INFORMATION: n is a, c, g, or t
<220> FEATURE:
<221> NAME/KEY: misc_feature
<222> LOCATION: (88)..(100)
<223> OTHER INFORMATION: n is a, c, g, or t
<220> FEATURE:

-continued

```
<221> NAME/KEY: misc_feature
<222> LOCATION: (107)..(132)
<223> OTHER INFORMATION: n is a, c, g, or t
<220> FEATURE:
<221> NAME/KEY: misc_feature
<222> LOCATION: (140)..(144)
<223> OTHER INFORMATION: n is a, c, g, or t

<400> SEQUENCE: 36

nnnnnnnnnn nnnnnnnnnn nnnnnnnnnn nnnnnnnnnn nnnnnnnnnn nnnnnnnnnn      60

naacatctga atatatattc agatattnnn nnnnnnnnnn taaactnnnn nnnnnnnnnn     120

nnnnnnnnnn nnactgaaan nnnnatg                                         147
```